(12) United States Patent
Liao et al.

(10) Patent No.: US 10,510,962 B2
(45) Date of Patent: Dec. 17, 2019

(54) COMPOUND AND ORGANIC ELECTRONIC DEVICE USING THE SAME

(71) Applicant: NICHEM FINE TECHNOLOGY CO., LTD., Jhubei, Hsinchu County (TW)

(72) Inventors: Liang-Di Liao, Jhubei (TW); Hui-Ling Wu, Jhubei (TW); Shwu-Ju Shieh, Jhubei (TW); Chi-Chung Chen, Jhubei (TW)

(73) Assignee: SHANGHAI NICHEM FINE CHEMICAL CO., LTD., Shanghai (CN)

( * ) Notice: Subject to any disclaimer, the term of this patent is extended or adjusted under 35 U.S.C. 154(b) by 252 days.

(21) Appl. No.: 15/828,986

(22) Filed: Dec. 1, 2017

(65) Prior Publication Data

US 2018/0159044 A1    Jun. 7, 2018

Related U.S. Application Data

(60) Provisional application No. 62/433,371, filed on Dec. 13, 2016, provisional application No. 62/430,982, filed on Dec. 7, 2016.

(51) Int. Cl.
| | | |
|---|---|---|
| H01L 51/50 | (2006.01) | |
| H01L 51/00 | (2006.01) | |
| C07D 311/82 | (2006.01) | |
| C07D 335/12 | (2006.01) | |
| C07D 405/04 | (2006.01) | |
| C07D 405/14 | (2006.01) | |
| C07D 409/04 | (2006.01) | |
| C07D 409/14 | (2006.01) | |
| C09K 11/06 | (2006.01) | |
| G01R 33/46 | (2006.01) | |

(52) U.S. Cl.
CPC ........ *H01L 51/0058* (2013.01); *C07D 311/82* (2013.01); *C07D 335/12* (2013.01); *C07D 405/04* (2013.01); *C07D 405/14* (2013.01); *C07D 409/04* (2013.01); *C07D 409/14* (2013.01); *C09K 11/06* (2013.01); *H01L 51/0054* (2013.01); *H01L 51/0057* (2013.01); *H01L 51/0067* (2013.01); *H01L 51/0068* (2013.01); *H01L 51/0071* (2013.01); *H01L 51/0072* (2013.01); *H01L 51/0073* (2013.01); *H01L 51/0074* (2013.01); *H01L 51/5072* (2013.01); *C09K 2211/1088* (2013.01); *C09K 2211/1092* (2013.01); *G01R 33/46* (2013.01); *H01L 51/5076* (2013.01)

(58) Field of Classification Search
None
See application file for complete search history.

(56) References Cited

FOREIGN PATENT DOCUMENTS

JP    2009-057300    *   3/2009   ........... C07D 311/94

\* cited by examiner

*Primary Examiner* — Gregory D Clark
(74) *Attorney, Agent, or Firm* — Birch, Stewart, Kolasch & Birch, LLP

(57) ABSTRACT

The present specification relates to a novel compound and an organic electronic device using the same.

18 Claims, 28 Drawing Sheets

COMPOUND AND ORGANIC ELECTRONIC DEVICE USING THE SAME

CROSS-REFERENCE TO RELATED APPLICATIONS

Pursuant to 35 U.S.C. § 119(e), this application claims the benefits of the priority to U.S. Provisional Patent Application No. 62/430,982, filed Dec. 7, 2016 and of the priority to U.S. Provisional Patent Application No. 62/433,371, filed Dec. 13, 2016. The contents of the prior applications are incorporated herein by their entirety.

BACKGROUND OF THE INVENTION

1. Field of the Invention

The present invention relates to a novel compound and an organic electronic device using the same, more particularly to a novel compound as electron-transporters and an organic electronic device using the same.

2. Description of the Prior Arts

With the advance of technology, various organic electronic devices that make use of organic materials have been energetically developed. Examples of organic electronic devices include organic light emitting devices (OLEDs), organic phototransistors, organic photovoltaic cells, and organic photodetectors.

OLED was initially invented and proposed by Eastman Kodak Company through a vacuum evaporation method. Dr. Ching Tang and Steven VanSlyke of Kodak Company deposited an electron transport material such as tris(8-hydroxyquinoline)aluminum(III) (abbreviated as $Alq_3$) on a transparent indium tin oxide glass (abbreviated as ITO glass) formed with a hole transport layer of organic aromatic diamine thereon, and subsequently deposited a metal electrode onto an electron transport layer to complete the fabrication of the OLED. OLEDs have attracted lots of attention due to their numerous advantages, such as fast response speed, light weight, compactness, wide viewing angle, high brightness, higher contrast ratio, no need of backlight, and low power consumption. However, the OLEDs still have the problems such as low efficiency and short lifetime.

To overcome the problem of low efficiency, one of the approaches is to interpose some interlayers between the cathode and the anode. With reference to FIG. 1, a modified OLED 1 may have a structure of a substrate 11, an anode 12, a hole injection layer 13 (abbreviated as HIL), a hole transport layer 14 (abbreviated as HTL), an emission layer 15 (abbreviated as EL), an electron transport layer 16 (abbreviated as ETL), an electron injection layer 17 (abbreviated as EIL), and a cathode 18 stacked in sequence. When a voltage is applied between the anode 12 and the cathode 18, the holes injected from the anode 12 move to the EL via HIL and HTL and the electrons injected from the cathode 18 move to the EL via EIL and ETL. Recombination of the electrons and the holes occurs in the EL to generate excitons, thereby emitting light when the excitons decay from excited state to ground state. Another approach is to modify the materials of ETL for OLEDs to render the electron transport materials to exhibit hole-blocking ability. Examples of conventional electron transport materials include 3,3'-[5'-[3-(3-Pyridinyl)phenyl][1,1':3',1''-terphenyl]-3,3''-diyl]bispyridine (TmPyPb), 1,3,5-tris(1-phenyl-1H-benzimidazol-2-yl)benzene(TPBi), tris(2,4,6-trimethyl-3-(pyridin-3-yl)phenyl)borane(3TPYMB), 1,3-bis(3,5-dipyrid-3-yl-phenyl)benzene (BmPyPb), and 9,10-bis(3-(pyridin-3-yl)phenyl)anthracene (DPyPA).

However, even using the foresaid electron transport materials, the current efficiency of OLEDs still needs to be improved. Therefore, the present invention provides a novel compound to mitigate or obviate the problems in the prior art.

SUMMARY OF THE INVENTION

An objective of the present invention is to provide a novel compound useful for an organic electronic device.

Another objective of the present invention is to provide an organic electronic device using the novel compound, so as to reduce the driving volatage and improve the efficiency of the organic electronic device.

To achieve the foresaid objectives, the present invention provides a novel compound represented by the following Formula (I):

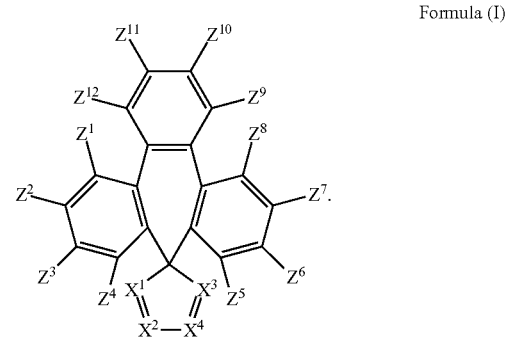

Formula (I)

In Formula (I), $X^1$ and $X^2$ are each independently $C(R^a)$, the two ($R^a$)s are the same or different, and the two ($R^a$)s are joined together to form an aryl ring.

In Formula (I), $X^3$ and $X^4$ are each independently $C(R^b)$, the two ($R^b$)s are the same or different, and the two ($R^b$)s are joined together to form a heteroaryl ring containing at least one furan group, at least one thiophene group, or at least one thiophene S,S-dioxide group.

In Formula (I), $Z^1$ to $Z^{12}$ are each independently selected from the group consisting of: a hydrogen atom, a deuterium atom, a trifuloromethyl group, a halogen group, a cyano group, a nitro group, an alkyl group having 1 to 40 carbon atoms, an alkenyl group having 2 to 40 carbon atoms, an alkynyl group having 2 to 40 carbon atoms, a cycloalkyl group having 3 to 60 ring carbon atoms, a heterocycloalkyl group having 3 to 60 ring carbon atoms, an aryl group having 6 to 60 ring carbon atoms, a heteroaryl group having 3 to 60 ring carbon atoms, an alkoxy group having 1 to 40 carbon atoms, an aryloxy group having 6 to 60 ring carbon atoms, an alkylsilyl group having 1 to 40 carbon atoms, an arylsilyl group having 6 to 60 ring carbon atoms, an alkylboron group having 1 to 40 carbon atoms, an arylboron group having 6 to 60 ring carbon atoms, a phosphine group having 1 to 40 carbon atoms, and a phosphine oxide group having 1 to 40 carbon atoms.

In accordance with the present invention, the double bond between $X^1$ and $X^2$ in Formula (I) and the bonds between the two joined ($R^a$)s are conjugated and commonly construct the aryl ring. Likely, the double bond between $X^3$ and $X^4$ in Formula (I) and the bonds between the two joined ($R^b$)s are conjugated and commonly construct the heteroaryl ring. In accordance with the present invention, the aryl ring extended from $X^1$ and $X^2$ and the heteroaryl ring extended from $X^3$ and $X^4$ are joined and fused, and the double bonds on the aryl ring and the heteroaryl ring are conjugated.

Preferably, $Z^1$ to $Z^{12}$ are each independently selected from the group consisting of: a hydrogen atom, a deuterium atom, a trifluoromethyl group, a halogen group, a cyano group, a nitro group, an alkyl group having 1 to 12 carbon atoms, an alkenyl group having 2 to 12 carbon atoms, an alkynyl group having 2 to 12 carbon atoms, a cycloalkyl group having 3 to 30 ring carbon atoms, a heterocycloalkyl group having 3 to 30 ring carbon atoms, an aryl group having 6 to 30 ring carbon atoms, a heteroaryl group having 3 to 30 ring carbon atoms, an alkoxy group having 1 to 12 carbon atoms, an aryloxy group having 6 to 30 ring carbon atoms, an alkylsilyl group having 1 to 12 carbon atoms, an arylsilyl group having 6 to 30 ring carbon atoms, an alkylboron group having 1 to 12 carbon atoms, an arylboron group having 6 to 30 ring carbon atoms, a phosphine group having 1 to 12 carbon atoms, and a phosphine oxide group having 1 to 12 carbon atoms.

Preferably, the heteroaryl ring extended from $X^3$ and $X^4$ in Formula (I) may contain at least one furan group. For example, the heteroaryl ring may be, but not limited to, benzofuran ring, dibenzofuran ring, or napththofuran ring.

In the case that the heteroaryl ring extended from $X^3$ and $X^4$ contains at least one furan group, the compound may be, for example, represented by any one of the following Formulae (I-I) to (I-VI):

Formula (I-I)

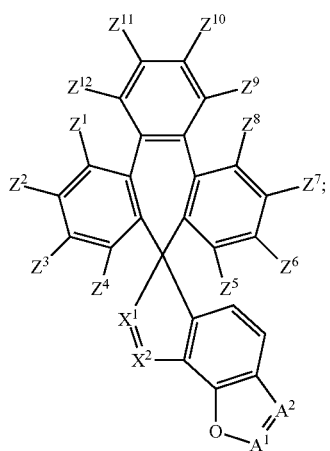

Formula (I-II)

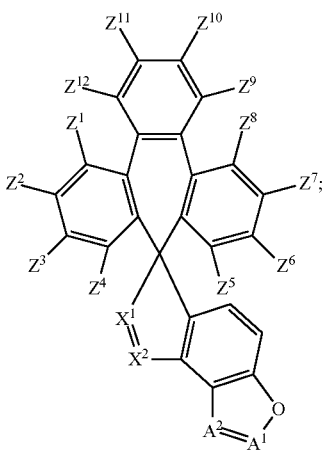

Formula (I-III)

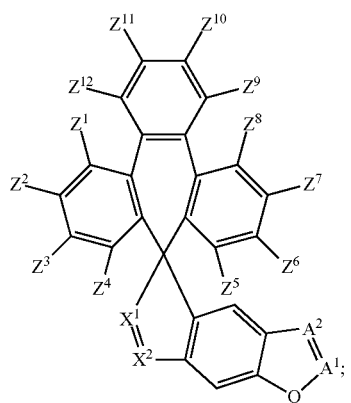

Formula (I-IV)

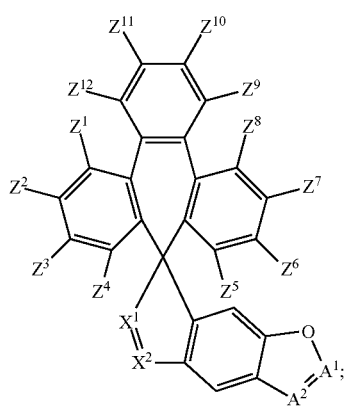

Formula (I-V)

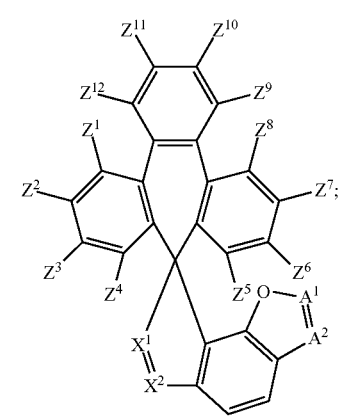

Formula (I-VI)

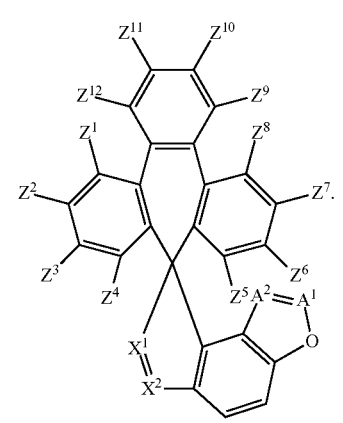

Preferably, the heteroaryl ring extended from $X^3$ and $X^4$ in Formula (I) may contain at least one thiophene group. For example, the heteroaryl ring may be, but not limited to, benzothiophene ring, dibenzothiophene ring, or napththothiophene ring.

In the case that the heteroaryl ring extended from $X^3$ and $X^4$ contains at least one thiophene group, the compound may be, for example, represented by any one of the following Formulae (I-VII) to (I-XII):

Formula (I-VII)

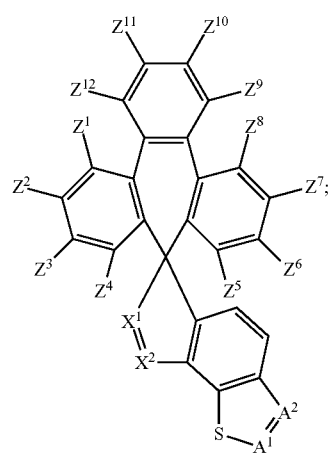

Formula (I-VIII)

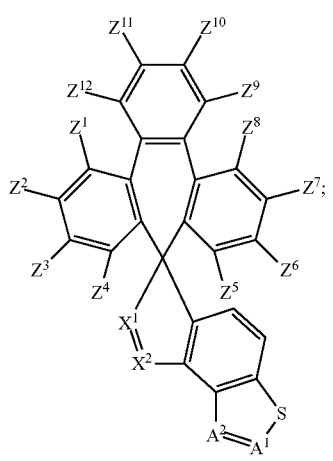

Formula (I-IX)

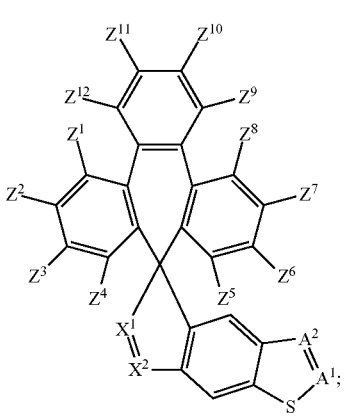

-continued

Formula (I-X)

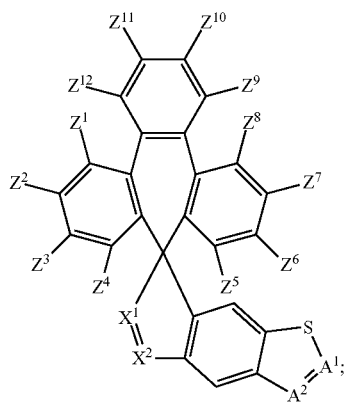

Formula (I-XI)

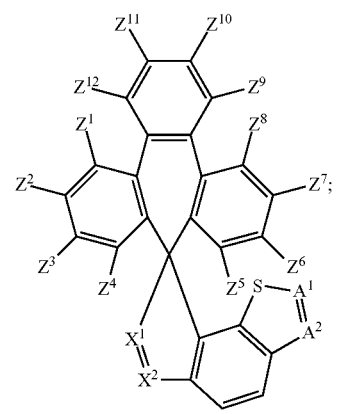

Formula (I-XII)

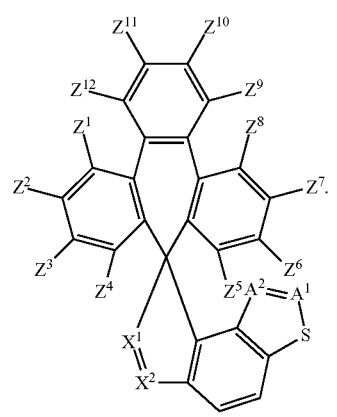

In the case that the heteroaryl ring extended from $X^3$ and $X^4$ contains at least one thiophene S,S-dioxide group, the compound may be, for example, represented by any one of the following Formulae (I-XIII) to (I-XVIII):

Formula (I-XIII)

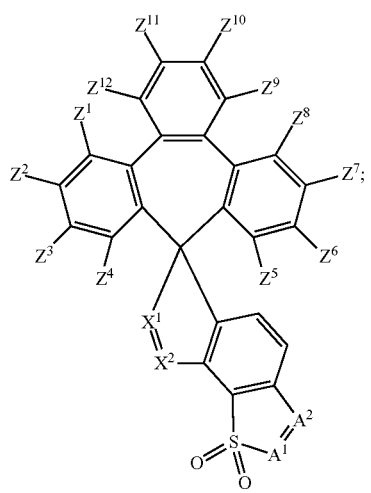

Formula (I-XIV)

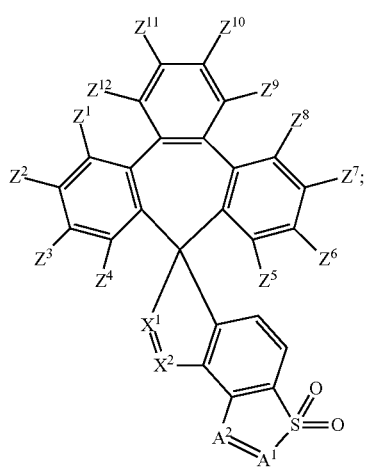

Formula (I-XV)

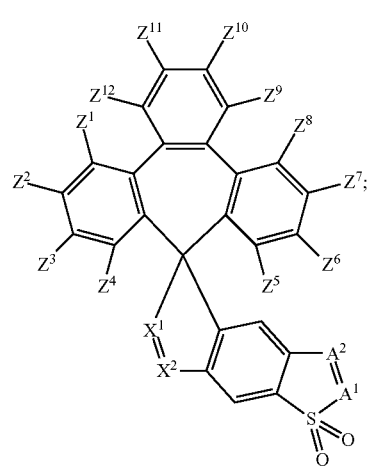

Formula (I-XVI)

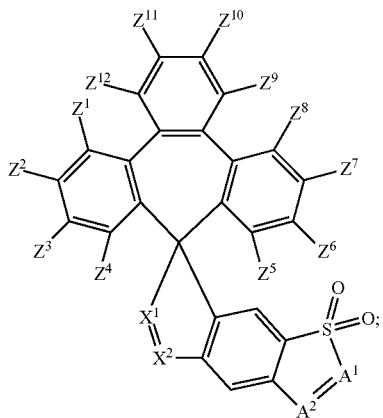

Formula (I-XVII)

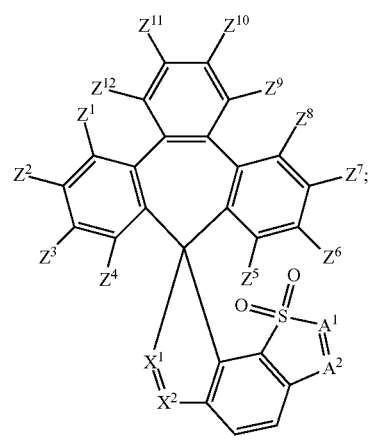

Formula (I-XVIII)

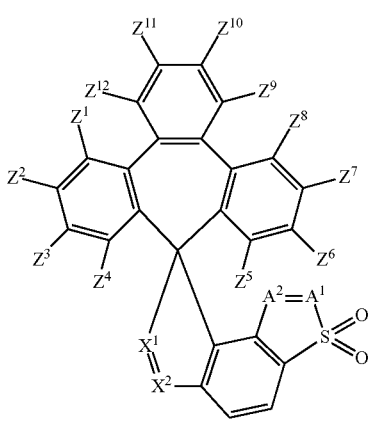

In accordance with the present invention, the foresaid $A^1$ and $A^2$ are each independently $C(R^c)$, the two $(R^c)$s are the same or different, and the two $(R^c)$s are joined together to form an aromatic structure contained in the heteroaryl ring.

Preferably, the aromatic structure may be a substituted or unsubstituted 6 to 20-membered carbon aromatic cyclic structure, for example, but not limited to, a substituted or unsubstituted benzene structure, a substituted or unsubstituted naphthalene structure, a substituted or unsubstituted anthracene structure, a substituted or unsubstituted phenanthrene structure, a substituted or unsubstituted fluorene structure, a substituted or unsubstituted pyrene structure, a substituted or unsubstituted benzophenanthrene structure, a substituted or unsubstituted benzopyrene structure, a substituted or unsubstituted fluoranthene structure, a substituted or unsubstituted benzofluoranthene structure. The substitution group on the 6 to 20-membered carbon aromatic cyclic structure may be, but not limited to, a halogen group, a cyano group, a nitro group, an alkyl group having 1 to 12 carbon atoms, an alkenyl group having 2 to 12 carbon atoms, or an alkynyl group having 2 to 12 carbon atoms.

Preferably, the aryl ring extended from $X^1$ and $X^2$ in any one of foresaid formulae is a substituted or unsubstituted 6 to 60-membered carbon ring, more preferably, a substituted or unsubstituted 6 to 20-membered carbon ring. For example, the substituted or unsubstituted 6 to 60-membered carbon ring may be, for example, a substituted or unsubstituted benzene ring, a substituted or unsubstituted naphthalene ring, a substituted or unsubstituted anthracene ring, a substituted or unsubstituted phenanthrene ring, a substituted or unsubstituted fluorene ring, a substituted or unsubstituted pyrene ring, a substituted or unsubstituted benzophenanthrene ring, a substituted or unsubstituted benzopyrene ring, a substituted or unsubstituted fluoranthene ring, or a substituted or unsubstituted benzofluoranthene ring, but is not limited thereto. More preferably, the substituted or unsubstituted 6 to 60-membered carbon ring is a substituted or unsubstituted benzene structure. The substitution group on the 6 to 20-membered carbon ring may be, but not limited to, a halogen group, a cyano group, a nitro group, an alkyl group having 1 to 12 carbon atoms, an alkenyl group having 2 to 12 carbon atoms, or an alkynyl group having 2 to 12 carbon atoms.

Preferably, at least one of $Z^1$ to $Z^8$ in any one of foresaid formulae may be selected from the group consisting of: an alkyl group having 1 to 40 carbon atoms and substituted with at least one functional group, an alkenyl group having 2 to 40 carbon atoms and substituted with at least one functional group, an alkynyl group having 2 to 40 carbon atoms and substituted with at least one functional group, a cycloalkyl group having 3 to 60 ring carbon atoms and substituted with at least one functional group, a heterocycloalkyl group having 3 to 60 ring carbon atoms and substituted with at least one functional group, an aryl group having 6 to 60 ring carbon atoms and substituted with at least one functional group, a heteroaryl group having 3 to 60 ring carbon atoms containing at least one nitrogen atom, an alkoxy group having 1 to 40 carbon atoms and substituted with at least one functional group, an aryloxy group having 6 to 60 ring carbon atoms and substituted with at least one functional group, an alkylsilyl group having 1 to 40 carbon atoms and substituted with at least one functional group, an arylsilyl group having 6 to 60 ring carbon atoms and substituted with at least one functional group, an alkylboron group having 1 to 40 carbon atoms and substituted with at least one functional group, an arylboron group having 6 to 60 ring carbon atoms, a phosphine group having 1 to 40 carbon atoms and substituted with at least one functional group, and a phosphine oxide group having 1 to 40 carbon atoms and substituted with at least one functional group; and the other of $Z^1$ to $Z^8$ in any one of foresaid formulae may be a hydrogen atom, a deuterium atom, or any other substitution groups as mentioned in the specification. Said functional group is selected from the group consisting of: a cyano group, a nitro group, a trifluoromethyl group, a fluoro group, and a chloro group.

More specifically, at least one of $Z^1$ to $Z^8$ in any one of foresaid formulae may be a specific aromatic substitution. The specific aromatic substitution may be selected from the group consisting of:

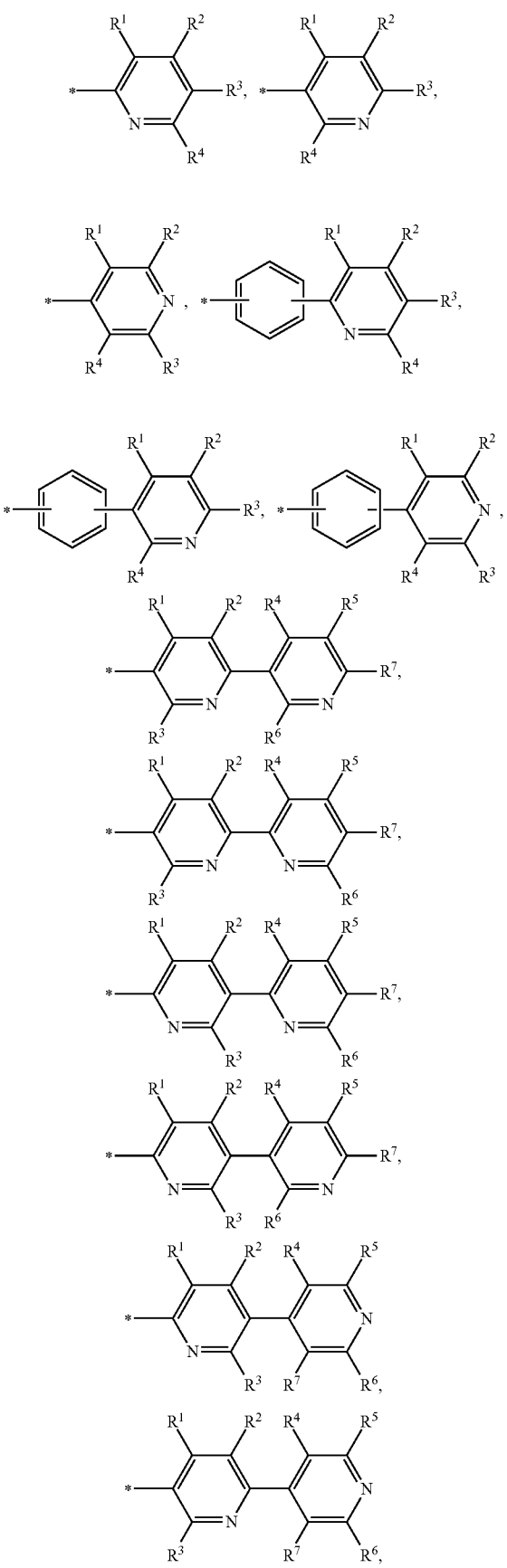

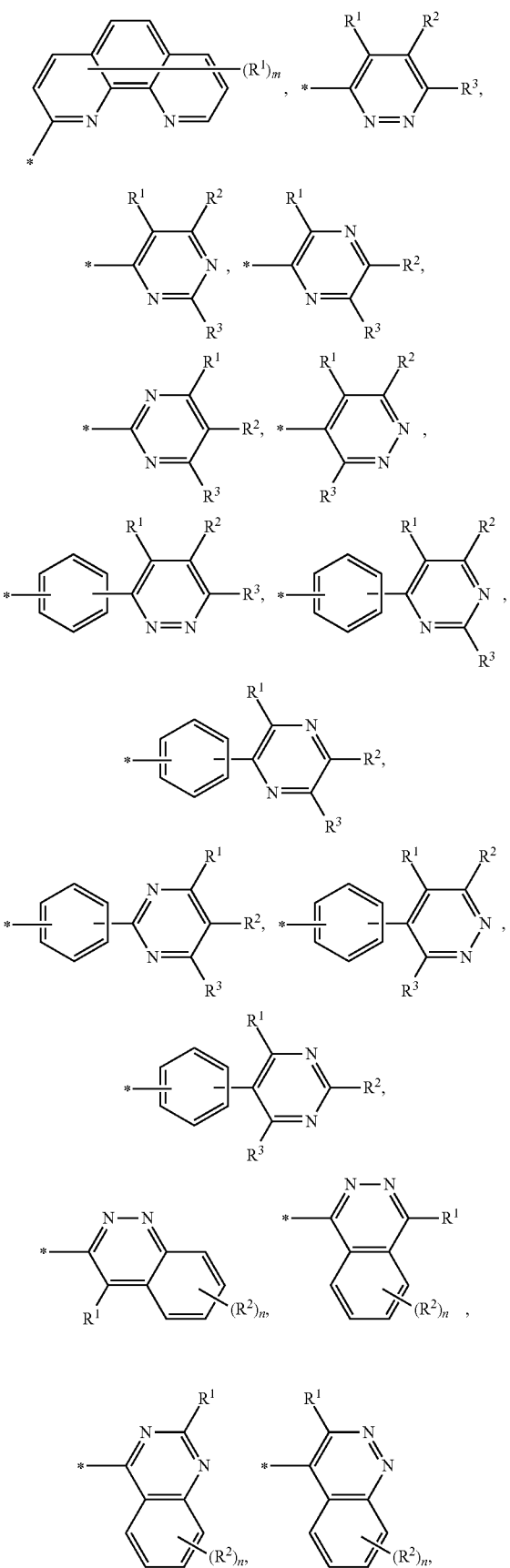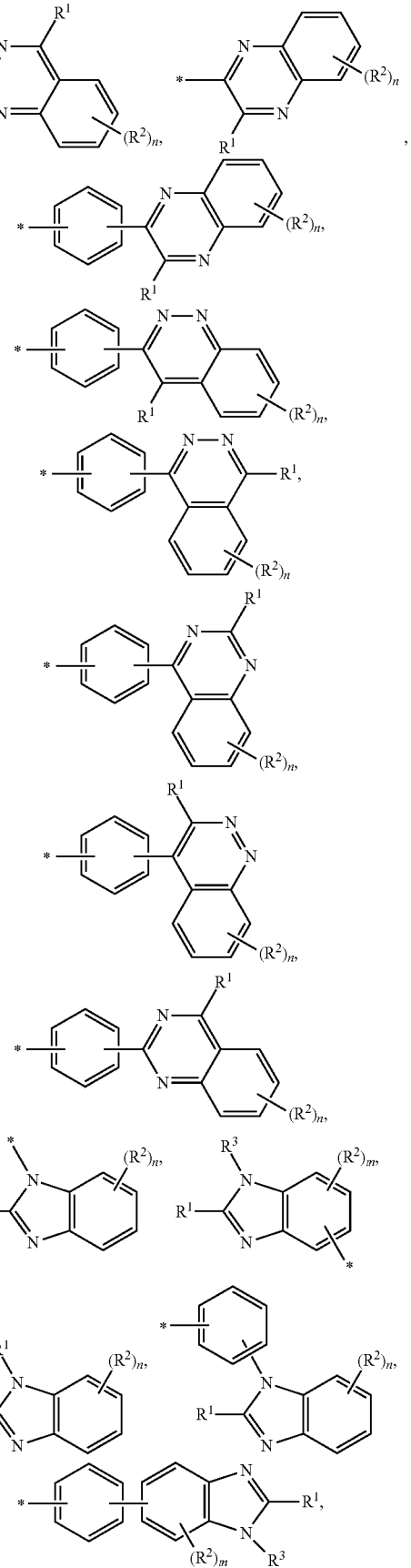

-continued

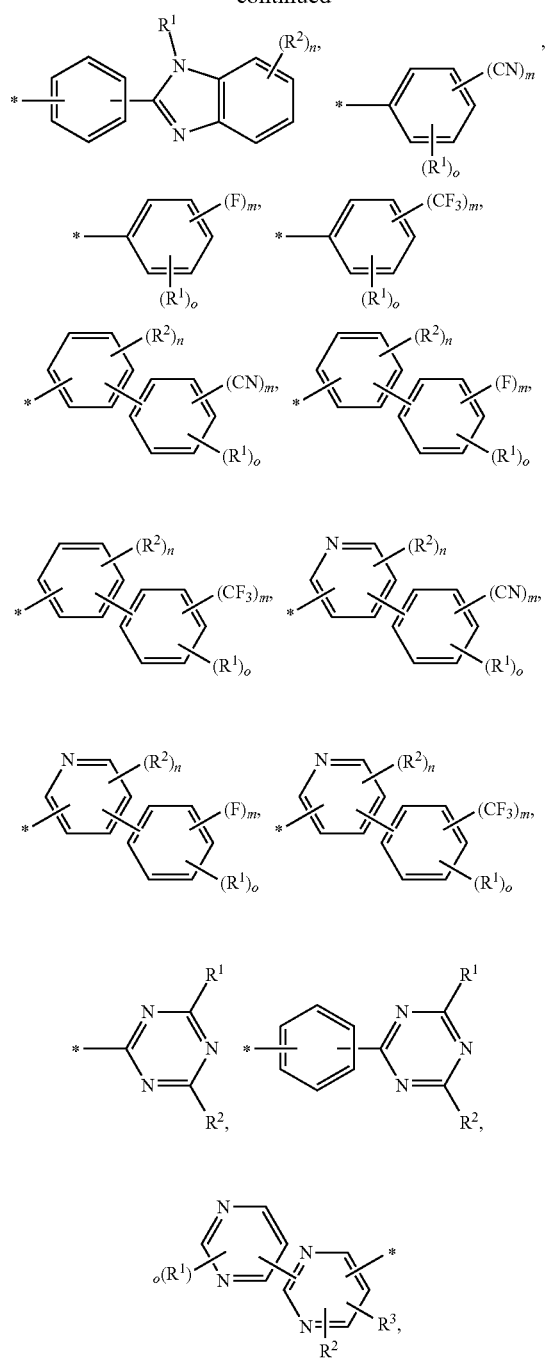

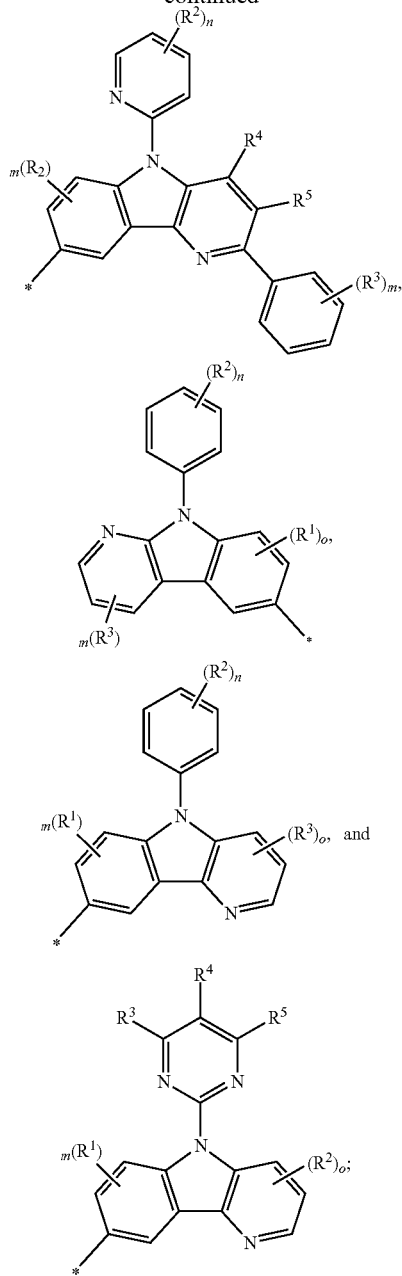

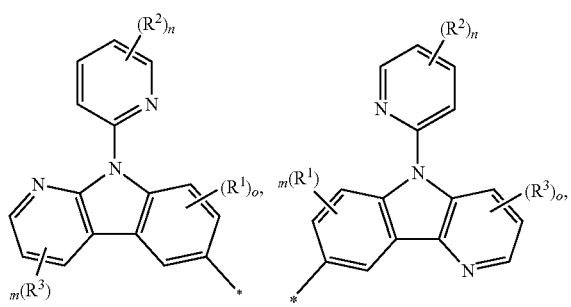

wherein $R^1$ to $R^7$ are each independently selected from the group consisting of: a hydrogen atom, a deuterium atom, a trifluoromethyl group, a halogen group, a cyano group, a nitro group, an alkyl group having 1 to 12 carbon atoms, an alkenyl group having 2 to 12 carbon atoms, an alkynyl group having 2 to 12 carbon atoms, a cycloalkyl group having 3 to 30 ring carbon atoms, a heterocycloalkyl group having 3 to 30 ring carbon atoms, an aryl group having 6 to 30 ring carbon atoms, a heteroaryl group having 3 to 20 ring carbon atoms, an alkoxy group having 1 to 40 carbon atoms, an aryloxy group having 6 to 30 carbon atoms, an alkylsilyl group having 1 to 40 carbon atoms, an arylsilyl group having 6 to 30 ring carbon atoms, an alkylboron group having 1 to 40 carbon atoms, an arylboron group having 6 to 30 carbon atoms, a phosphine group having 1 to 30 carbon atoms, and a phosphine oxide group having 1 to 30 carbon atoms;

wherein n is a positive integral from 0 to 4, m is a positive integral from 0 to 3, o is a positive integral from 0 to 3, and the total of m and o is not more than 5.

Preferably, $R^1$ to $R^3$ each may independently be, for example, but not limited to, phenyl group, pyridine group, pyrimidine group, pyrazine group, pyridazine group, phenylpyridine group, phenylpyrimidine group, phenylpyrazine group, or phenylpyridazine group.

In an embodiment, at least one of $Z^1$ to $Z^8$ in any one of foresaid formulae may preferably be

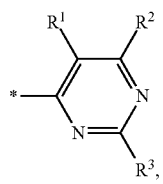

wherein $R^1$ may be pyridinyl group or cyanophenyl group, and $R^2$ and $R^3$ may be any substitution group as stated above.

In another embodiment, at least one of $Z^1$ to $Z^8$ in any one of foresaid formulae may preferably be

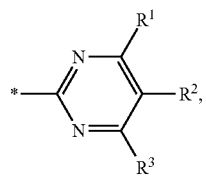

wherein $R^2$ may be pyridinyl group or cyanophenyl group, and $R^1$ and $R^3$ may be any substitution group as stated above.

In further another embodiment, at least one of $Z^1$, $Z^2$, $Z^3$, $Z^6$, $Z^7$, and $Z^8$ in any one of foresaid formulae may be a substituted triazine group with two phenyl groups, two pyridine groups, two pyrimidine groups, two pyrazine groups, two pyridazine groups, two phenylpyridine groups, two phenylpyrimidine groups, two phenylpyrazine groups, or two phenylpyridazine groups.

Preferably, at least one of $Z^1$, $Z^2$, $Z^3$, $Z^6$, $Z^7$, and $Z^8$ in any one of foresaid formulae may be the specific aromatic substitution as stated above, and $Z^4$ and $Z^5$ are each independently selected from the group consisting of: a hydrogen atom, a deuterium atom, a halogen group, a cyano group, a nitro group, an alkyl group having 1 to 12 carbon atoms, an alkenyl group having 2 to 12 carbon atoms, and an alkynyl group having 2 to 12 carbon atoms. Or, at least one of $Z^2$, $Z^3$, $Z^6$, and $Z^7$ in any one of foresaid formulae may be the specific aromatic substitution as stated above, and $Z^1$, $Z^4$, $Z^5$, $Z^8$ are each independently selected from the group consisting of: a hydrogen atom, a deuterium atom, an alkyl group having 1 to 12 carbon atoms, an alkenyl group having 2 to 12 carbon atoms, and an alkynyl group having 2 to 12 carbon atoms.

Preferably, at least one of $Z^2$, $Z^3$, $Z^6$, and $Z^7$ in any one of foresaid formulae is selected from the group consisting of:

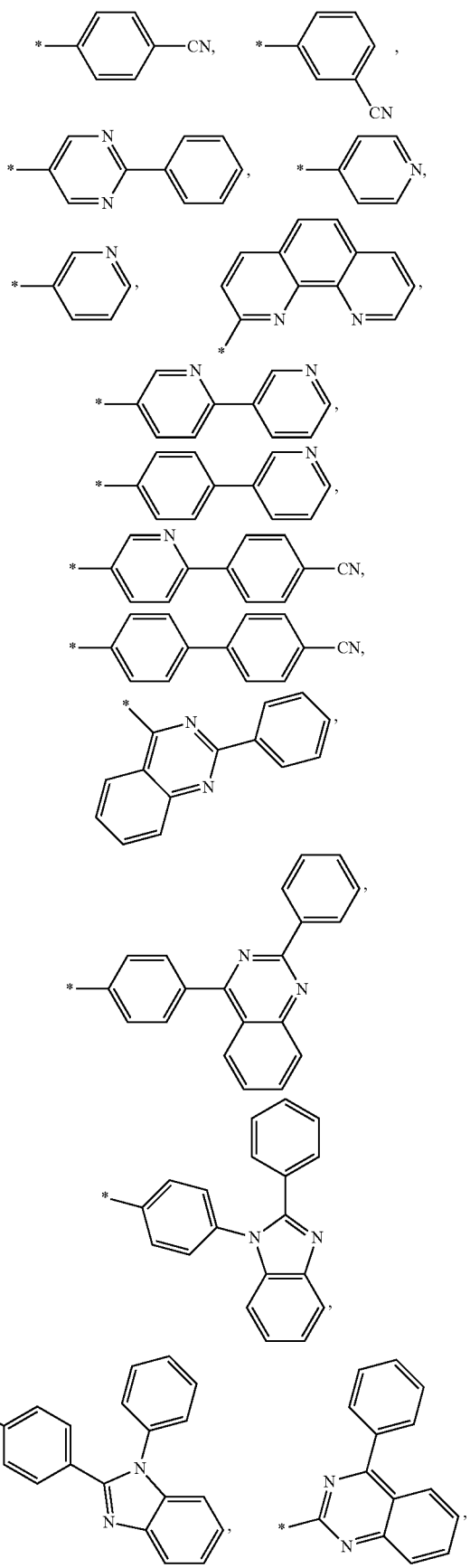

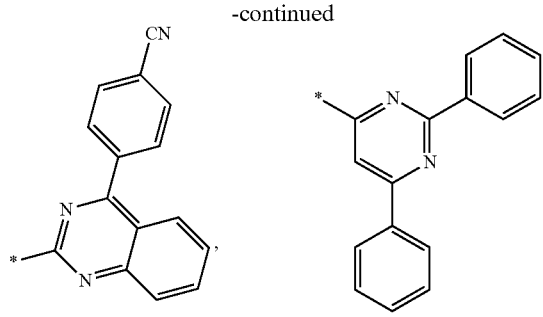
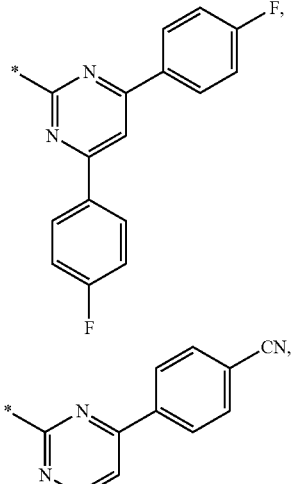
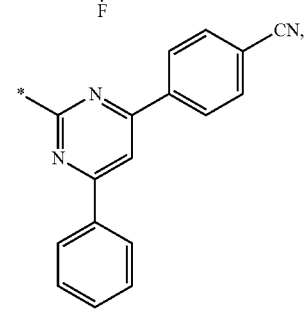
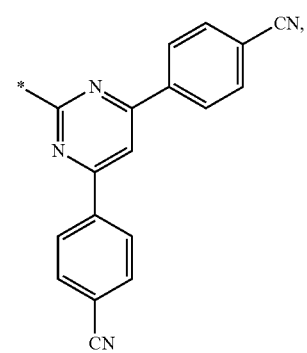
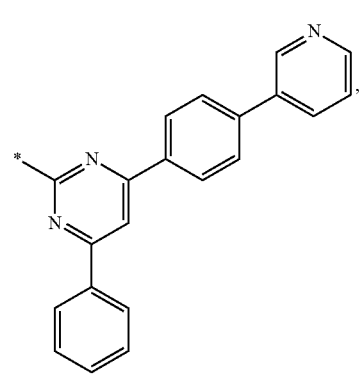
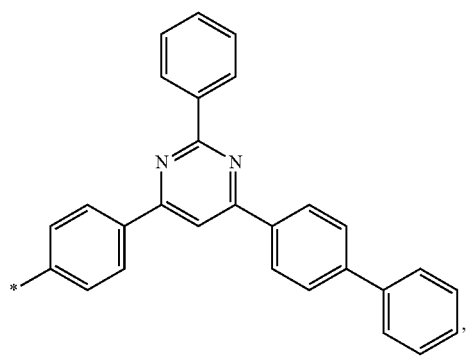
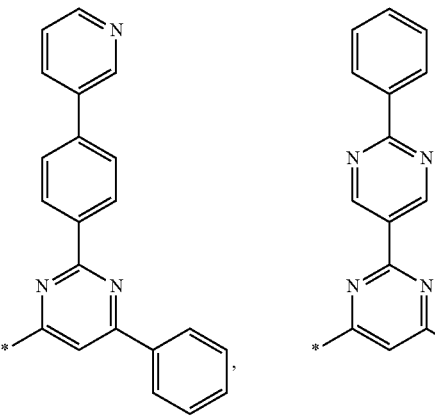
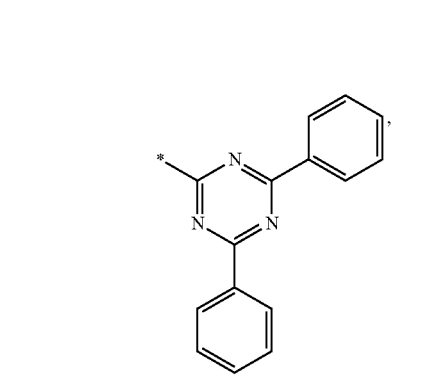
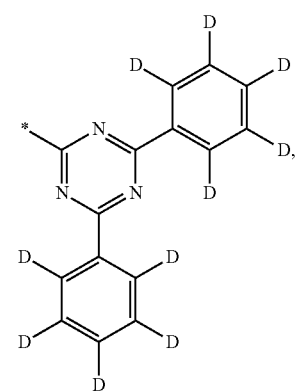

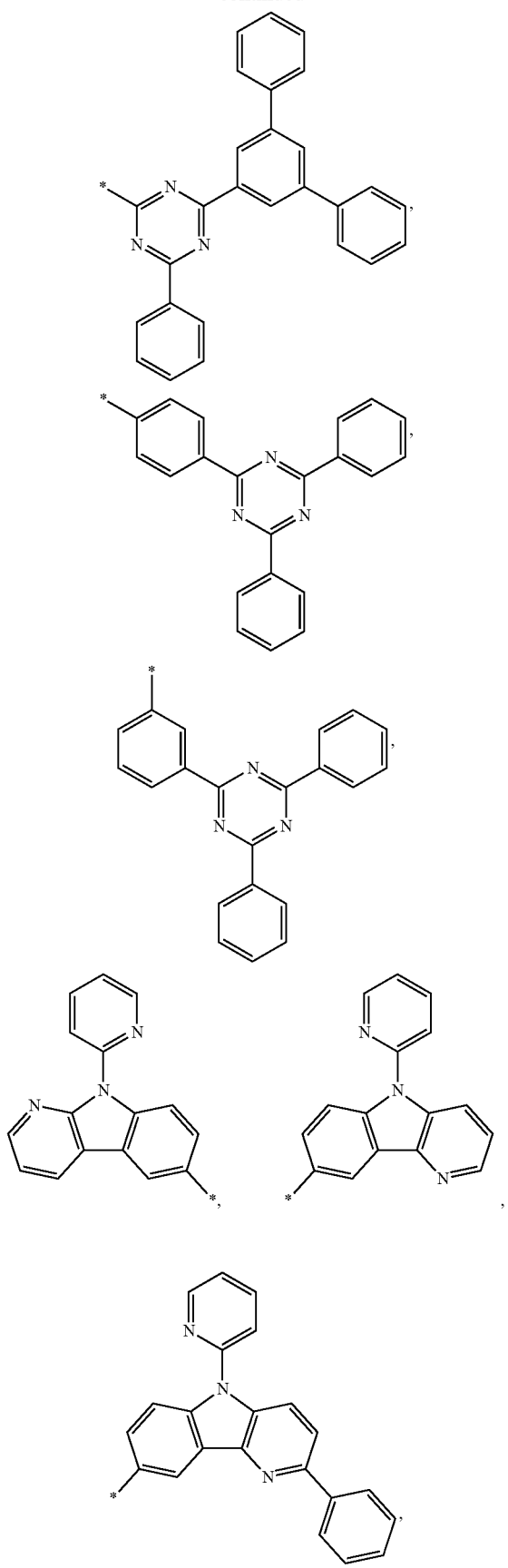

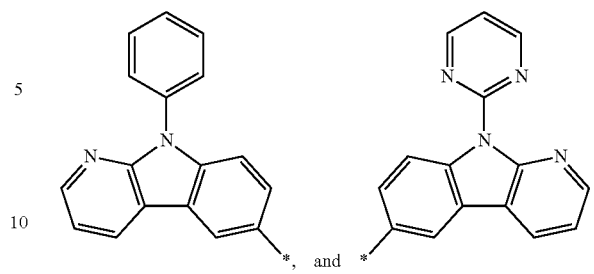

Preferably, $Z^9$ to $Z^{12}$ in any one of foresaid formulae are each independently selected from the group consisting of: a hydrogen atom, a deuterium atom, a halogen group, a cyano group, a nitro group, an alkyl group having 1 to 12 carbon atoms, an alkenyl group having 2 to 12 carbon atoms, and an alkynyl group having 2 to 12 carbon atoms. In accordance with the present invention, $Z^1$ and $Z^8$ may be the same or different. In accordance with the present invention, $Z^2$ and $Z^7$ may be the same or different. In accordance with the present invention, $Z^3$ and $Z^6$ may be the same or different. In one embodiment, any two of $Z^1$, $Z^2$, $Z^3$, $Z^6$, $Z^7$, and $Z^8$ may be the same substitution as stated above, and the others of $Z^1$, $Z^2$, $Z^3$, $Z^6$, $Z^7$, and $Z^8$ may be a hydrogen atom, a deuterium atom, a halogen group, a cyano group, a nitro group, an alkyl group having 1 to 12 carbon atoms, an alkenyl group having 2 to 12 carbon atoms, or an alkynyl group having 2 to 12 carbon atoms.

For example, $Z^1$, $Z^4$ to $Z^8$ are each independently a hydrogen atom or a deuterium atom, and $Z^2$ and/or $Z^3$ may be a specific aromatic substitution. Or, $Z^1$, $Z^2$, $Z^4$, $Z^5$, $Z^7$, and $Z^8$ are each independently a hydrogen atom or a deuterium atom, and $Z^3$ and $Z^6$ are both the above specific aromatic substitutions.

For example, the compound may be selected from the group consisting of:

Compound I

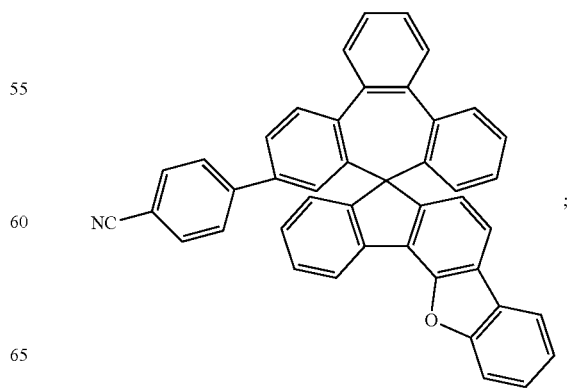

Compound II
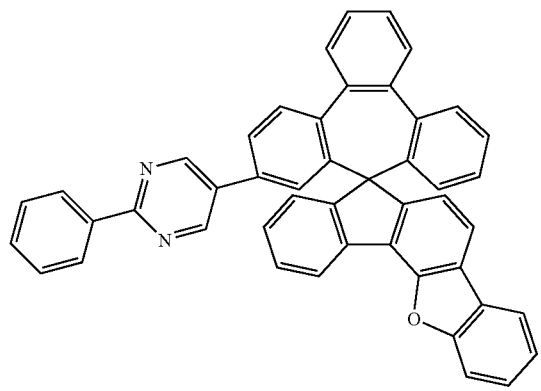
Compound III
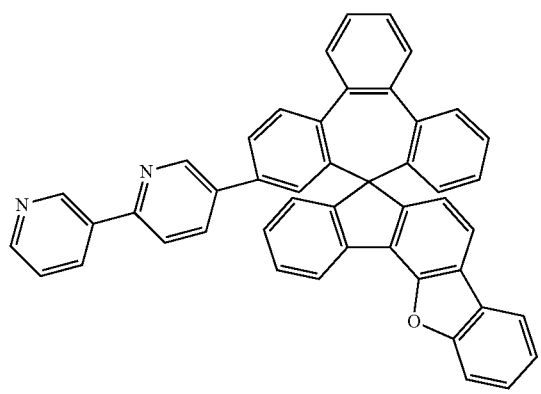
Compound IV
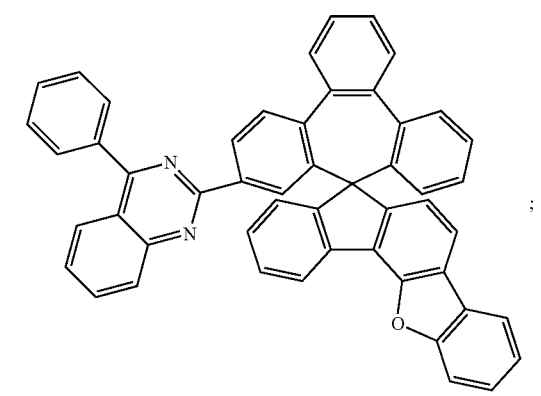
Compound V
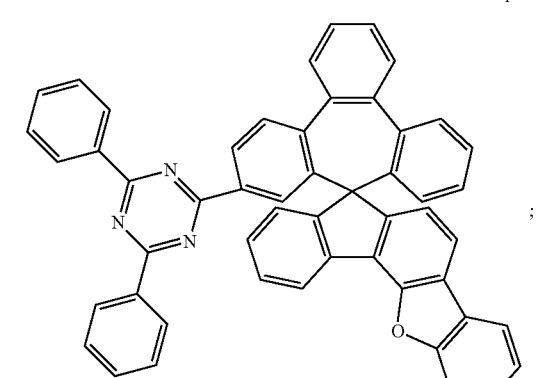
Compound VI
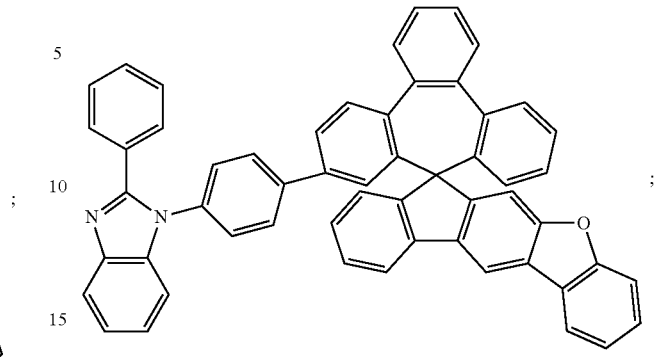
Compound VII
Compound VIII
Compound IX Compound X
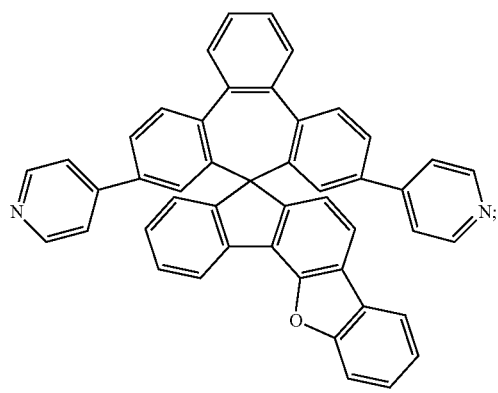
Compound XI
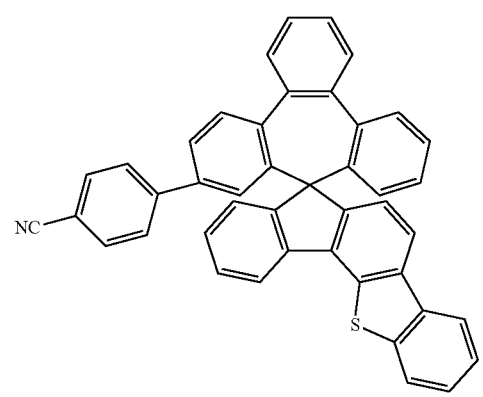
Compound XII
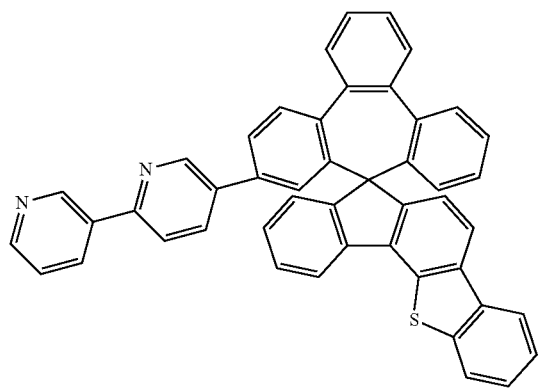
Compound XIII
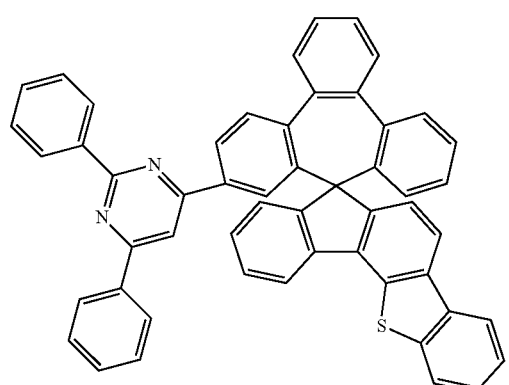
Compound XIV
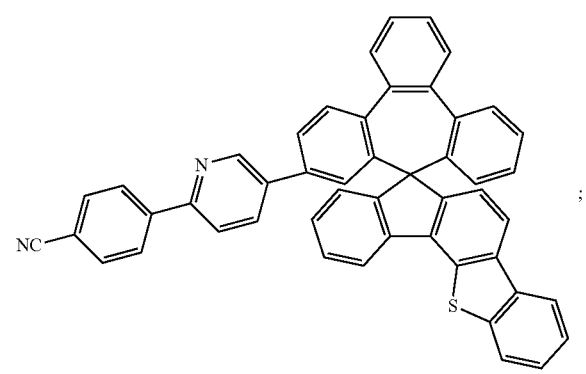
Compound XV
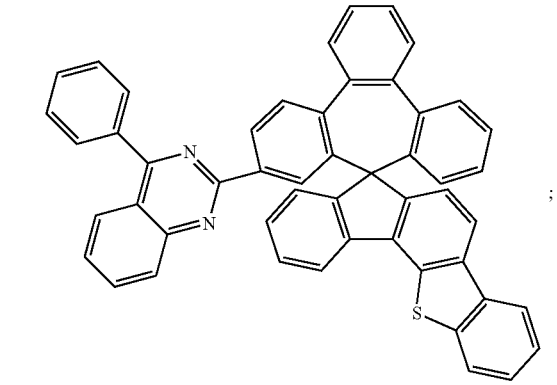
Compound XVI
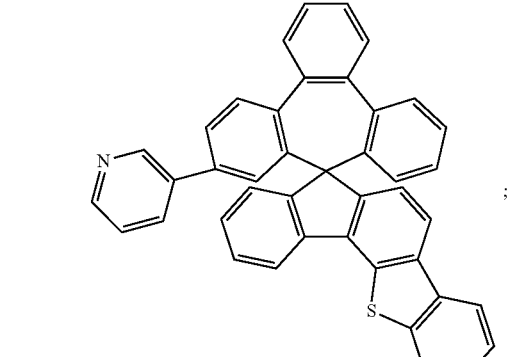
Compound XVII Compound XVIII
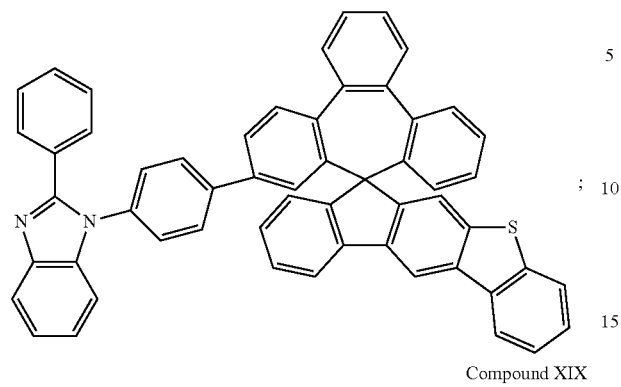
Compound XIX
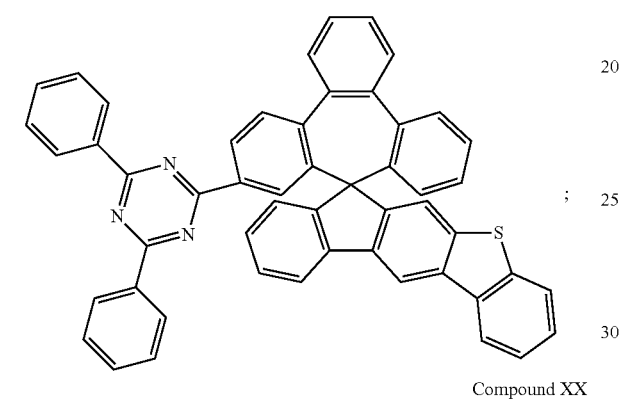
Compound XX
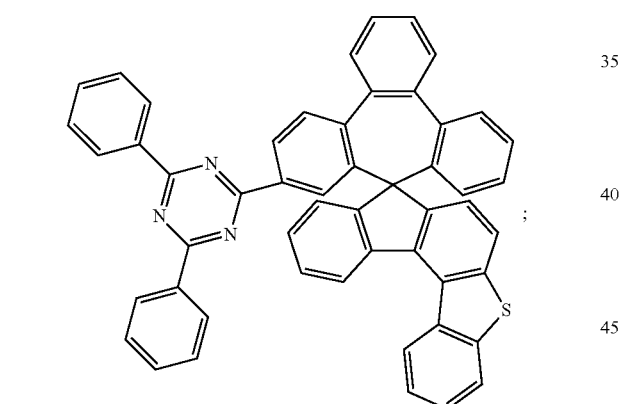
Compound XXI
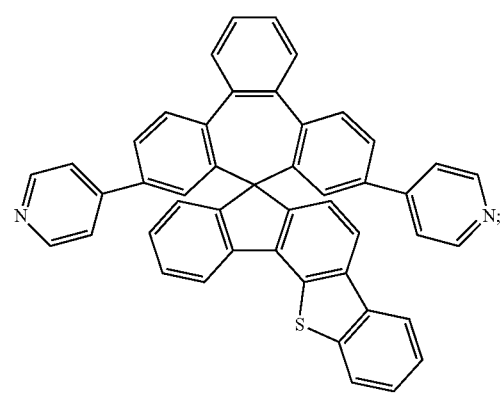
Compound XXII
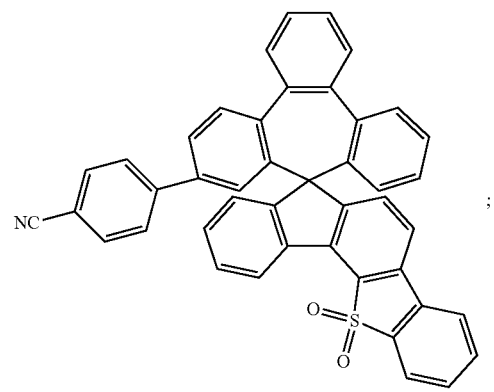
Compound XXIII
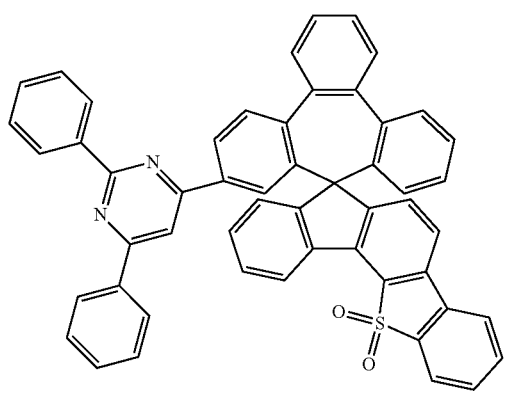
Compound XXIV
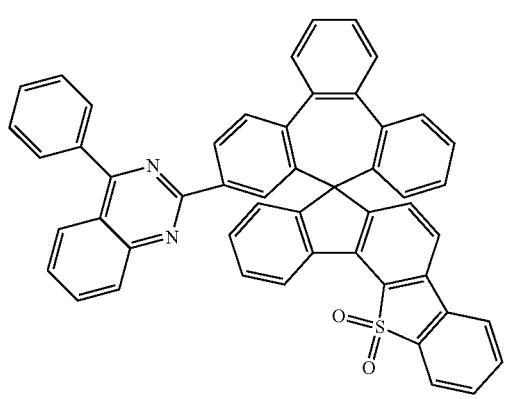
Compound XXV
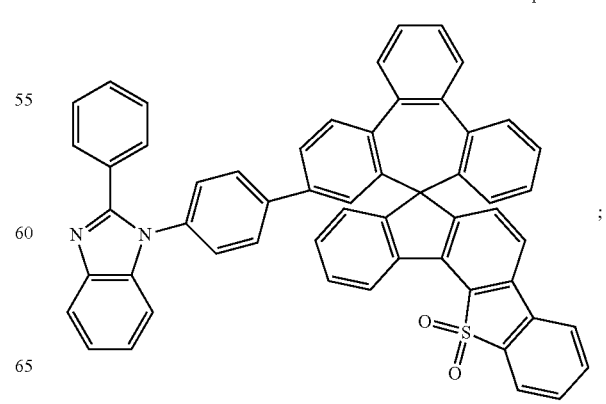

Compound XXVI
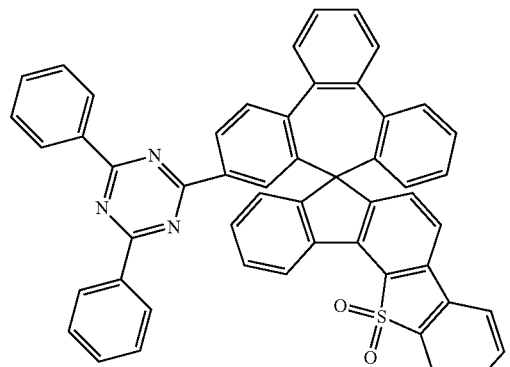
Compound XXVII
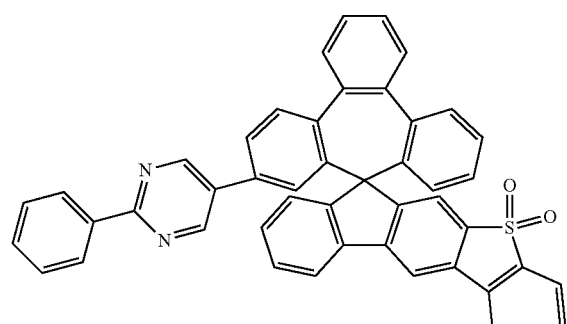
Compound XXVIII
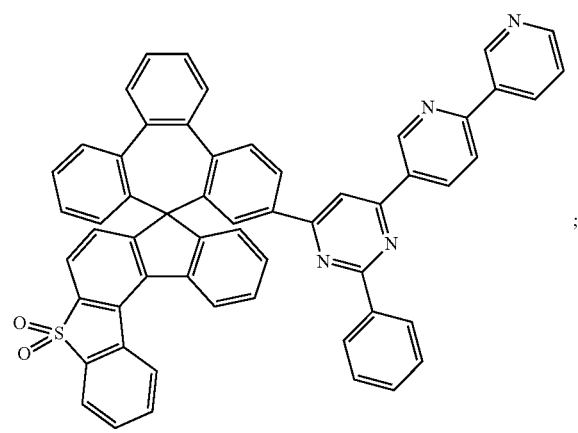
Compound XXIX
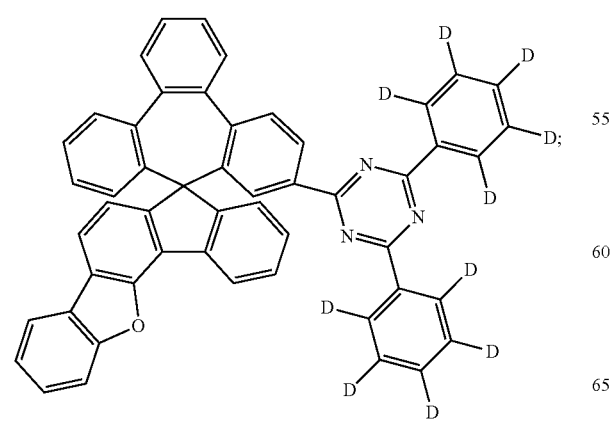
Compound XXX
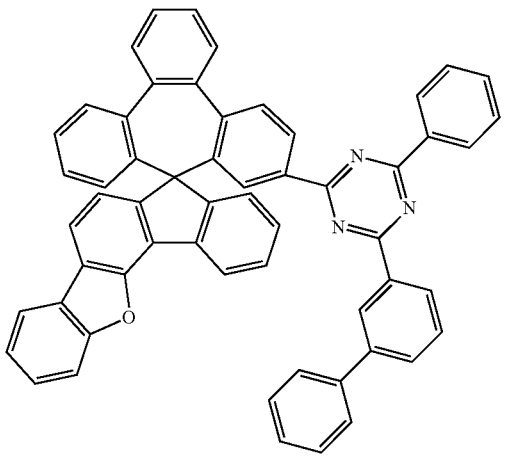
Compound XXXI
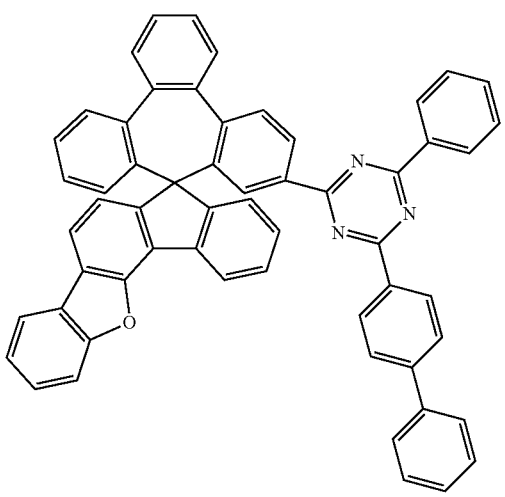
Compound XXXII
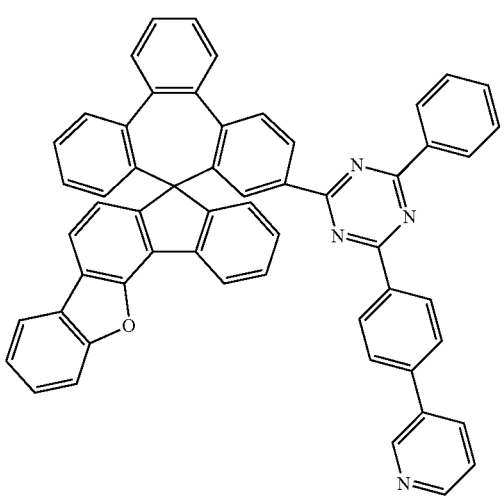

Compound XXXIII
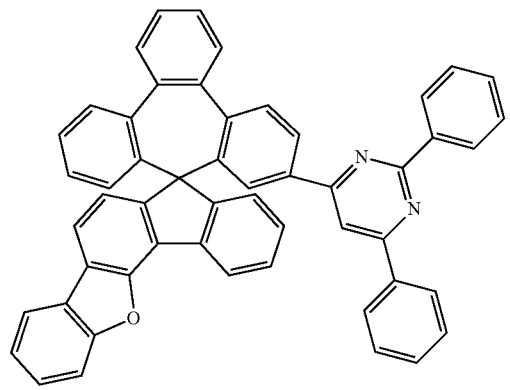
Compound XXXIV
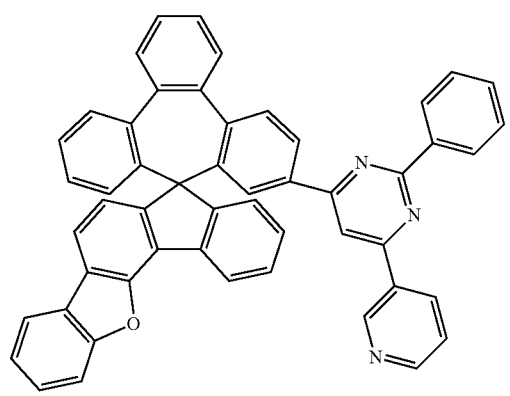
Compound XXXV
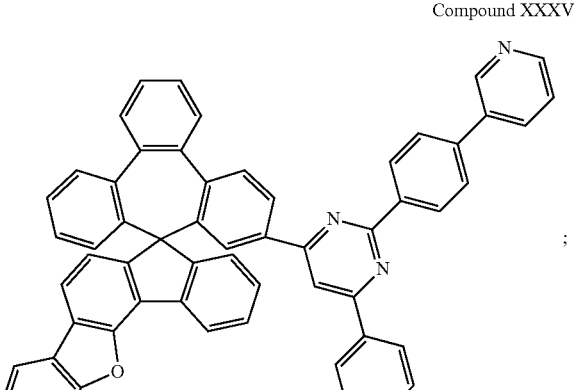
Compound XXXVI
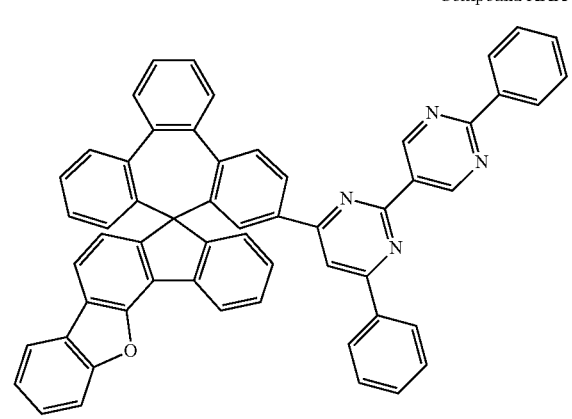
Compound XXXVII
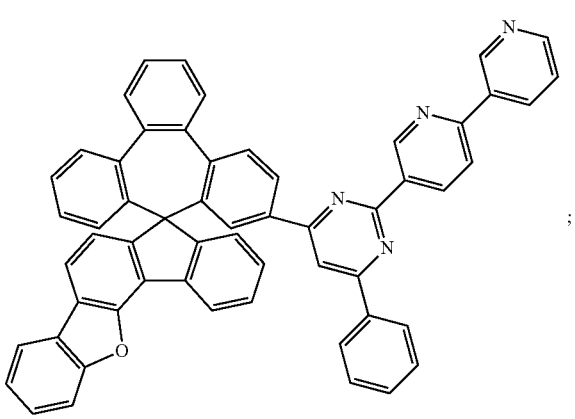
Compound XXXVIII
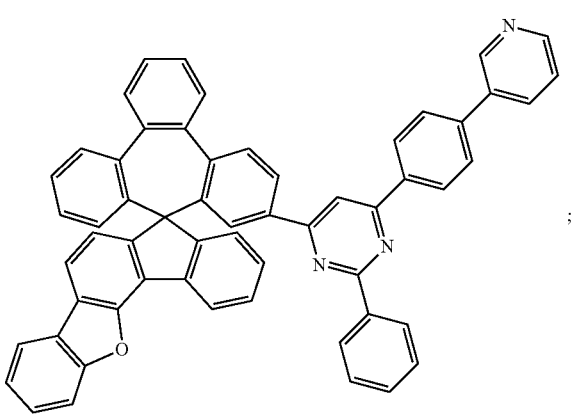
Compound XXXIX
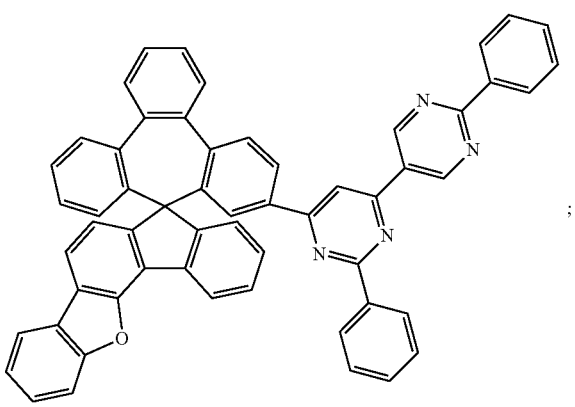

Compound XL
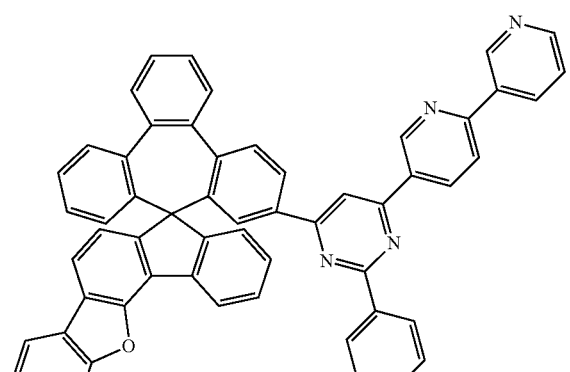
Compound XLI
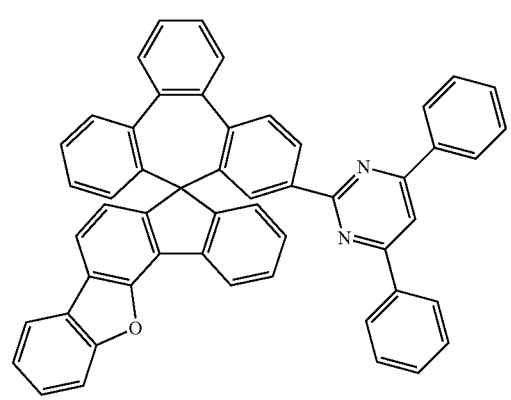
Compound XLII
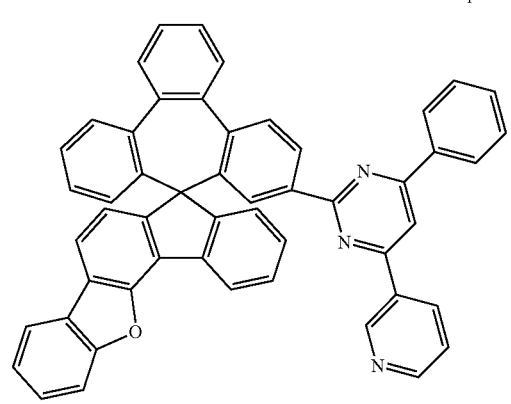
Compound XLIII
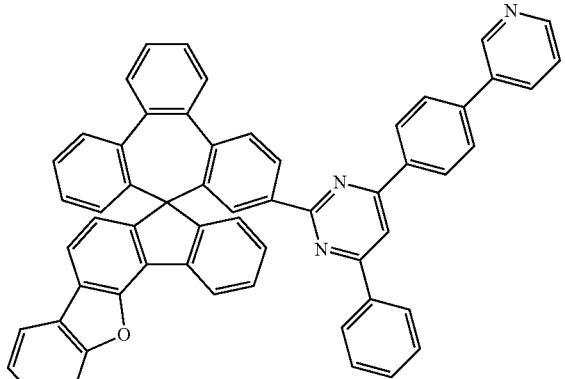
Compound XLIV
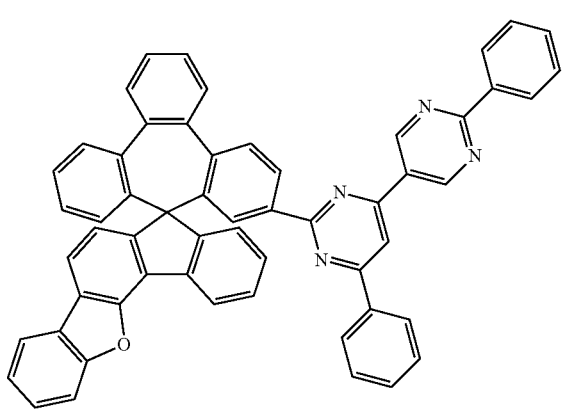
Compound XLV
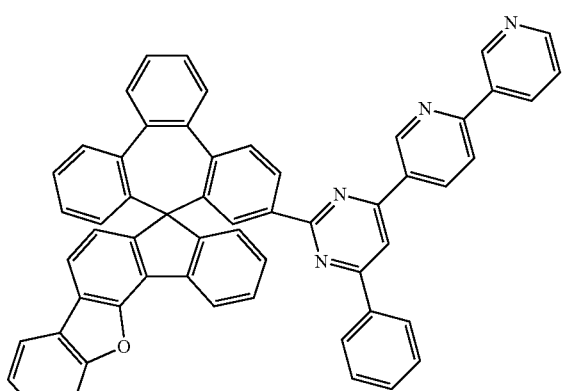

Compound XLVI
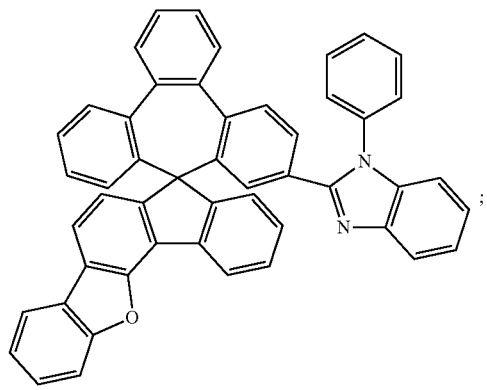
Compound XLVII
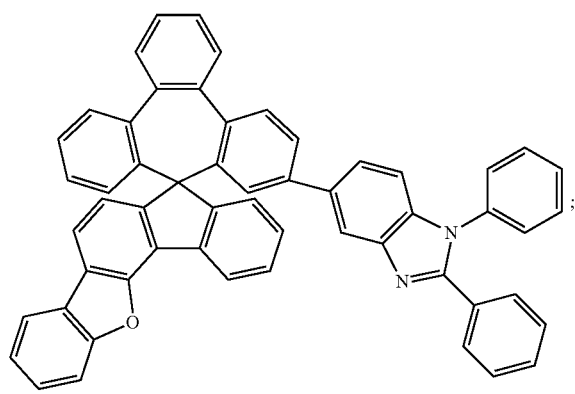
Compound XLVIII
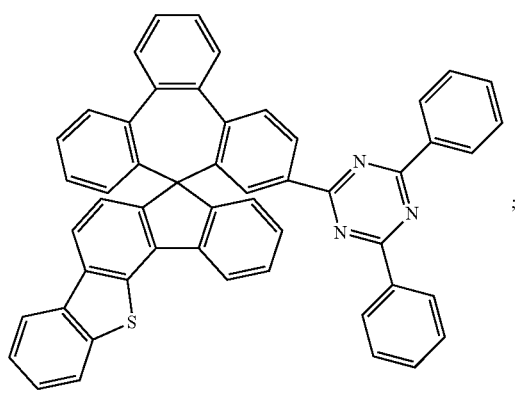
Compound IL
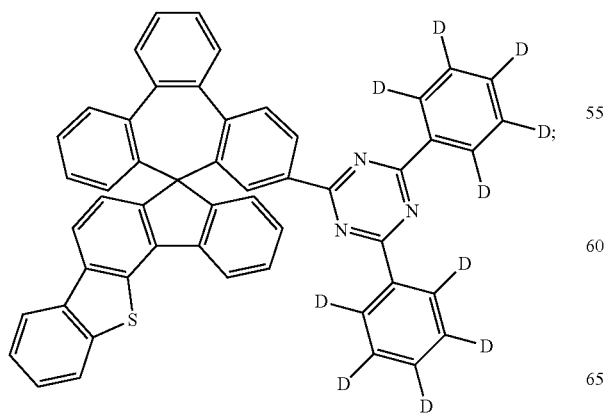
Compound L
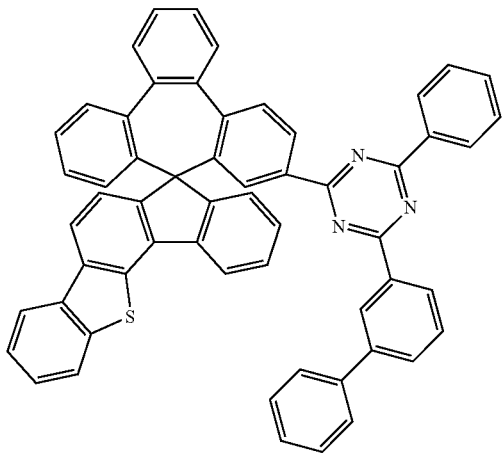
Compound LI
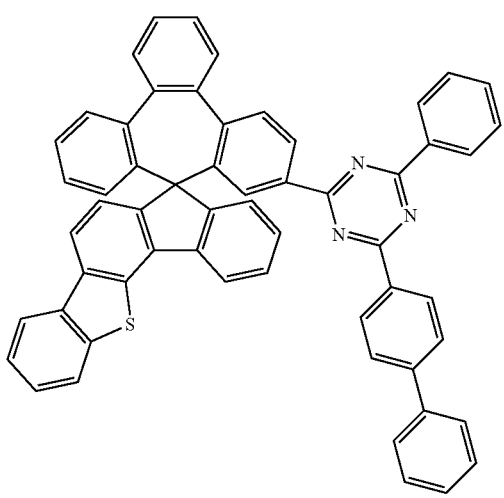
Compound LII
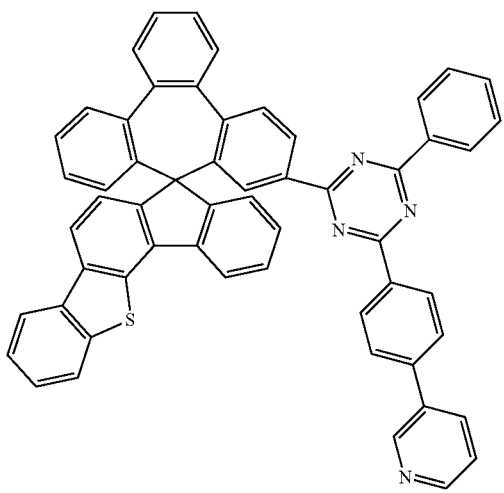

Compound LIII
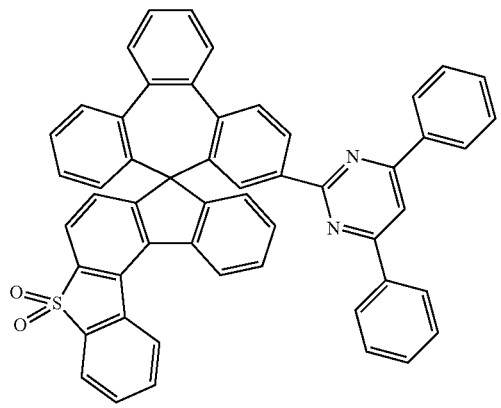
Compound LIV
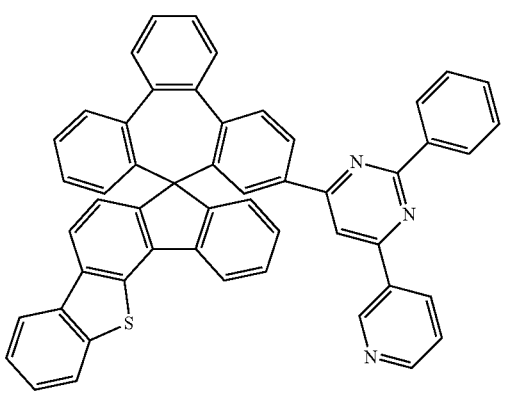
Compound LV
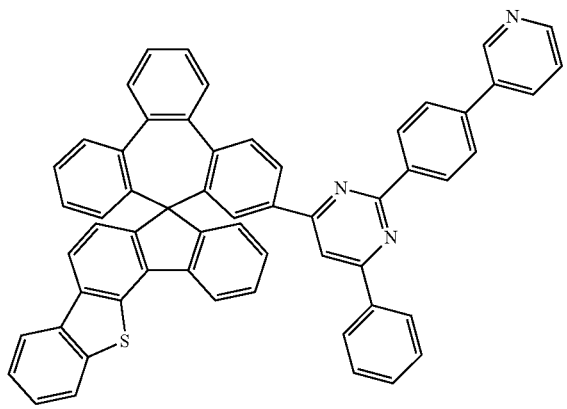
Compound LVI
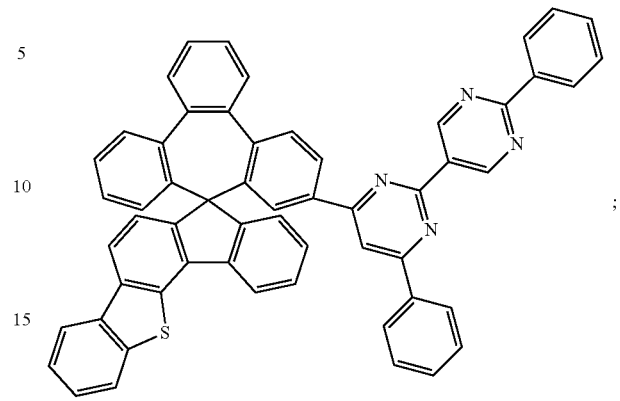
Compound LVII
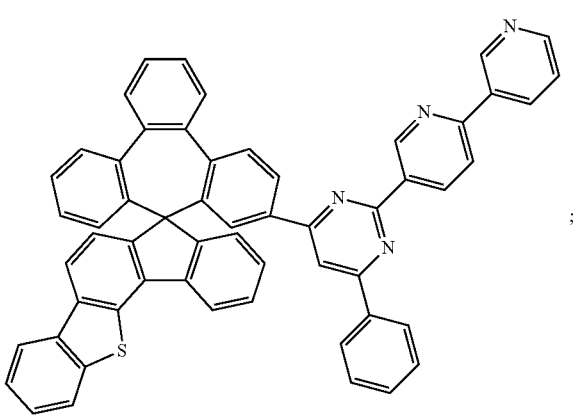
Compound LVIII
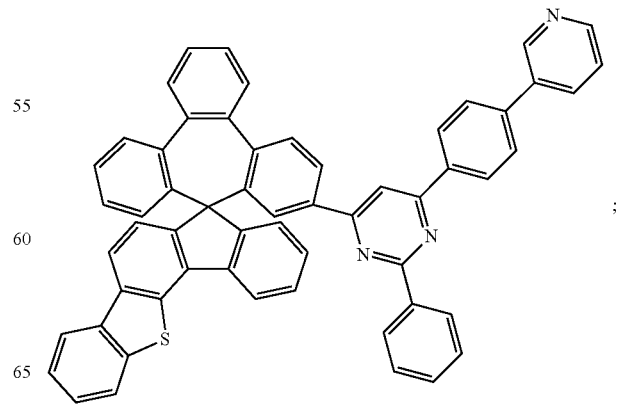

Compound LIX
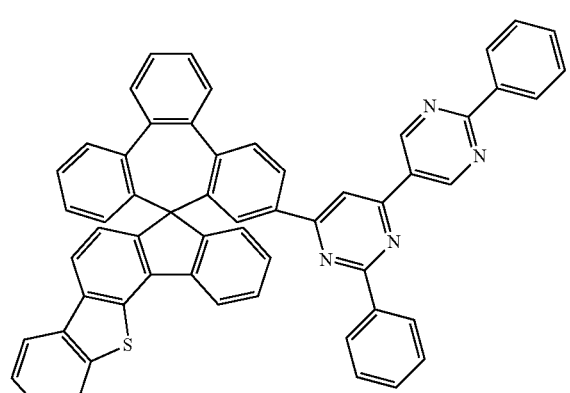
Compound LX
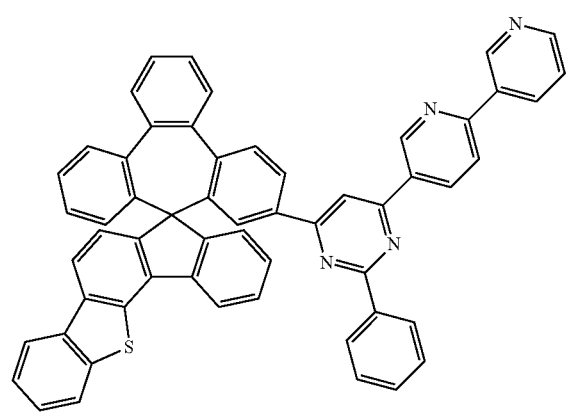
Compound LXI
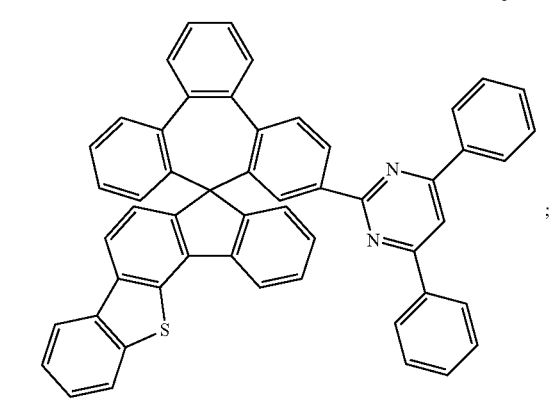
Compound LXII
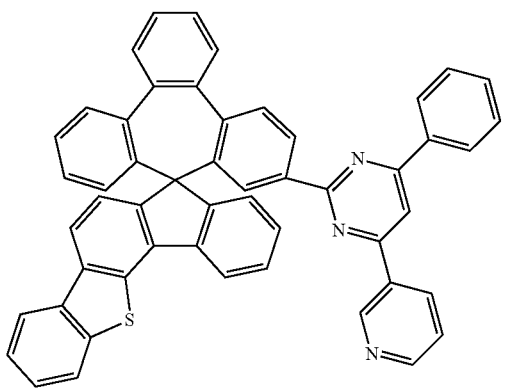
Compound LXIII
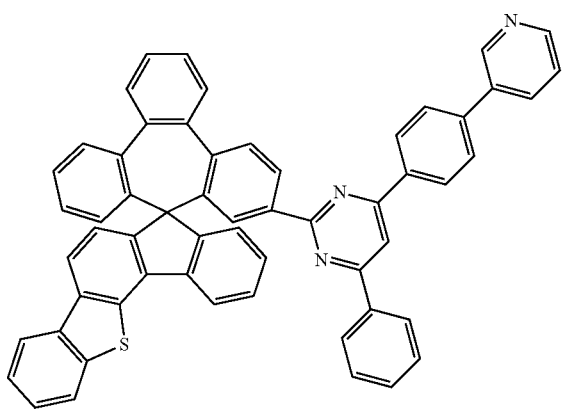
Compound LXIV
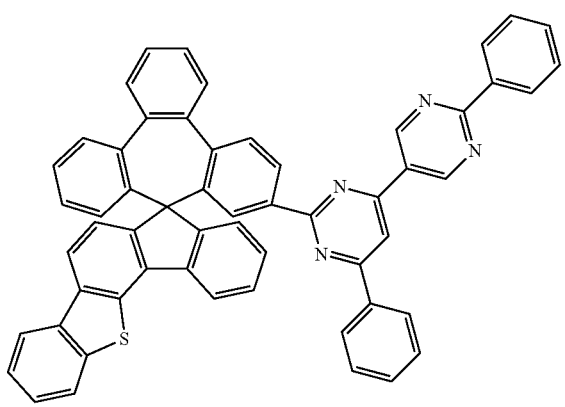

Compound LXV
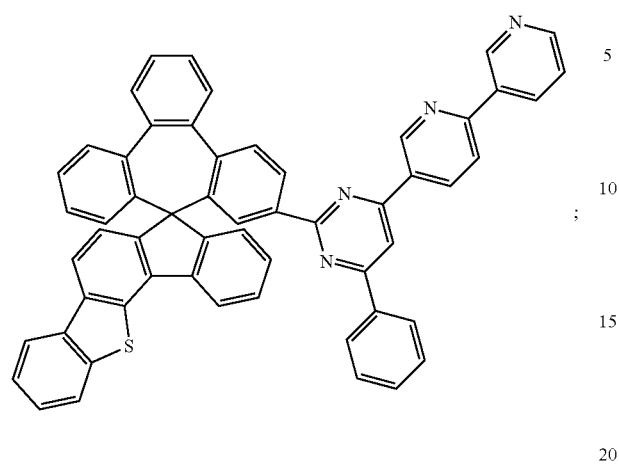
Compound LXVIII
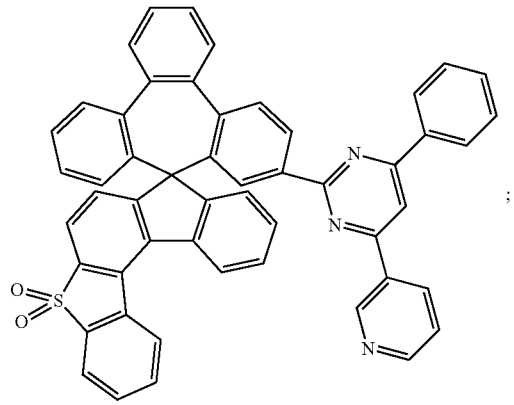
Compound LXVI
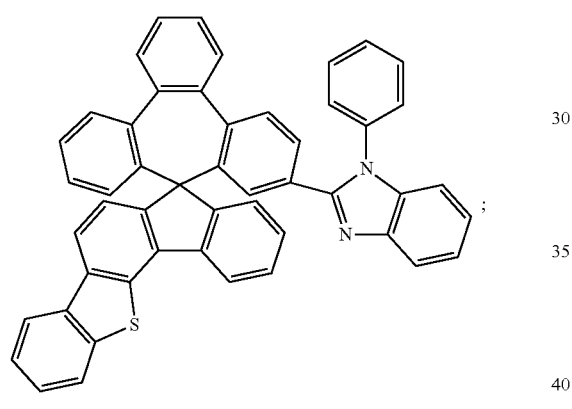
Compound LXIX
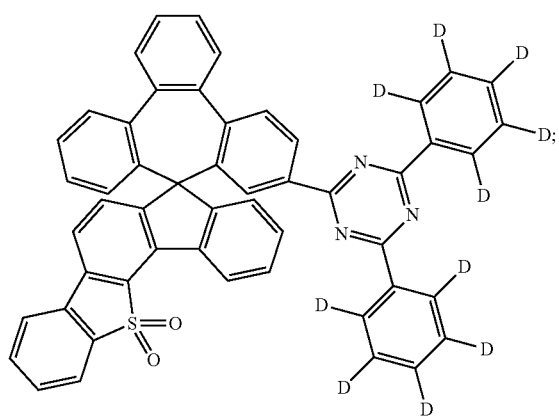
Compound LXVII
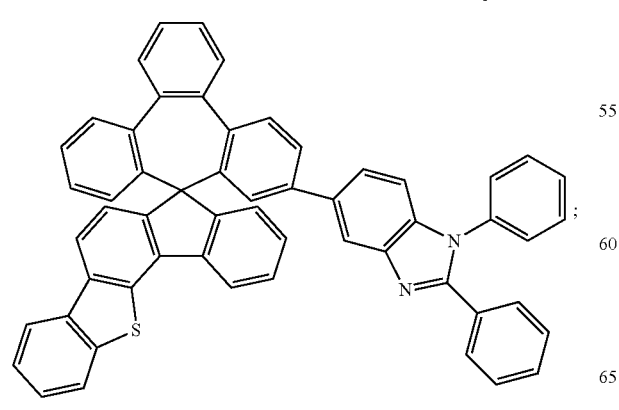
Compound LXX
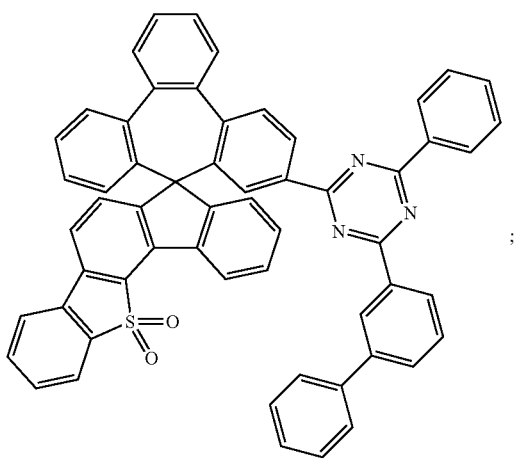

Compound LXXI
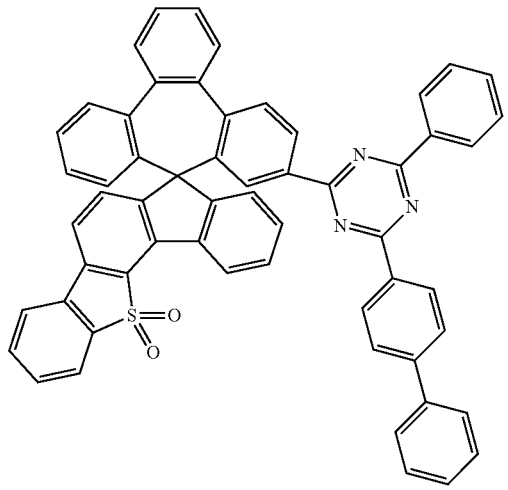
Compound LXXII
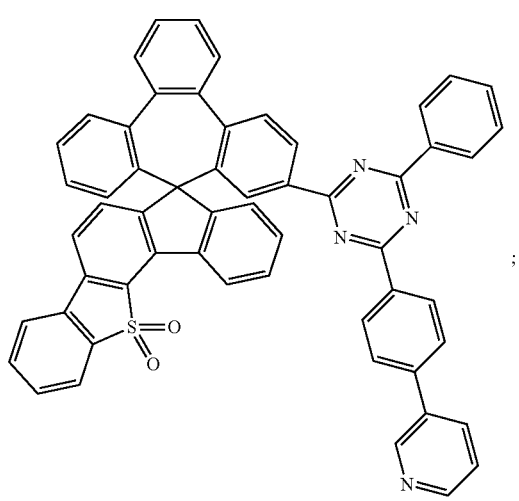
Compound LXXIII
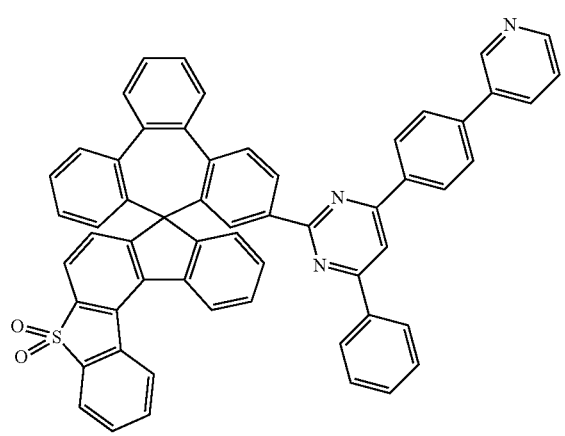
Compound LXXIV
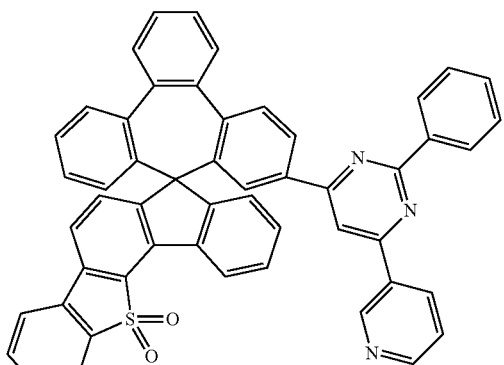
Compound LXXV
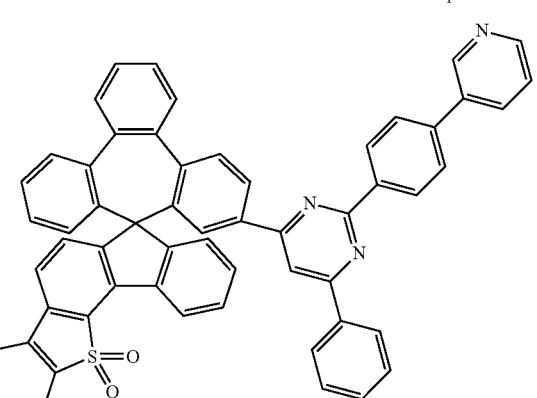
Compound LXXVI
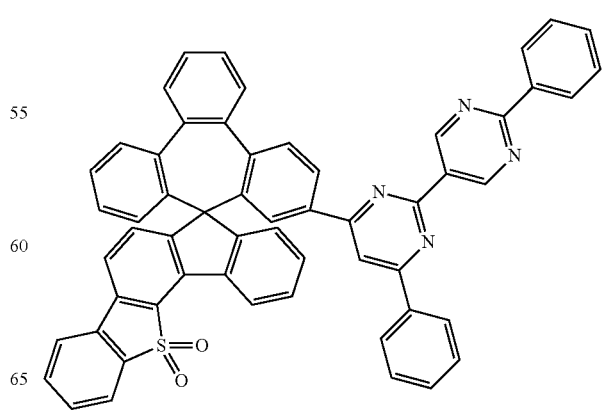

Compound LXXVII
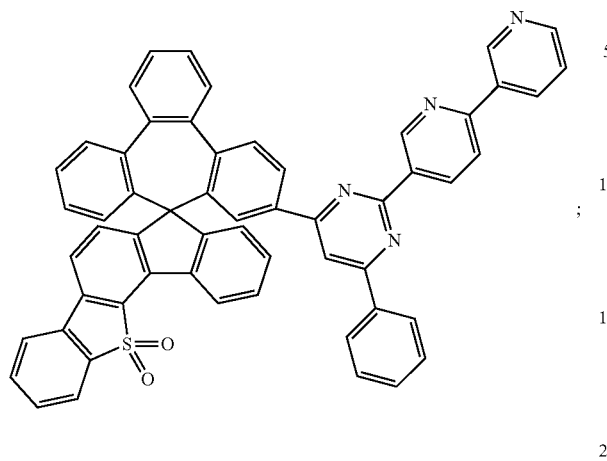
Compound LXXVIII
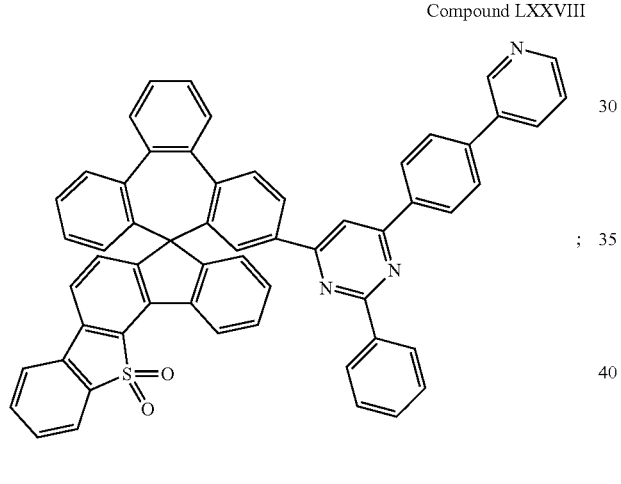
Compound LXXIX
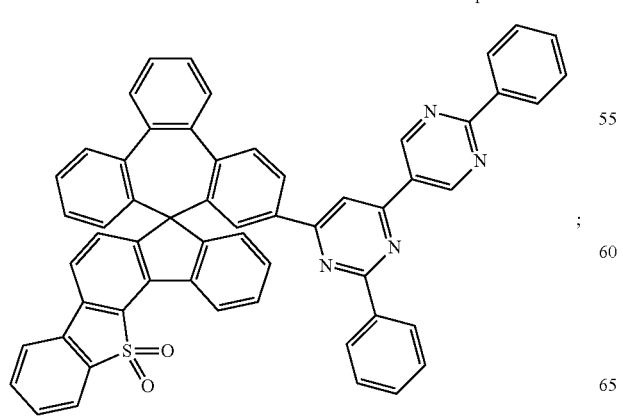
Compound LXXX
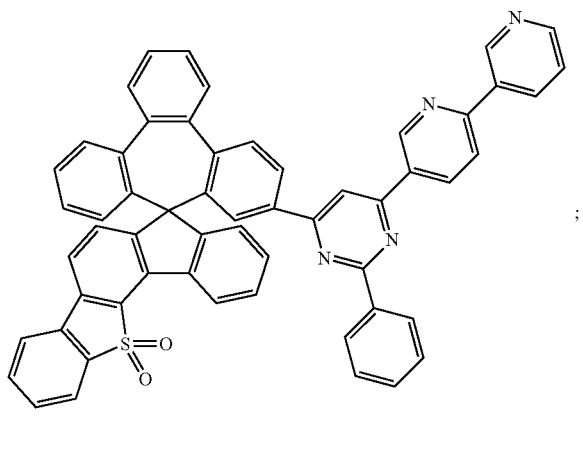
Compound LXXXI
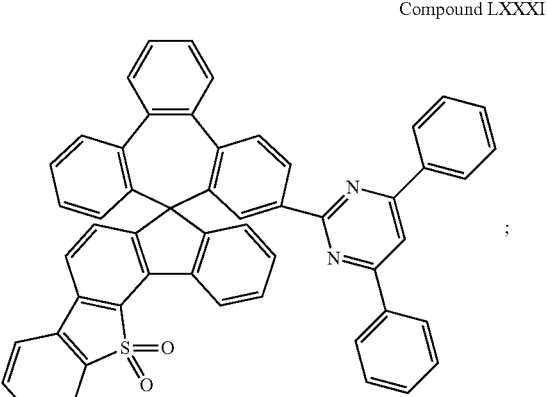
Compound LXXXII
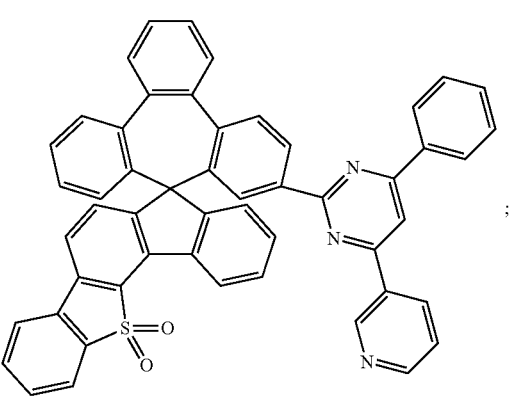

Compound LXXXIII
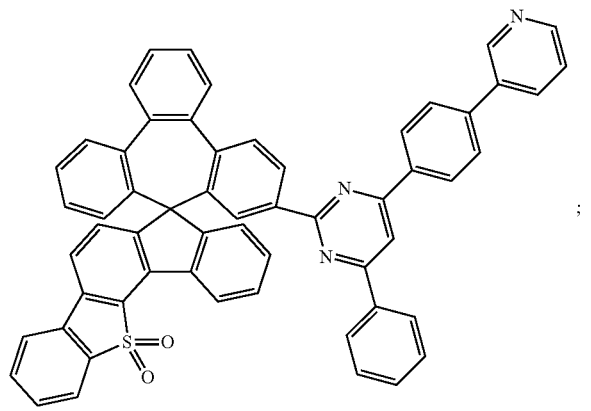
Compound LXXXIV
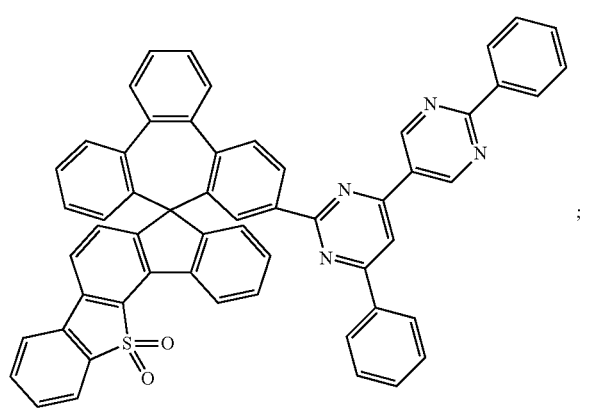
Compound LXXXV
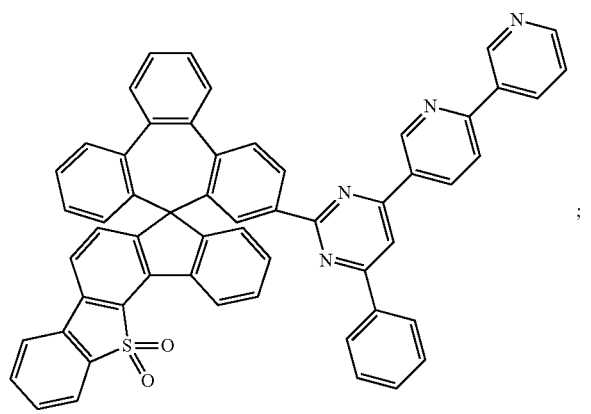
Compound LXXXVI
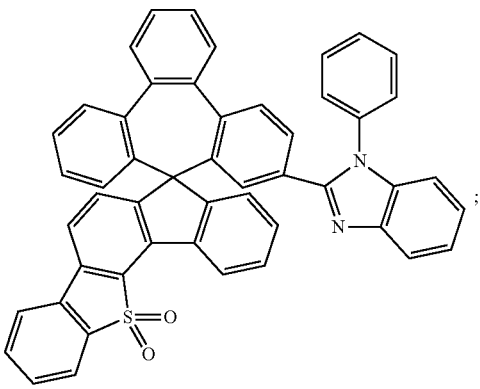
Compound LXXXVII
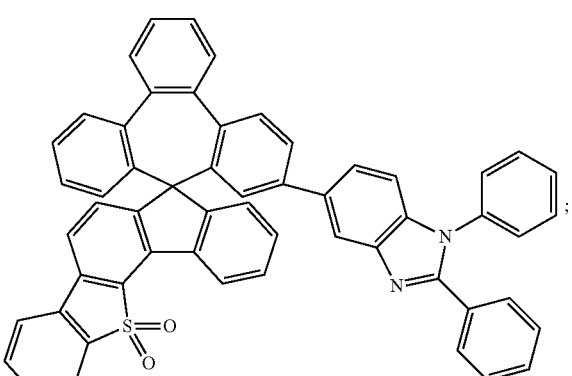
Compound LXXXVIII
Compound LXXXIX
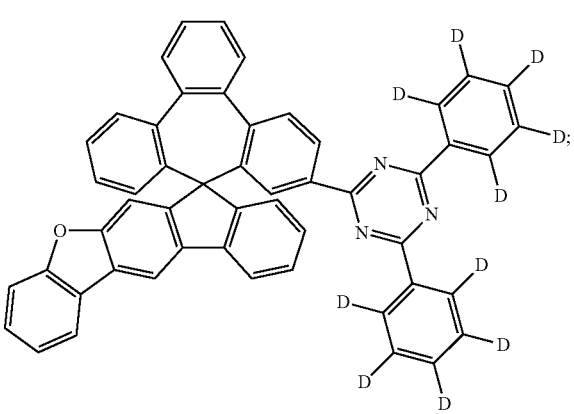

Compound XC
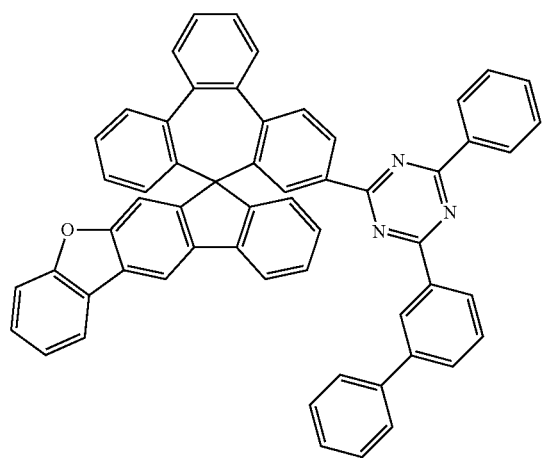
Compound XCIII
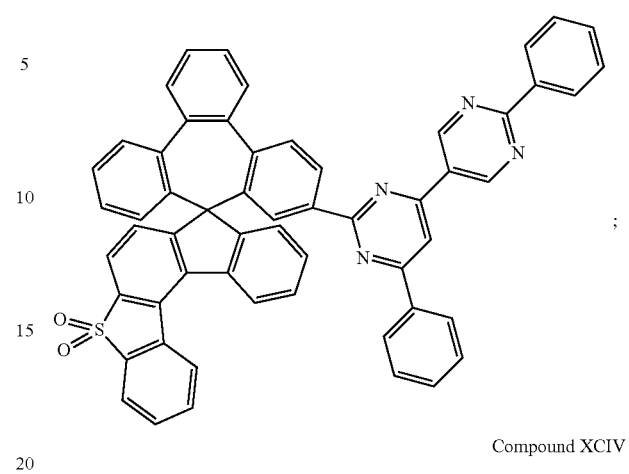
Compound XCI
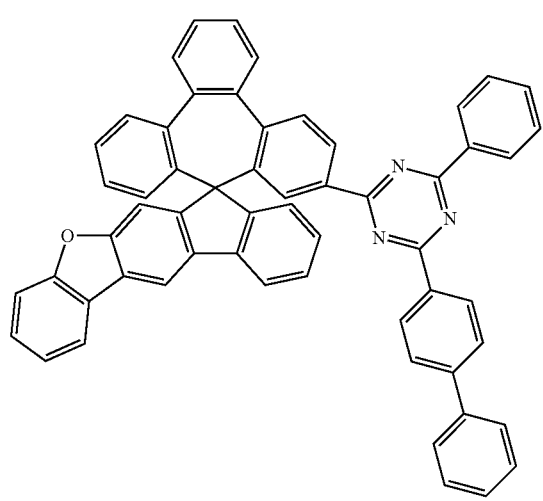
Compound XCIV
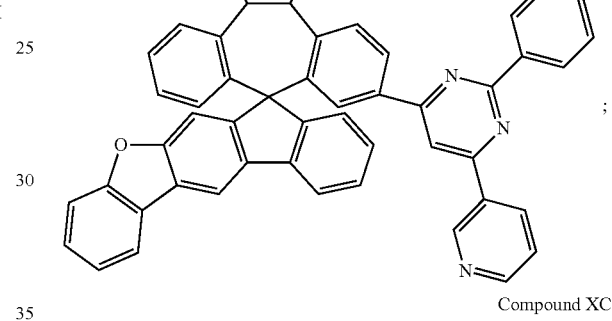
Compound XCV
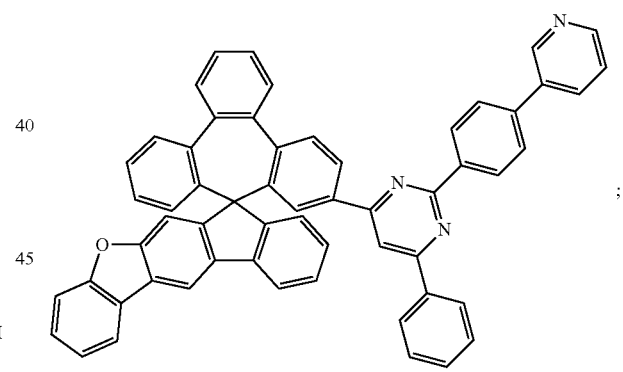
Compound XCII
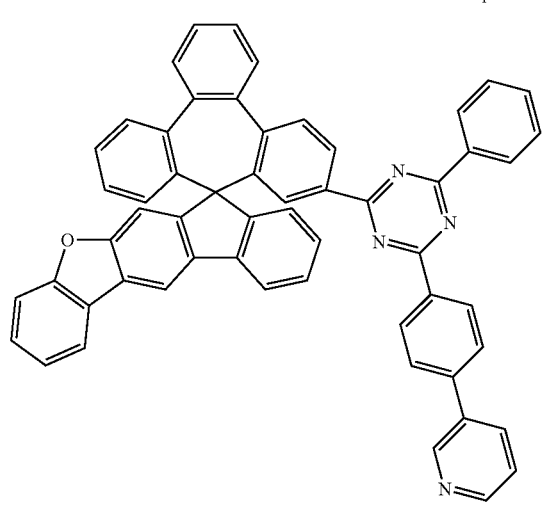
Compound XCVI
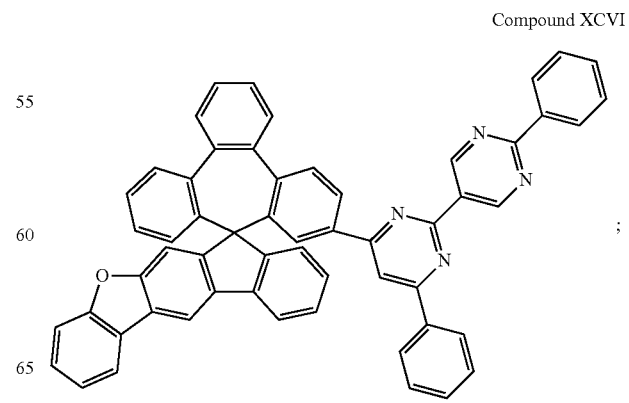

Compound XCVII
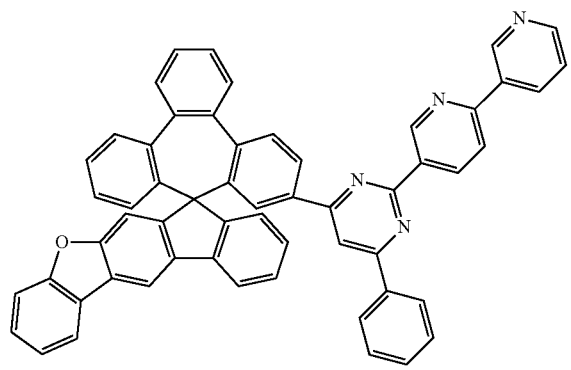
Compound XCVIII
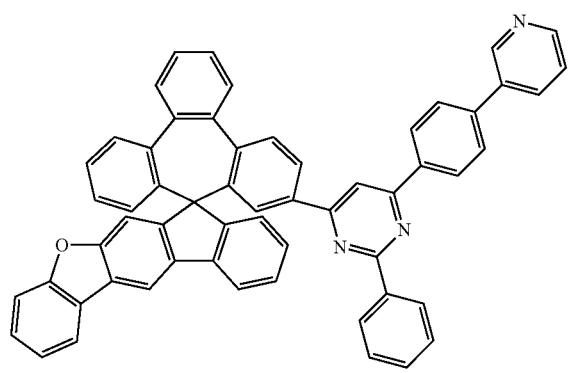
Compound IC
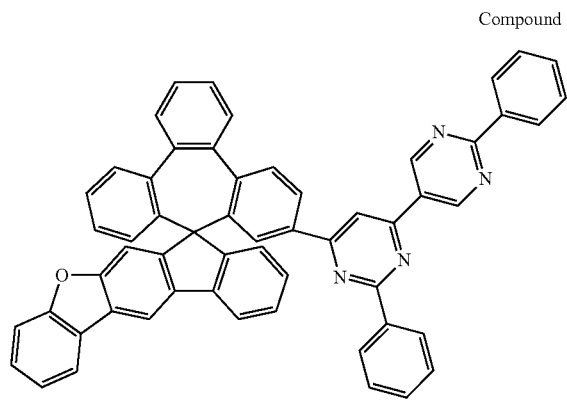
Compound C
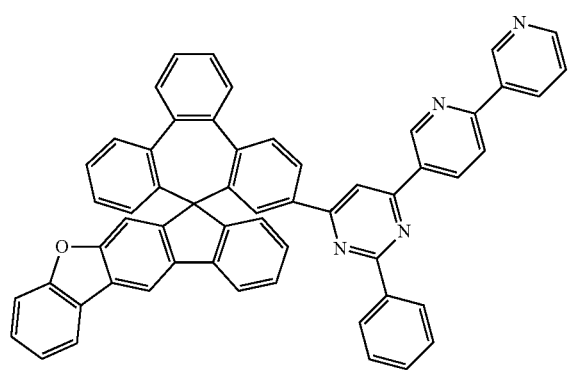
Compound CI
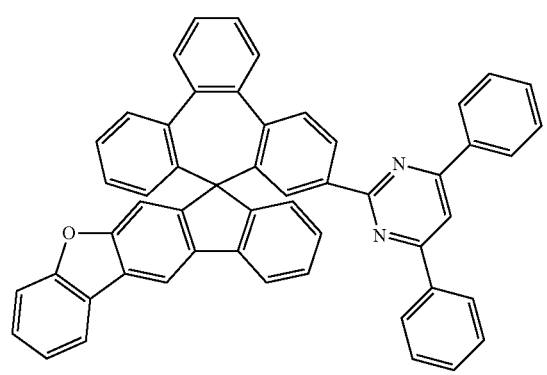
Compound CII
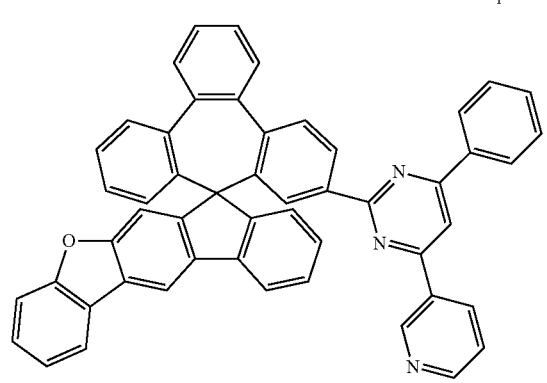
Compound CIII
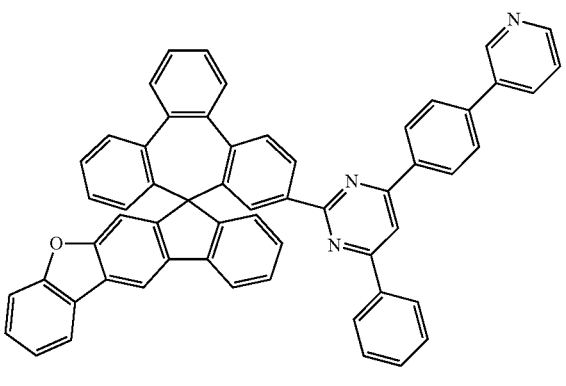
Compound CIV
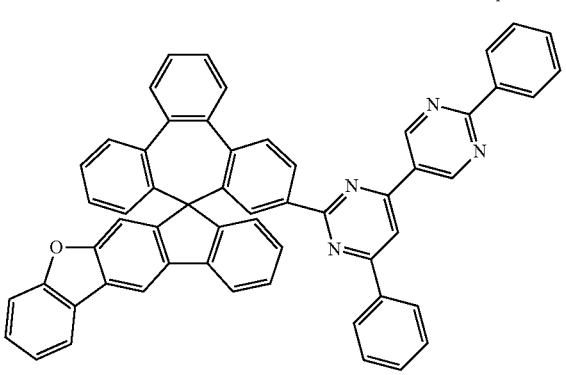

Compound CV
Compound CVI
Compound CVII
Compound CVIII
Compound CIX
Compound CX
Compound CXI
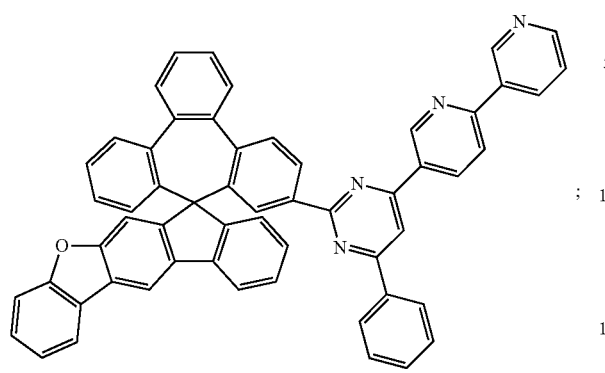
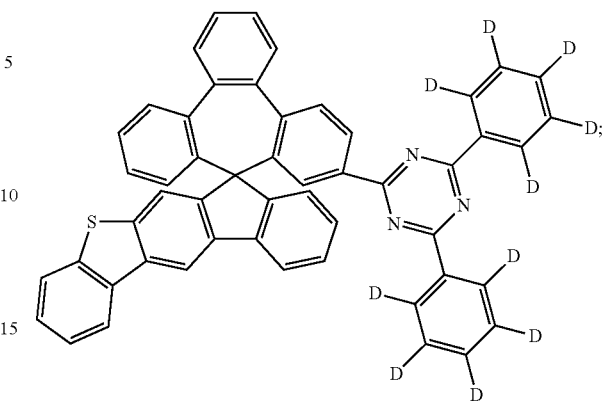

Compound CXII
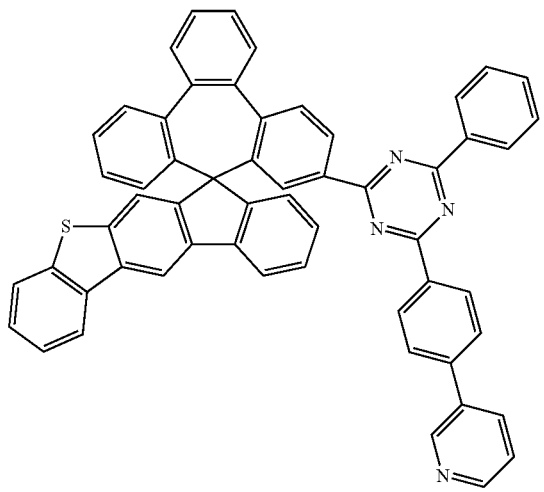
Compound CXV
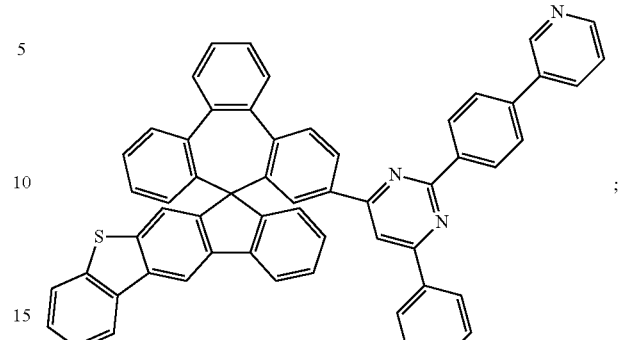
Compound CXVI
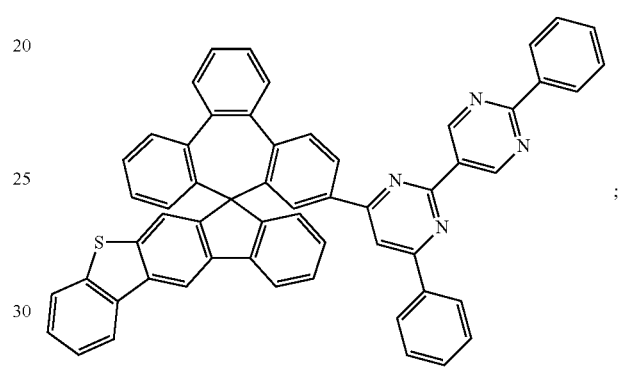
Compound CXIII
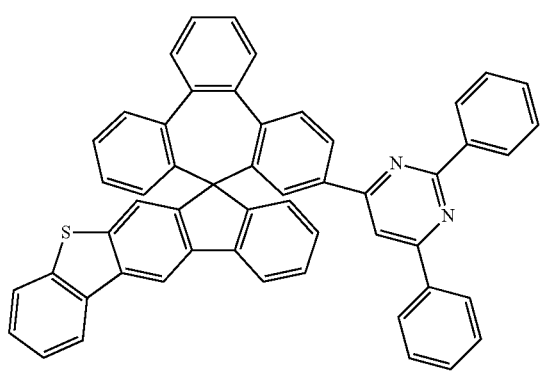
Compound CXVII
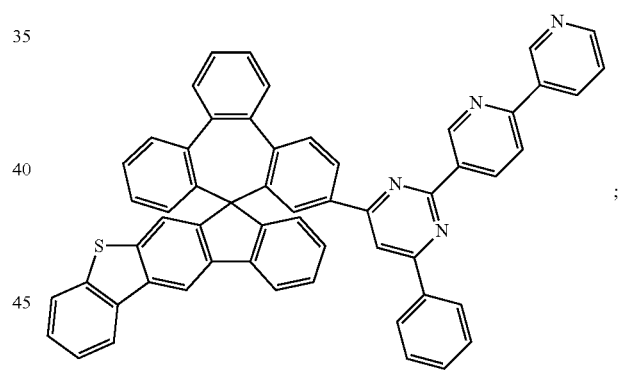
Compound CXIV
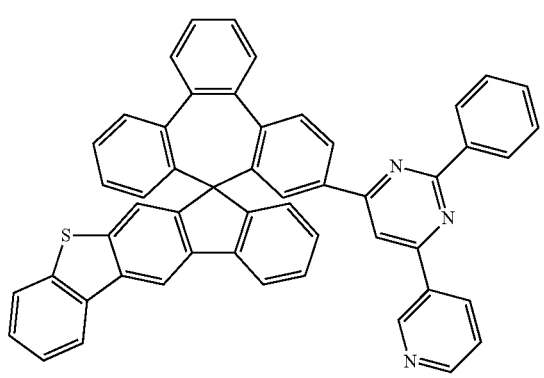
Compound CXVIII
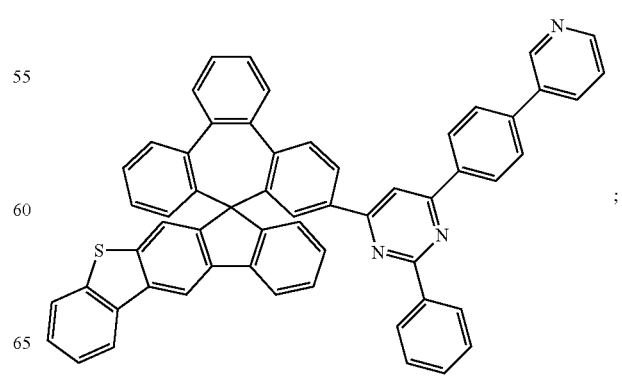

-continued
Compound CXIX
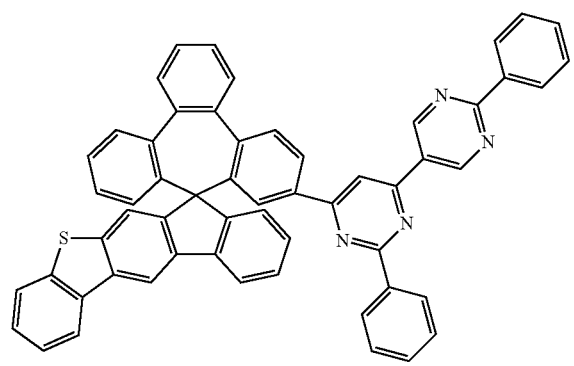
Compound CXX
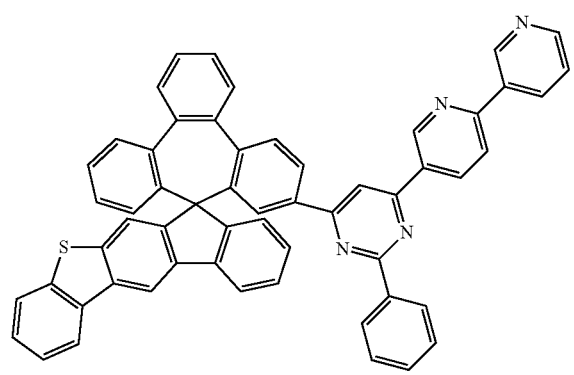
Compound CXXI
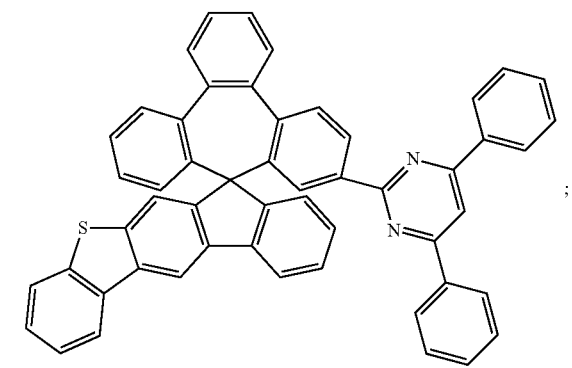
Compound CXXII
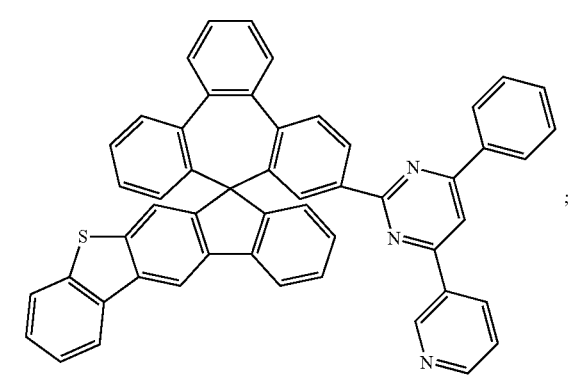
Compound CXXIII
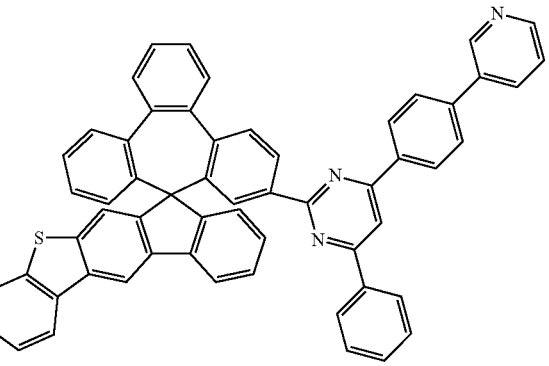
Compound CXXIV
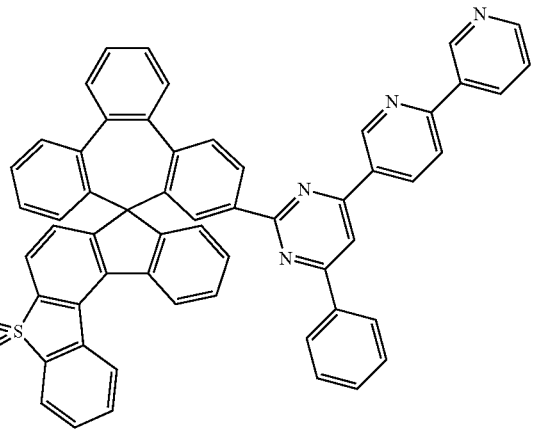
Compound CXXV
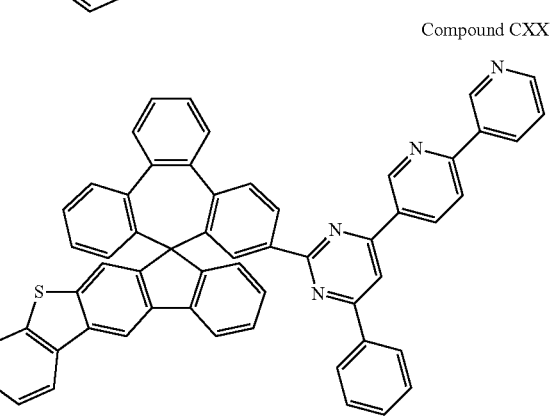
Compound CXXVI
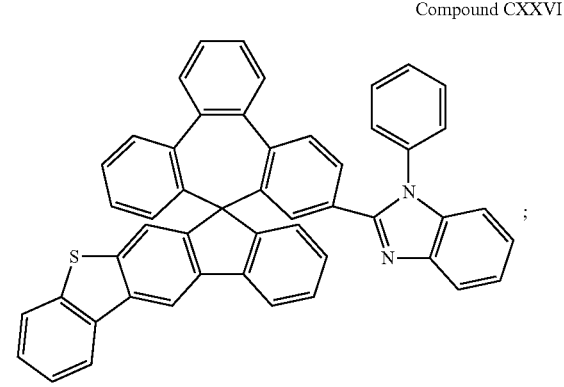

Compound CXXVII
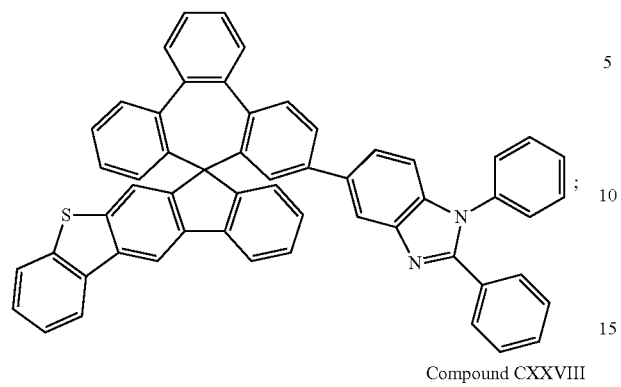
Compound CXXVIII
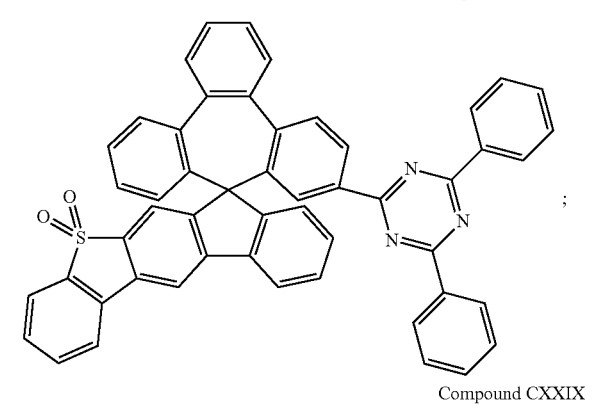
Compound CXXIX
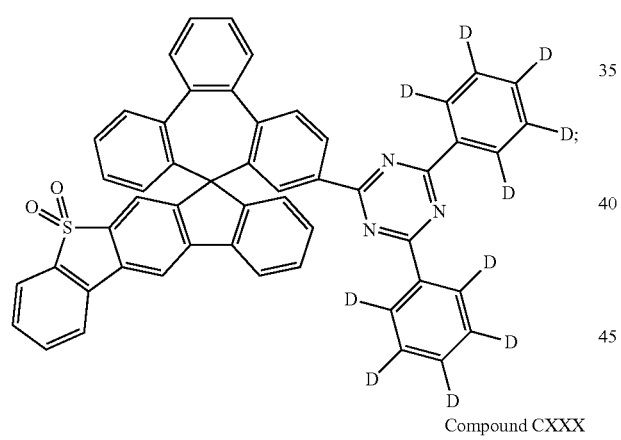
Compound CXXX
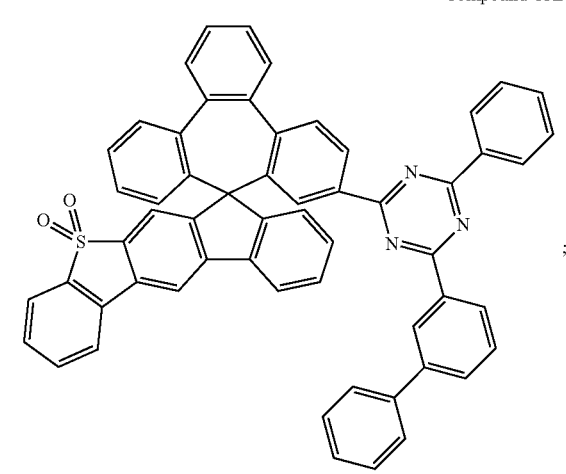
Compound CXXXI
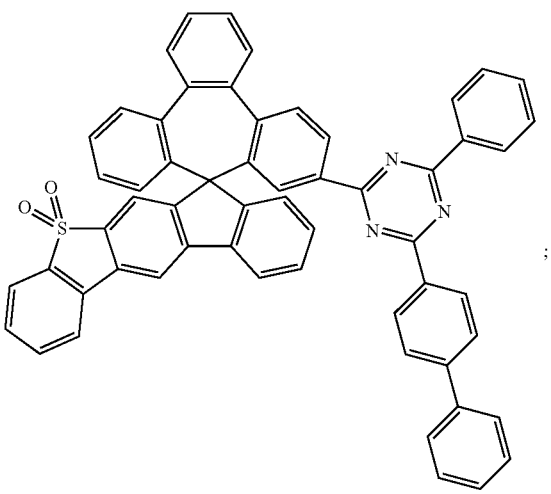
Compound CXXXII
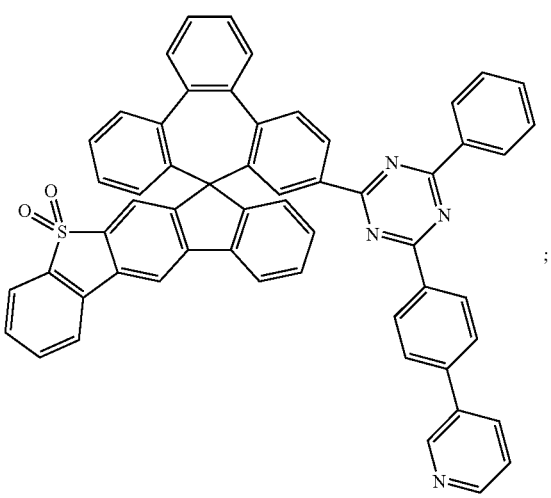
Compound CXXXIII Compound CXXXIV
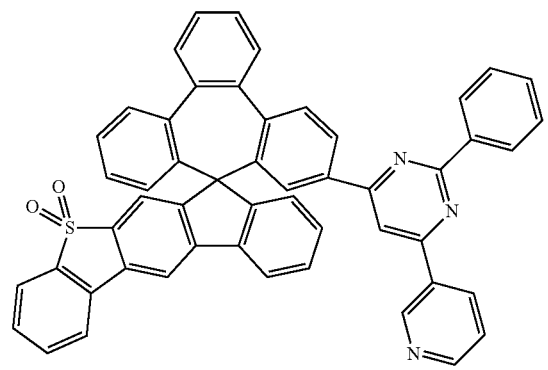
Compound CXXXVIII
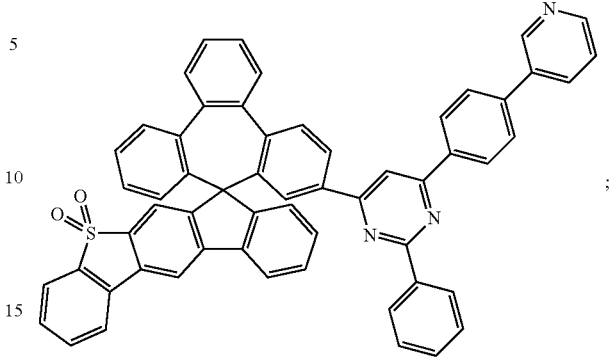
Compound CXXXV
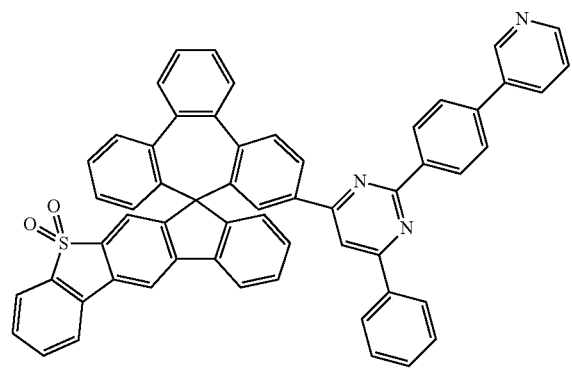
Compound CXXXIX
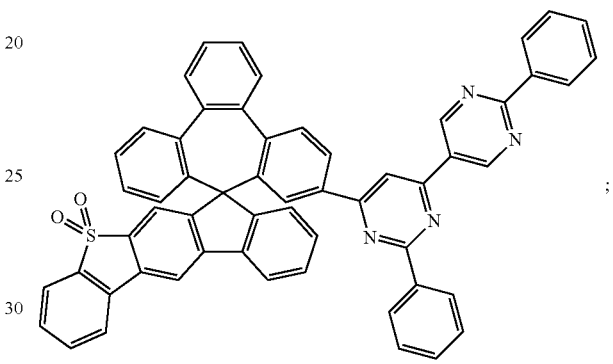
Compound CXXXVI
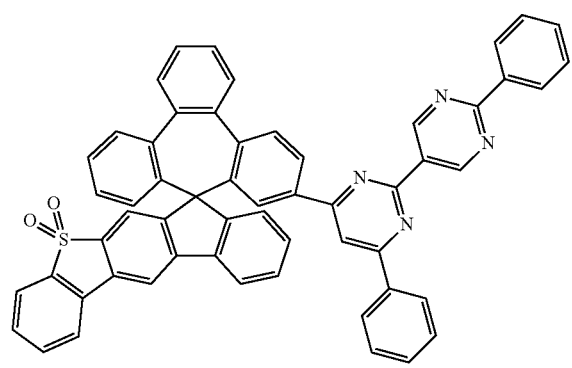
Compound CXL
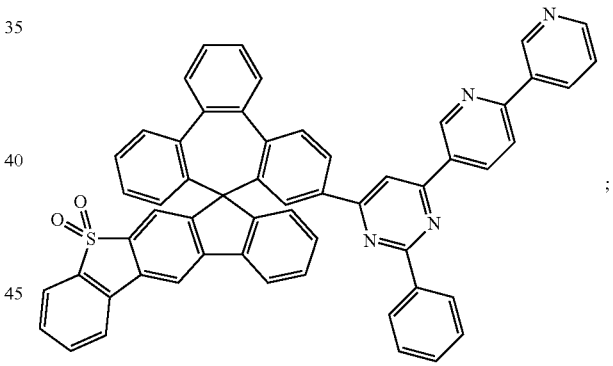
Compound CXXXVII
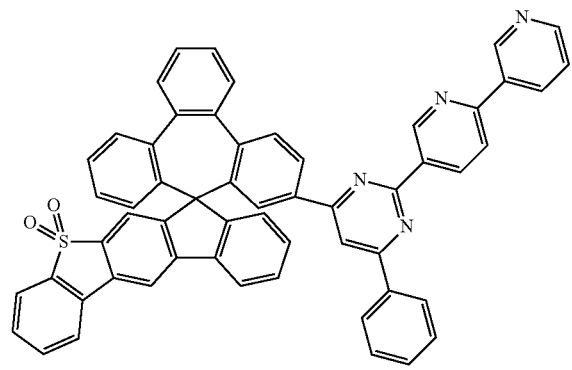
Compound CXLI
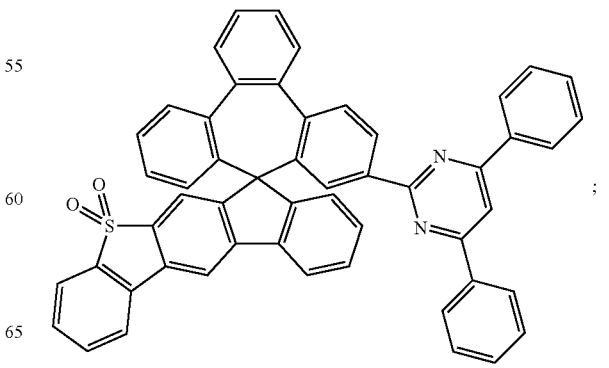

Compound CXLII
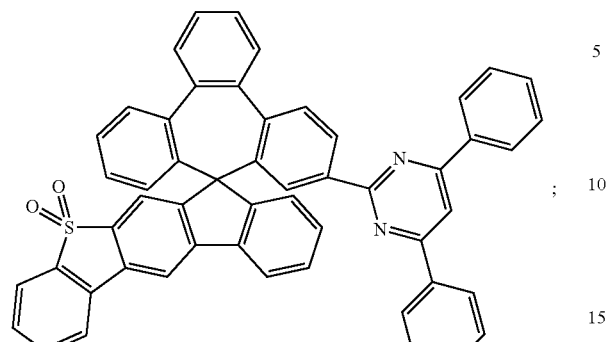
Compound CXLIII
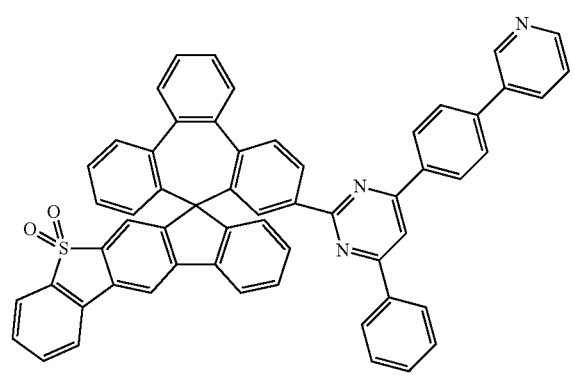
Compound CXLIV
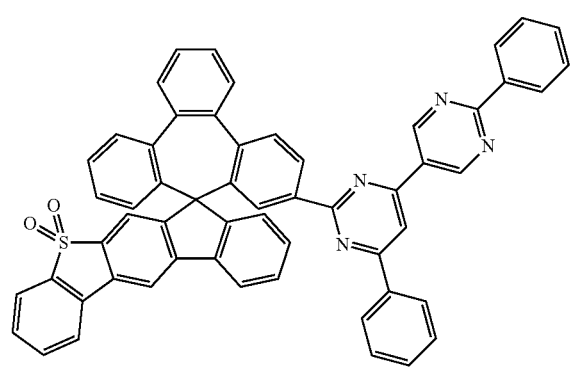
Compound CXLV
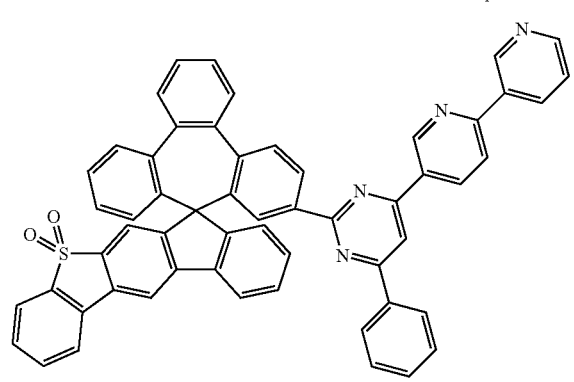
Compound CXLVI
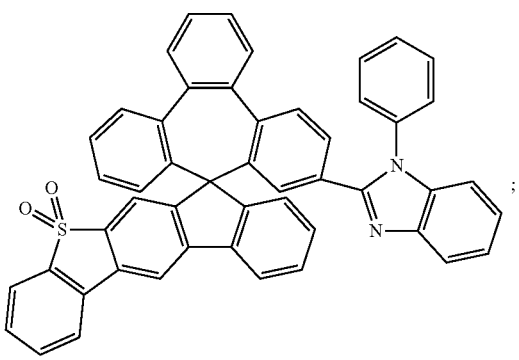
Compound CXLVII
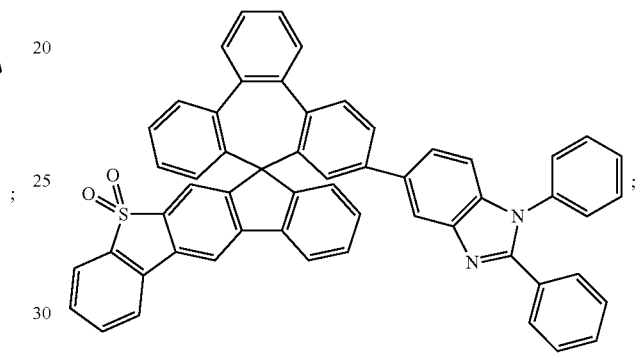
Compound CXLVIII
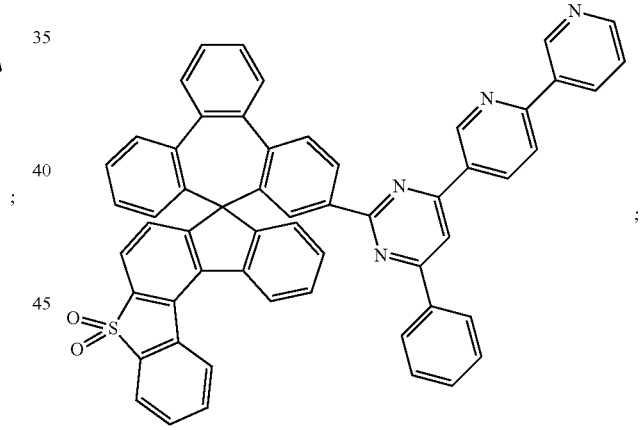
Compound CIL
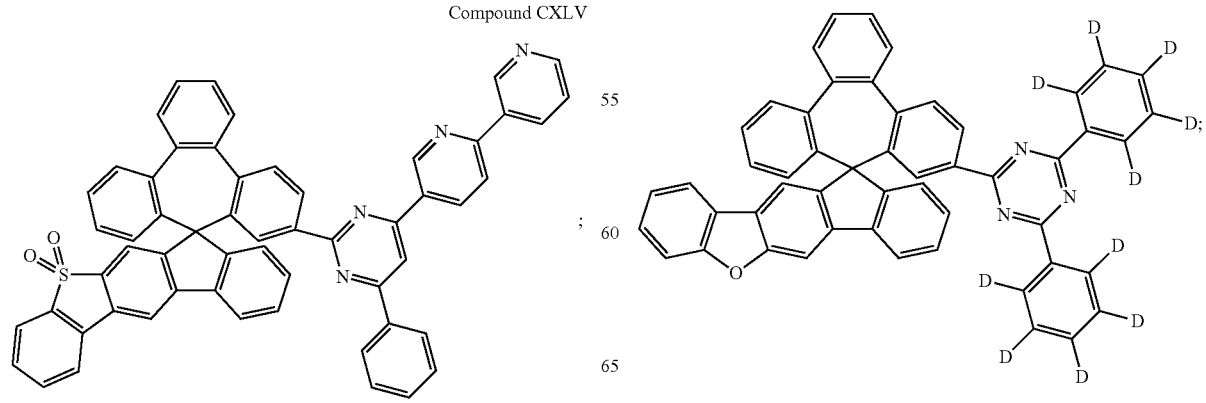

Compound CL
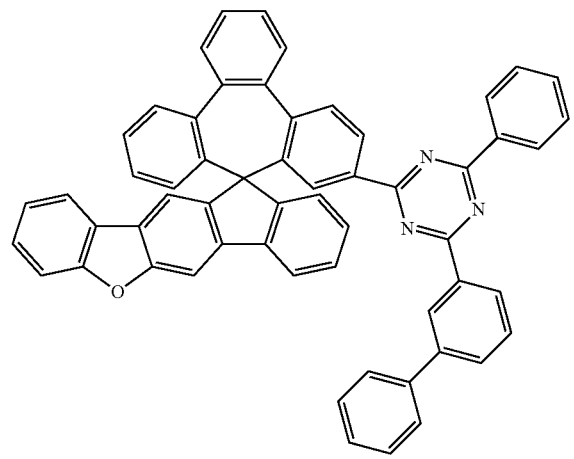
Compound CLI
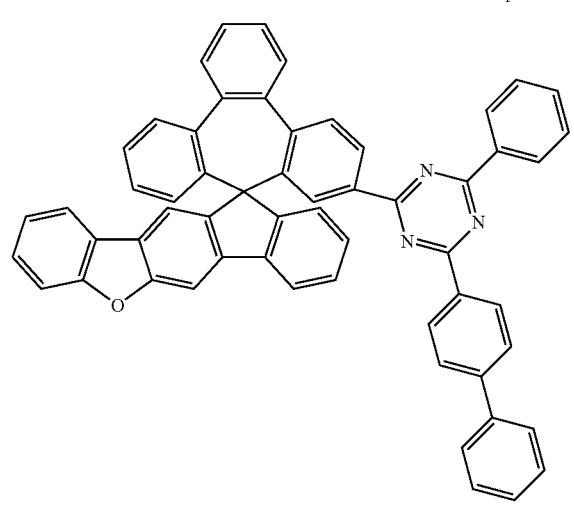
Compound CLII
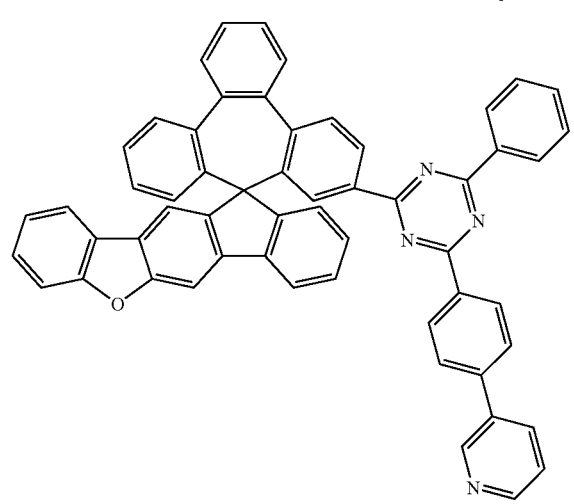
Compound CLIII
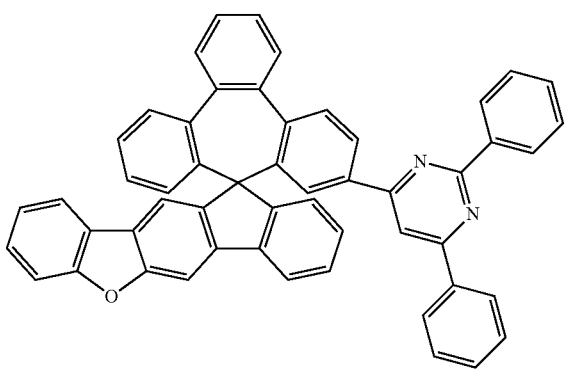
Compound CLIV
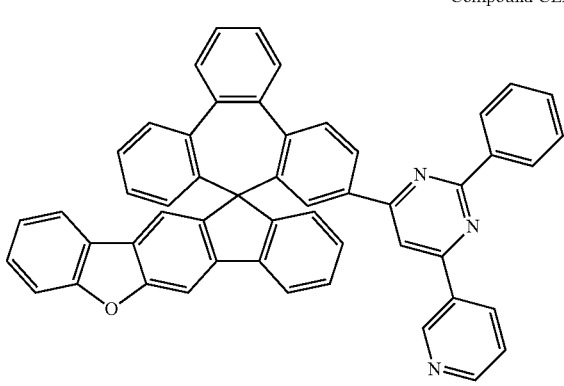
Compound CLV
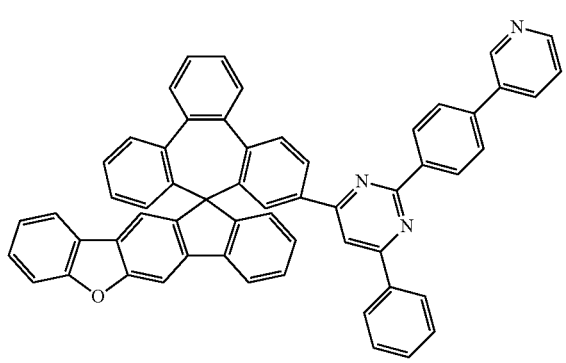
Compound CLVI
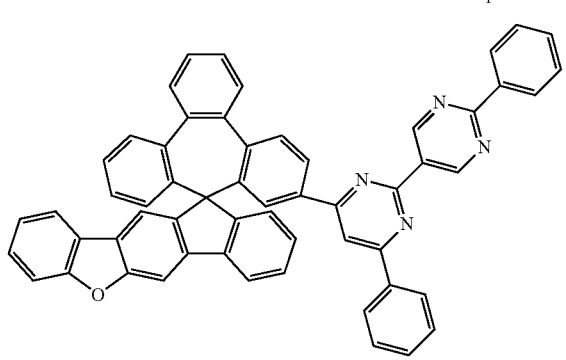

Compound CLVII
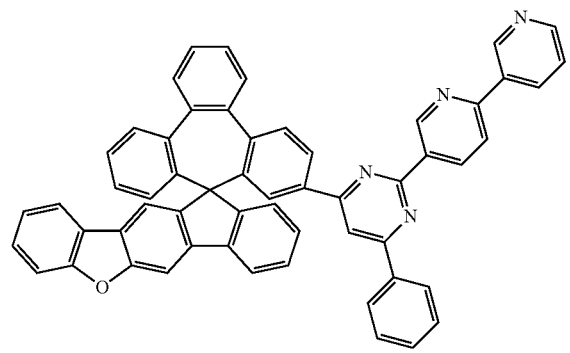
Compound CLVIII
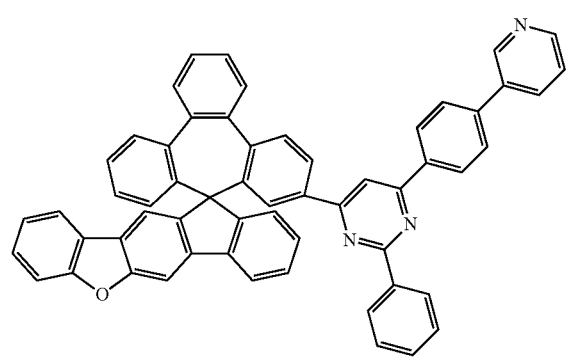
Compound CLIX
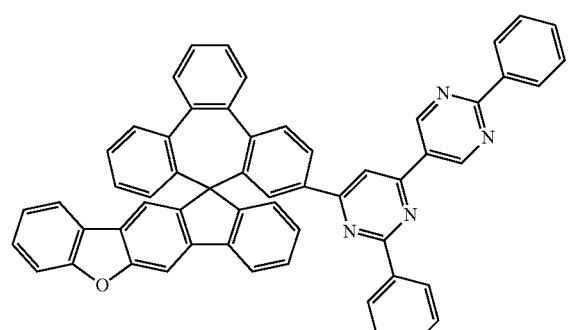
Compound CLX
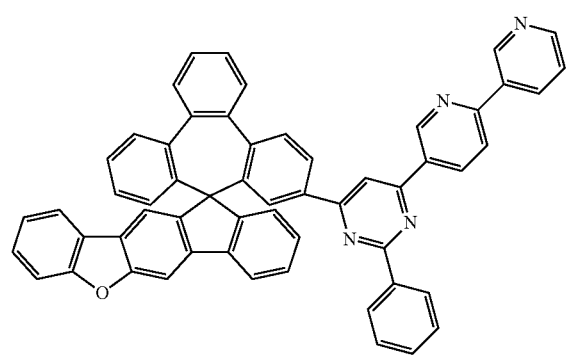
Compound CLXI
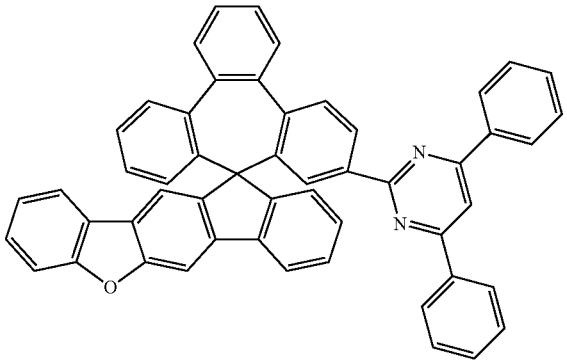
Compound CLXII
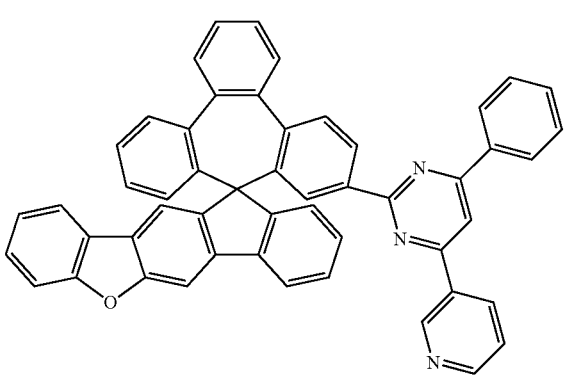
Compound CLXIII
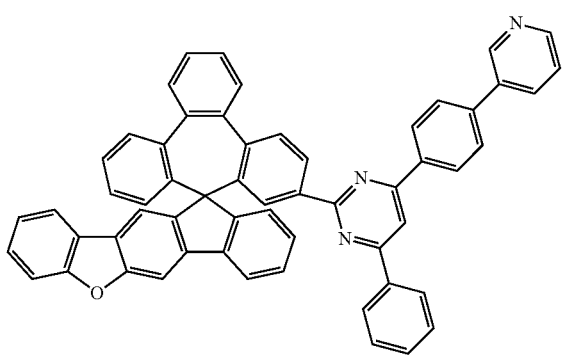
Compound CLXIV
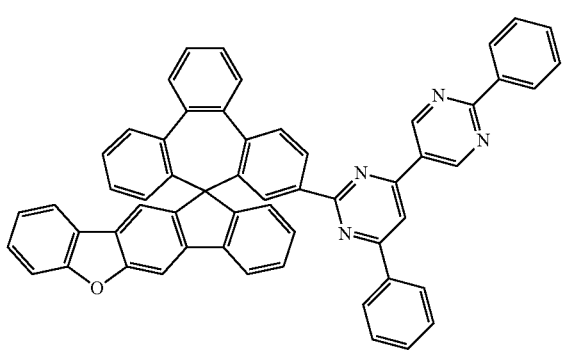

-continued
Compound CLXV
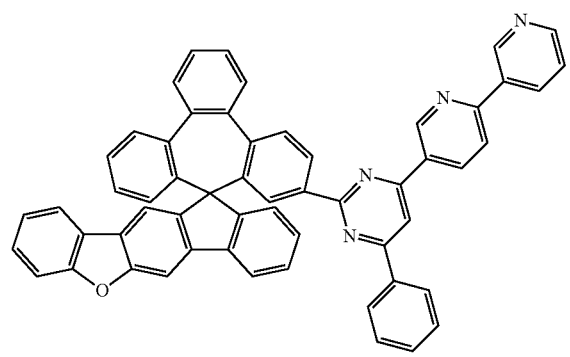
Compound CLXVI
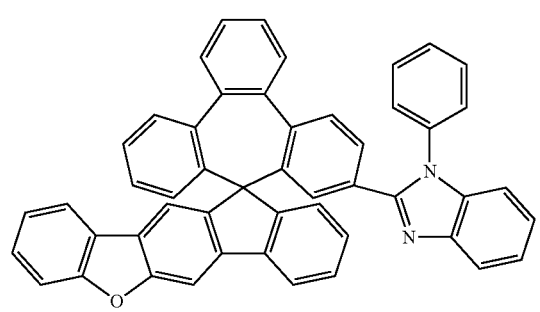
Compound CLXVII
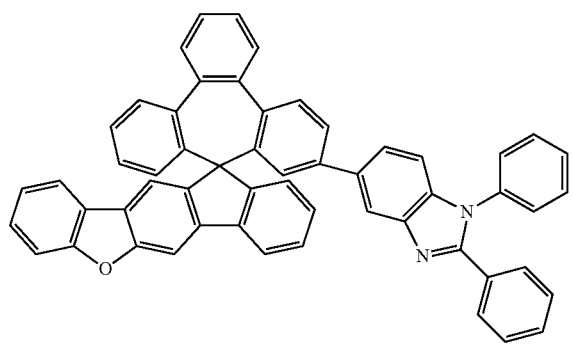
Compound CLXVIII
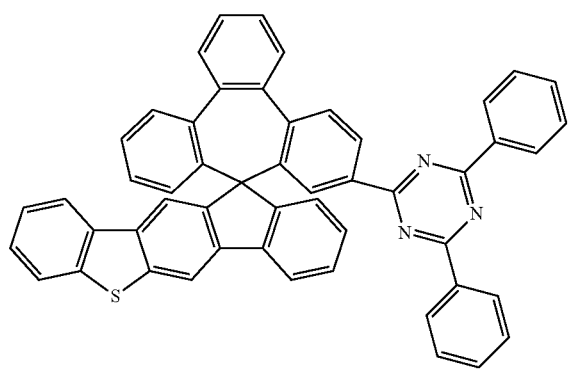
-continued
Compound CLXIX
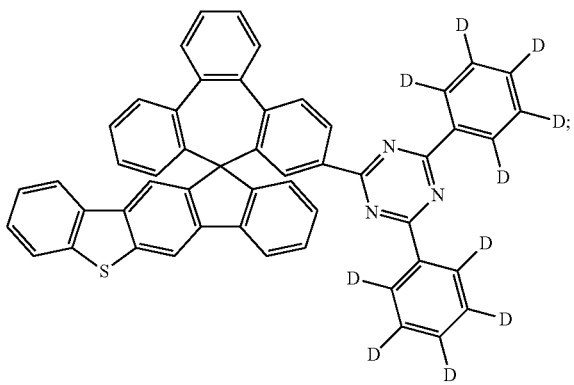
Compound CLXX
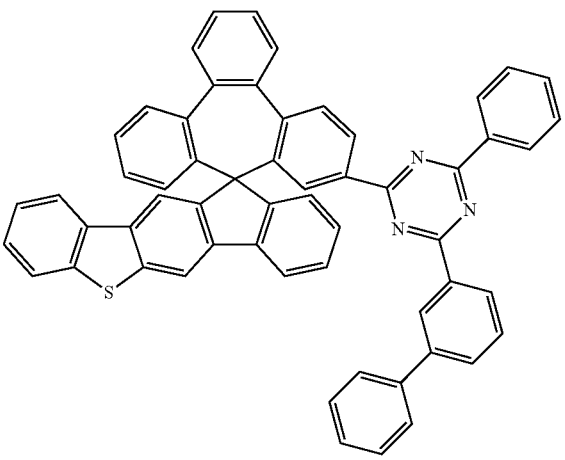
Compound CLXXI
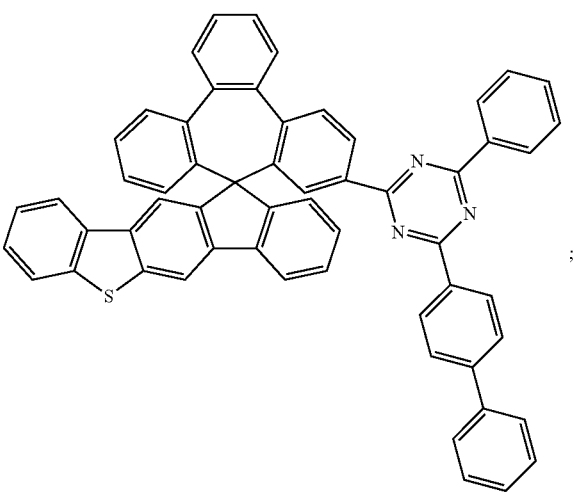

Compound CLXXII
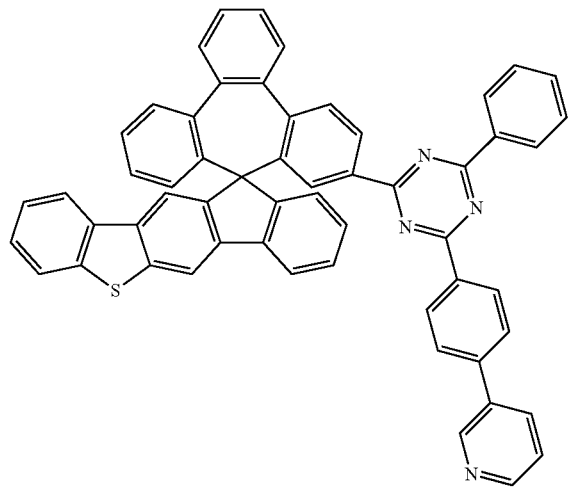
Compound CLXXIII
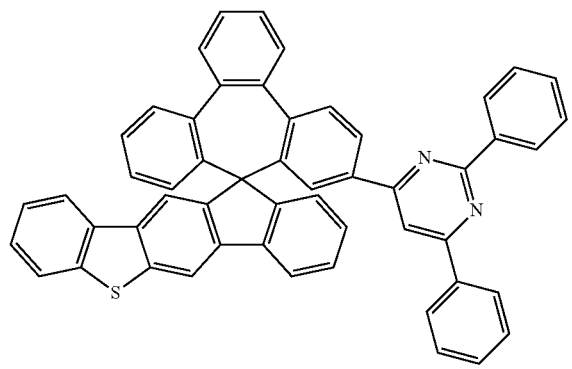
Compound CLXXIV
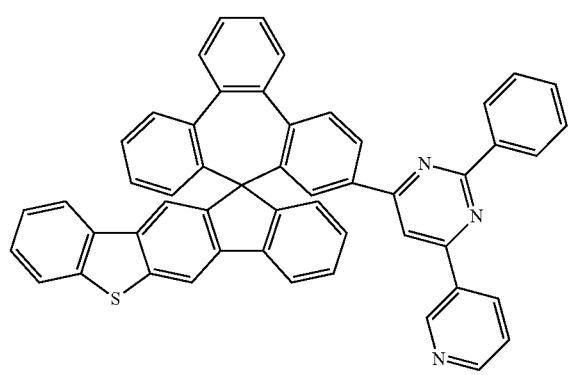
Compound CLXXV
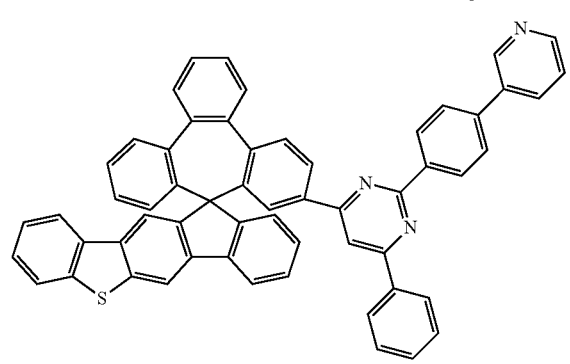
Compound CLXXVI
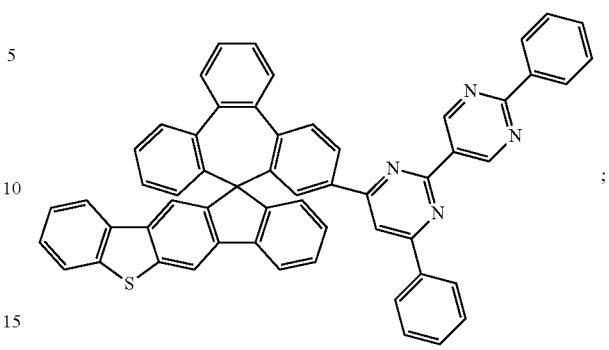
Compound CLXXVII
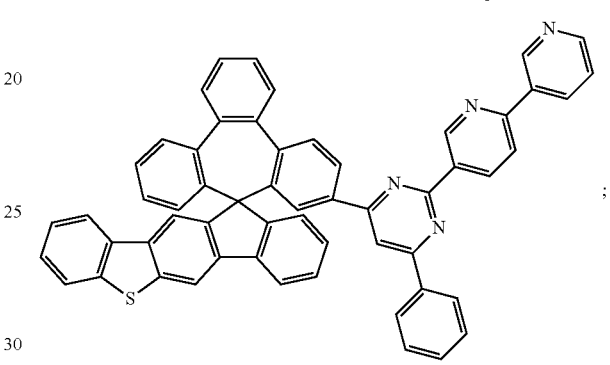
Compound CLXXVIII
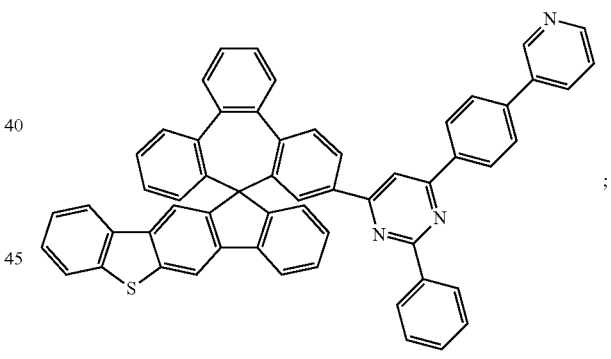
Compound CLXXIX
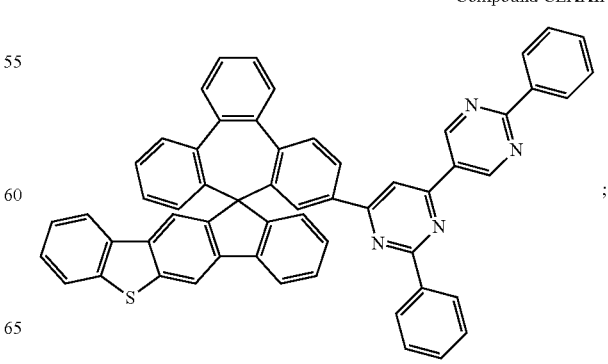

Compound CLXXX
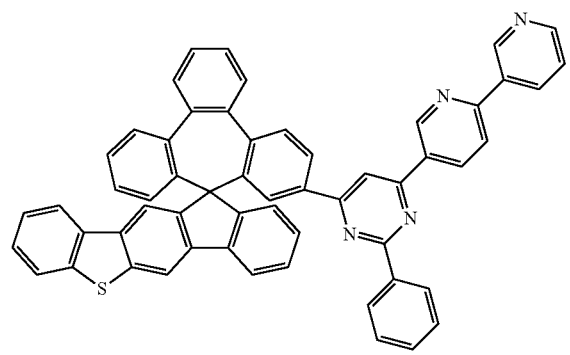
Compound CLXXXI
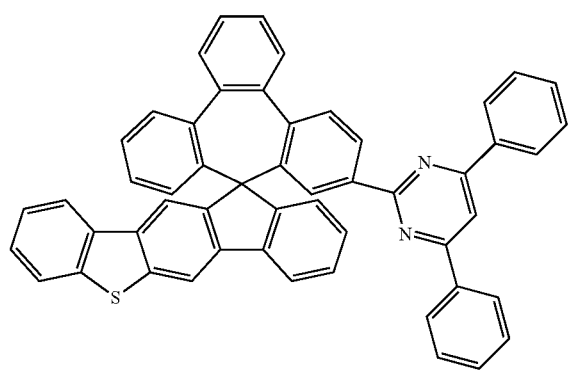
Compound CLXXXII
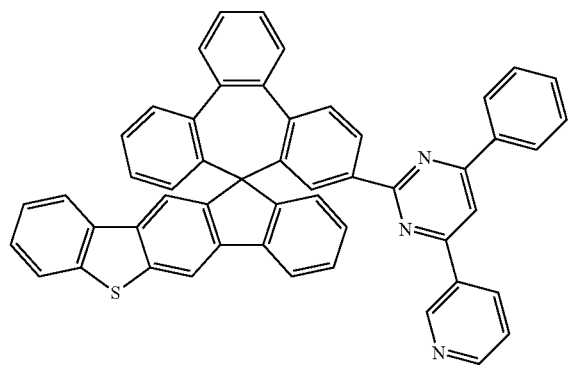
Compound CLXXXIII
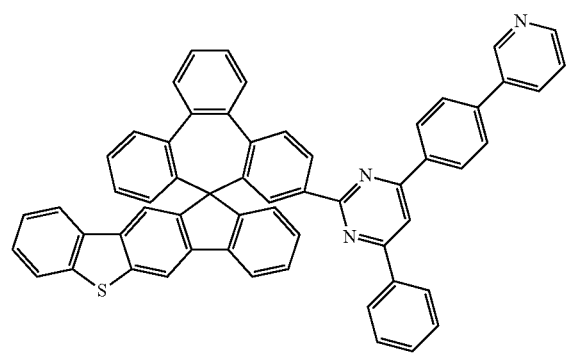
Compound CLXXXIV
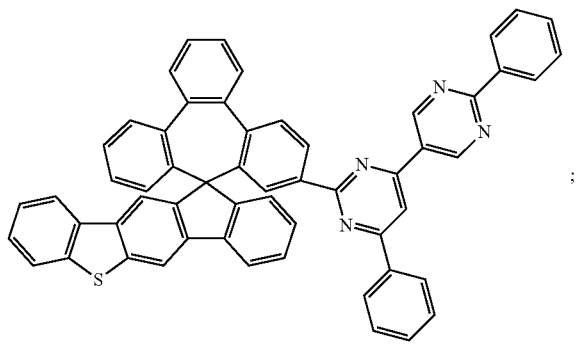
Compound CLXXXV
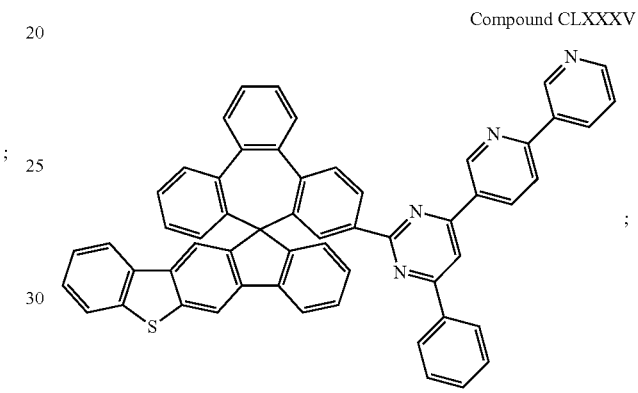
Compound CLXXXVI
Compound CLXXXVII
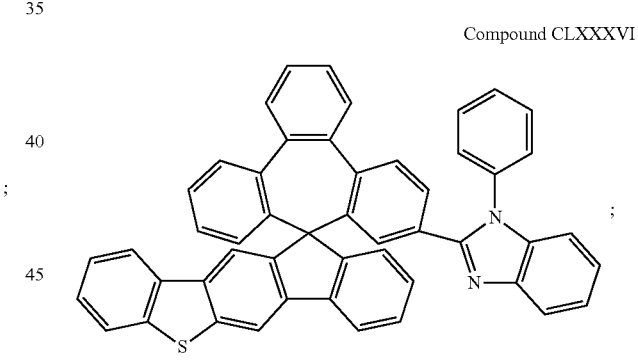

Compound CLXXXVIII
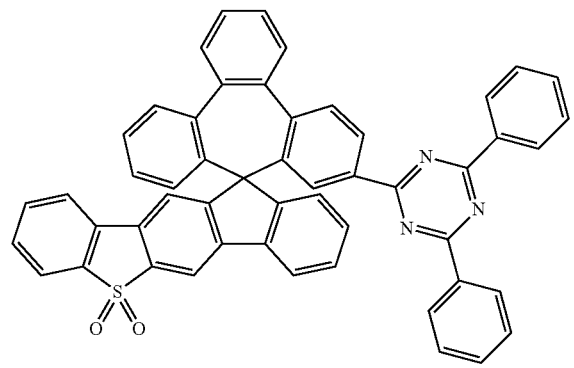
Compound CLXXXIX
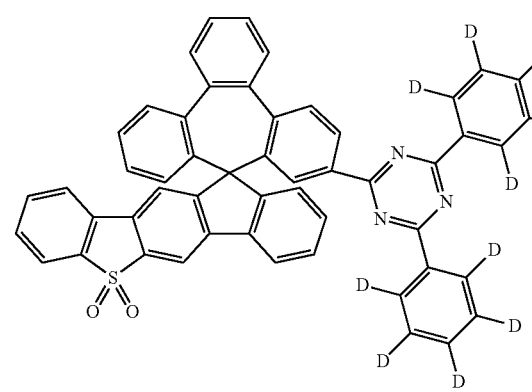
Compound CXC
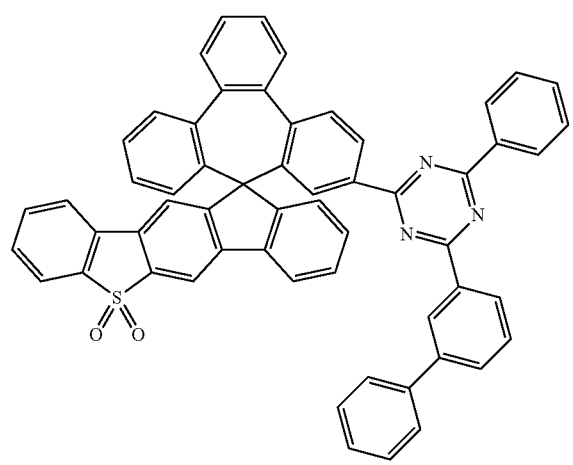
Compound CXCI
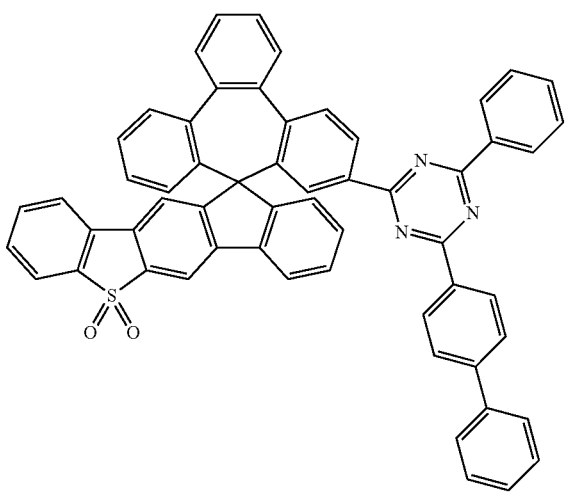
Compound CXCII
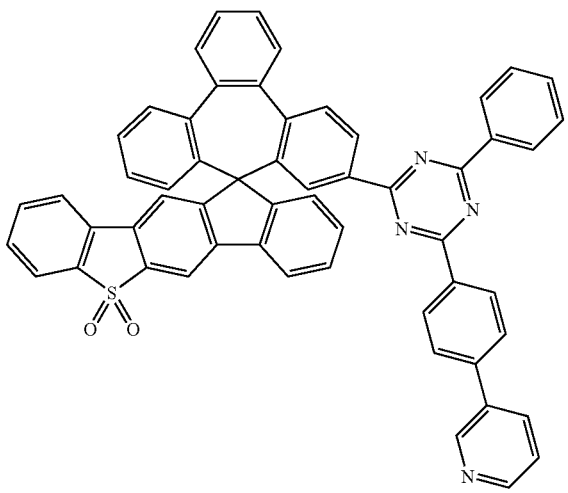
Compound CXCIII
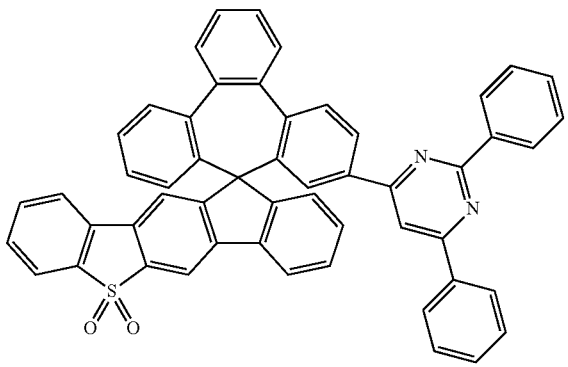

-continued
Compound CXCIV
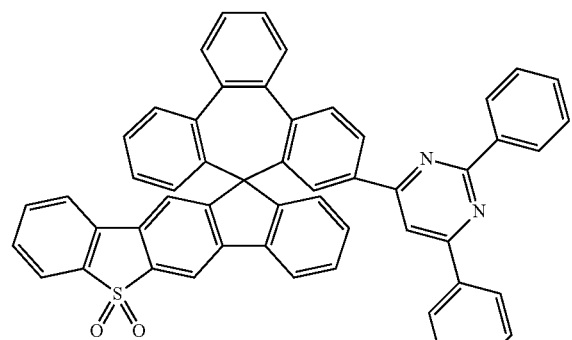
;
Compound CXCV
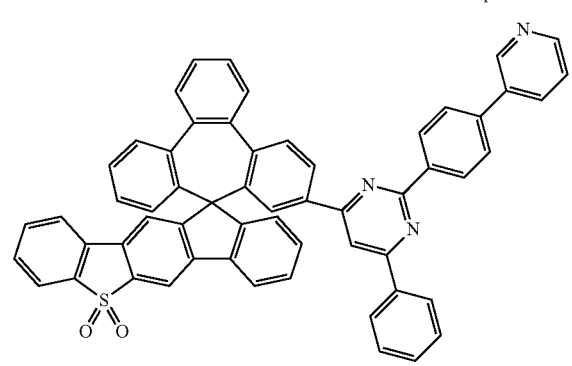
;
Compound CXCVI
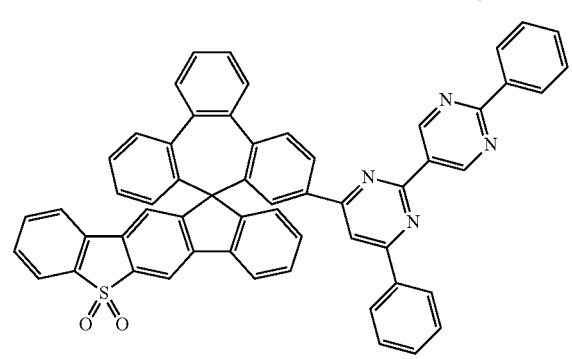
;
Compound CXCVII
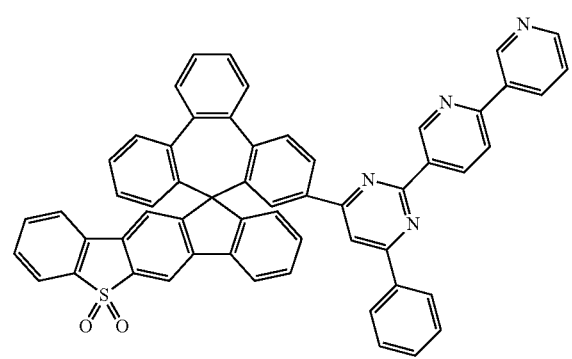
;
Compound CXCVIII
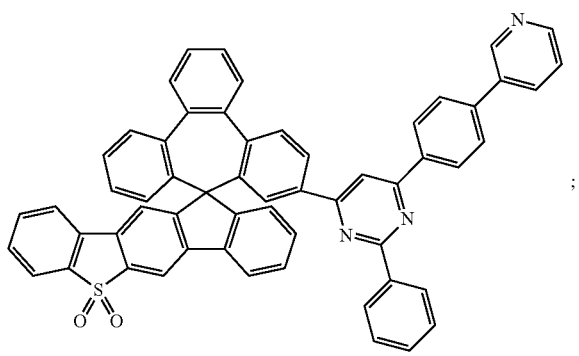
;
Compound CIC
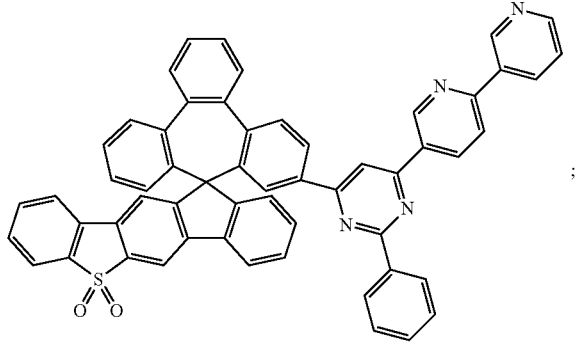
;
Compound CC
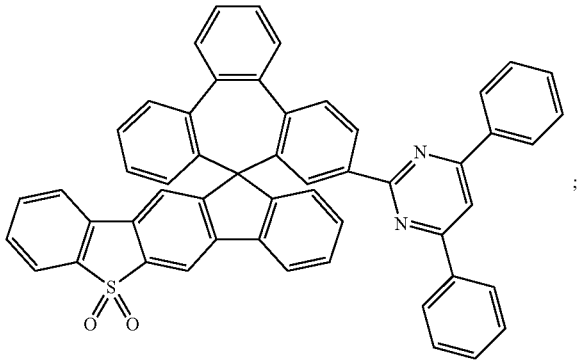
;
Compound CCI Compound CCII
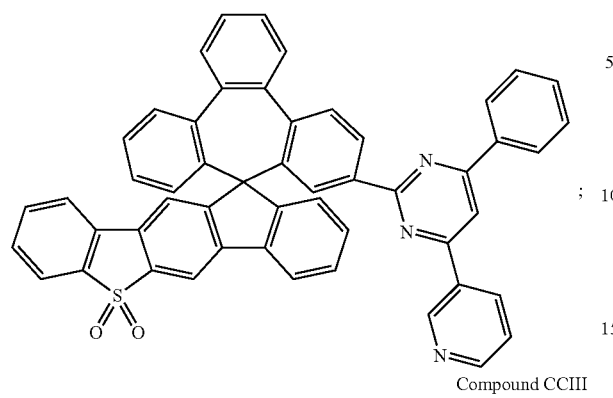
Compound CCIII
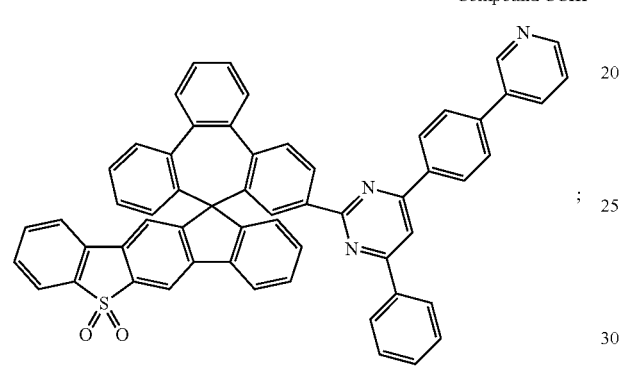
Compound CCIV
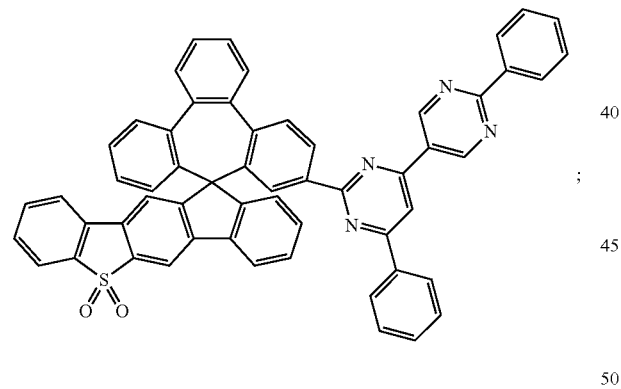
Compound CCV
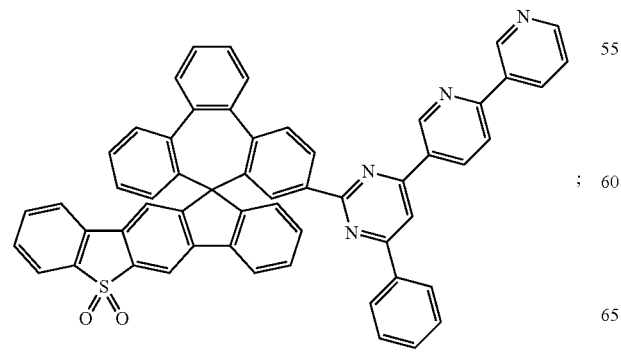
Compound CCVI
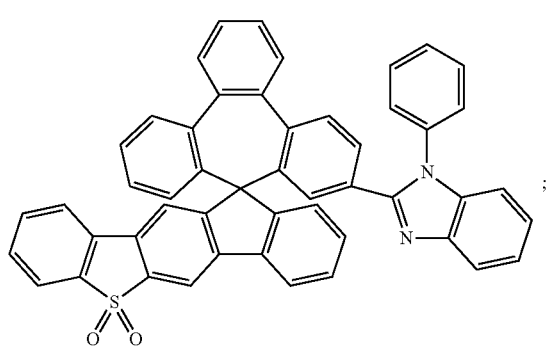
Compound CCVII
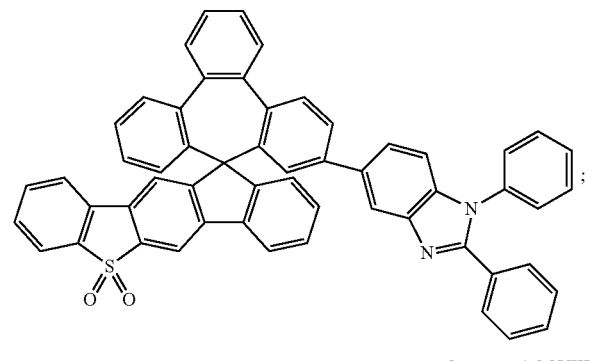
Compound CCVIII
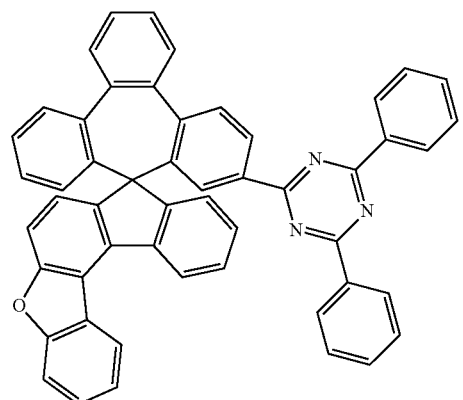
Compound CCIX
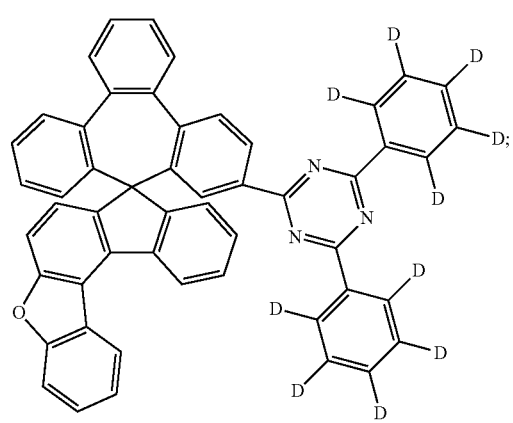

Compound CCX
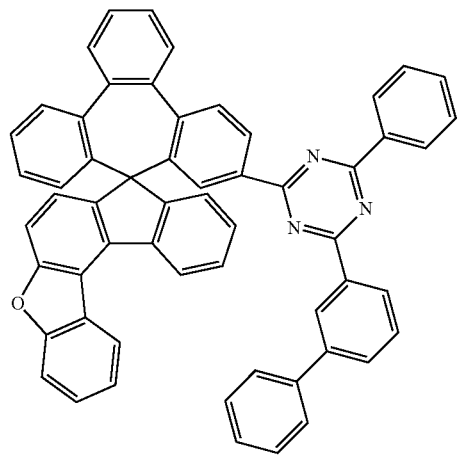
Compound CCI
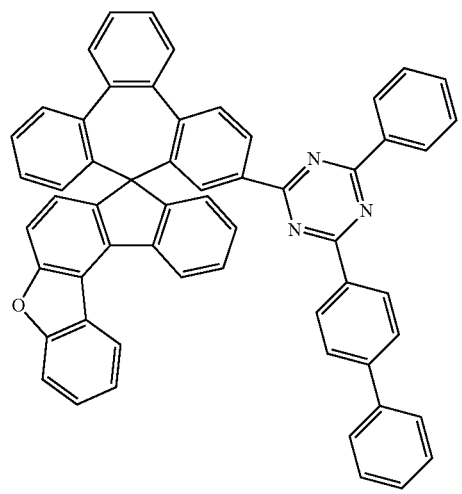
Compound CCII
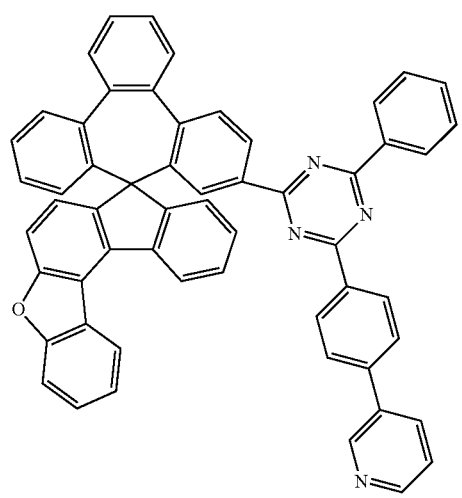
Compound CCIII
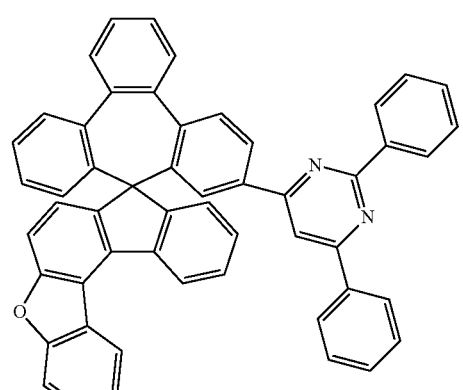
Compound CCIV
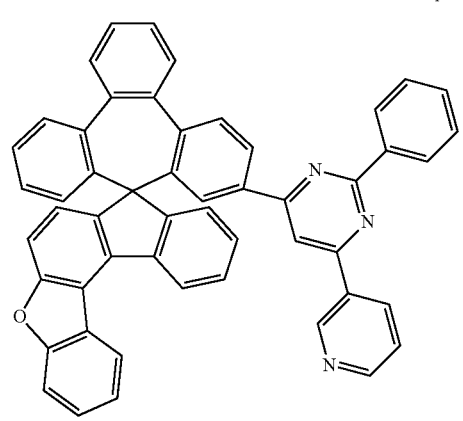
Compound CCV
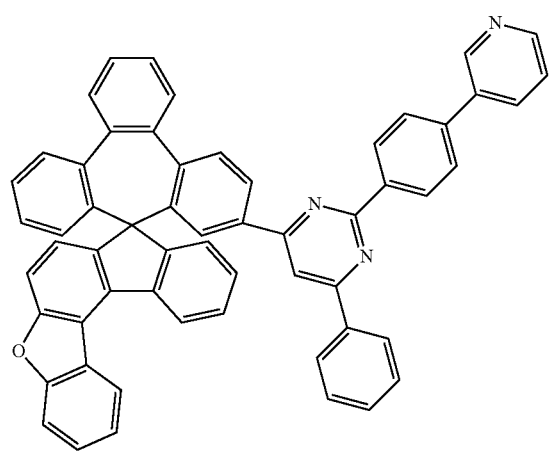

Compound CCVI
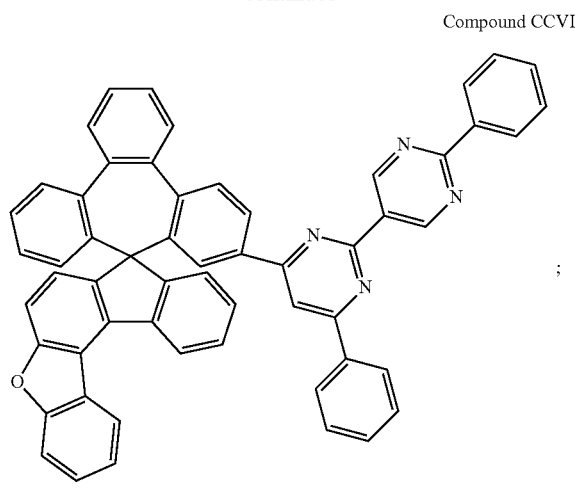
Compound CCVII
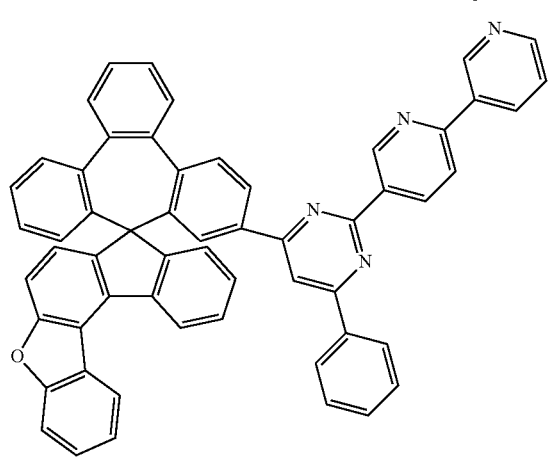
Compound CCVIII
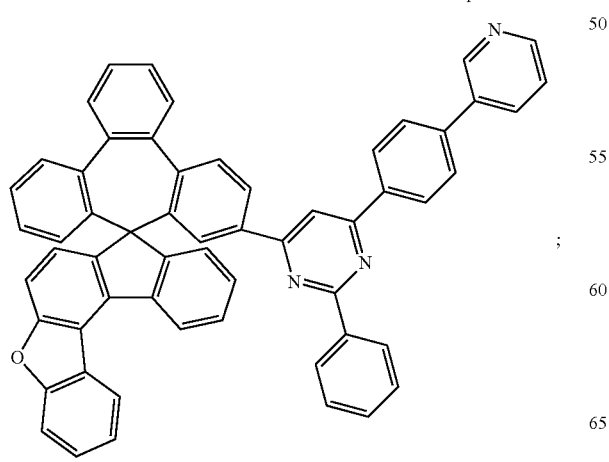
Compound CCIX
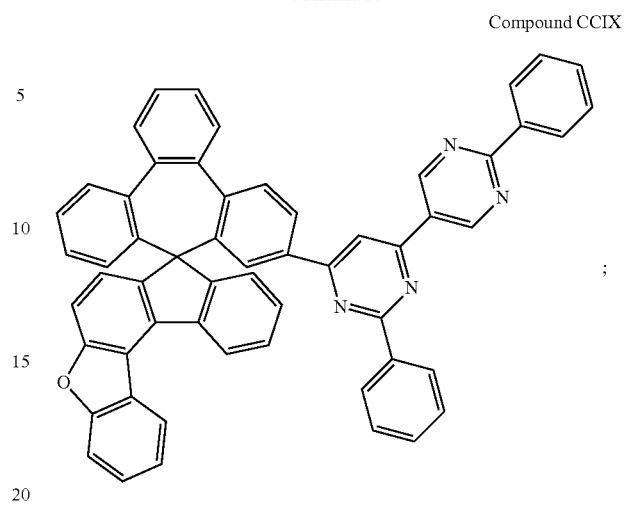
Compound CCX
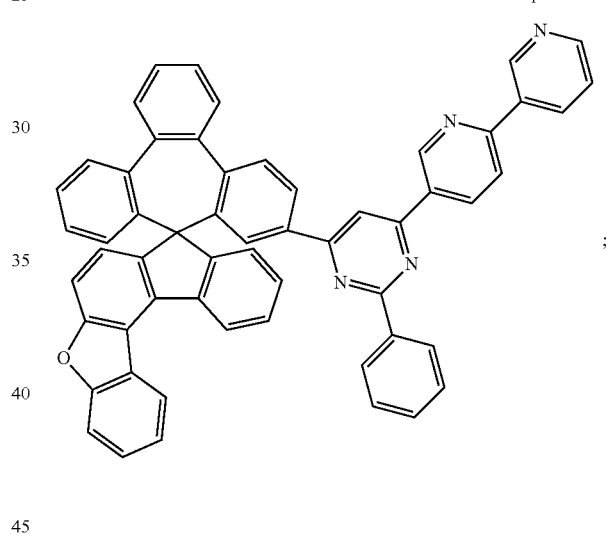
Compound CCXI
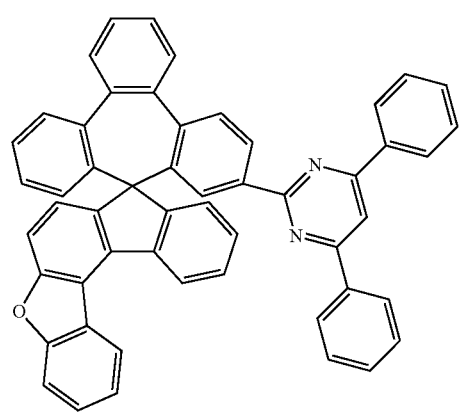

Compound CCXII
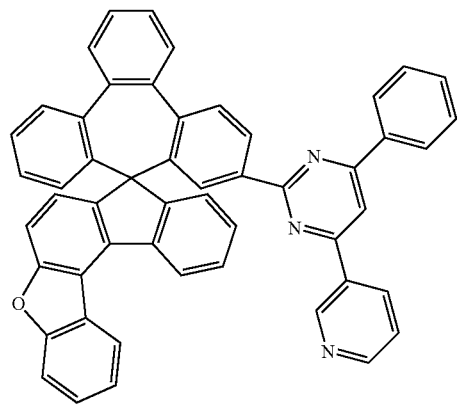
Compound CCXIII
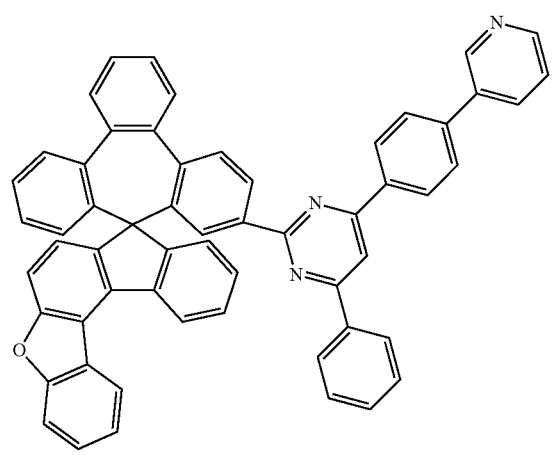
Compound CCXIV
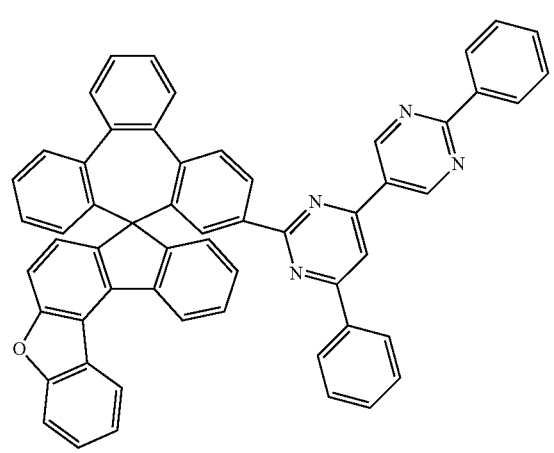
Compound CCXV
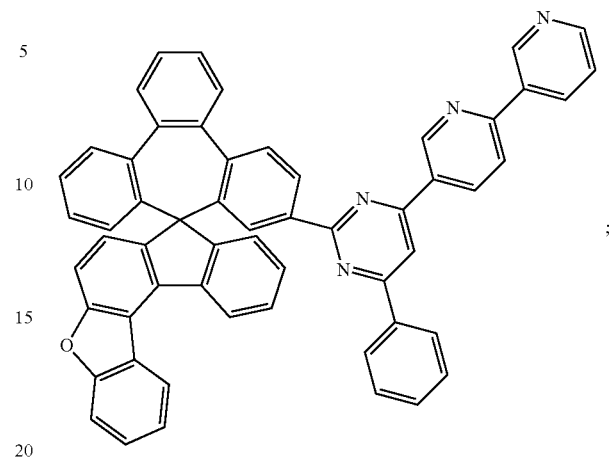
Compound CCXVI
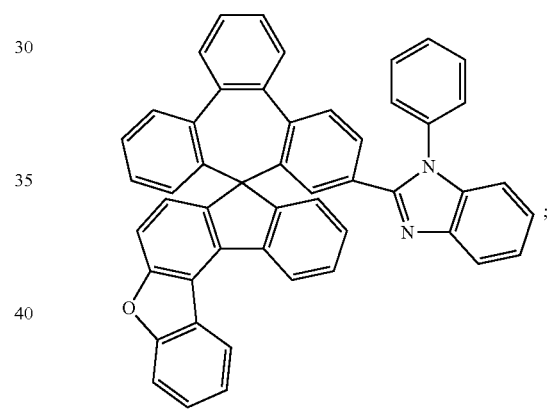
Compound CCXVII
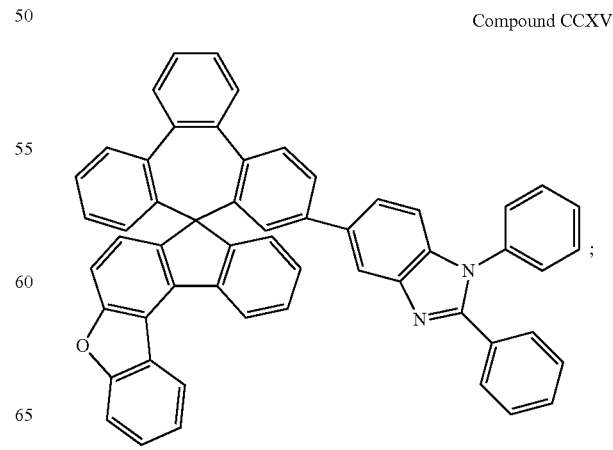

Compound CCXVIII
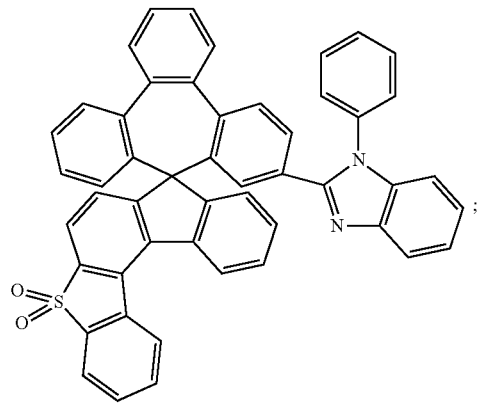
Compound CCXIX
Compound CCXX
Compound CCXXI
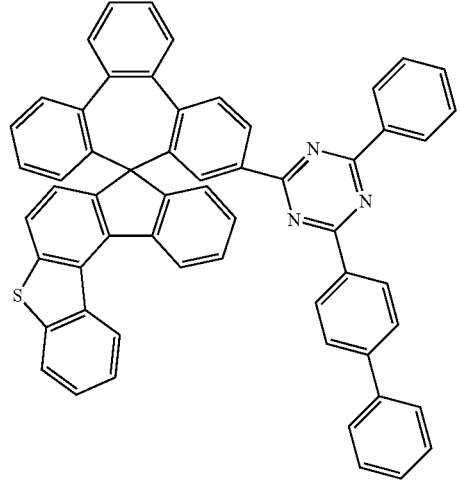
Compound CCXXII
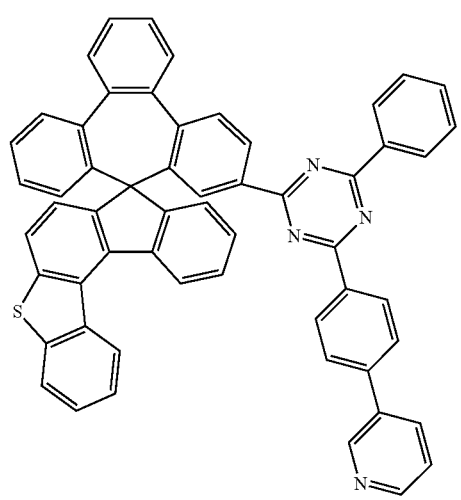
Compound CCXXIII
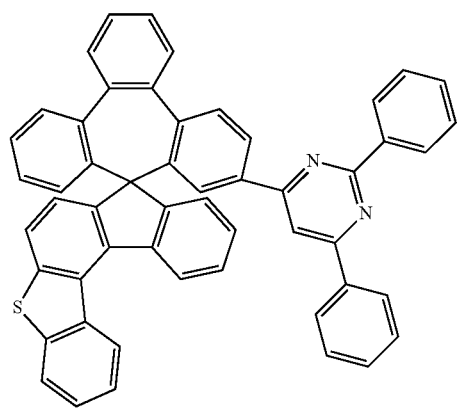

Compound CCXXIV
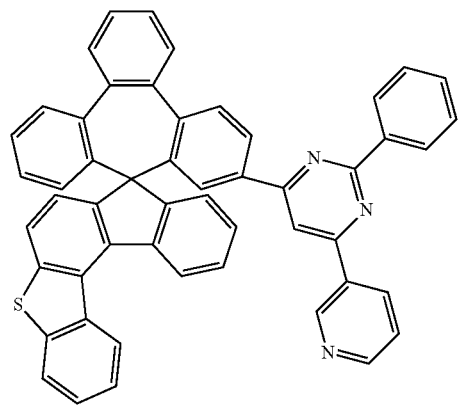
Compound CCXXV
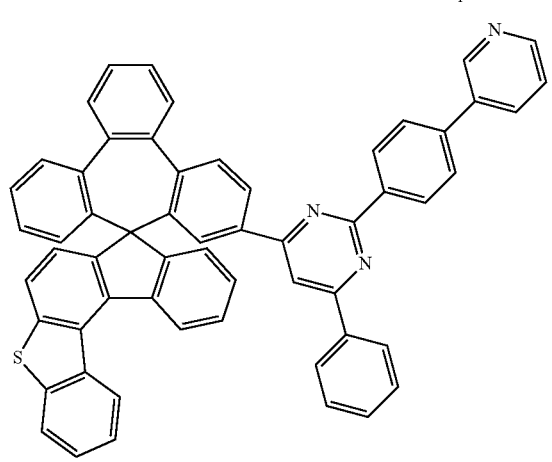
Compound CCXXVI
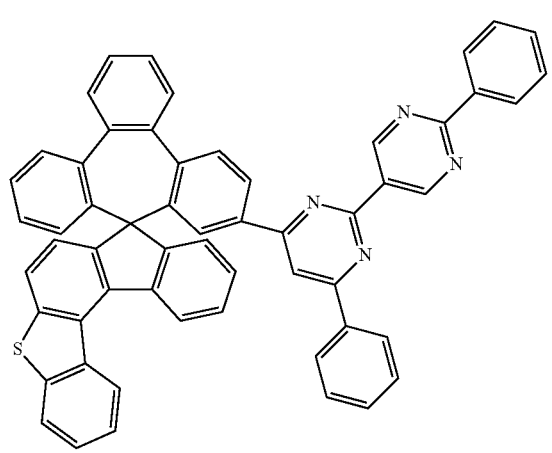
Compound CCXXVII
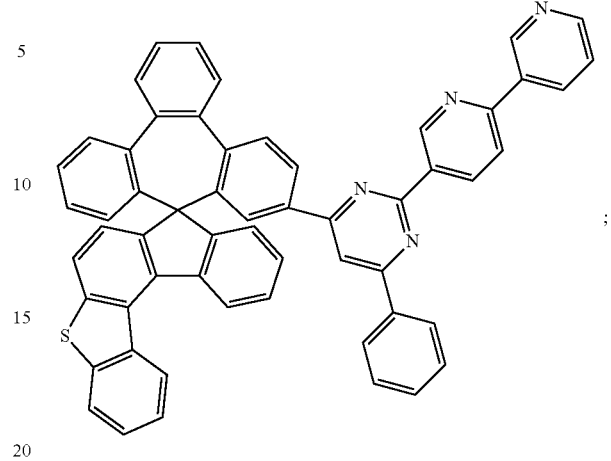
Compound CCXXVIII
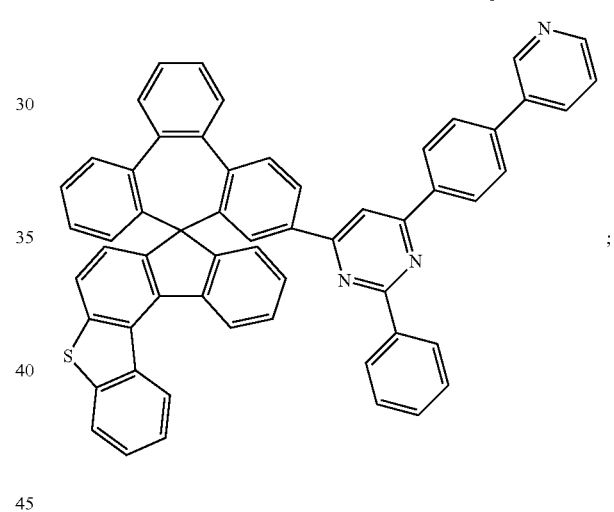
Compound CCXXIX
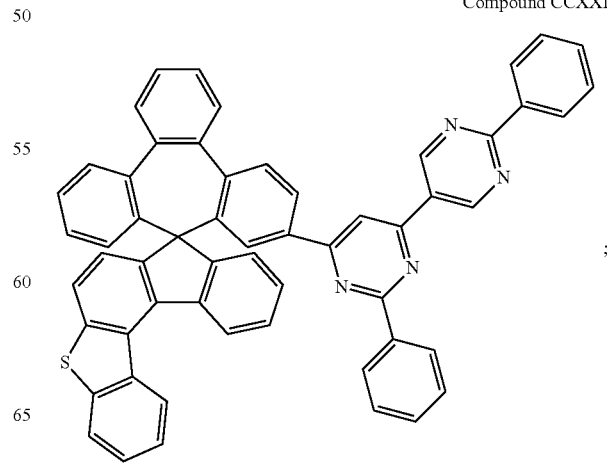

Compound CCXXX
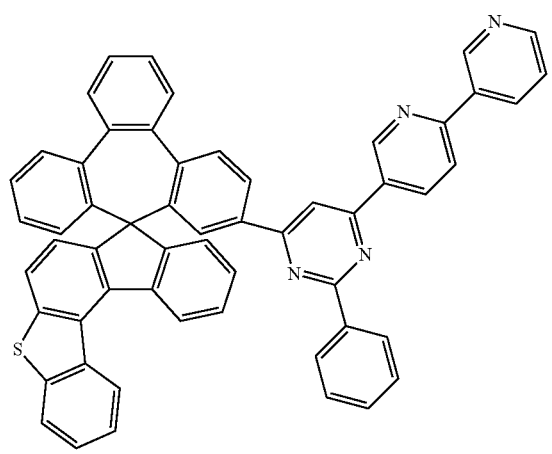
Compound CCXXXIII
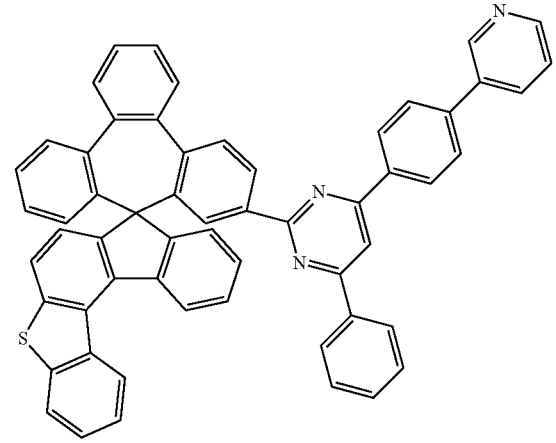
Compound CCXXXI
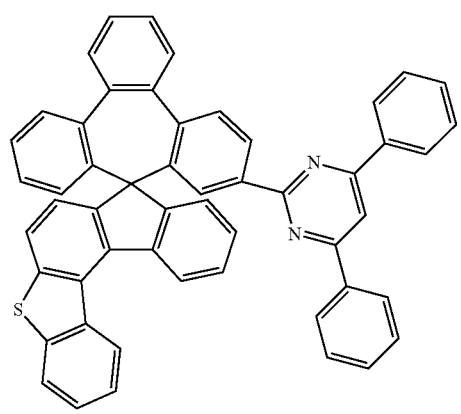
Compound CCXXXIV
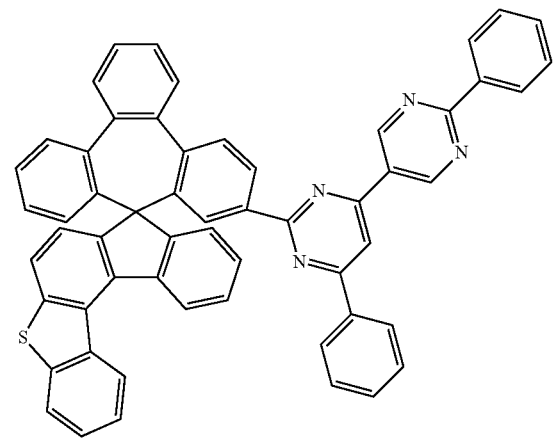
Compound CCXXXII
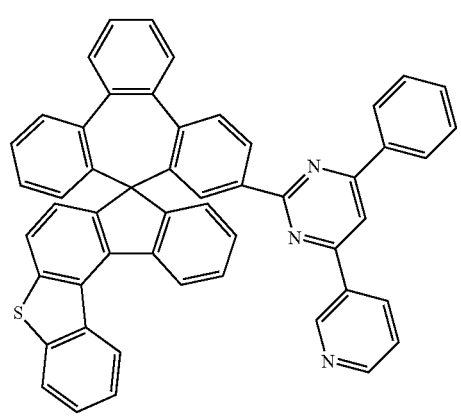
Compound CCXXXV
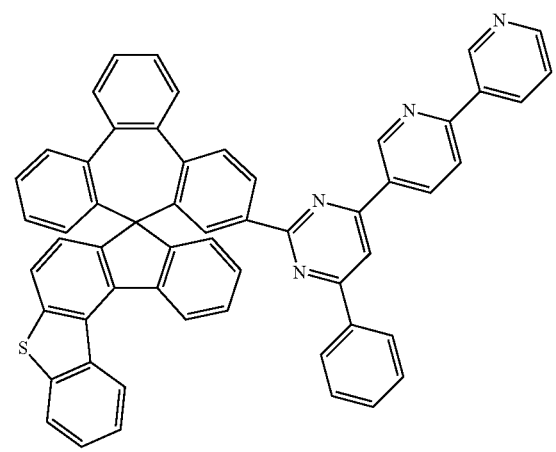

Compound CCXXXVI
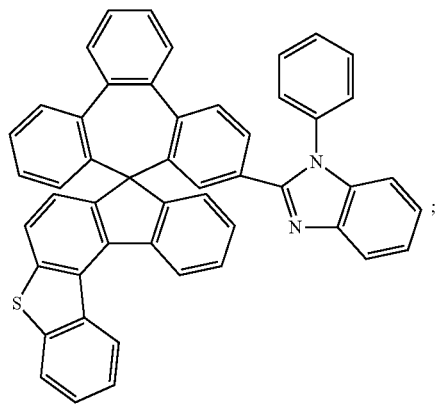
Compound CCXXXVII
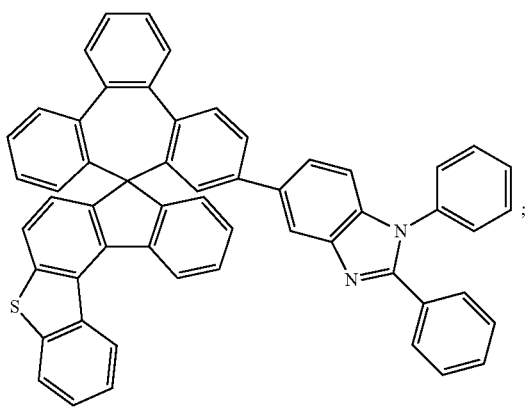
Compound CCXXXVIII
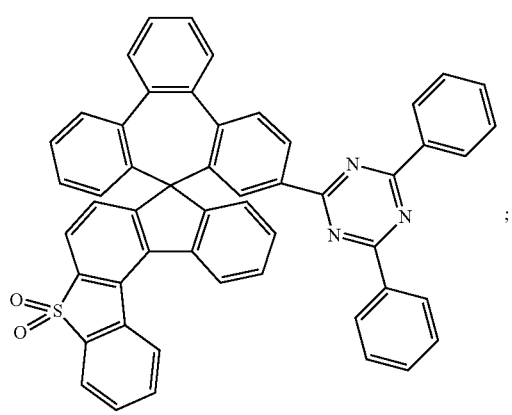
Compound CCXXXIX
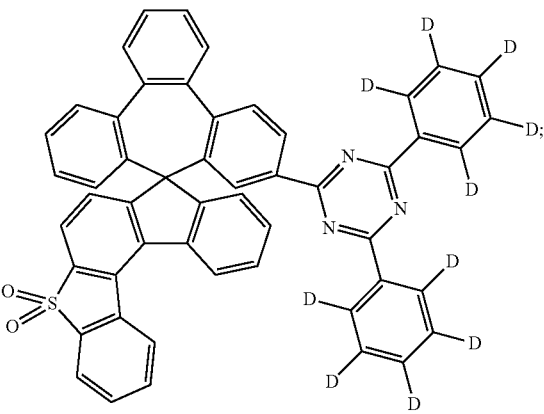
Compound CCXL
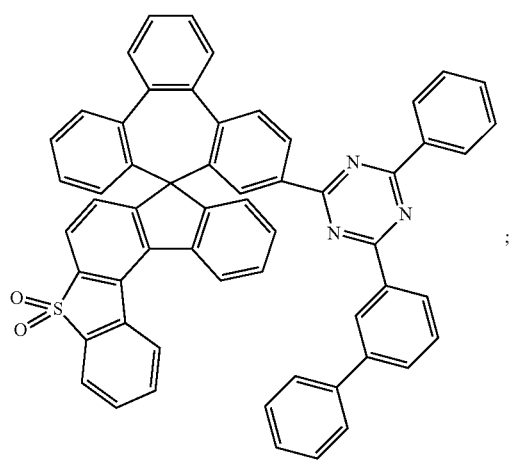
Compound CCXLI
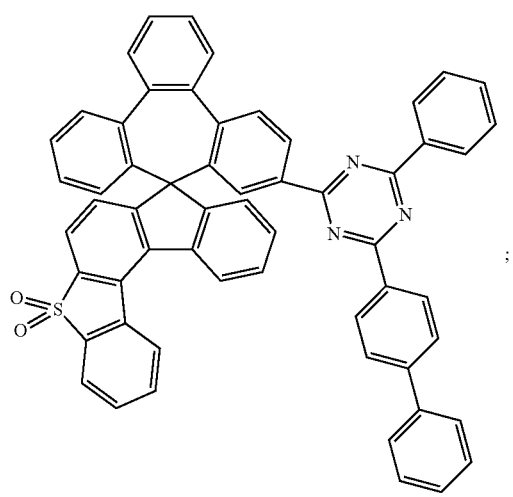

Compound CCXLII
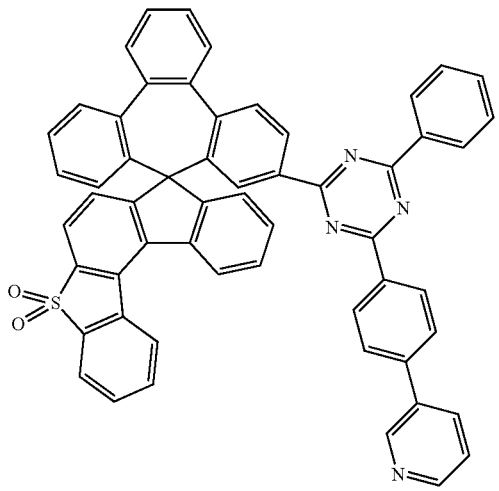
Compound CCXLIII
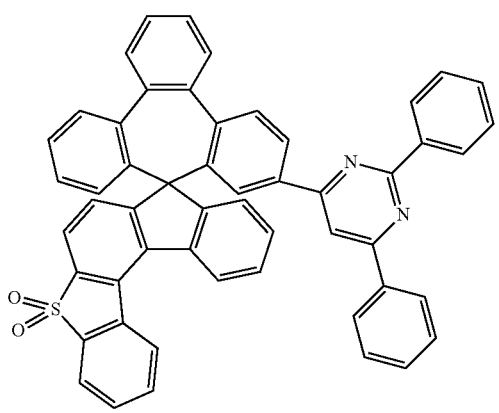
Compound CCXLIV
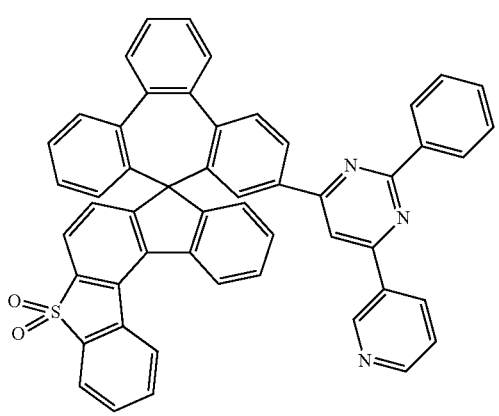
Compound CCXLV
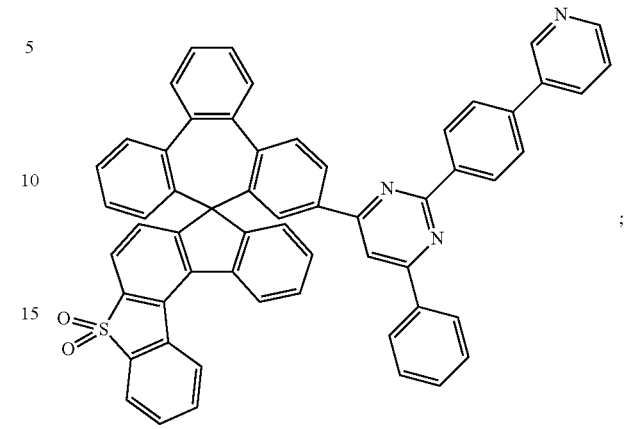
Compound CCXLVI
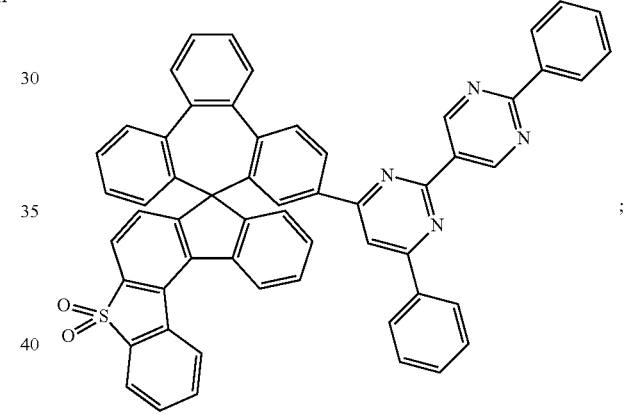
Compound CCXLVII
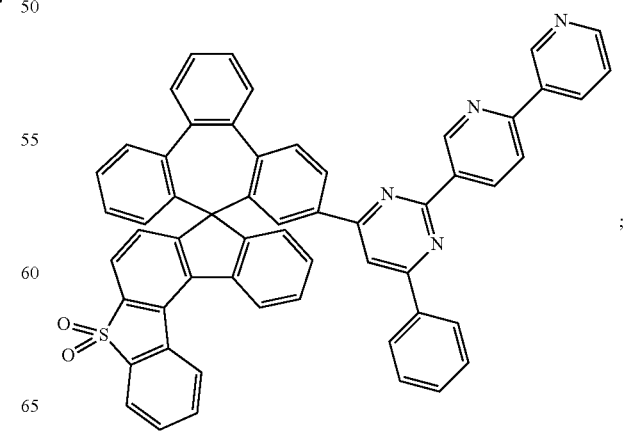

Compound CCXLVIII
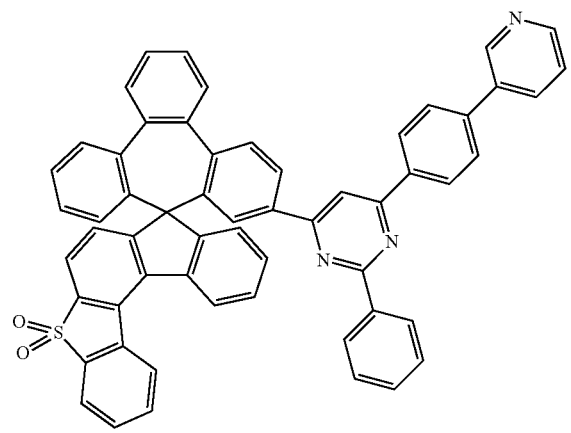
Compound CCIL
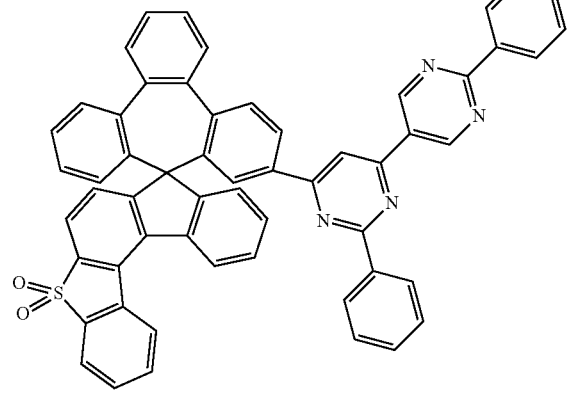
Compound CCL
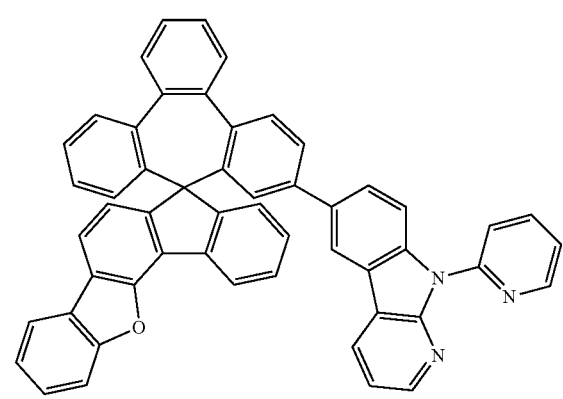
Compound CCLI
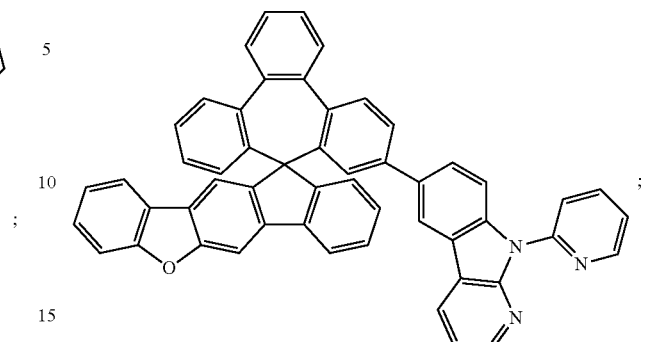
Compound CCLII
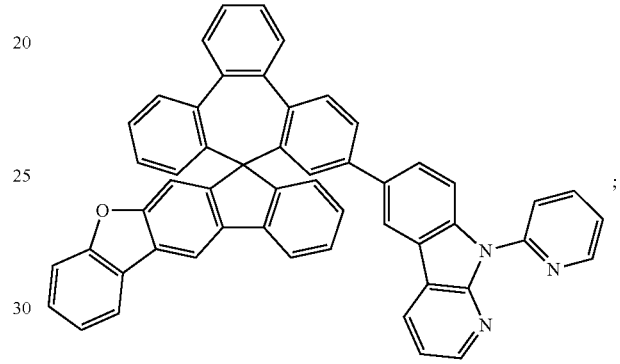
Compound CCLIII
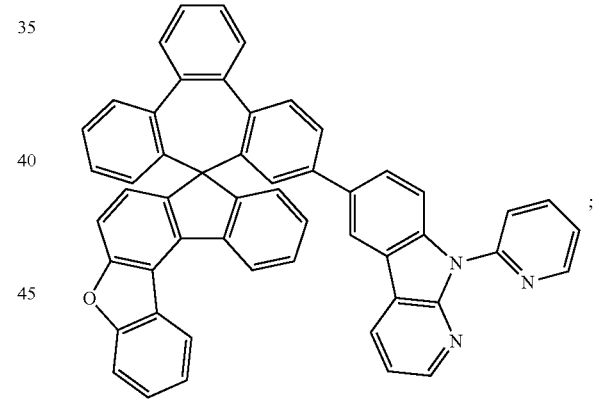
Compound CCLIV
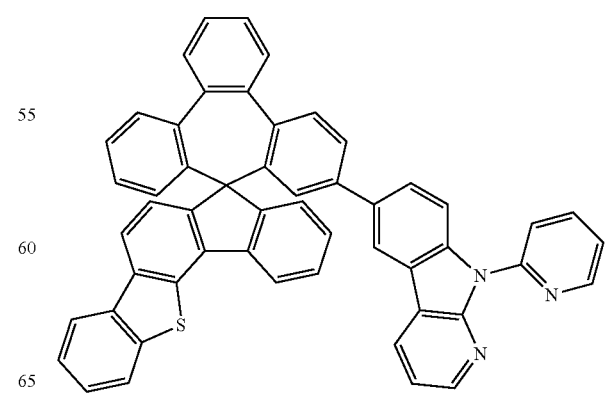

Compound CCLV
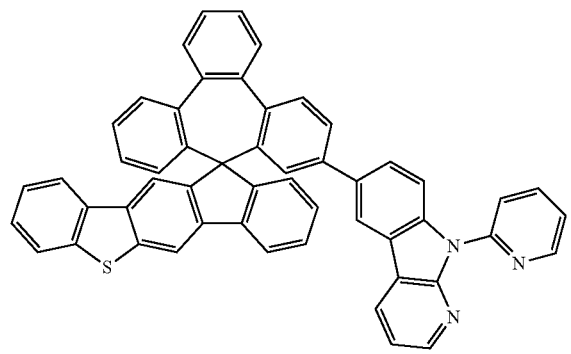
Compound CCLVI
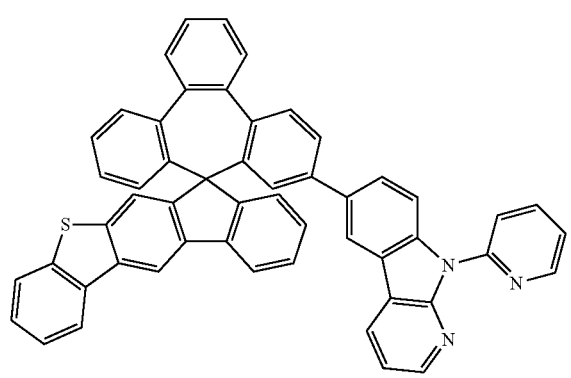
Compound CCLVII
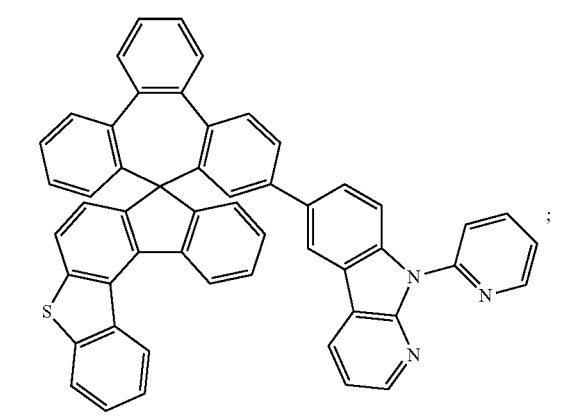
Compound CCLVIII
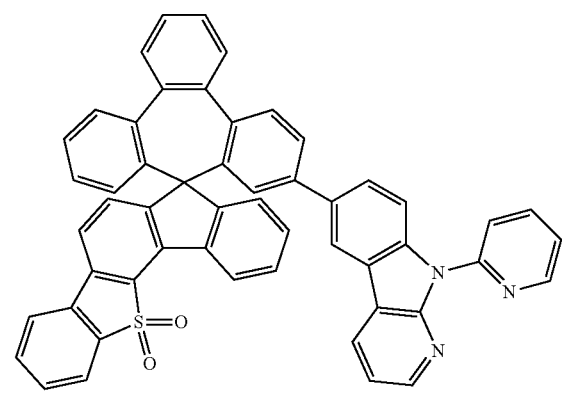
Compound CCLIX
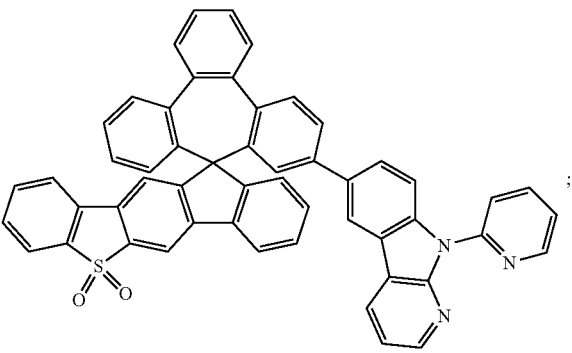
Compound CCLX
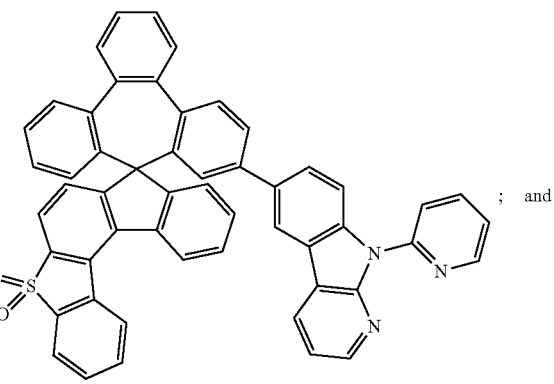
Compound CCLXI
; and
Compound CCLXII
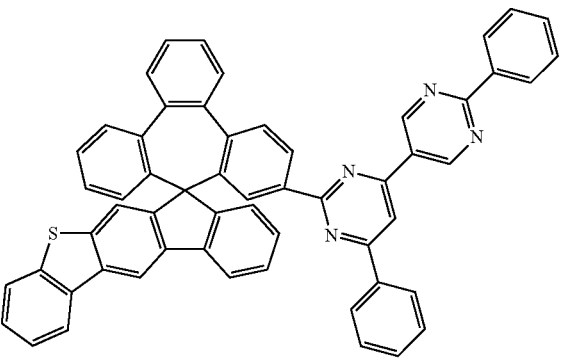
.
The present invention also provides an organic electronic device, comprising a first electrode, a second electrode, and an organic layer disposed between the first electrode and the second electrode. The organic layer comprises the novel compound as described above.

Preferably, the organic electronic device is an organic light emitting device (OLED). More preferably, the novel compound of the present invention may be used as an electron transport material or a hole blocking layer.

Specifically, the organic light emitting device may comprise:
a hole injection layer formed on the first electrode;
a hole transport layer formed on the hole injection layer;
an emission layer formed on the hole transport layer;
an electron transport layer formed on the emission layer;
an electron injection layer formed between the electron transport layer and the second electrode.

In one embodiment, the organic layer may be the electron transport layer, i.e., the electron transport layer comprises the novel compound as stated above.

Preferably, the hole injection layer may be a two-layered structure, i.e., the OLED comprises a first hole injection layer and a second hole injection layer disposed between the first electrode and the hole transport layer.

Preferably, the hole transport layer may be a two-layered structure, i.e., the OLED comprises a first hole transport layer and a second hole transport layer disposed between the two-layered hole injection layer and the emission layer.

Preferably, the electron transport layer is made of the novel compound such as Compounds I to CCLXII. The OLEDs using the novel compound as the electron transport material can have an improved efficiency compared to commercial OLEDs using known electron transport material, such as 2-(4-(9,10-di(naphthalen-2-yl)anthracen-2-yl)phenyl)-1-phenyl-1H-benzo[d]imidazole; bis(2-methyl-8-quinolinolato)(p-phenylphenolato) aluminum; and 2-(4-biphenylyl)-5-(4-tert-butylphenyl)-1,3,4-oxadiazole (PBD), as the electron transport material.

Preferably, the OLED comprises a hole blocking layer formed between the electron transport layer and the emission layer, to block holes overflow from the emission layer to the electron transport layer. Said hole blocking layer may be made of the foresaid novel compound, 2,9-dimethyl-4,7-diphenyl-1,10-phenanthroline (BCP) or 2,3,5,6-tetramethyl-phenyl-1,4-(bis-phthalimide) (TMPP), but not limited thereto. In another embodiment, the organic layer may be the hole blocking layer, i.e., the hole blocking layer comprises the novel compound as stated above.

Preferably, the OLED comprises an electron blocking layer formed between the hole transport layer and the emission layer, to block electrons overflow from the emission layer to the hole transport layer. Said electron blocking layer may be made of 9,9'-[1,1'-biphenyl]-4,4'-diylbis-9H-carbazole(CBP) or 4,4',4''-tri(N-carbazolyl)-triphenylamine (TCTA), but not limited thereto.

In the presence of such a hole blocking layer and/or an electron blocking layer in an OLED, the OLED has a higher luminous efficiency compared to a typical OLED.

Said first and second hole transport layers may be made of, for example, but not limited to: $N^1,N^{1'}$-(biphenyl-4,4'-diyl)bis($N^1$-(naphthalen-1-yl)-$N^4,N^{4'}$-diphenylbenzene-1,4-diamine); or $N^4,N^{4'}$-di(naphthalen-1-yl)-$N^4,N^{4'}$-diphenylbiphenyl-4,4'-diamine (NPB).

Said first and second hole injection layers may be made of, for example, but not ited to, polyaniline or polyethylenedioxythiophene.

Said emission layer can be made of an emission material including a host and a dopant. The host of the emission material is, for example, but not limited to, 9-(4-(naphthalen-1-yl)phenyl)-10-(naphthalen-2-yl)anthracene.

For red OLEDs, the dopant of the emission material is, for example, but not limited to: organometallic compounds of iridium (H) having perylene ligands, fluoranthene ligands, or periflanthene ligands. For green OLEDs, the dopant of the emission material is, for example, but not limited to: diaminofluorenes; diaminoanthracenes; or organometallic compounds of iridium (II) having phenylpyridine ligands. For blue OLEDs, the dopant of the emission material is, for example, but not limited to: diaminofluorenes; diaminoanthracenes; diaminopyrenes; or organicmetallic compounds of iridium (II) having phenylpyridine ligands. With various host materials of the emission layer, the OLED can emit lights in red, green or blue.

Said electron injection layer may be made of an electron injection material, for example, but not limited to (8-oxidonaphthalen-1-yl)lithium(II).

Said first electrode is, for example, but not limited to, an indium-doped tin oxide electrode.

Said second electrode has a work function lower than that of the first electrode. The second electrode is, for example, but not limited to, an aluminum electrode, an indium electrode, or a magnesium electrode.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
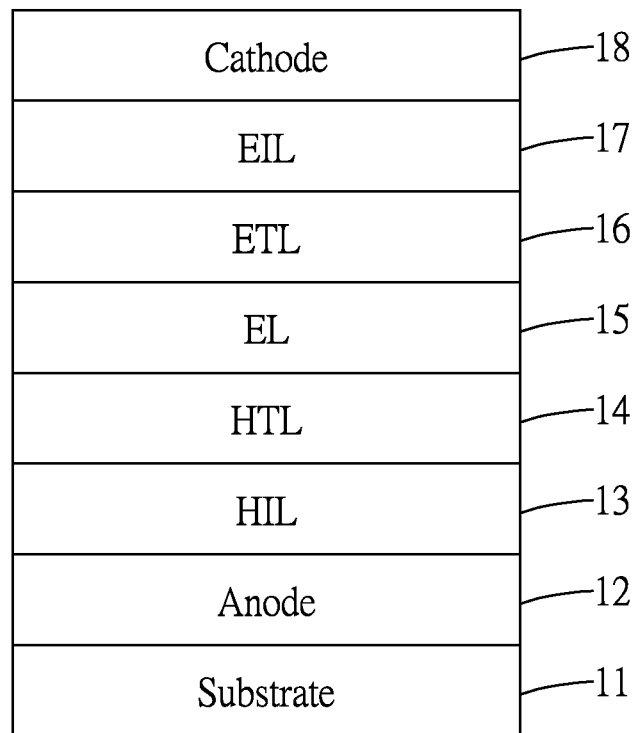
FIG. 1 illustrates a schematic cross-sectional view of an OLED.

Hereinafter, one skilled in the arts can easily realize the advantages and effects of a novel compound and an organic light emitting device using the same in accordance with the present invention from the following examples. It should be understood that the descriptions proposed herein are just preferable examples only for the purpose of illustrations, not intended to limit the scope of the invention. Various modifications and variations could be made in order to practice or apply the present invention without departing from the spirit and scope of the invention.

Synthesis of Intermediate A1

Intermediate A1 used for preparing a novel compound was synthesized by the following steps. The synthesis pathway of the Intermediate A1 was summarized in Scheme A1.

Scheme A1

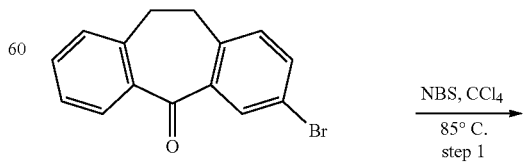

3-bromodibenzo[a,d]cyclohepten-5-one
[3973-53-3]

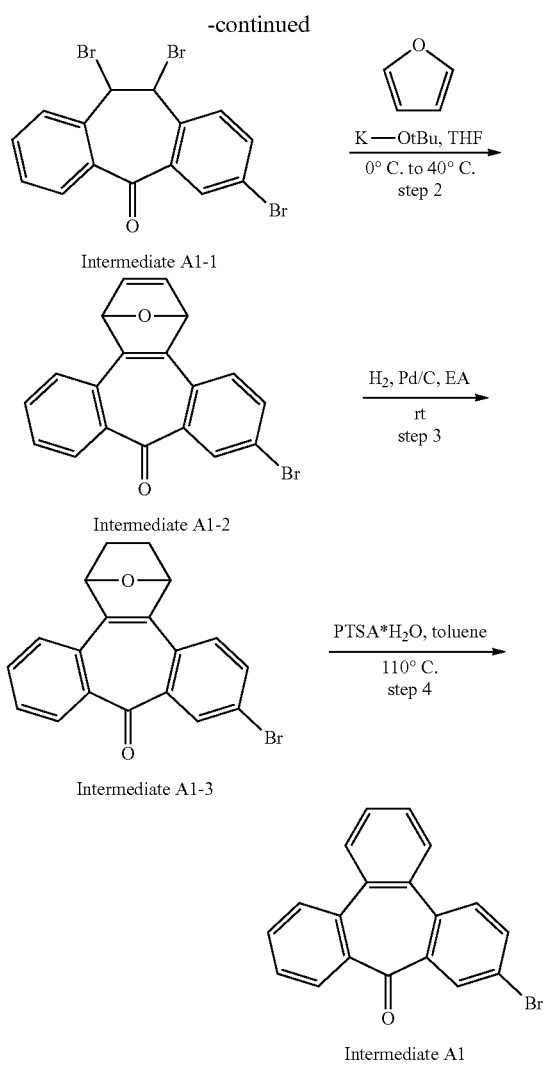

Intermediate A1-1

Intermediate A1-2

Intermediate A1-3

Intermediate A1

Step 1: Synthesis of Intermediate A1-1

A mixture of 3-bromodibenzo[a,d]cyclohepten-5-one (86 g, 1.0 eq), N-bromosuccinimide (NBS) (106 g, 2 eq), benzyl peroxide (0.7 g, 0.01 eq) in carbon tetrachloride ($CCl_4$) (5 times of starting material) was heated to 85° C. The reaction progress was monitored by high performance liquid chromatography (HPLC). After completion of the reaction, the precipitate was separated by filtration and washed with $CH_3OH$, which was then purified by recrystallization. The purified product was concentrated to dryness, whereby white solid products were obtained in an amount of 123 g and a yield of 92.3%.

The solid product was identified as Intermediate A1-1 by a field desorption mass spectroscopy (FD-MS) analysis. FD-MS analysis: $C_{15}H_9Br_3O$: theoretical value of 444.94 and observed value of 444.94.

Step 2: Synthesis of Intermediate A1-2

The obtained Intermediate A1-1 (116.0 g, 1.0 eq) and furan (1.5 eq) were dissolved in THF (1.0 M), the reaction was cooled to 0° C. and then treated with potassium tert-butoxide (K-OtBu) (87.8 g, 3.0 eq). The reaction was allowed to stir at 0° C. for 1 hour, and then stirred at room temperature for additional 12 hours. After completion of the reaction, the reaction was quenched by DI water and the organic layer was recovered by solvent extraction operation and dried over sodium sulfate. The solvent was removed from the organic layer by distillation under reduced pressure, and the resulting residue was purified by silica gel column chromatography. The purified product was concentrated to dryness, whereby a light yellow solid product was obtained in a yield of 60.3%.

The solid product was identified as Intermediate A1-2 by FD-MS analysis. FD-MS analysis $C_{19}H_{11}BrO_2$: theoretical value of 351.19 and observed value of 351.19.

Step 3: synthesis of Intermediate A1-3

A suspension of Intermediate A1-2 (1.0 eq) and 5% Pd/C (0.025 eq) in ethyl acetate (EA, 2.0 M) was stirred for 3 hours to 6 hours under a hydrogen atmosphere ($H_2$) provided by a balloon of hydrogen. The resulting mixture was filtered through a pad of celite and washed with EA, and the filtrate was concentrated under reduced pressure to obtain 100 g (100%) of a yellow solid product.

The solid product was identified as Intermediate A1-3 by FD-MS analysis. FD-MS analysis $C_{19}H_{13}BrO_2$: theoretical value of 353.21 and observed value of 353.21. The intermediate A1-3 can be directly used in the following step without further purification.

Step 4: Synthesis of Intermediate A1-4

Intermediate A1-3 (53 g, 1.0 eq) and p-toluenesulfonic acid (PTSA) (2.0 eq) in 530 ml of toluene was heated to reflux for 12 hours. The reaction mixture was cooled to room temperature and then quenched with a saturated aqueous solution of $NaHCO_3$ and extracted with $CH_2Cl_2$. The organic layer was washed with water, brine and dried with anhydrous $Na_2SO_4$ subsequently. Then the resulting solution was concentrated under reduced pressure and purified by column chromatography on silica gel with $CH_2Cl_2$/hexane 1/1 (v/v) as eluent, whereby a light yellow solid product was obtained in an amount of 46.0 g and a yield of 91.5%.

The solid product was identified as Intermediate A1 by FD-MS analysis. FD-MS analysis $C_{19}H_{11}BrO$: theoretical value of 335.19 and observed value of 335.19.

Synthesis of Intermediate A2

Intermediate A2 used for preparing a novel compound was synthesized in a similar manner as Intermediate A1 through steps 1 to 4, except that the starting material 3-bromodibenzo[a,d]cyclohepten-5-one was replaced by 2-bromodibenzo[a,d]cyclohepten-5-one (CAS No. 198707-82-3). The synthesis pathway of Intermediate A2 was summarized in Scheme A2. All intermediates were analyzed according to the methods as described above, and the results were listed in Table 1.

Scheme A2

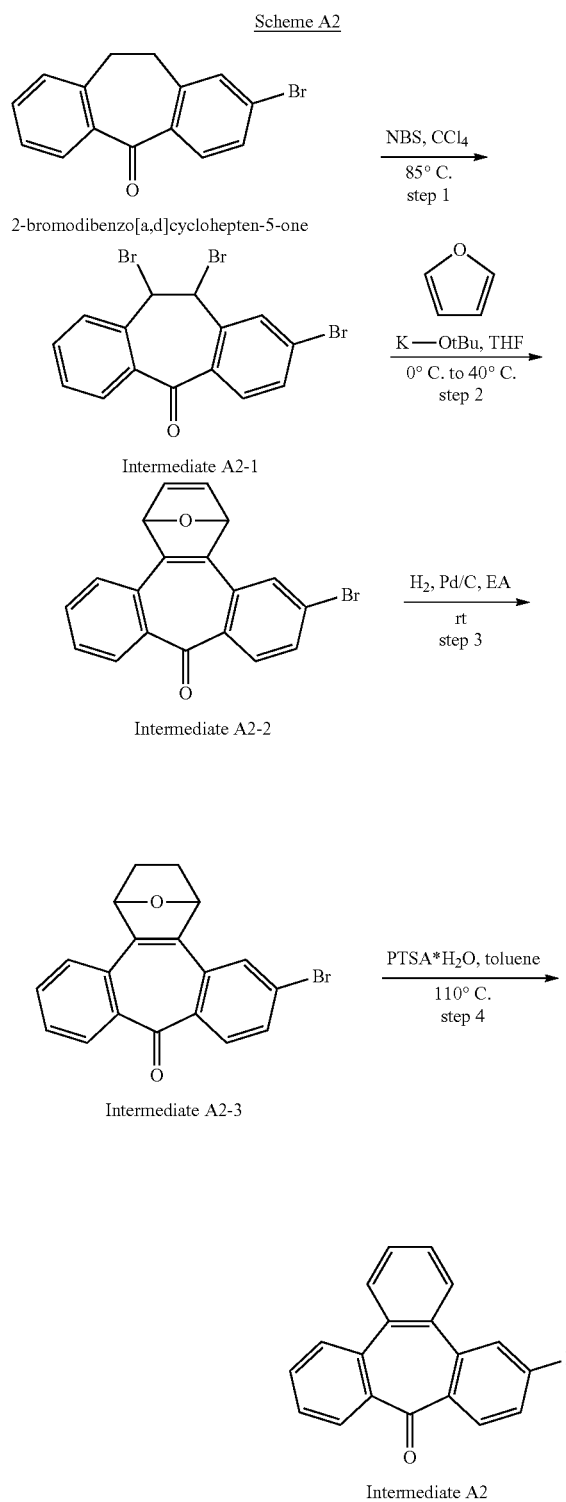

Synthesis of Intermediate A3

Intermediate A3 used for preparing a novel compound was synthesized in a similar manner as Intermediate A1 through steps 1 to 4, except that the starting material 3-bromodibenzo[a,d]cyclohepten-5-one was replaced by 3,7-dibromodibenzo[a,d]cyclohepten-5-one (CAS No. 226946-20-9). The synthesis pathway of Intermediate A3 was summarized in Scheme A3. All intermediates were analyzed as described above, and the results were listed in Table 1.

Scheme A3

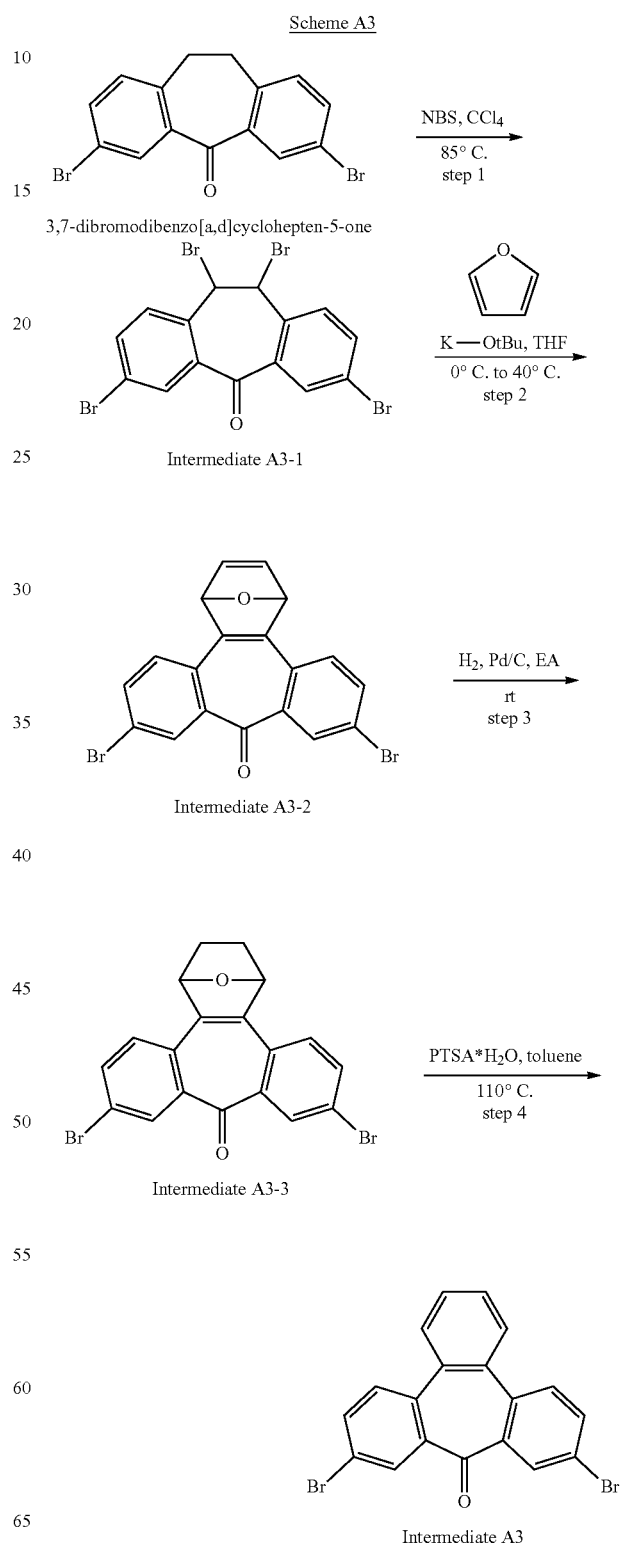

TABLE 1 chemical structures, yields, formulae, and mass (M⁺) analyzed by FD-MS of intermediates.

| Intermediate | A1-1 | A1-2 | A1-3 | A1 |
|---|---|---|---|---|
| Chemical Structure | (structure) | (structure) | (structure) | (structure) |
| Yield | 92.3% | 60.3% | NA | 91.5% |
| Formula | $C_{15}H_9Br_3O$ | $C_{19}H_{11}BrO_2$ | $C_{19}H_{13}BrO_2$ | $C_{19}H_{11}BrO$ |
| Mass(M⁺) | 444.94 | 351.19 | 353.21 | 335.19 |
| Intermediate | A2-1 | A2-2 | A2-3 | A2 |
| Chemical Structure | (structure) | (structure) | (structure) | (structure) |
| Yield | 91.5% | 58.2% | NA | 93.5% |
| Formula | $C_{15}H_9Br_3O$ | $C_{19}H_{11}BrO_2$ | $C_{19}H_{13}BrO_2$ | $C_{19}H_{11}BrO$ |
| Mass(M⁺) | 444.94 | 351.19 | 353.21 | 335.19 |
| Intermediate | A3-1 | A3-2 | A3-3 | A3 |
| Chemical Structure | (structure) | (structure) | (structure) | (structure) |
| Yield | 93.7% | 75.8% | NA | 93.0% |
| Formula | $C_{15}H_8Br_4O$ | $C_{19}H_{10}Br_2O_2$ | $C_{19}H_{12}Br_2O_2$ | $C_{19}H_{10}Br_2O$ |
| Mass(M⁺) | 523.84 | 430.09 | 432.11 | 414.09 |

Modifications of Intermediates A1 to A3

In addition to the Intermediates A1 to A3, one person skilled in the art can adopt other starting materials and successfully synthesize other desired intermediates through a reaction mechanism similar to Schemes A1 to A3. Applicable modifications of Intermediates A1 to A3 may be, for example, but not limited to, Intermediates A4 to A15 as follows.

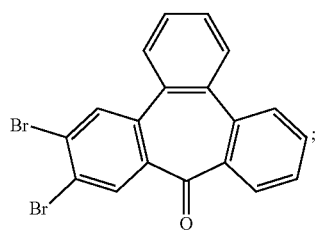

Intermediate A4

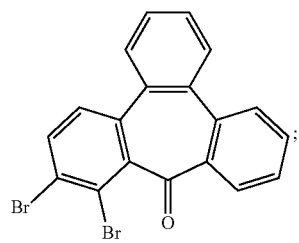

Intermediate A5

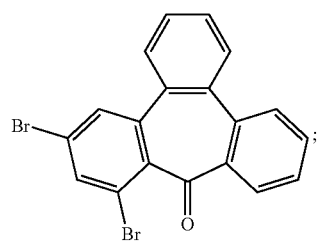

Intermediate A6

Intermediate A7

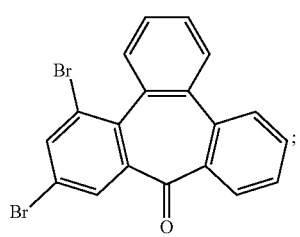

Intermediate A8

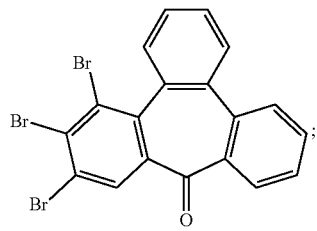

Intermediate A9

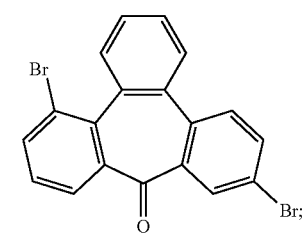 [SMILES: O=c1c2ccccc2c2ccccc2c2ccc(Br)cc12]

Intermediate A10

Intermediate A11

Intermediate A12

Intermediate A13

Intermediate A14

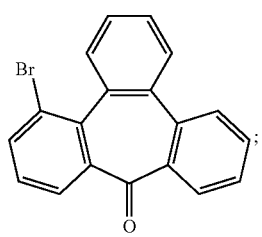

Intermediate A15

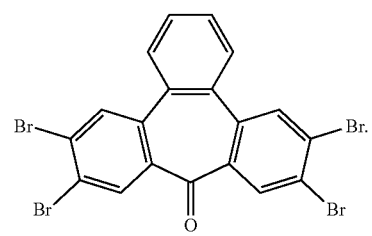

Synthesis of Intermediates B1 to B6

Intermediates B1 to B6 were synthesized by reacting 1-bromo-2-iodobenzene and heteroarylboronic acid (Reactant An). A general synthesis pathway for Intermediate Bn was summarized in Scheme B. In the following Scheme B, "Reactant An" may be any one of Reactants A1 to A6 as listed in Table 2 or the like, and "Intermediate Bn" may be any one of Intermediates B1 to B6.

Scheme B

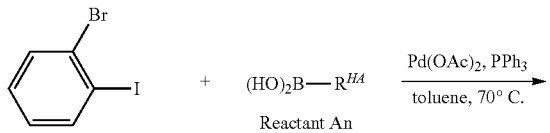

1-bromo-2-iodobenzene    Reactant An

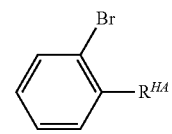

$R^{HA}$: heteroaryl ring containing furan or thiofuran group
Intermediate Bn

According to the Scheme B, each of the Intermediates B1 to B6 was synthesized by the steps as follows.

Water and toluene were poured into a round-bottomed flask, fitted with a condenser and argon flow, and bubbled through with argon. Potassium carbonate (1.5 eq), 1-bromo-2-iodobenzene (1.0 eq), Reactant An (1.2 eq), potassium carbonate (3.0 eq), 200 ml of toluene, PPh$_3$(0.06 eq)and Pd(OAc)$_2$ (0.015 eq) were mixed and stirred at 70° C. for 5 hours in an oil bath. After reaction was completed, the reaction mixture was allowed to be cooled to room temperature, and an organic layer was extracted with saturated aqueous solution of sodium chloride and EA and dried over magnesium sulfate, followed by filtering with silica gel. After a solid prepared by concentrating the filtrate under reduced pressure was suspended in hexane, the suspension was filtered again and washed with hexane to obtain Intermediate Bn. All intermediates Bn, including Intermediates B1 to B6, were analyzed according to the methods as described above, and the results were listed in Table 2.

TABLE 2

Reactant An used for preparing Intermediates B1 to B6, and the chemical structures, yields, formulae, and mass analyzed by FD-MS of Intermediates B1 to B6.

| Reactant An Chemical Structure | Intermediate Bn | | |
|---|---|---|---|
| | Chemical Structure | Yield | Formula/ Mass (M+) |
| 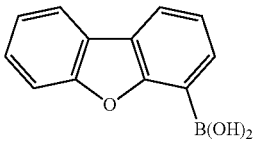 Reactant A1 | 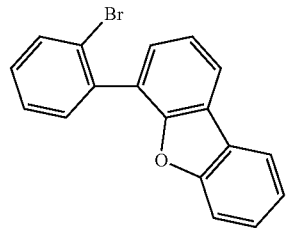 Intermediate B1 | 85% | $C_{18}H_{11}BrO$/ 323.18 |
| 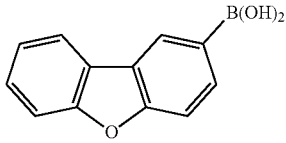 Reactant A2 | 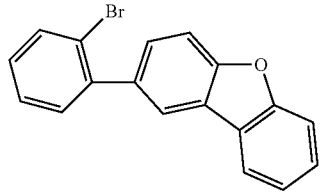 Intermediate B2 | 87% | $C_{18}H_{11}BrO$/ 323.18 |
| 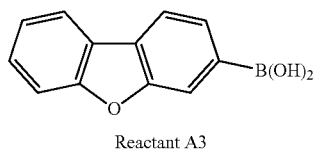 Reactant A3 | 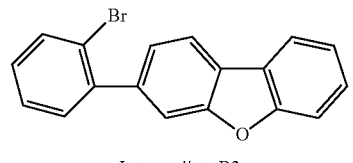 Intermediate B3 | 80% | $C_{18}H_{11}BrO$/ 323.18 |
| 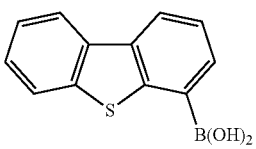 Reactant A4 | 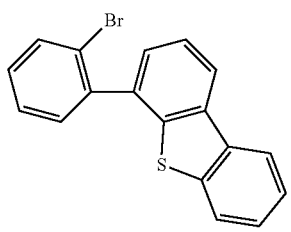 Intermediate B4 | 88% | $C_{18}H_{11}BrS$/ 339.25 |
| 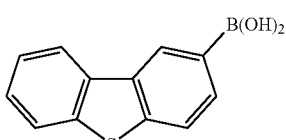 Reactant A5 | 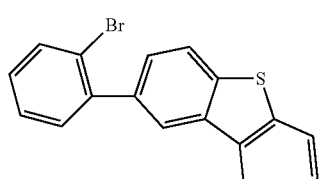 Intermediate B5 | 84% | $C_{18}H_{11}BrS$/ 339.25 |

TABLE 2-continued

Reactant An used for preparing Intermediates B1 to B6, and the chemical structures, yields, formulae, and mass analyzed by FD-MS of Intermediates B1 to B6.

| | Intermediate Bn | | |
|---|---|---|---|
| Reactant An Chemical Structure | Chemical Structure | Yield | Formula/ Mass (M+) |
| 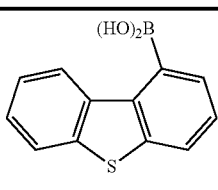<br>Reactant A6 | 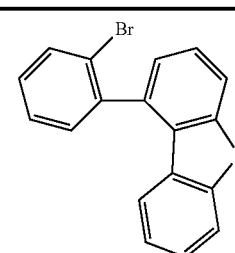<br>Intermediate B6 | 63% | $C_{18}H_{11}BrS$/ 339.25 |

Modifications of Intermediates B1 to B6

In addition to the Intermediates B1 to B6, one person skilled in the art can adopt any dihalobenzenes other than 1-bromo-2-iodobenzene and any heteroarylboronic acids other than Reactants A1 to A6 to successfully synthesize other desired Intermediate Bn through a reaction mechanism similar to Scheme B. Applicable modifications of Intermediates B1 to B6 may be, for example, but not limited to, Intermediates B7 and B8 as follows.

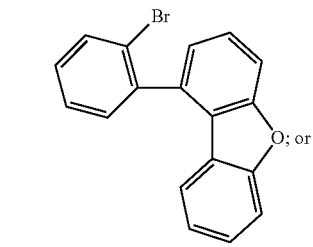

Intermediate B7

Intermediate B8

Synthesis of Intermediate C

The foresaid Intermediates B1 to B8, especially Intermediates B1 to B6, could be further adopted to synthesize Intermediate Cn. A general synthesis pathway for Intermediate Cn was summarized in Scheme C1. In the following Scheme C1, "Inteiniediate An" may be any one of foresaid Intermediates A1 to A15 or the like, "Intermediate Bn" may be any one of foresaid Intermediates B1 to B8 or the like, and "Intermediate Cn" may be any one of Intermediates C1 to C9 as listed in Table 3-1 or the like. Intermediates C1 to C9 were each synthesized by the following steps.

Scheme C1

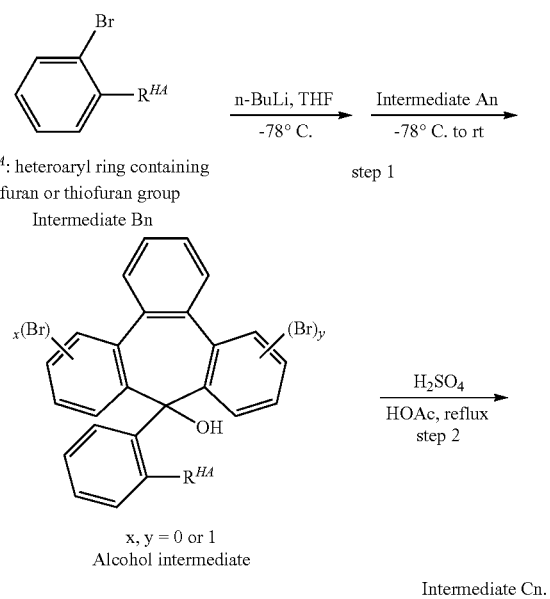

$R^{HA}$: heteroaryl ring containing furan or thiofuran group x, y = 0 or 1
Alcohol intermediate Intermediate Cn.

Step 1: Synthesis of Alcohol Intermediate

Intermediate Bn (1.0 eq) was dissolved in 120 mL of anhydrous THF (0.4M), and cooled to −78° C. n-Butyl-lithium (n-BuLi)(2.5 M,1.0 eq) was slowly added to the above cooled solution, and reaction mass was stirred for 1 h. After 1 h of stirring, Intermediate An (0.7 eq) was added to the reaction solution and stirred for additional 3 h at room temperature. After completion of the reaction, it was quenched by saturated solution of ammonium chloride, and extracted with organic solvent. The organic layer was separated, concentrated, and recrystallized with petroleum ether to obtain a white solid product.

The white solid product was identified as alcohol intermediate by FD-MS analysis. Take Intermediate C1-1 as an example, FD-MS analysis: $C_{37}H_{23}BrO_2$: theoretical value of 579.48 and observed value of 579.48.

The alcohol intermediate could be directly used in step 2 without further purification. Each alcohol intermediate synthesized by reacting different Intermediates An with Intermediate Bn was identified by FD-MS. The chemical structure of each alcohol intermediate was listed in Table 3-1.

Step 2: Synthesis of Intermediate Cn

Alcohol intermediate (1.0 eq), acetic acid (w/v=1/3 to the reactant) and $H_2SO_4$ (5 drops) were mixed, and the mixture was stirred at 110° C. for 6 h. The solvent was then removed under reduced pressure, and the residue was purified with column chromatography. The residual mass was recrystallized with toluene to obtain a white solid product.

The solid product was identified by FD-MS analysis. The chemical structures, yields, formulae, and mass analyzed by FD-MS of Intermediates C1 to C9 were listed in Table 3-1.

TABLE 3-1

Intermediates An and Bn used for preparing Intermediates C1 to C9, chemical structures of alcohol intermediates, and chemical structures, yields, formulae, and mass analyzed by FD-MS of Intermediates C1 to C9.

| Intermediate An | Intermediate Bn | Alcohol intermediate Chemical Structure | Yield (%) | Intermediate Cn Chemical Structure/ Formula/Mass (M+) | Yield (%) |
|---|---|---|---|---|---|
| A1 | B1 | 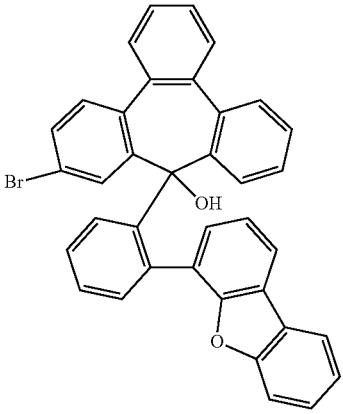 Intermediate C1-1 | 86 | 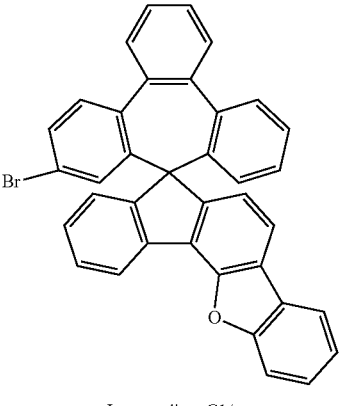 Intermediate C1/ $C_{37}H_{21}BrO$/ 561.47 | 95 |
| A2 | B1 | 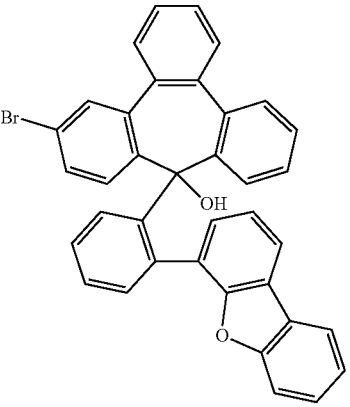 Intermediate C2-1 | 76 | 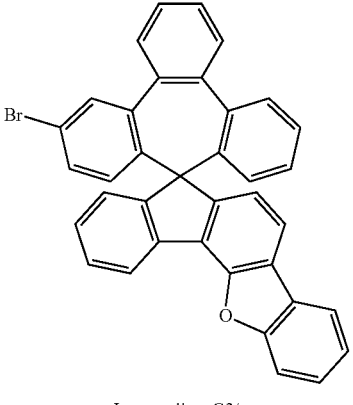 Intermediate C2/ $C_{37}H_{21}BrO$/ 561.47 | 87 |

TABLE 3-1-continued

Intermediates An and Bn used for preparing Intermediates C1 to C9, chemical structures of alcohol intermediates, and chemical structures, yields, formulae, and mass analyzed by FD-MS of Intermediates C1 to C9.

| Intermediate An | Intermediate Bn | Alcohol intermediate Chemical Structure | Yield (%) | Intermediate Cn Chemical Structure/ Formula/Mass (M+) | Yield (%) |
|---|---|---|---|---|---|
| A1 | B2 | 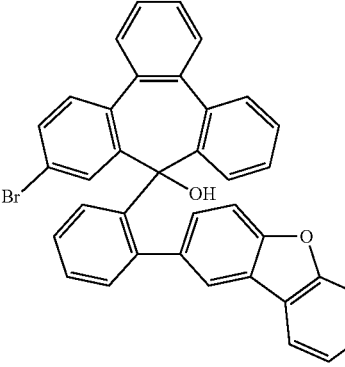<br>Intermediate C3-1 | 85 | 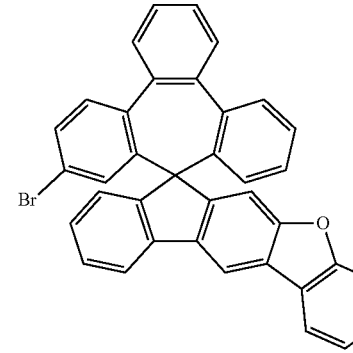<br>Intermediate C3/<br>C₃₇H₂₁BrO/<br>561.47 | 91 |
| A1 | B3 | 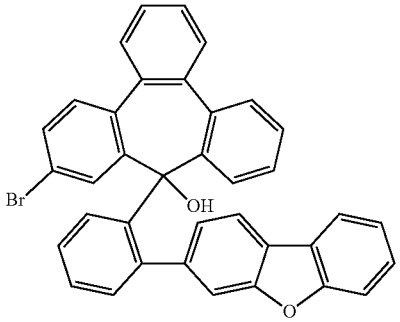<br>Intermediate C4-1 | 74 | 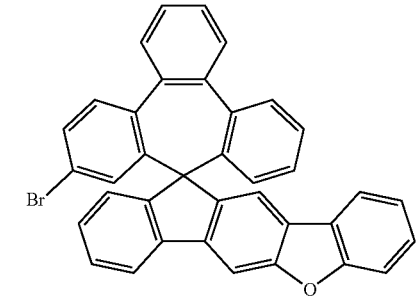<br>Intermediate C4/<br>C₃₇H₂₁BrO/<br>561.47 | 81 |
| A3 | B1 | 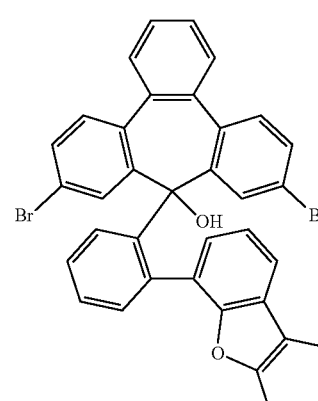<br>Intermediate C5-1 | 83 | 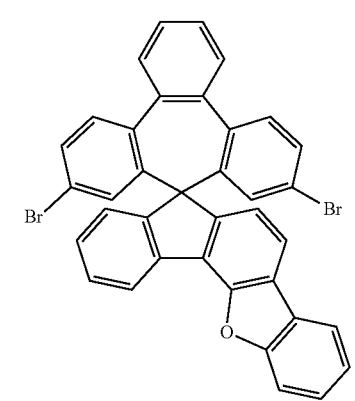<br>Intermediate C5/<br>C₃₇H₂₀Br₂O/<br>640.36 | 76 |

TABLE 3-1-continued

Intermediates An and Bn used for preparing Intermediates C1 to C9, chemical structures of alcohol intermediates, and chemical structures, yields, formulae, and mass analyzed by FD-MS of Intermediates C1 to C9.

| Intermediate An | Intermediate Bn | Alcohol intermediate Chemical Structure | Yield (%) | Intermediate Cn Chemical Structure/ Formula/Mass (M+) | Yield (%) |
|---|---|---|---|---|---|
| A1 | B4 | 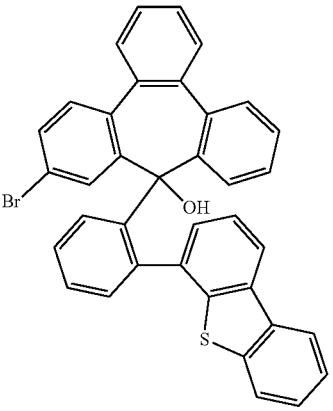 Intermediate C6-1 | 83 | 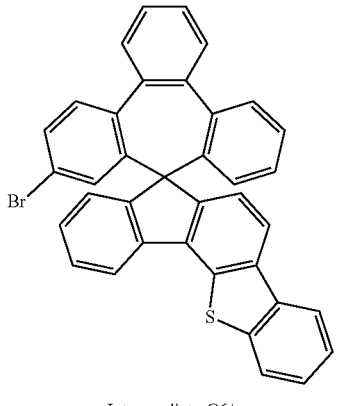 Intermediate C6/ $C_{37}H_{21}BrS$/ 577.53 | 95 |
| A1 | B5 | 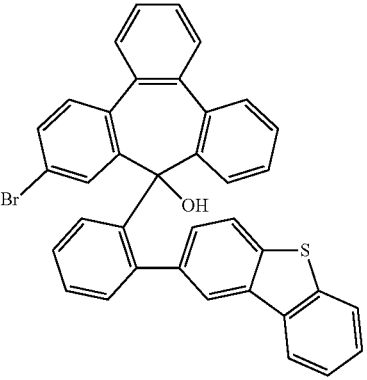 Intermediate C7-1 | 88 | 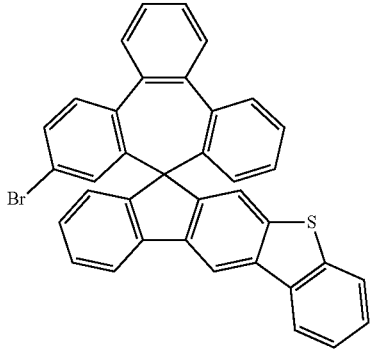 Intermediate C7/ $C_{37}H_{21}BrS$/ 577.53 | 83 |
| A1 | B6 | 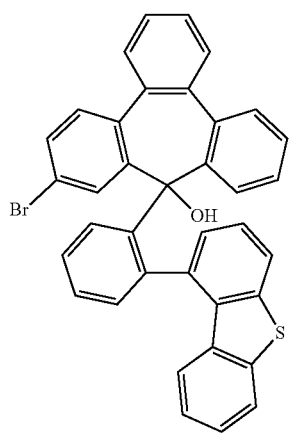 Intermediate C8-1 | 62 | 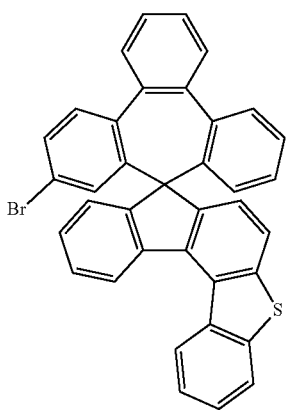 Intermediate C8/ $C_{37}H_{21}BrS$/ 577.53 | 85 |

TABLE 3-1-continued

Intermediates An and Bn used for preparing Intermediates C1 to C9, chemical structures of alcohol intermediates, and chemical structures, yields, formulae, and mass analyzed by FD-MS of Intermediates C1 to C9.

| Interme-diate An | Interme-diate Bn | Alcohol intermediate | | Intermediate Cn | |
|---|---|---|---|---|---|
| | | Chemical Structure | Yield (%) | Chemical Structure/ Formula/Mass (M+) | Yield (%) |
| A3 | B4 | 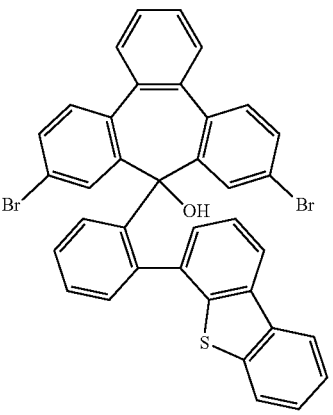 Intermediate C9-1 | 88 | 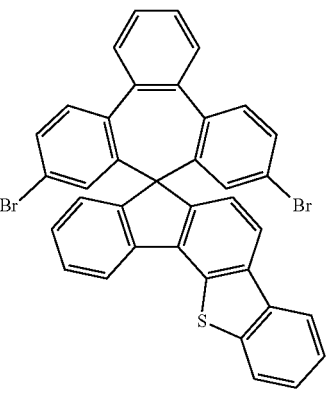 Intermediate C9/ $C_{37}H_{21}BrS$/ 577.53 | 84 |

Modifications of Intermediates C1 to C9

In addition to the Intermediates C1 to C9, one person skilled in the art can adopt any intermediate An other than Intermediates A1 to A3 and/or any Intermediate Bn other than Intermediates B1 to B6 to successfully synthesize other desired Intermediate Cn through a reaction mechanism similar to Scheme C1. Applicable modifications of Intermediates C1 to C9 may be, for example, but not limited to, Intermediates C10 to C33 as follows.

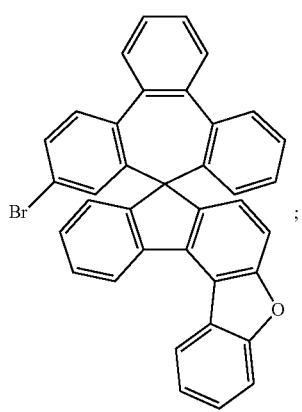

Intermediate C10

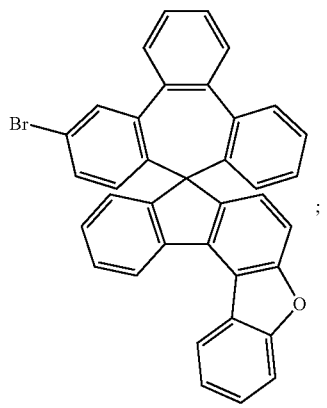

Intermediate C11

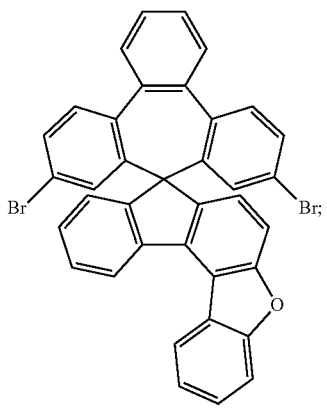

Intermediate C12

Intermediate C13
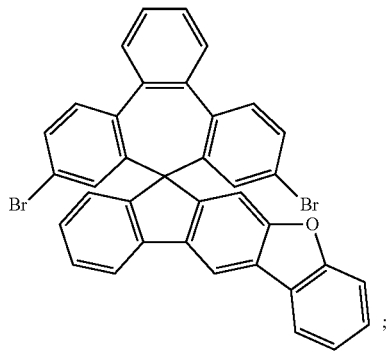
Intermediate C14
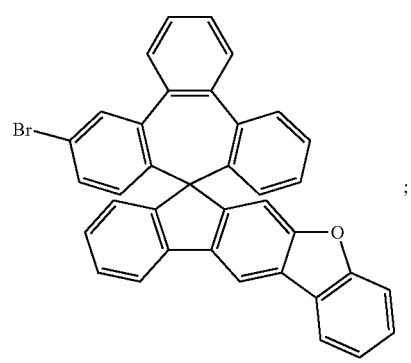
Intermediate C15
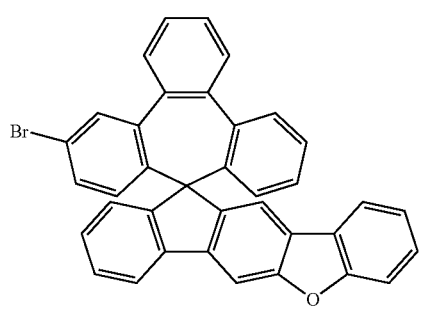
Intermediate C16
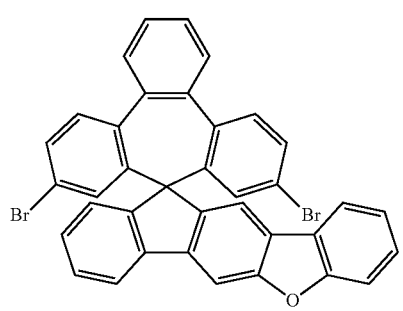
Intermediate C17
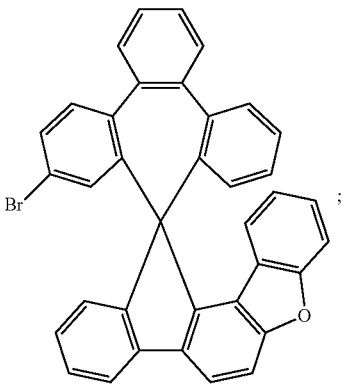
Intermediate C18
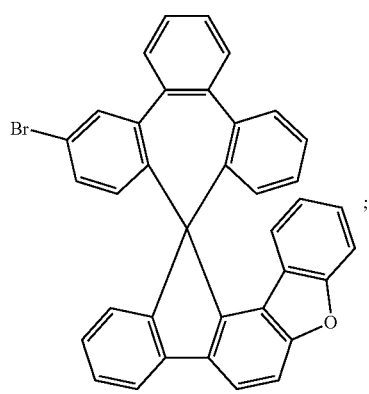
Intermediate C19
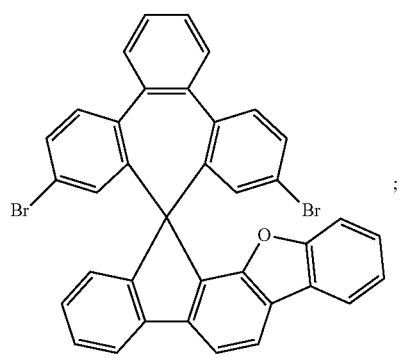
Intermediate C20
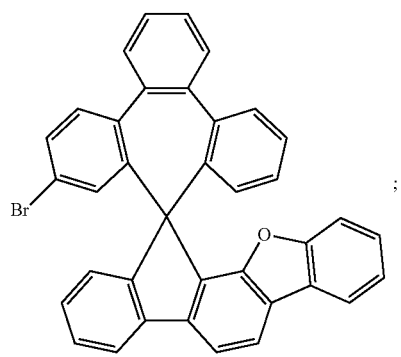

Intermediate C21
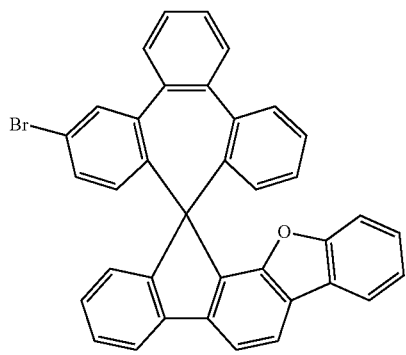
Intermediate C22
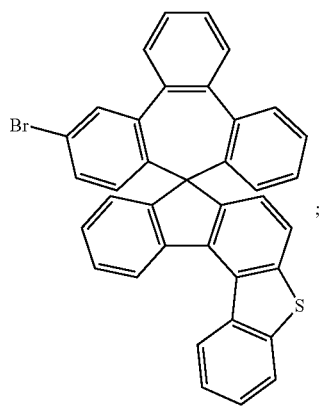
Intermediate C23
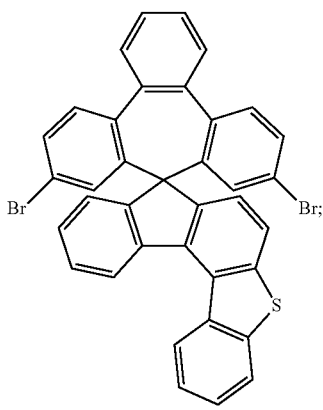
Intermediate C24
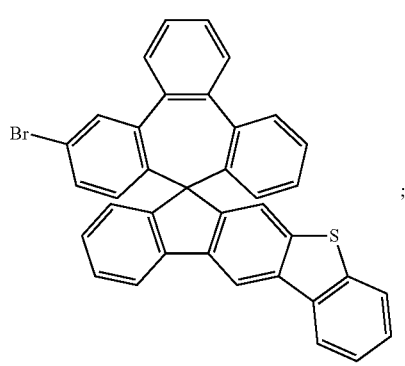
Intermediate C25
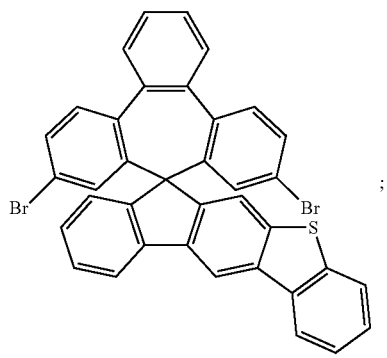
Intermediate C26
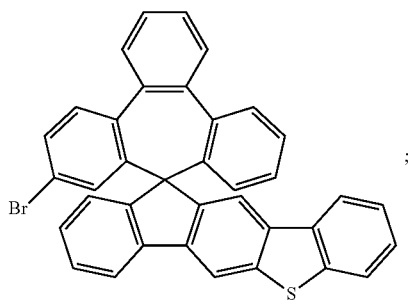
Intermediate C27
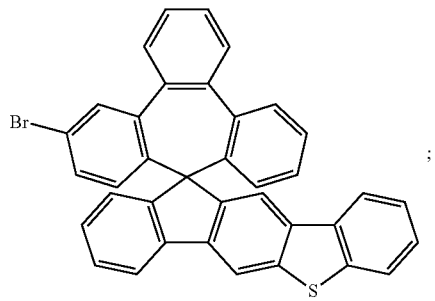
Intermediate C28
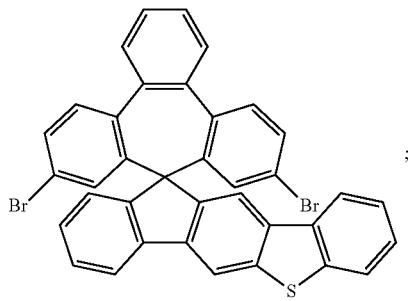

-continued

Intermediate C29
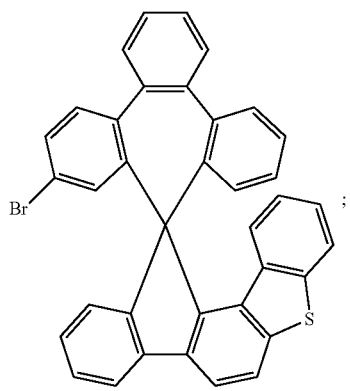

Intermediate C30
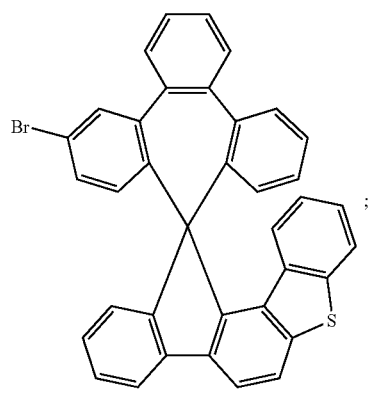

Intermediate C31
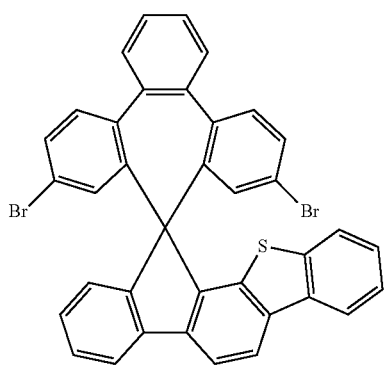

Intermediate C32
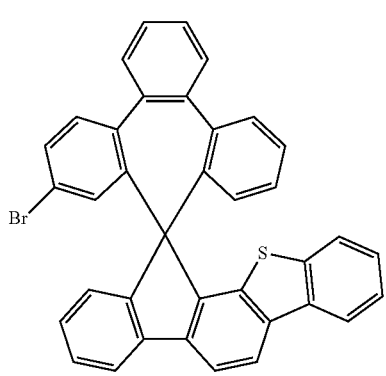

-continued

Intermediate C33
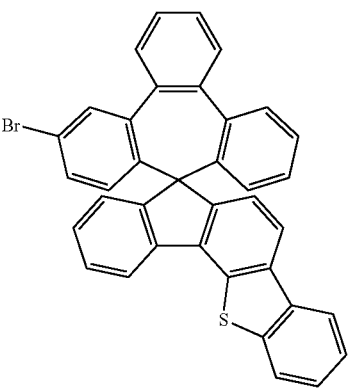

The foresaid Intermediates C6 to C9 and C22 to C33 could be further oxidized to synthesize other Intermediates Cn. Take Intermediates C6 and C7 as examples, the Intermediates C6 and C7 could be oxidized into Intermediates C34 and C35 by methods of Scheme C2 and C3, respectively.

Synthesis of Intermediate C34

Scheme C2

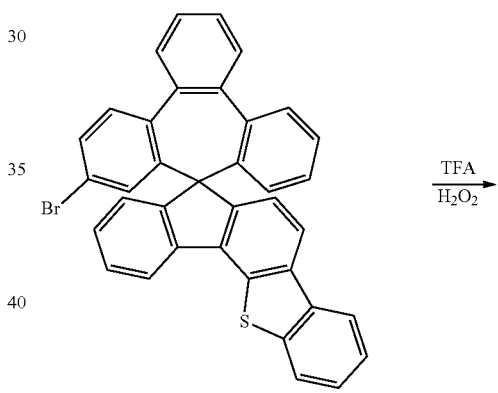

Intermediate C6

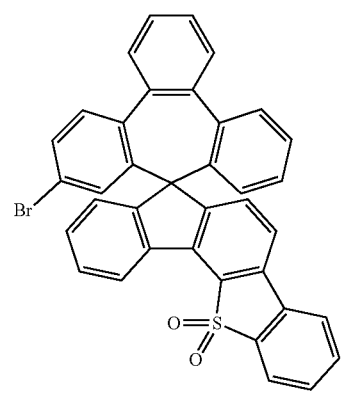

Intermediate C34

Trifluoroperacetic acid was prepared by the dropwise addition of 30% aqueous hydrogen peroxide (15.2 ml) to trifluoroacetic acid (75 ml) at 0° C. The ice bath was removed after the completion of the addition of peroxide. Then Intermediate C6 (5 g, 1 eq) was added slowly with stirring to the solution. After the completion of the reaction, the reaction mixture was washed with water, followed by filtering to get solid. The crude mixture was purified by silica-gel column chromatography to obtain Intermediate C34 (3.3 g, yield: 62.5%). The solid product was identified as Intermediate C34 by FD-MS analysis. FD-MS analysis: $C_{37}H_{21}BrO_2S$: theoretical value of 609.53 and observed value of 609.53.

Synthesis of Intermediate C35

Scheme C3

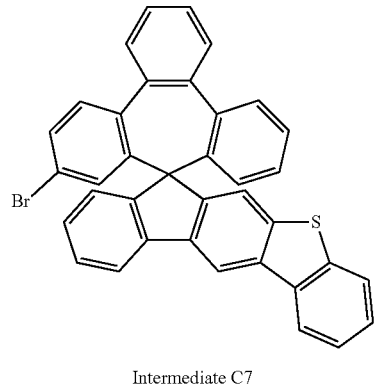

Intermediate C7

TFA
H₂O₂

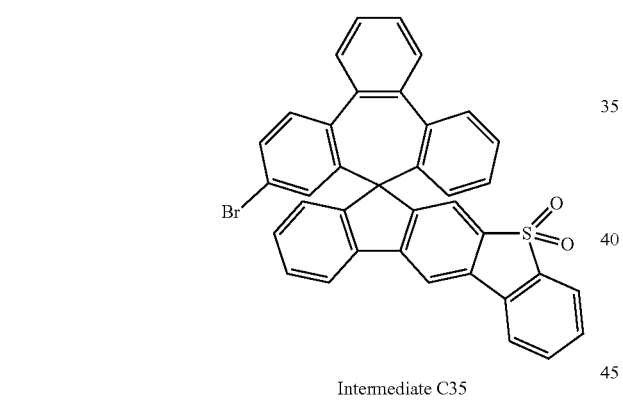

Intermediate C35

Intermediate C35 was synthesized in a similar manner as Intermediate C34, except that the Intermediate C6 was replaced by Intermediate C7.

The solid product was identified as intermediate C35 (yield 85%) by FD-MS analysis. FD-MS analysis: $C_{37}H_{21}BrO_2S$: theoretical value of 609.53 and observed value of 609.53.

Modifications of Intermediates C34 and C35

In addition to the Intermediates C34 and C35, one person skilled in the art can adopt other Intermediates Cn including thiofuran group, such as Intermediates C8, C9, C22 to C33 to synthesize other desired Intermediates Cn through a reaction mechanism similar to Scheme C2 or Scheme C3. Applicable modifications of Intermediates C34 and C35 may be, for example, but not limited to, Intermediates C36 to C46 as follows.

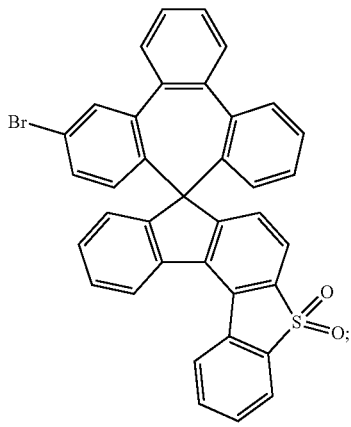

Intermediate C36

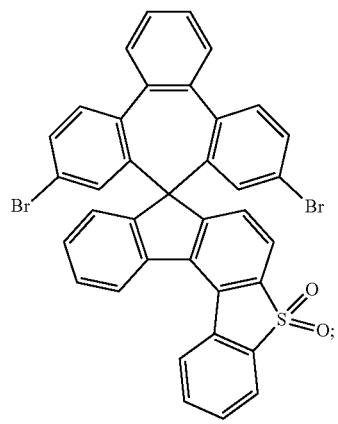

Intermediate C37

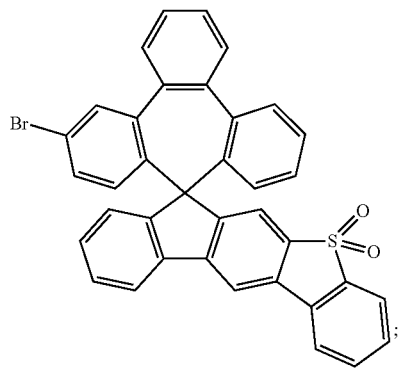

Intermediate C38

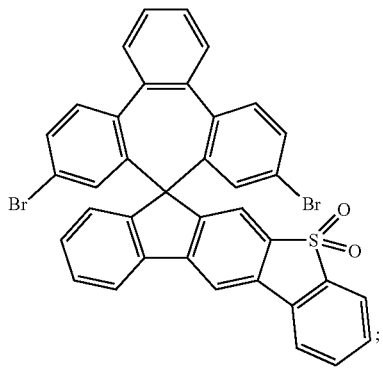

Intermediate C39

Intermediate C40

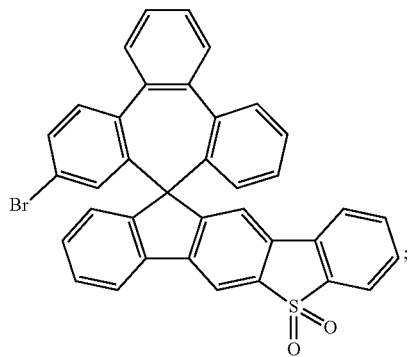

Intermediate C41

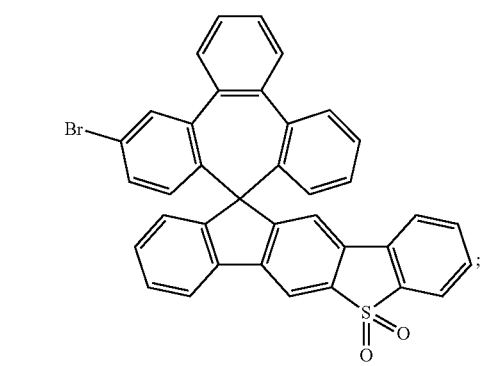

Intermediate C42

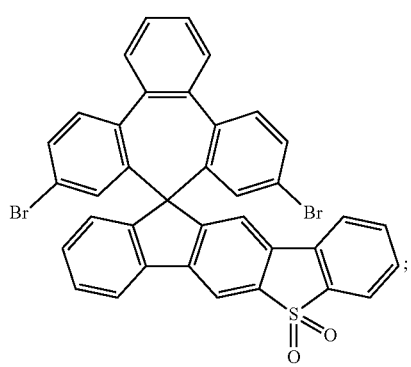

Intermediate C43

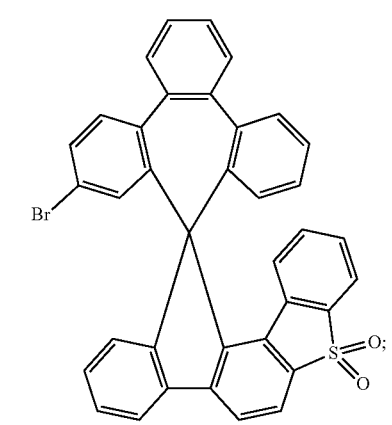

Intermediate C44

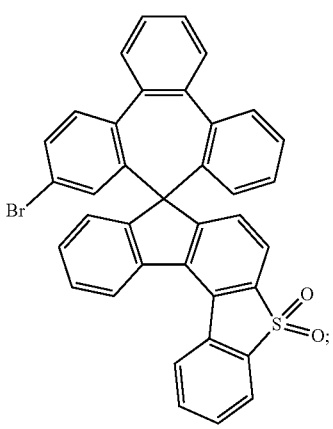

Intermediate C45

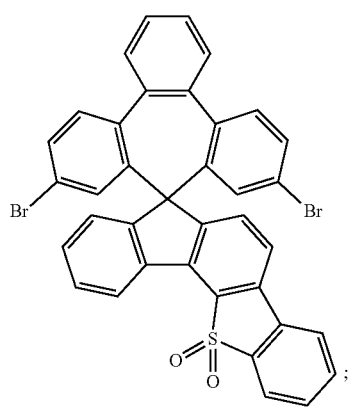

Intermediate C46

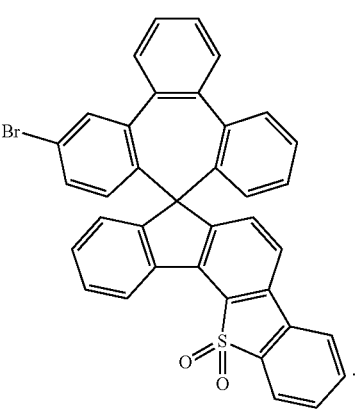

Synthesis of Intermediate Cn-B

The foresaid Intermediate Cn could be further modified into an Intermediate Cn-B through Miyaura borylation reaction. "Intermediate Cn-B" was directed to a compound derived from Intermediate Cn whose bromo group was replaced by (pinacolato)boron group. A synthesis pathway of Intermediate Cn-B was summarized in Scheme C1-B. Intermediate Cn-B was synthesized by the following steps.

Scheme C1-B

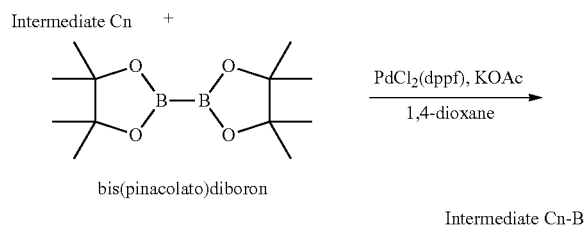

A mixture of bis(pinacolato)diboron (1.2 eq), Intermediate Cn(1.0 eq), 1,1-bis(diphenylphosphino)-ferrocene dichloropalladium (II) (PdCl$_2$(dppf)) (0.015 eq), and potassium acetate (KOAc) (3.0 eq) in anhydrous 1,4-dioxane (0.3 M) was stirred at 110° C. for 8 hours under nitrogen atmosphere. After cooling to room temperature, the solvent was then removed under reduced pressure, and the residue was purified via column chromatography to obtain a pale yellow solid product.

The pale yellow solid product was identified by FD-MS analysis. The chemical structures, yields, formulae, and mass analyzed by FD-MS of Intermediates Cn-B were listed in Table 3-2.

TABLE 3-2

Intermediate Cn used for preparing Intermediate Cn-B and chemical structures, yields, formulae, and mass analyzed by FD-MS of Intermediates Cn-B.

| Intermediate Cn | | Intermediate Cn-B | | |
|---|---|---|---|---|
| Chemical Structure | Yield (%) | Chemical Structure | Yield (%) | Formula/ Mass (M$^+$) |
| Intermediate C2 | 87 | Intermediate C2-B | 93 | C$_{43}$H$_{33}$BO$_3$/ 608.53 |
| Intermediate C3 | 91 | Intermediate C3-B | 98 | C$_{43}$H$_{33}$BO$_3$/ 608.53 |

TABLE 3-2-continued

Intermediate Cn used for preparing Intermediate Cn-B and chemical structures, yields, formulae, and mass analyzed by FD-MS of Intermediates Cn-B.

| Intermediate Cn | | Intermediate Cn-B | | |
|---|---|---|---|---|
| Chemical Structure | Yield (%) | Chemical Structure | Yield (%) | Formula/ Mass (M+) |
| 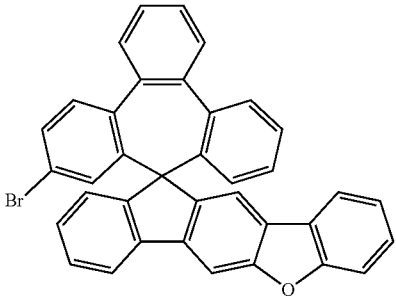<br>Intermediate C4 | 81 | 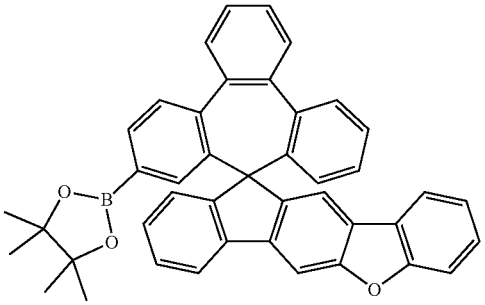<br>Intermediate C4-B | 96 | $C_{43}H_{33}BO_3$/ 608.53 |
| 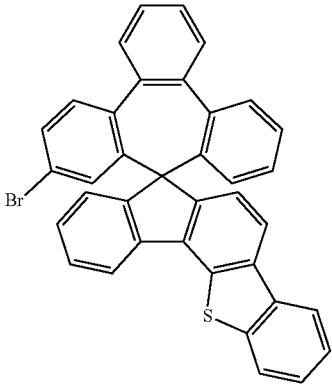<br>IntermediateC6 | 95 | 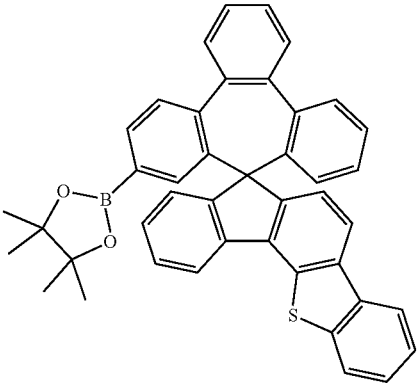<br>Intermediate C6-B | 91 | $C_{43}H_{33}BO_2S$/ 624.60 |
| 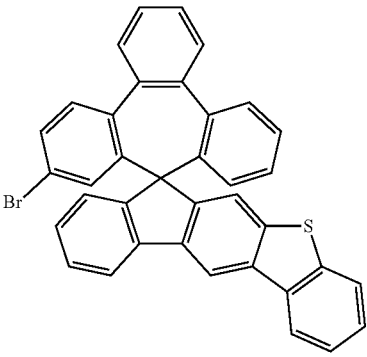<br>Intermediate C7 | 83 | 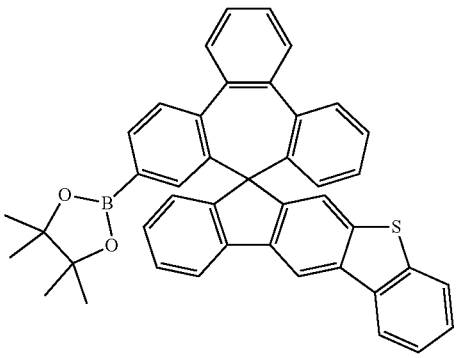<br>Intermediate C7-B | 91 | $C_{43}H_{33}BO_2S$/ 624.60 |

TABLE 3-2-continued

Intermediate Cn used for preparing Intermediate Cn-B and chemical structures, yields, formulae, and mass analyzed by FD-MS of Intermediates Cn-B.

| Intermediate Cn | | Intermediate Cn-B | | |
|---|---|---|---|---|
| Chemical Structure | Yield (%) | Chemical Structure | Yield (%) | Formula/ Mass (M+) |
| 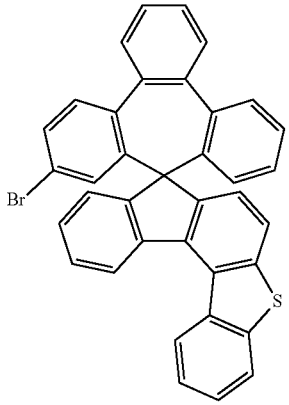 Intermediate C8 | 85 | 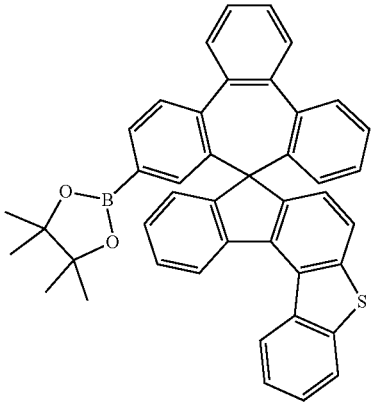 Intermediate C8-B | 92 | $C_{43}H_{33}BO_2S$/ 624.60 |

Modifications of Intermediate Cn-B

In addition to the Intermediate Cn-B, one person skilled in the art can adopt any one of foresaid Inteimediates Cn to undergo a Miyaura borylation reaction to successfully synthesize other desired intermediates Cn-B as follows.

Intermediate C1-B

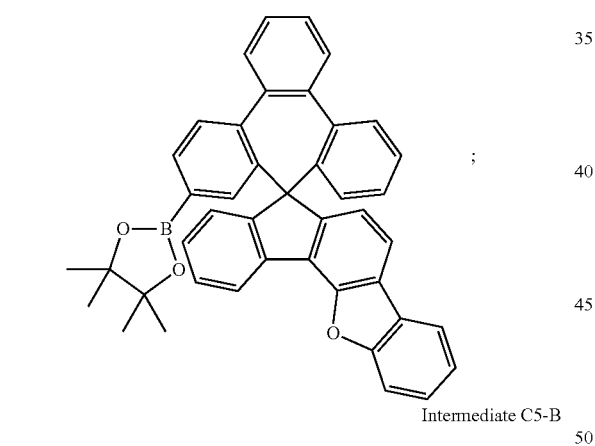

;

Intermediate C5-B

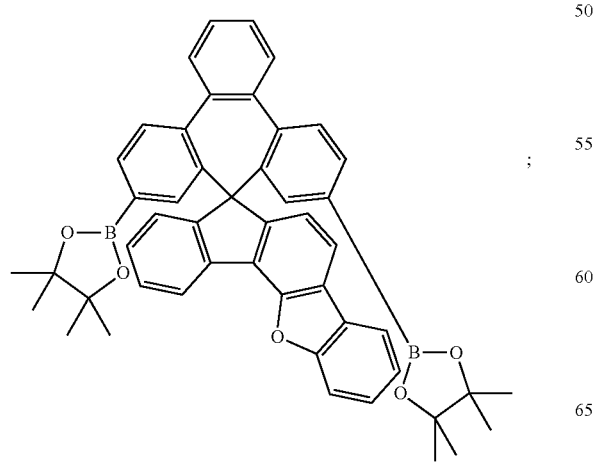

;

-continued

Intermediate C34-B

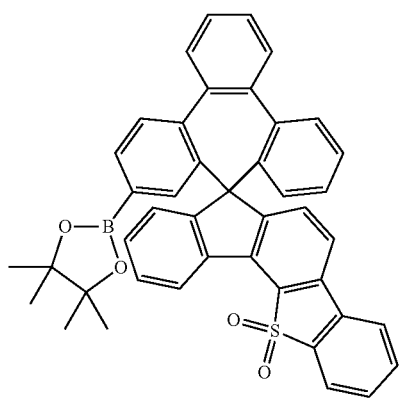

Intermediate C36-B

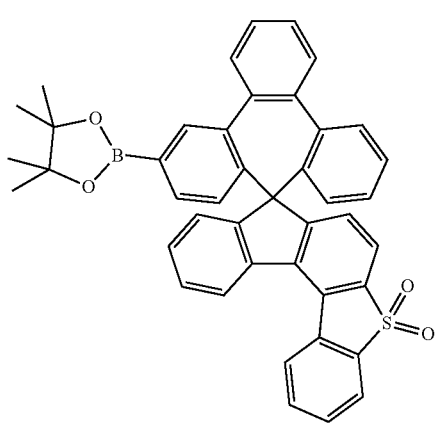

Intermediate C37-B

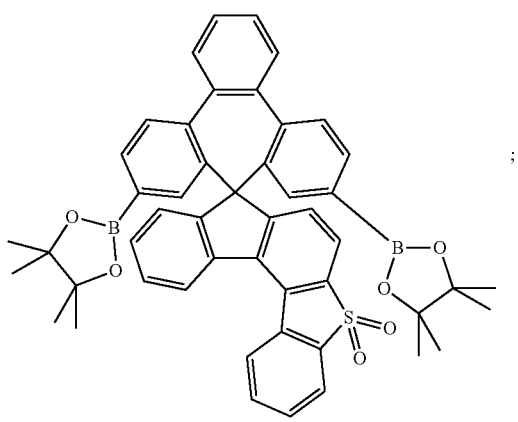

-continued

Intermediate C44-B

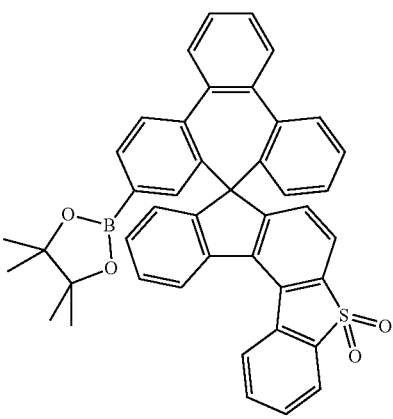

Synthesis of Novel Compounds

Each of the foresaid Intermediates Cn and Cn-B could be reacted with various reactants to synthesize various claimed novel compounds. The general synthesis pathway of the claimed novel compound was summarized in Scheme I. In the following Scheme I, "Reactant B" may be any one of Reactants B1 to B34 as listed in Table 4, and "Intermediate C" may be any one of the foresaid Intermediates Cn and Cn-B or the like. The compounds were each synthesized by the following steps.

Scheme I

Reactant Bn + Intermediate C $\xrightarrow[K_2CO_3, \text{toluene/EtOH}]{Pd(OAc)_2, P(Cy_2)(2\text{-biPh})}$ Claimed Compound

TABLE 4 chemical structure and CAS No. of Reactants B1 to B34.

| Reactant No. | Reactant B1 | Reactant B2 | Reactant B3 | Reactant B4 |
|---|---|---|---|---|
| Chemical Structure | (HO)₂B—⟨⟩—CN | pinacol boronate-pyridyl-phenyl | pyridyl-Bpin | pyridyl-phenyl-Bpin |
| CAS No. | [126747-14-6] | [1319255-85-0] | [181219-01-2] | [1260106-29-3] |
| Reactant No. | Reactant B5 | Reactant B6 | Reactant B7 | Reactant B8 |
| Chemical Structure | 4-phenyl-2-chloroquinazoline | 1-(4-bromophenyl)-2-phenylbenzimidazole | 2-chloro-4,6-diphenyl-1,3,5-triazine | 2-chloro-4,6-diphenylpyrimidine |
| CAS No. | [29874-83-7] | [867044-33-5] | [3842-55-5] | [29509-91-9] |
| Reactant No. | Reactant B9 | Reactant B10 | Reactant B11 | Reactant B12 |
| Chemical Structure | 5-bromo-2-(4-cyanophenyl)pyridine | 3-pyridyl-Bpin | 3-cyanophenylboronic acid | 4'-cyano-4-biphenylboronic acid |
| CAS No. | [916653-46-8] | [329214-79-1] | [150255-96-2] | [406482-73-3] |
| Reactant No. | Reactant B13 | Reactant B14 | Reactant B15 | Reactant B16 |

TABLE 4-continued chemical structure and CAS No. of Reactants B1 to B34.

| Chemical Structure | | | | |
|---|---|---|---|---|
| CAS No. | [952514-79-3] | [1588407-97-9] | [1300115-09-6] | [6484-25-9] |
| Reactant No. | Reactant B17 | Reactant B18 | Reactant B19 | Reactant B20 |

| Chemical Structure | | | | |
|---|---|---|---|---|
| CAS No. | [3114-52-1] | [7089-68-1] | [1616231-57-2] | [1421599-34-9] |
| Reactant No. | Reactant B21 | | | Reactant B22 |

TABLE 4-continued chemical structure and CAS No. of Reactants B1 to B34.

| Chemical Structure | ![B22 structure: 2-phenyl-4-(4-chlorophenyl)quinazoline] | | ![B travel structure: 4-(pyridin-3-yl)phenylboronic acid with B(OH)2] |
|---|---|---|---|
| CAS No. | [99682-89-0] | | [170230-28-1] |
| Reactant No. | Reactant B23 | | |

| Chemical Structure | ![B24: 2-chloro-4-(4-cyanophenyl)-6-phenylpyrimidine] | ![B25: 2-chloro-4-[4-(pyridin-3-yl)phenyl]-6-phenylpyrimidine] | ![B26: 2-phenyl-4-(3-chlorophenyl)-6-phenyltriazine] |
|---|---|---|---|
| Reactant No. | Reactant B24 | Reactant B25 | Reactant B26 |

| Chemical Structure | ![B27: 2-chloro-4-(4-cyanophenyl)quinazoline with NC] | | ![B28: 2-chloro-4,6-bis(4-cyanophenyl)pyrimidine] |
|---|---|---|---|
| Reactant No. | Reactant B27 | | Reactant B28 |

| Chemical Structure | ![B29: 2-chloro-4,6-bis(biphenyl-3-yl)triazine] | | |
|---|---|---|---|
| Reactant No. | Reactant B29 | | Reactant B30 |

TABLE 4-continued chemical structure and CAS No. of Reactants B1 to B34.

| Chemical Structure | | |
|---|---|---|
| CAS No. | [774-53-8] | [867044-33-5] |
| Reactant No. | Reactant B31 | Reactant B32 |
| Chemical Structure | | |
| Reactant No. | Reactant B33 | Reactant B34 |
| Chemical Structure | | |
| CAS No. | [1009033-87-7] | — |

A mixture of Intermediate Cn (1.0 eq), Pd(OAc)$_2$(0.01 eq), P(Cy)$_2$(2-biphenyl) 0.04 eq), toluene/ethanol (0.5M, v/v=10/1),3.0 M potassium carbonate solution, and Reactant Bn (1.2 eq) was stirred at 100° C. for 12h under nitrogen atmosphere. After the completion of the reaction, water and toluene were added to the reaction mass. Subsequently, the organic layer was recovered by solvent extraction operation and dried over sodium sulfate. The solvent was then removed from the organic layer under reduced pressure, and the resulting residue was purified by silica gel column chromatography. The obtained residue was recrystallized with toluene to obtain white solid as the claimed novel compound.

Figure 2:
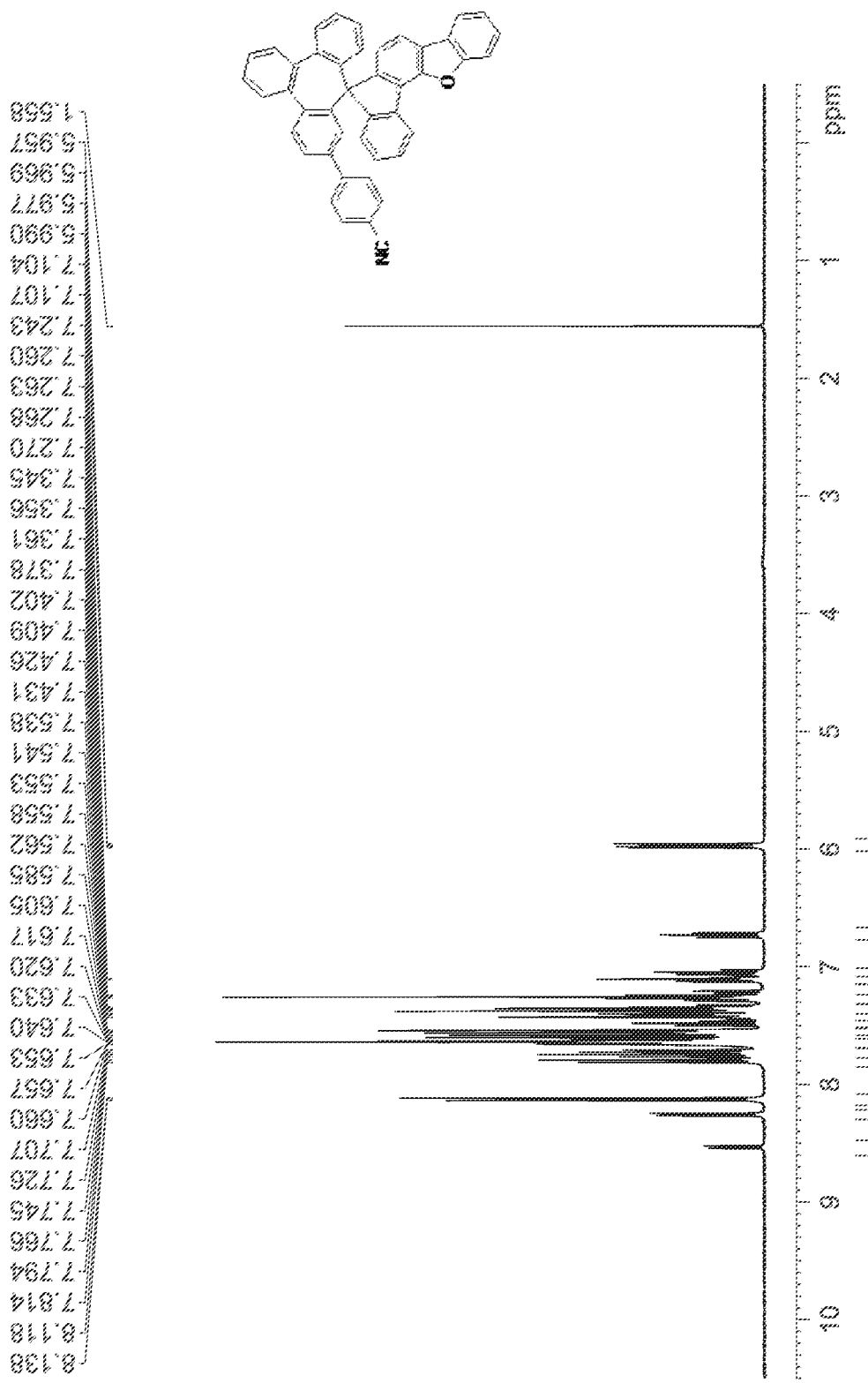
FIGS. 2 to 28 are respectively $^1$H nuclear magnetic resonance (NMR) spectra of Compounds I to XXVII.
Figure 3:
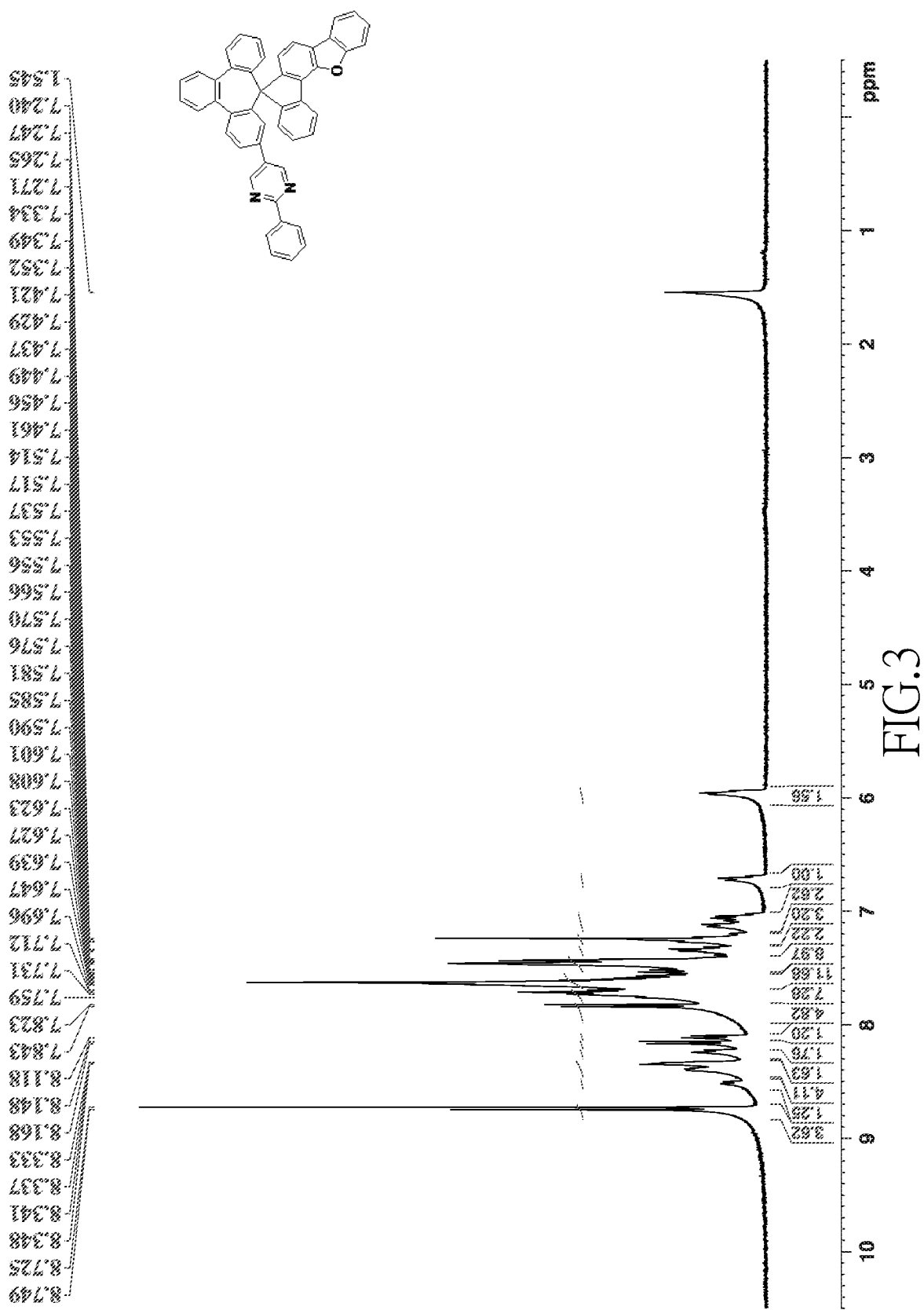
Figure 4:
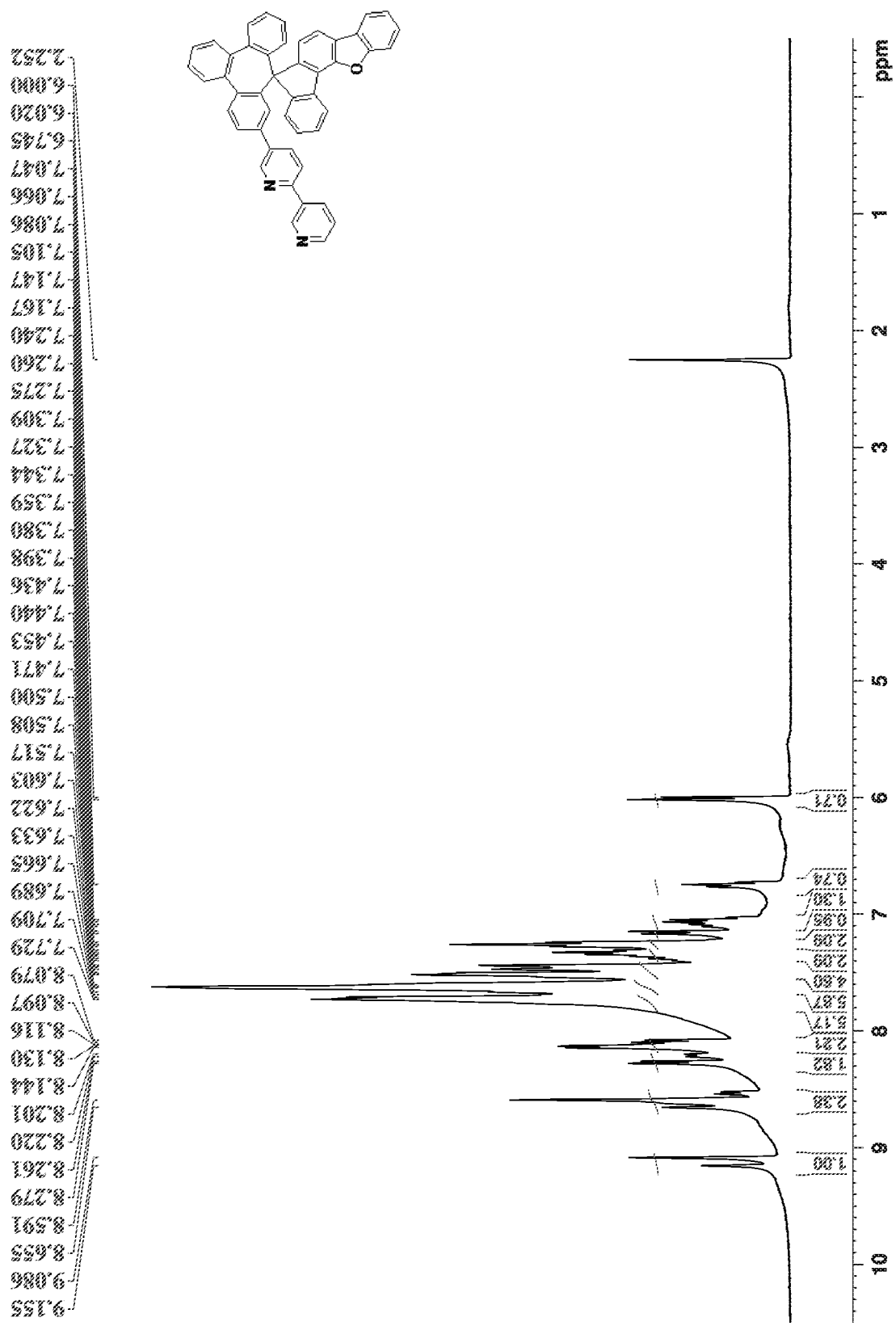
Figure 5:
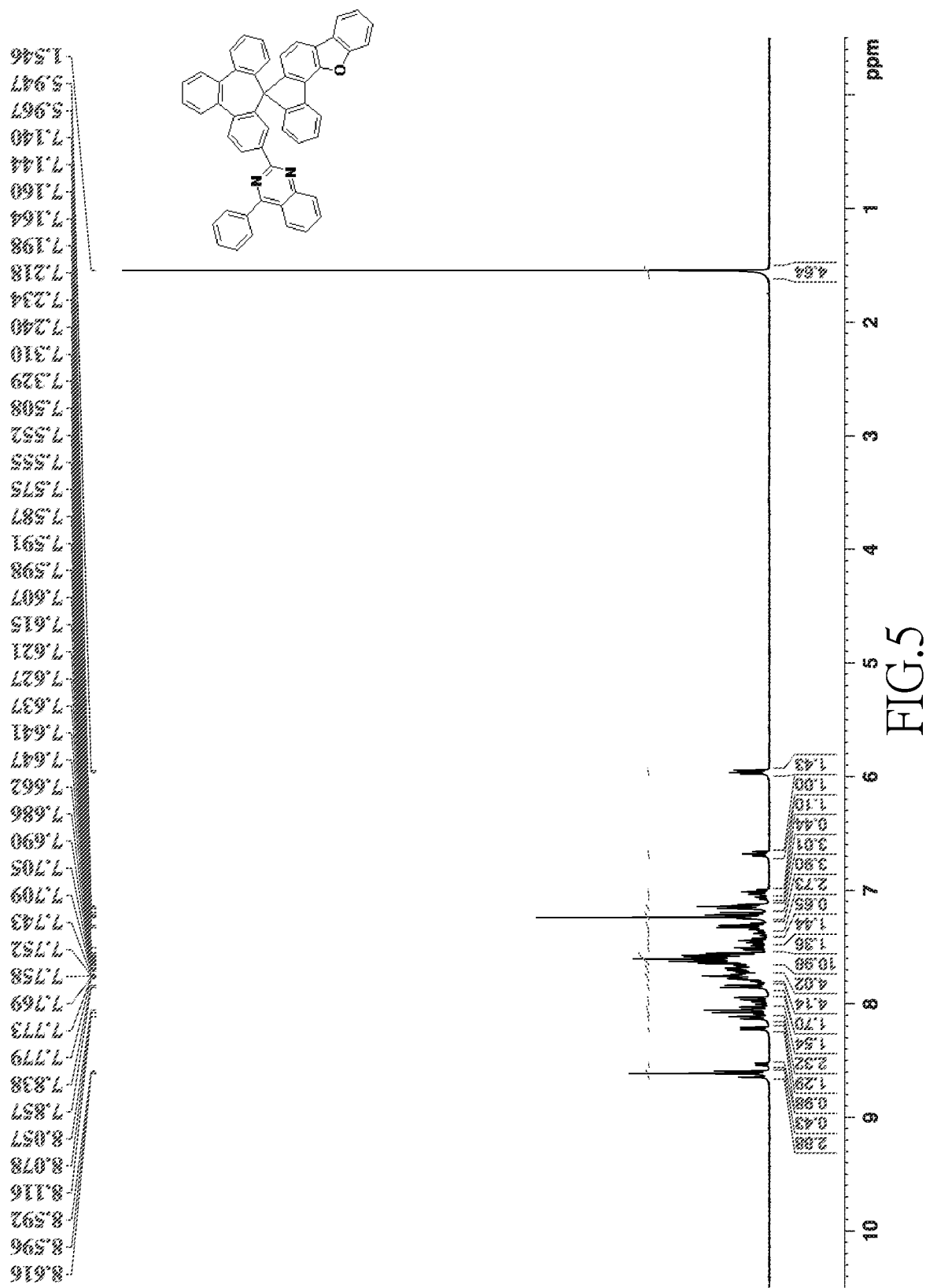
Figure 6:
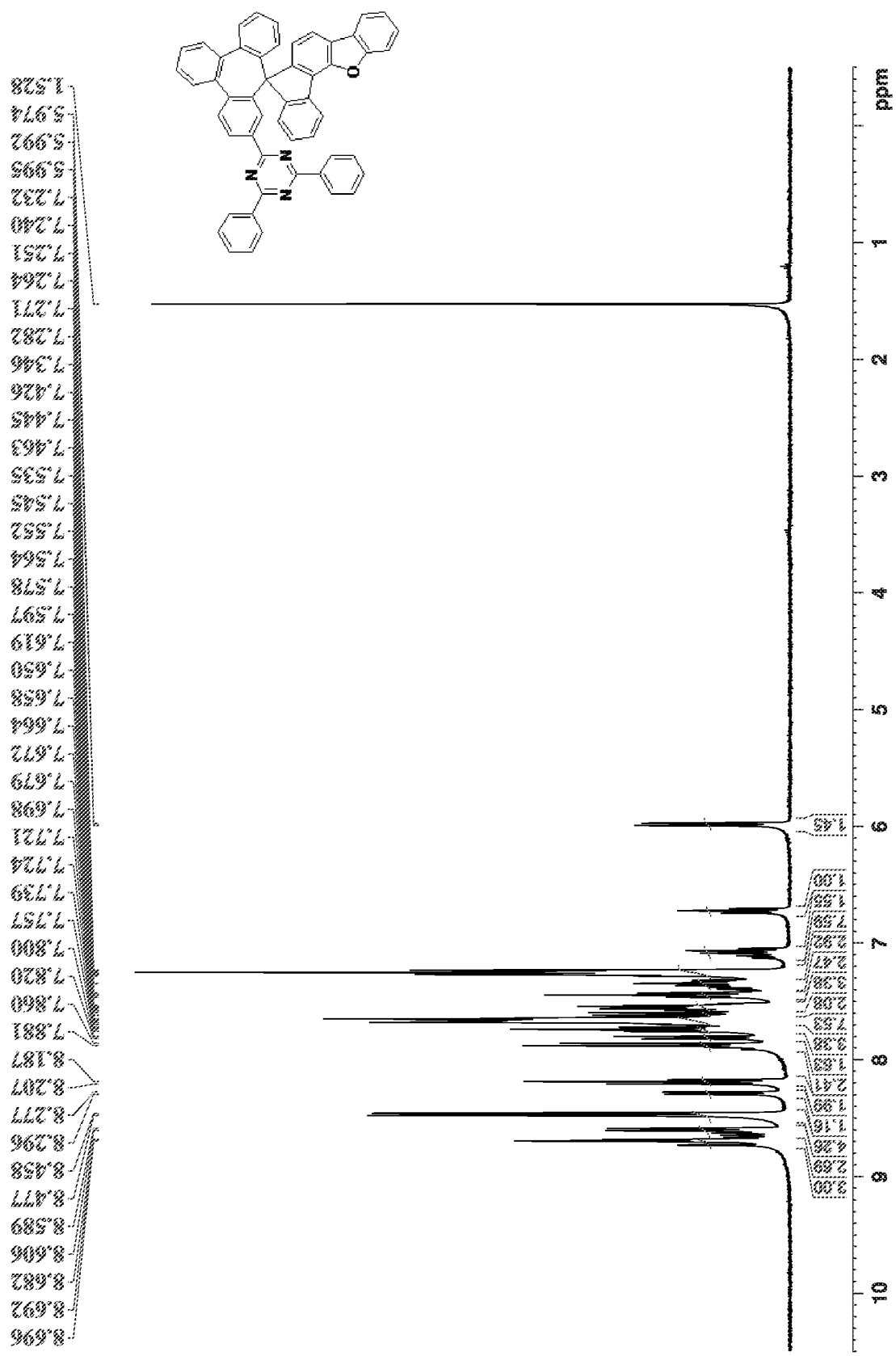
Figure 7:
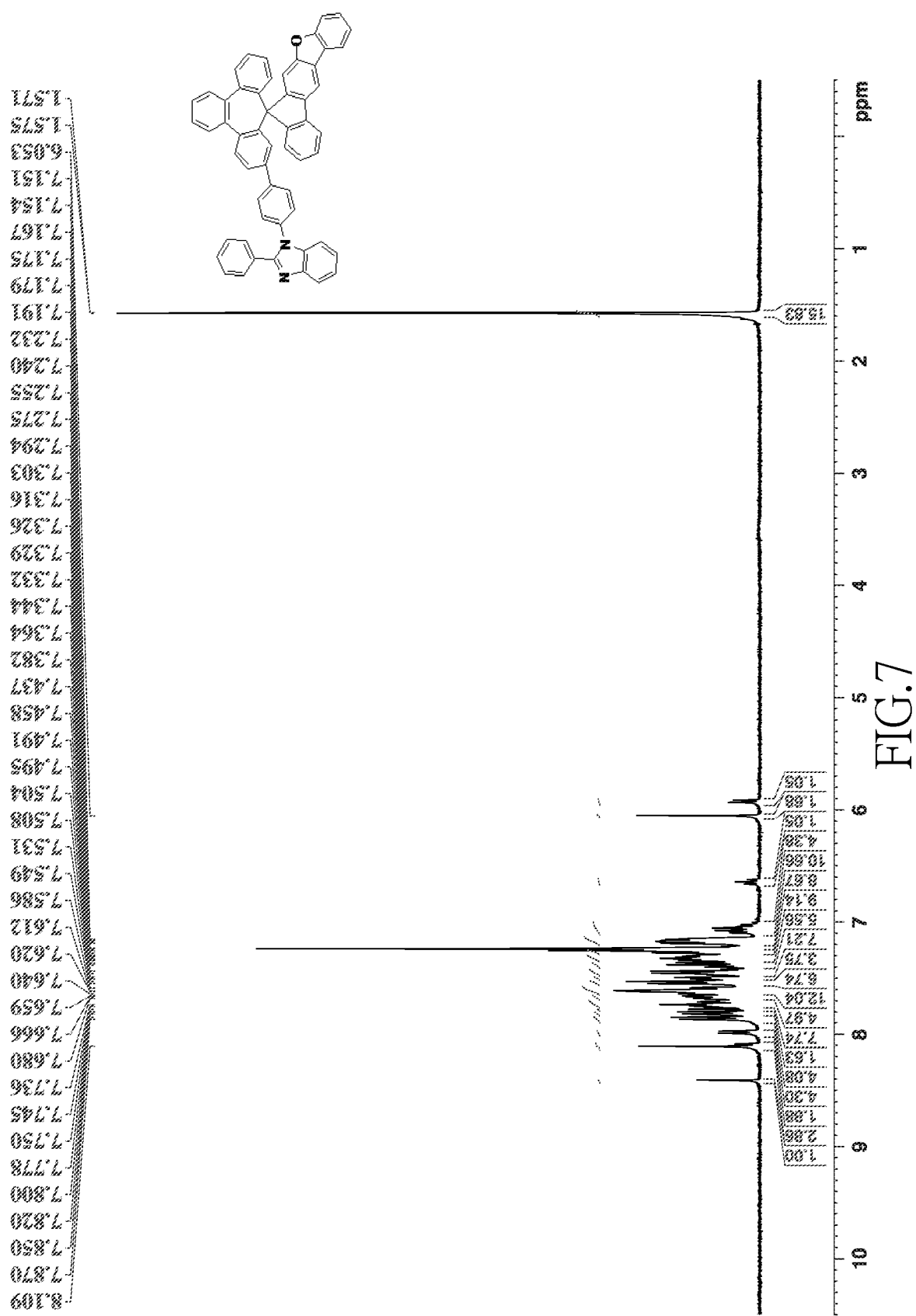
Figure 8:
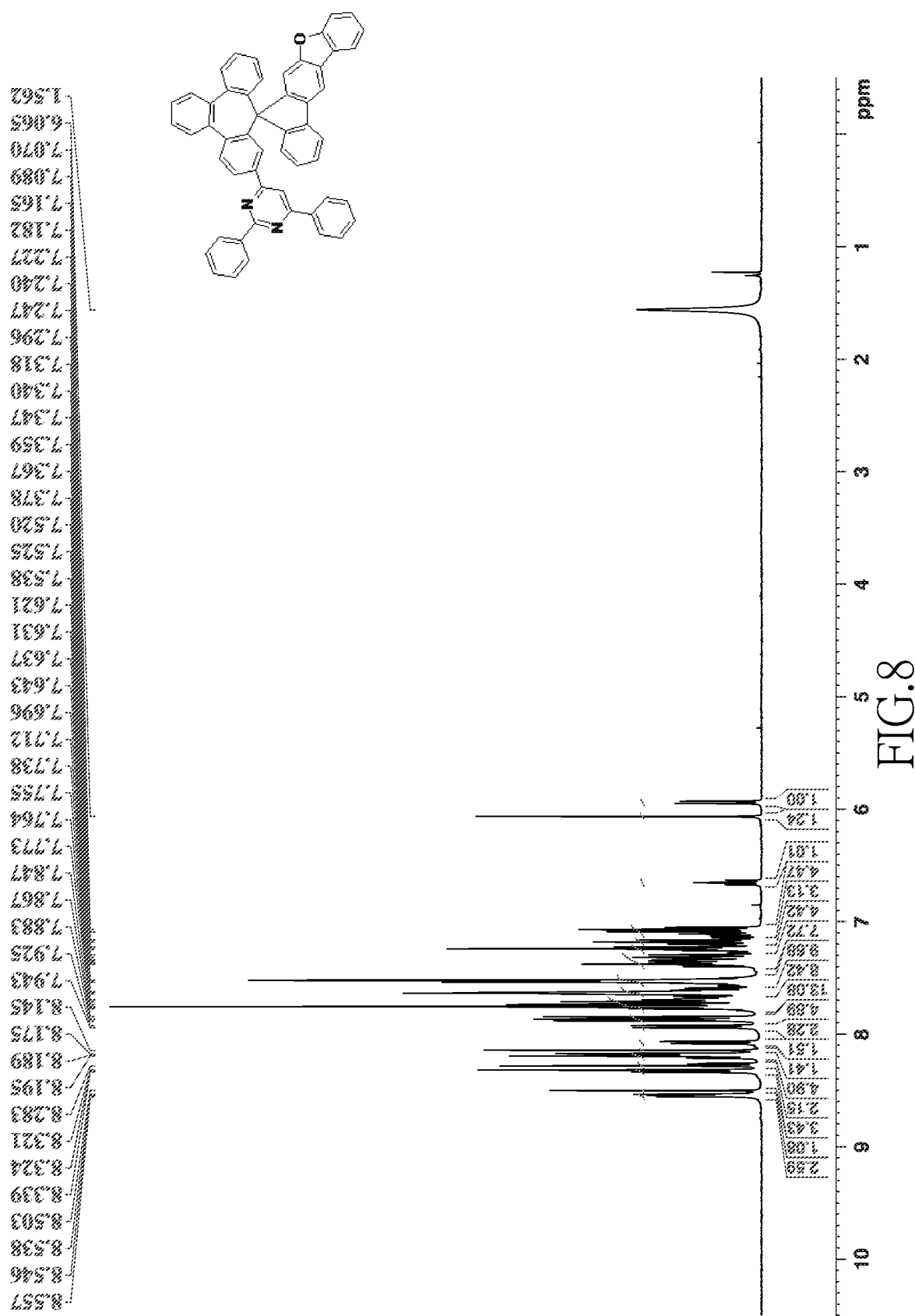
Figure 9:
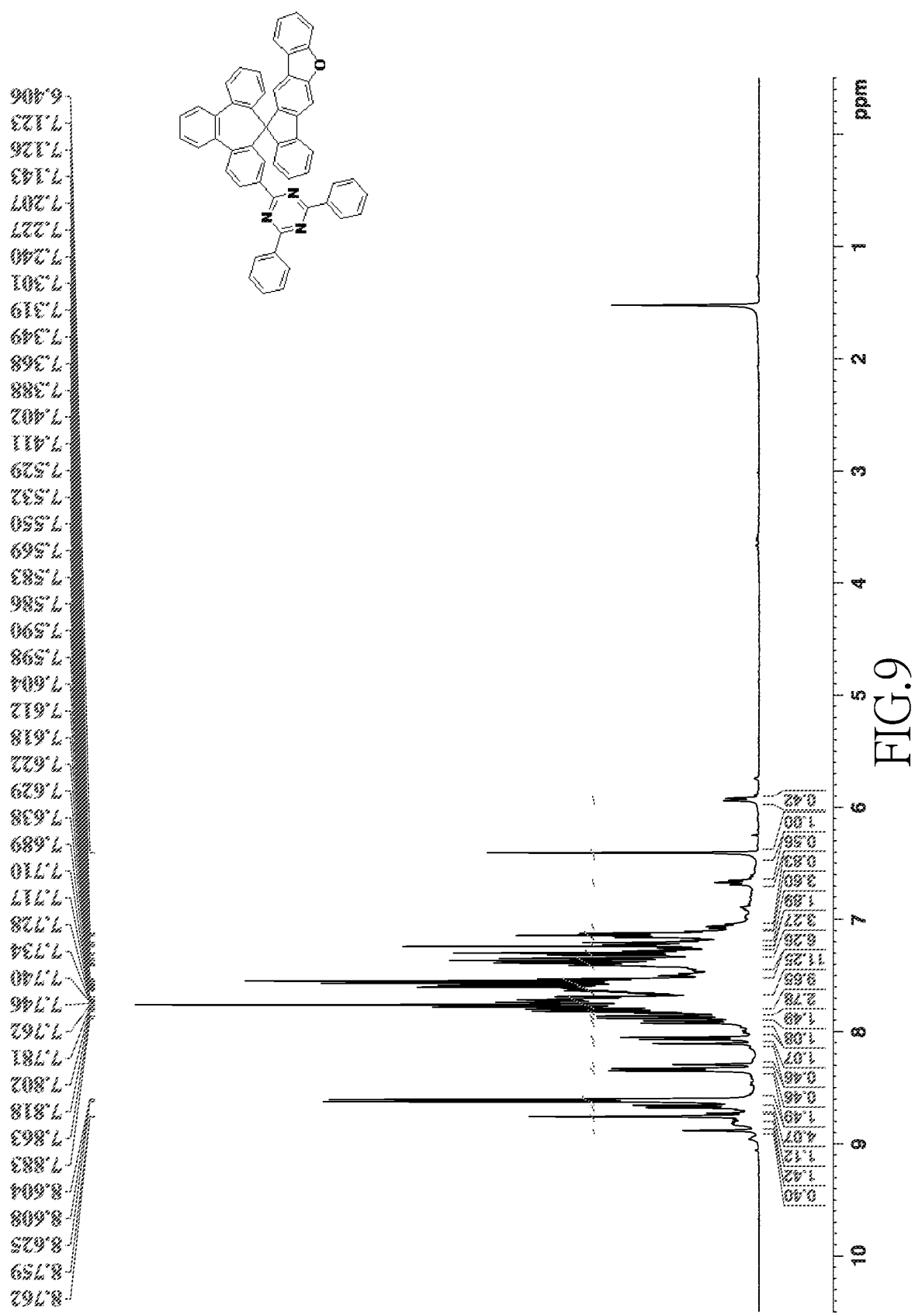
Figure 10:
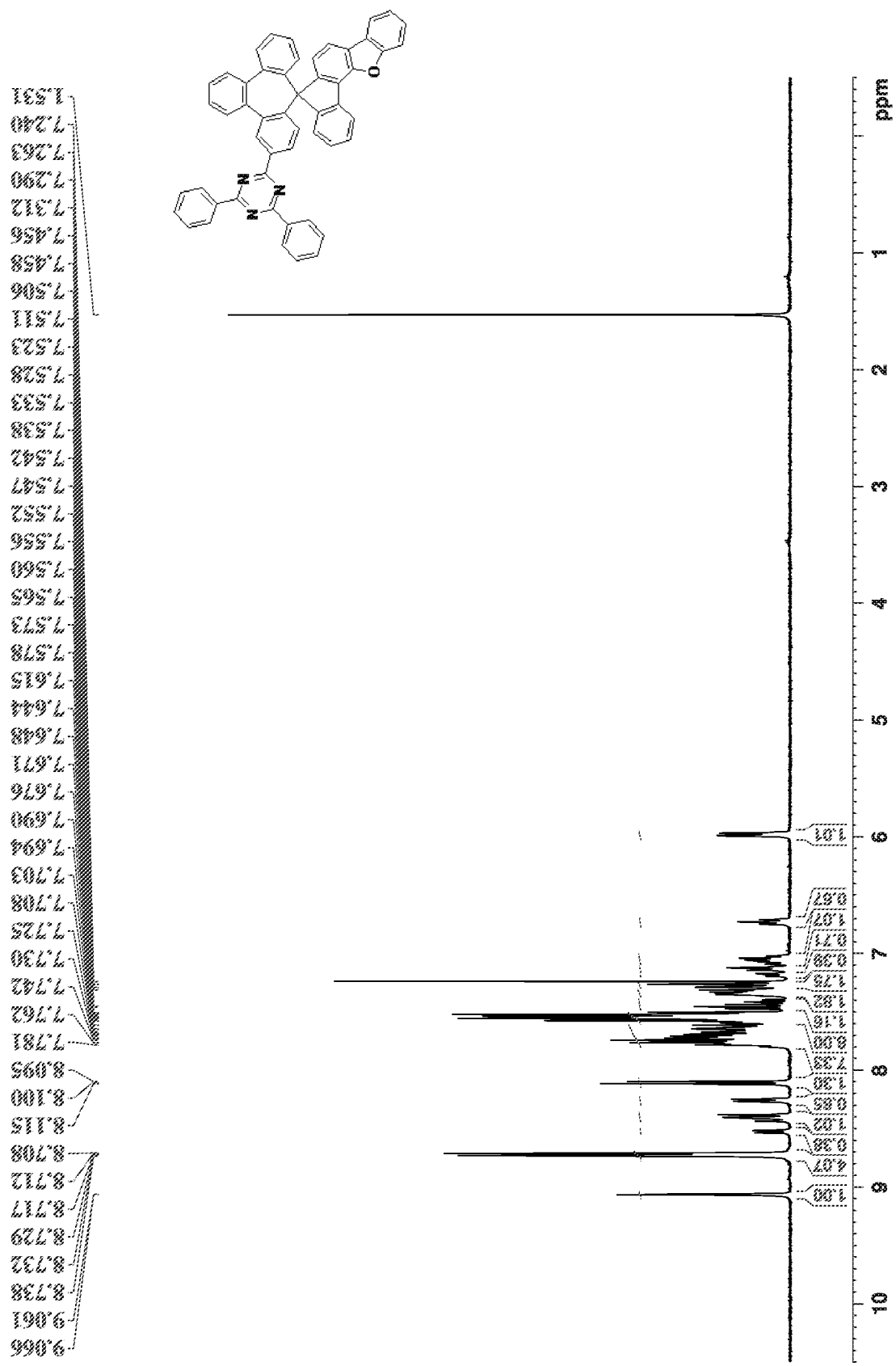
Figure 11:
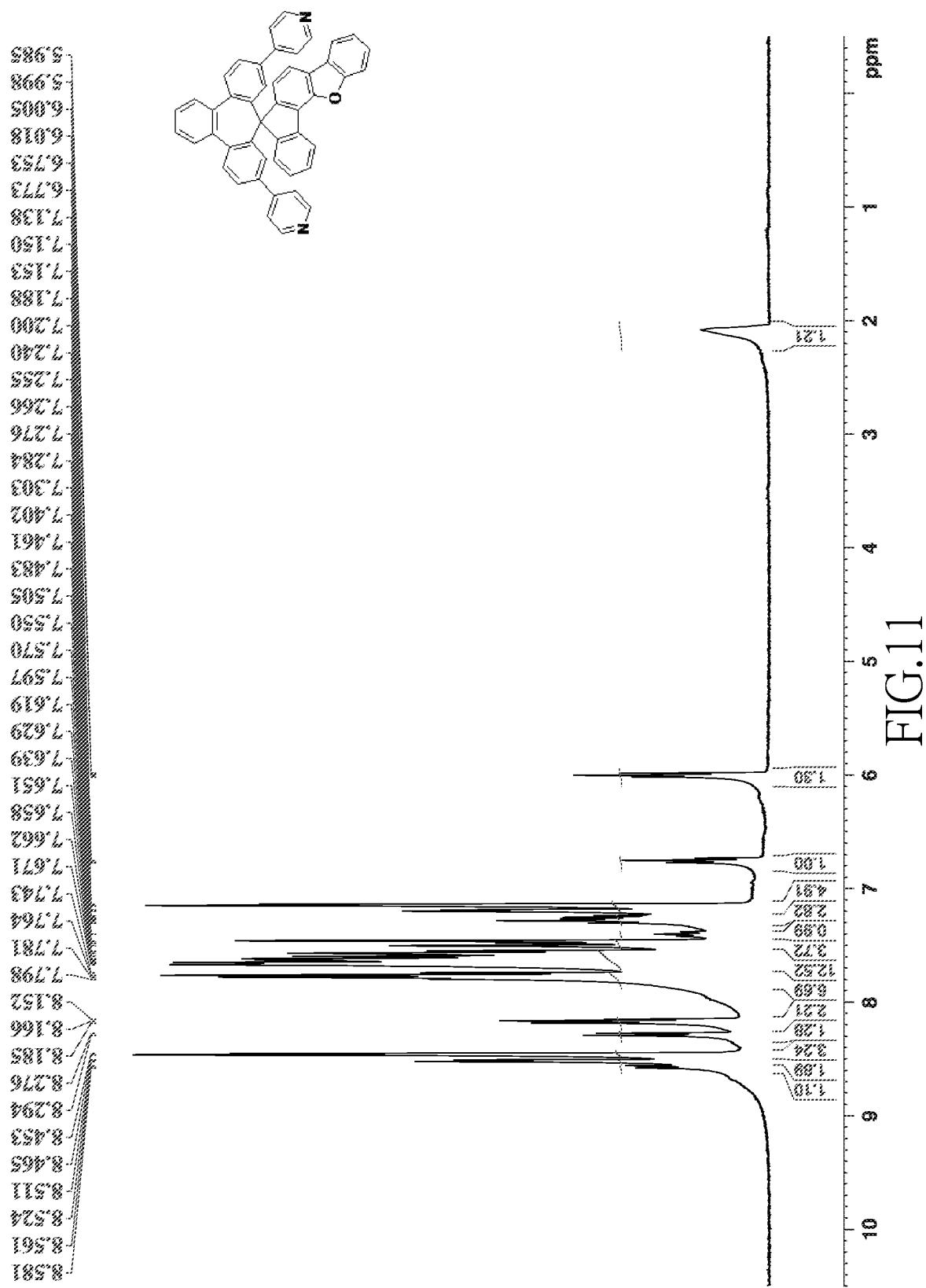
Figure 12:
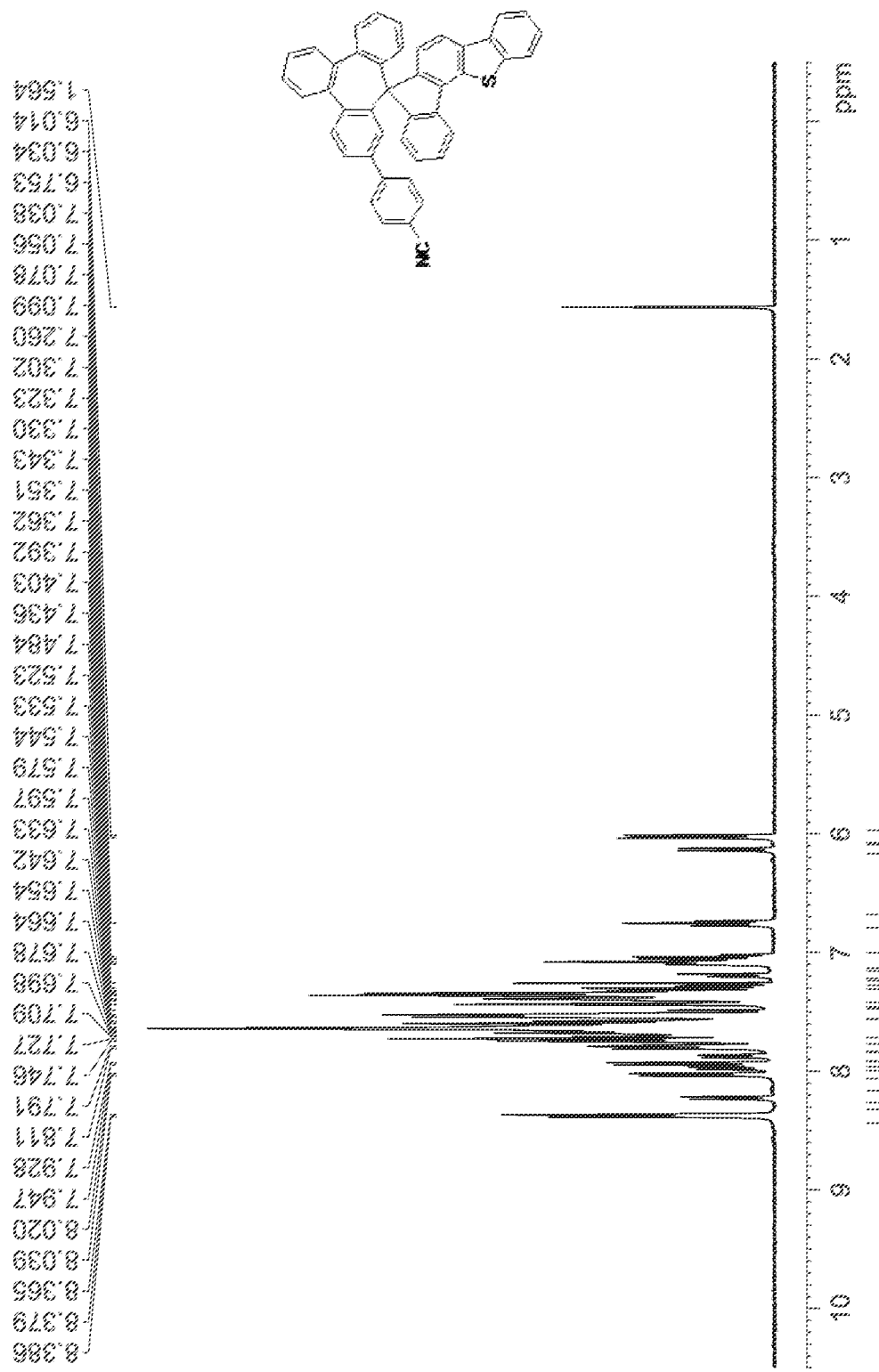
Figure 13:
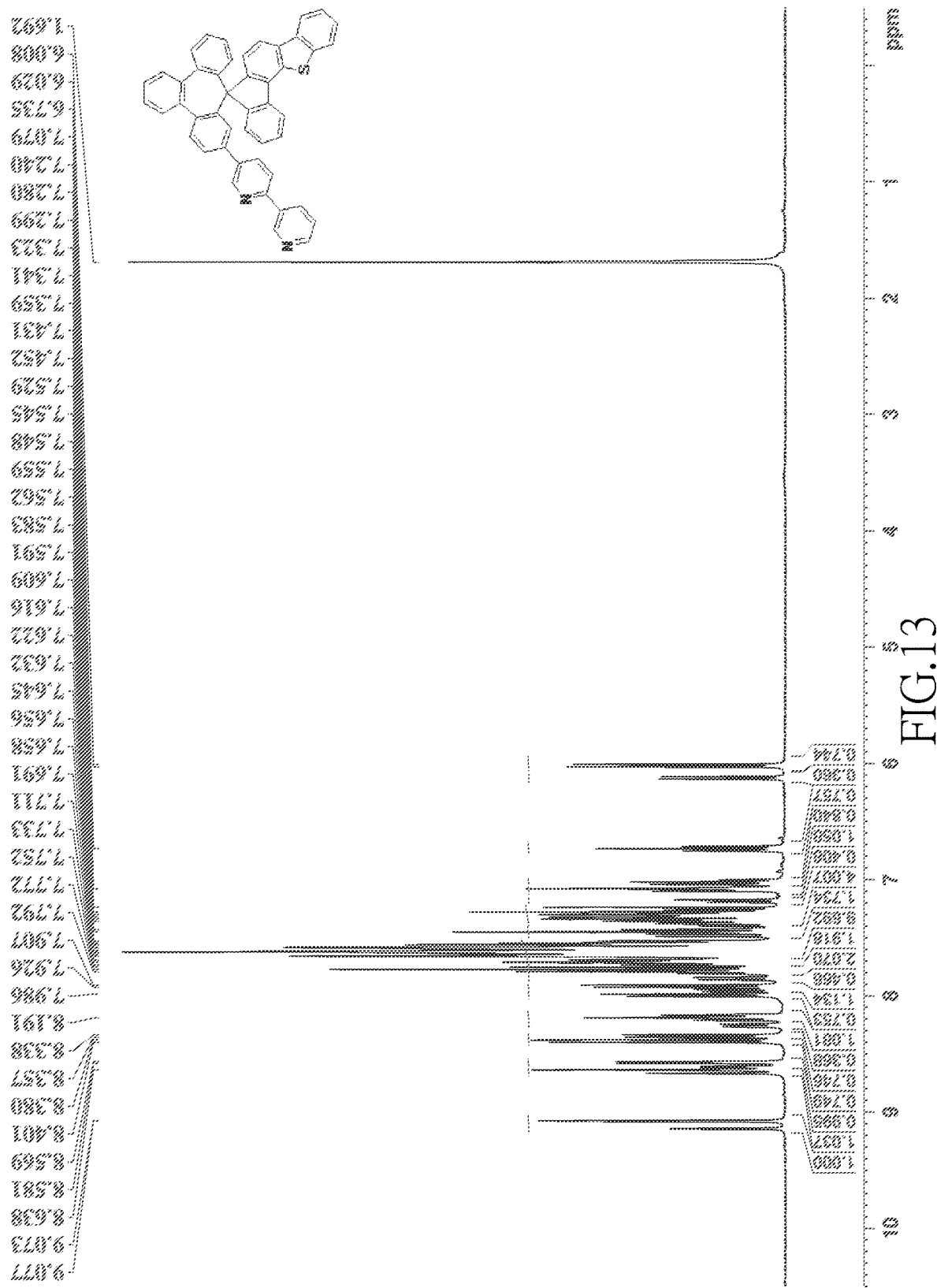
Figure 14:
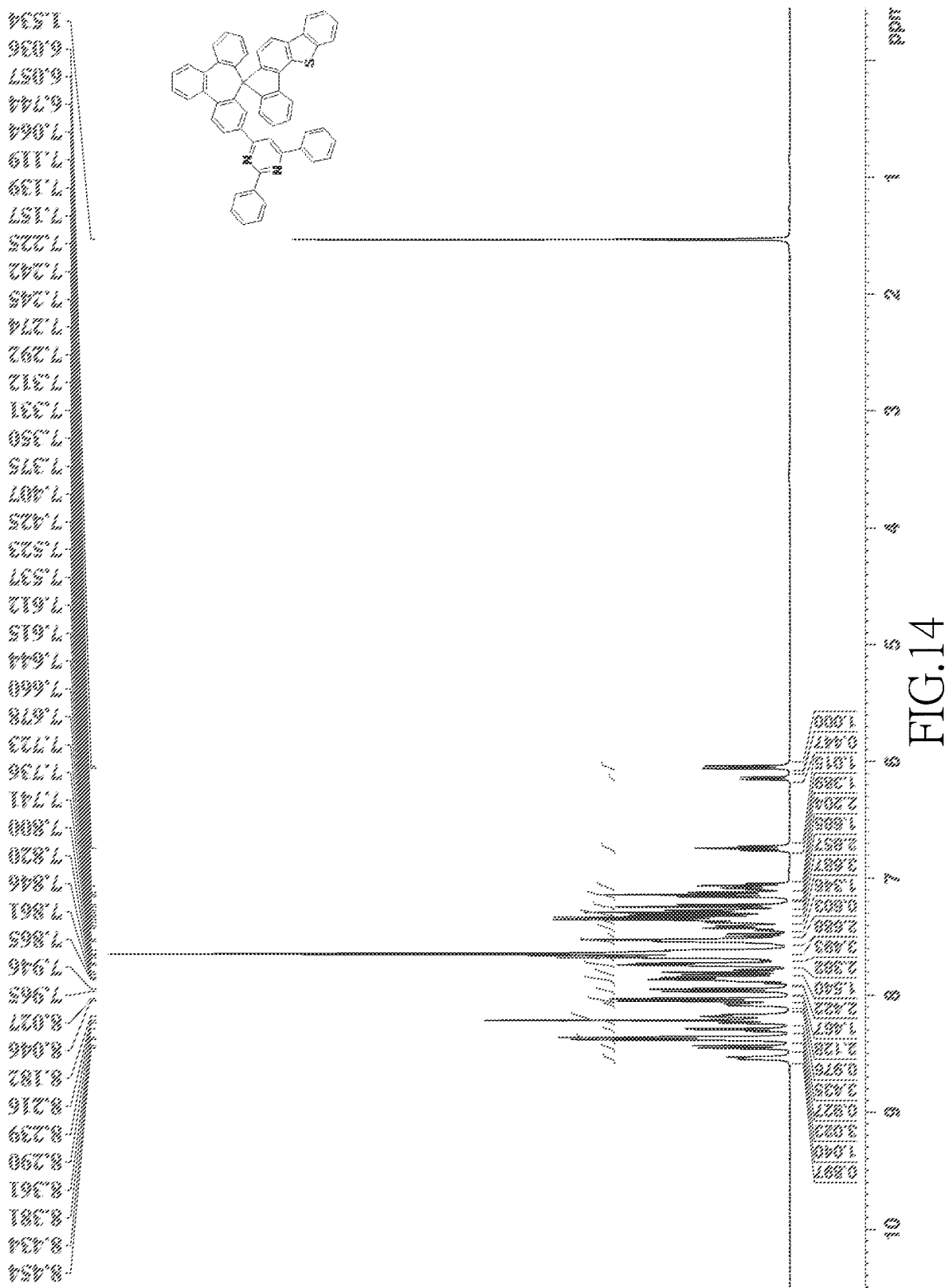
Figure 15:
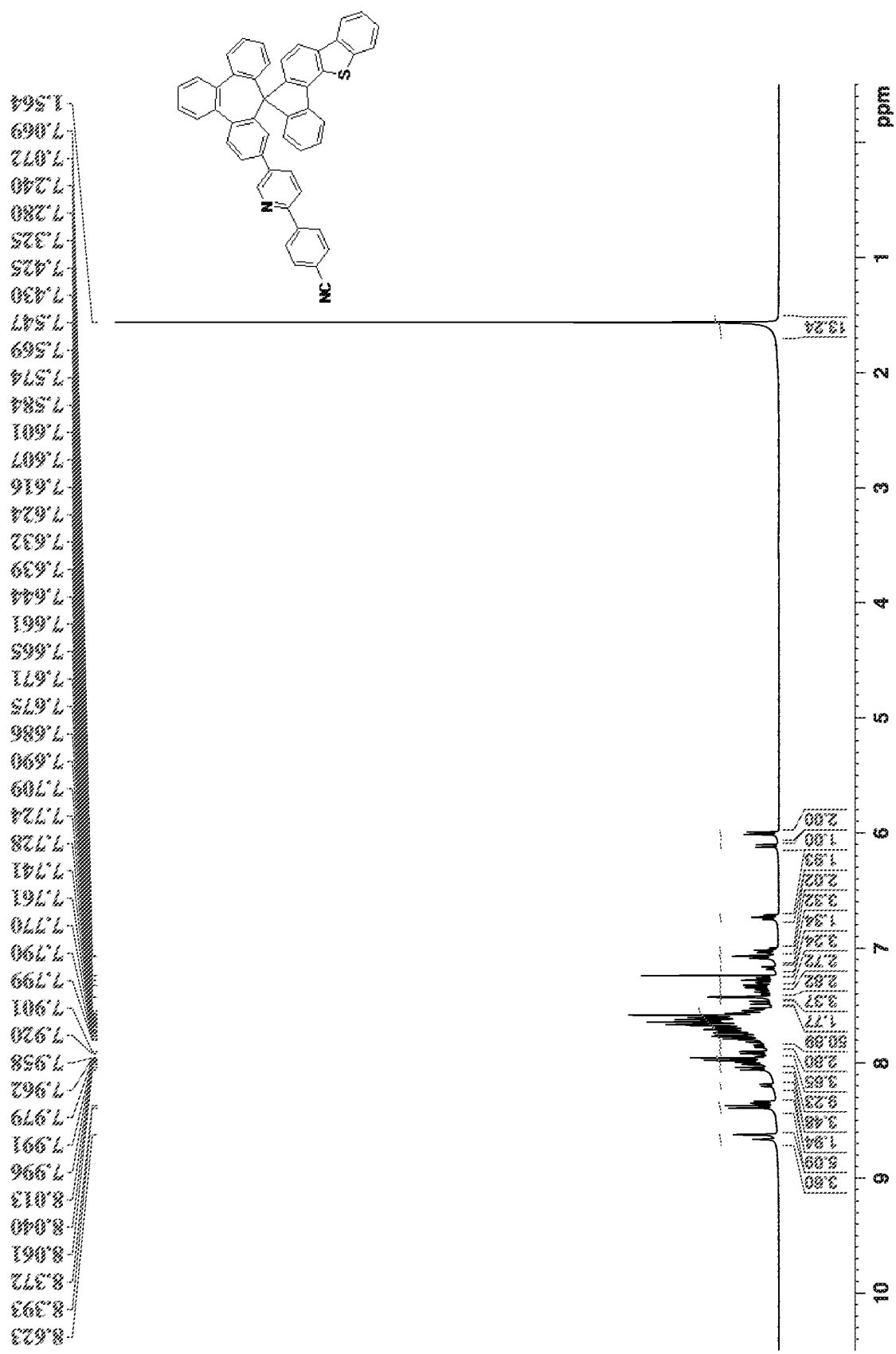
Figure 16:
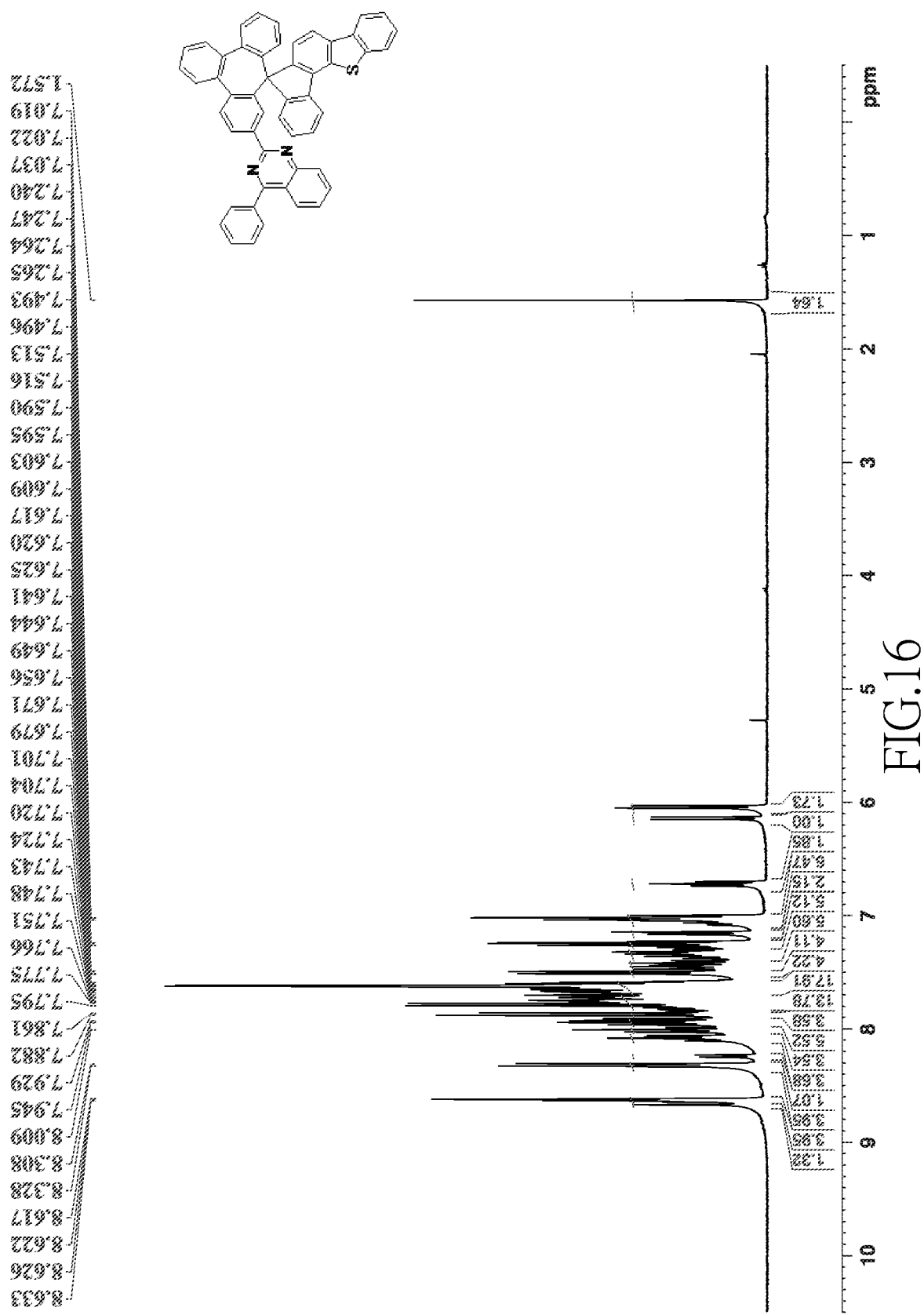
Figure 17:
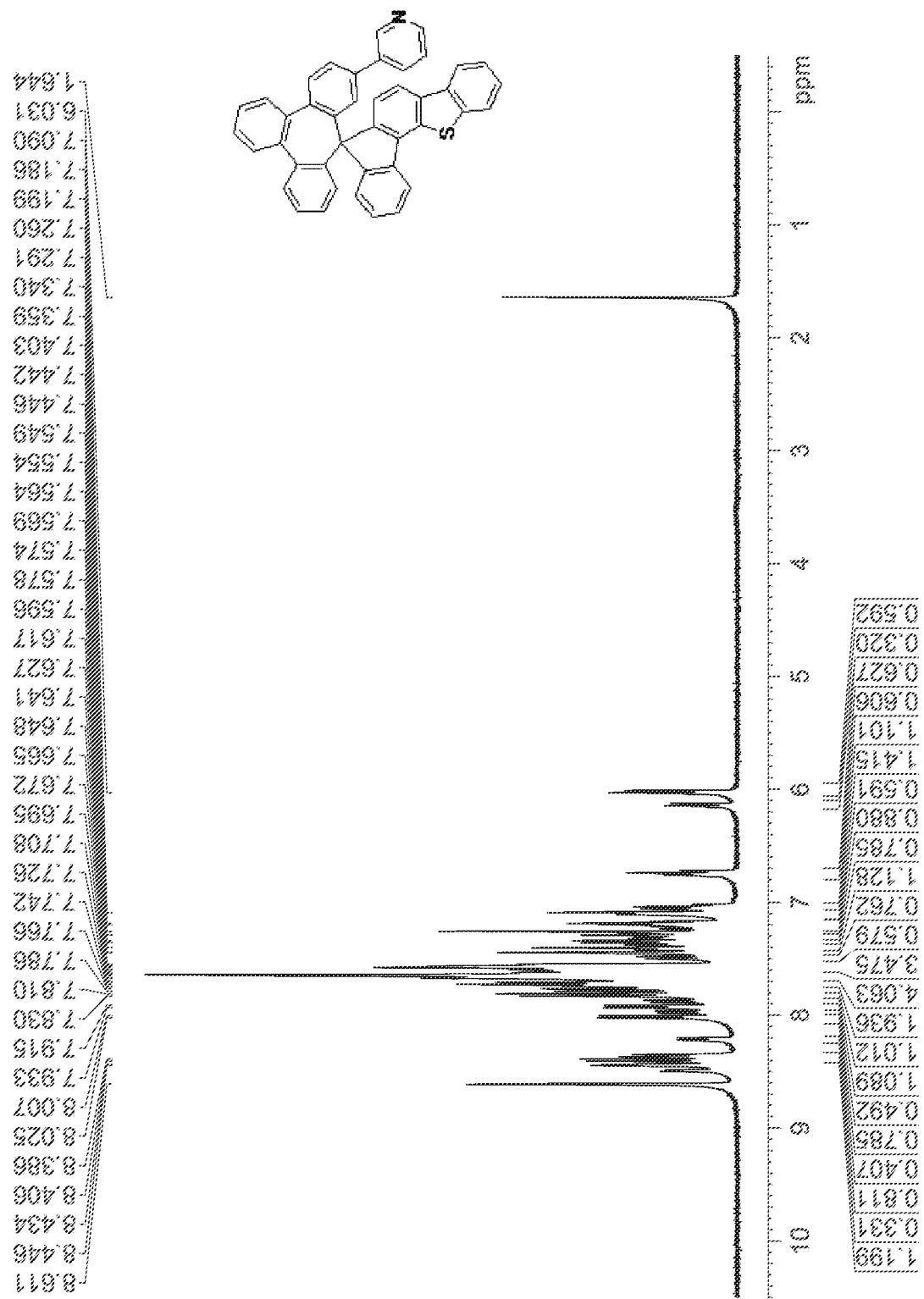
Figure 18:
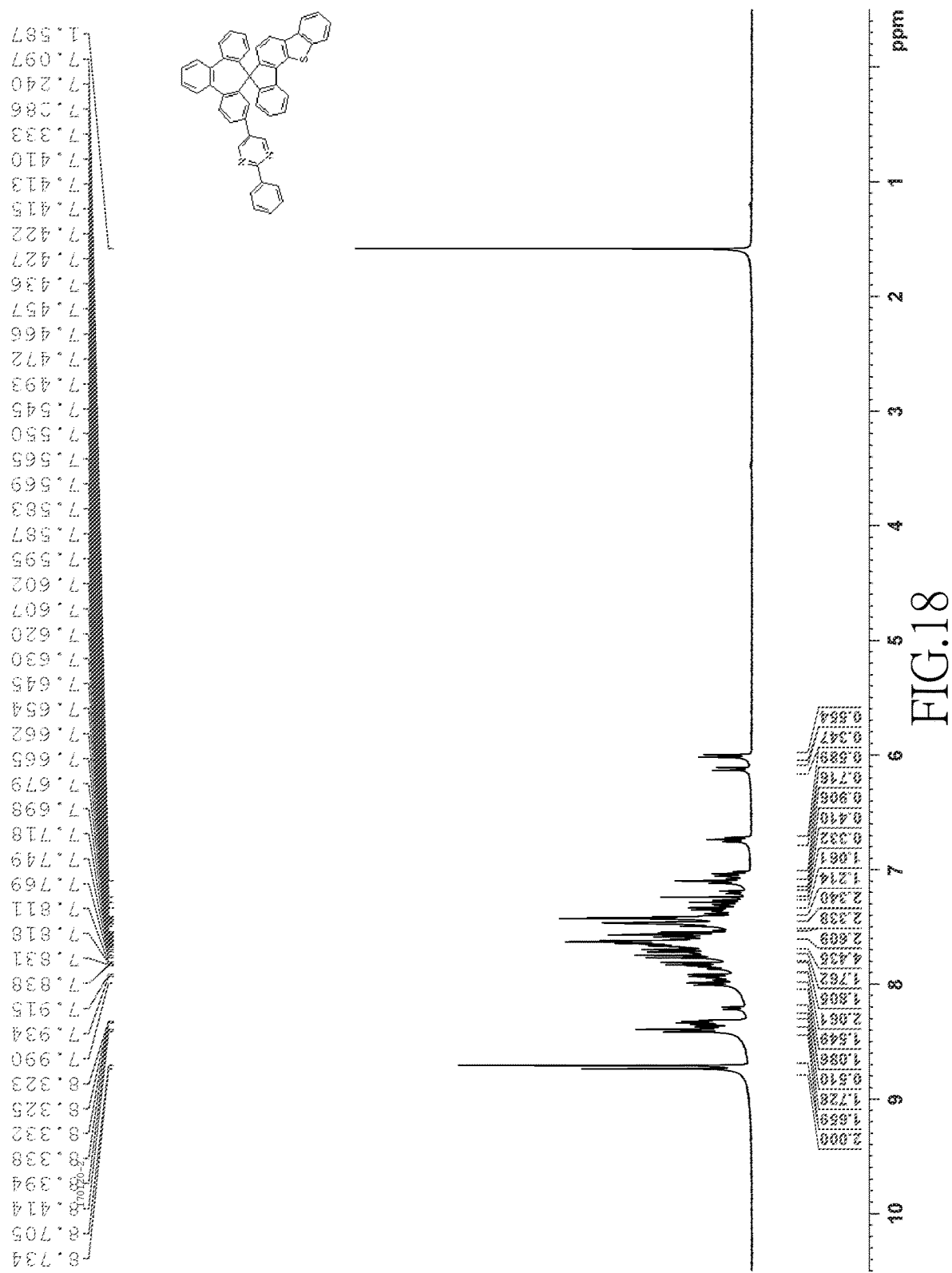
Figure 19:
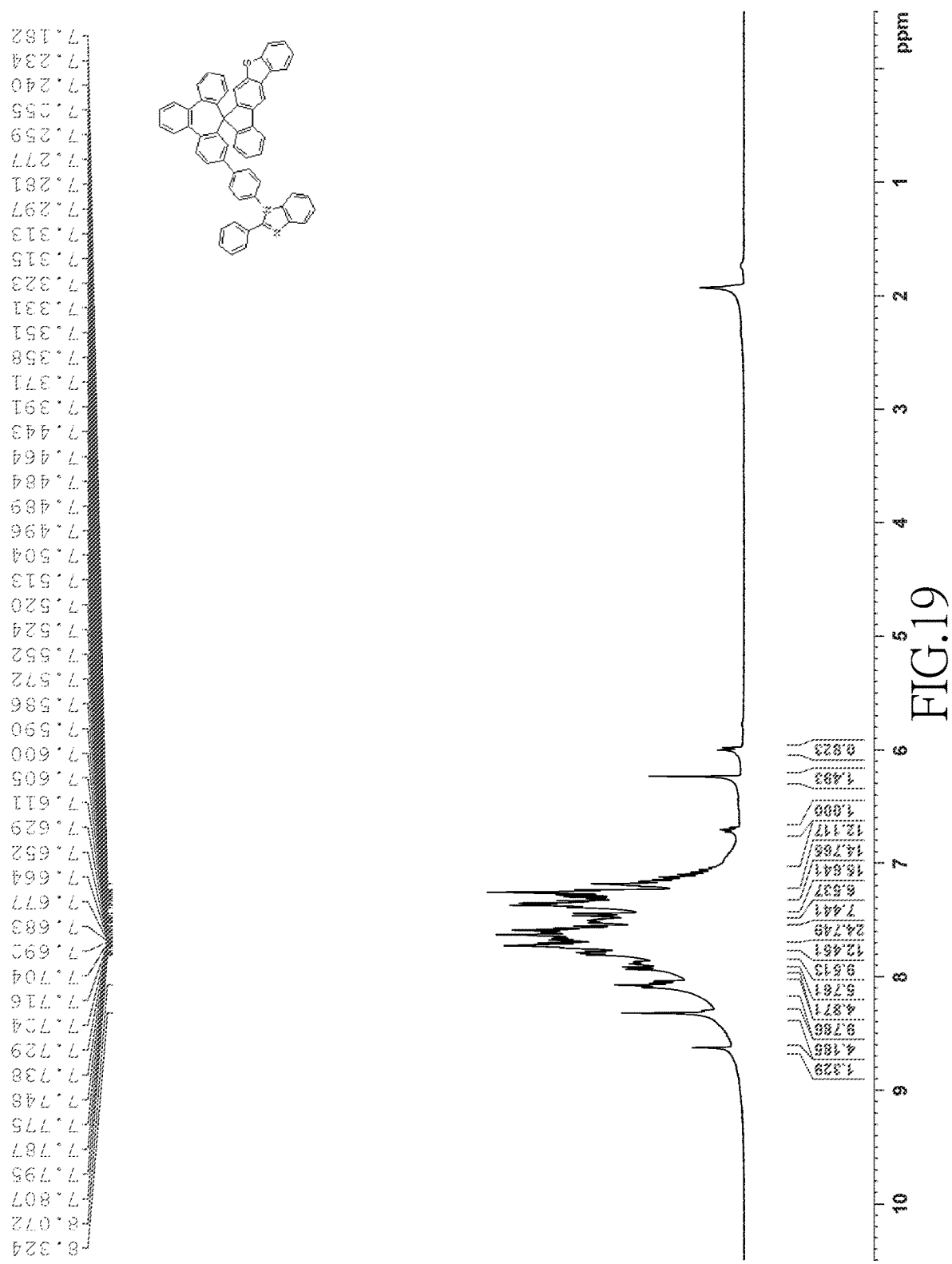
Figure 20:
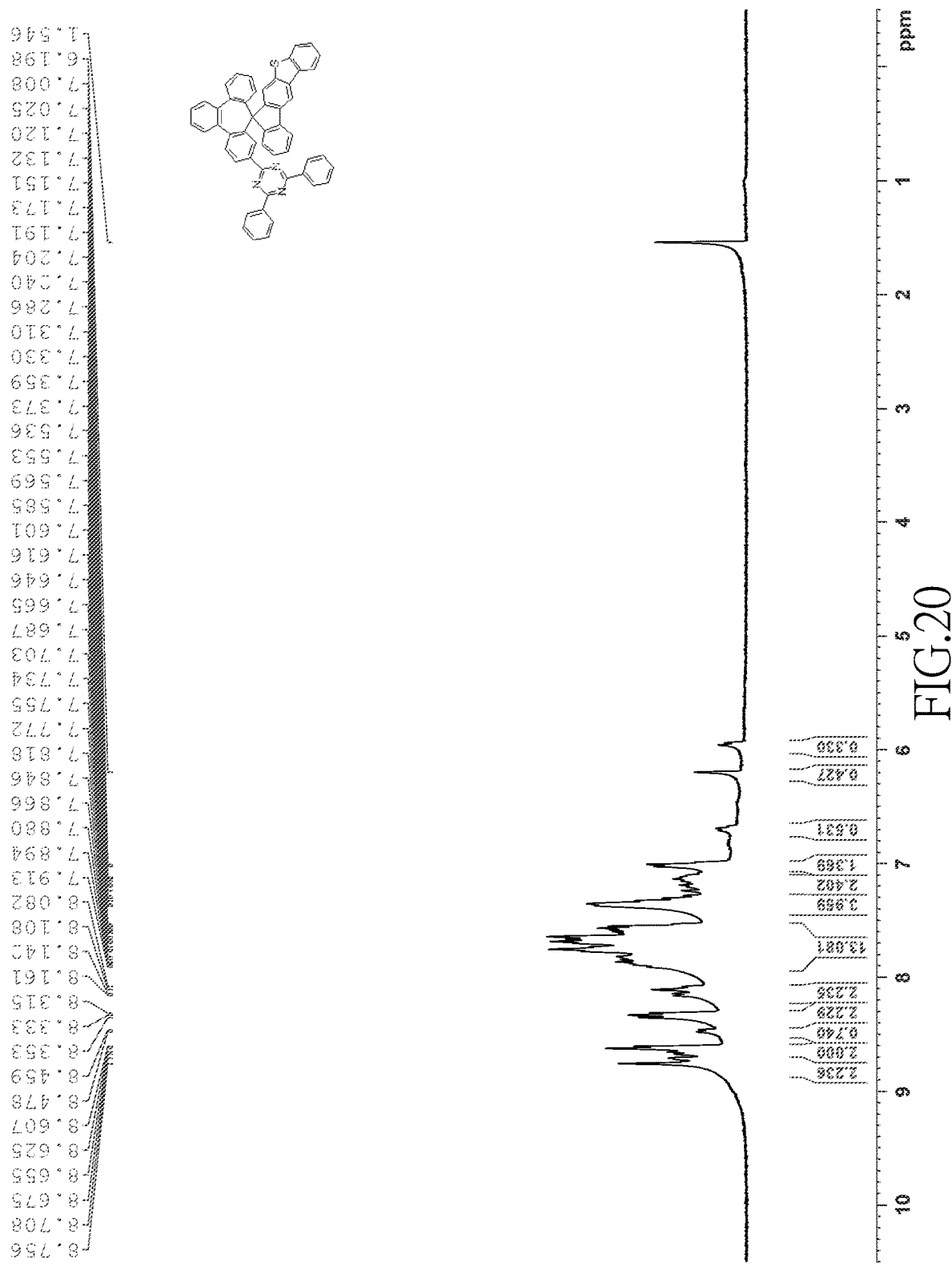
Figure 21:
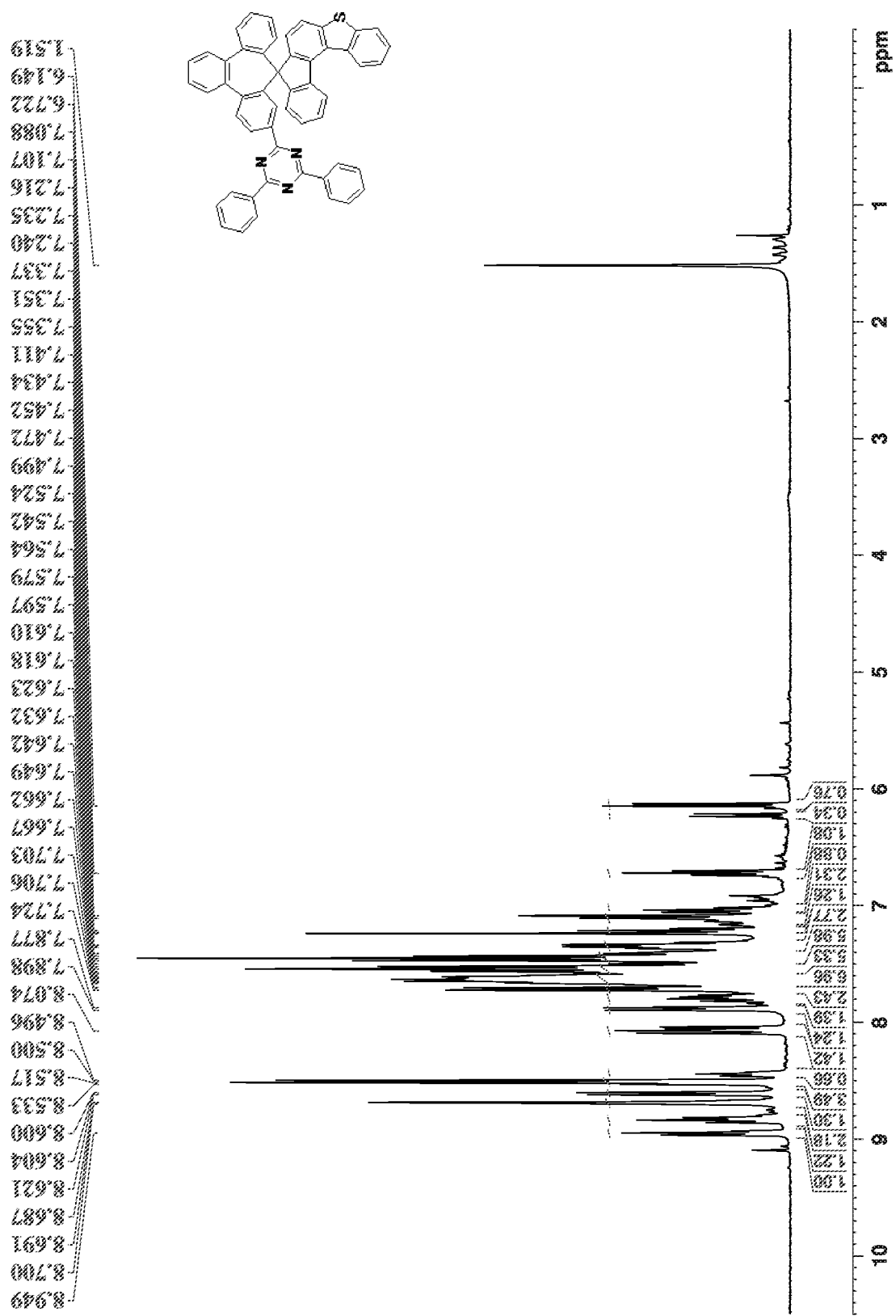
Figure 22:
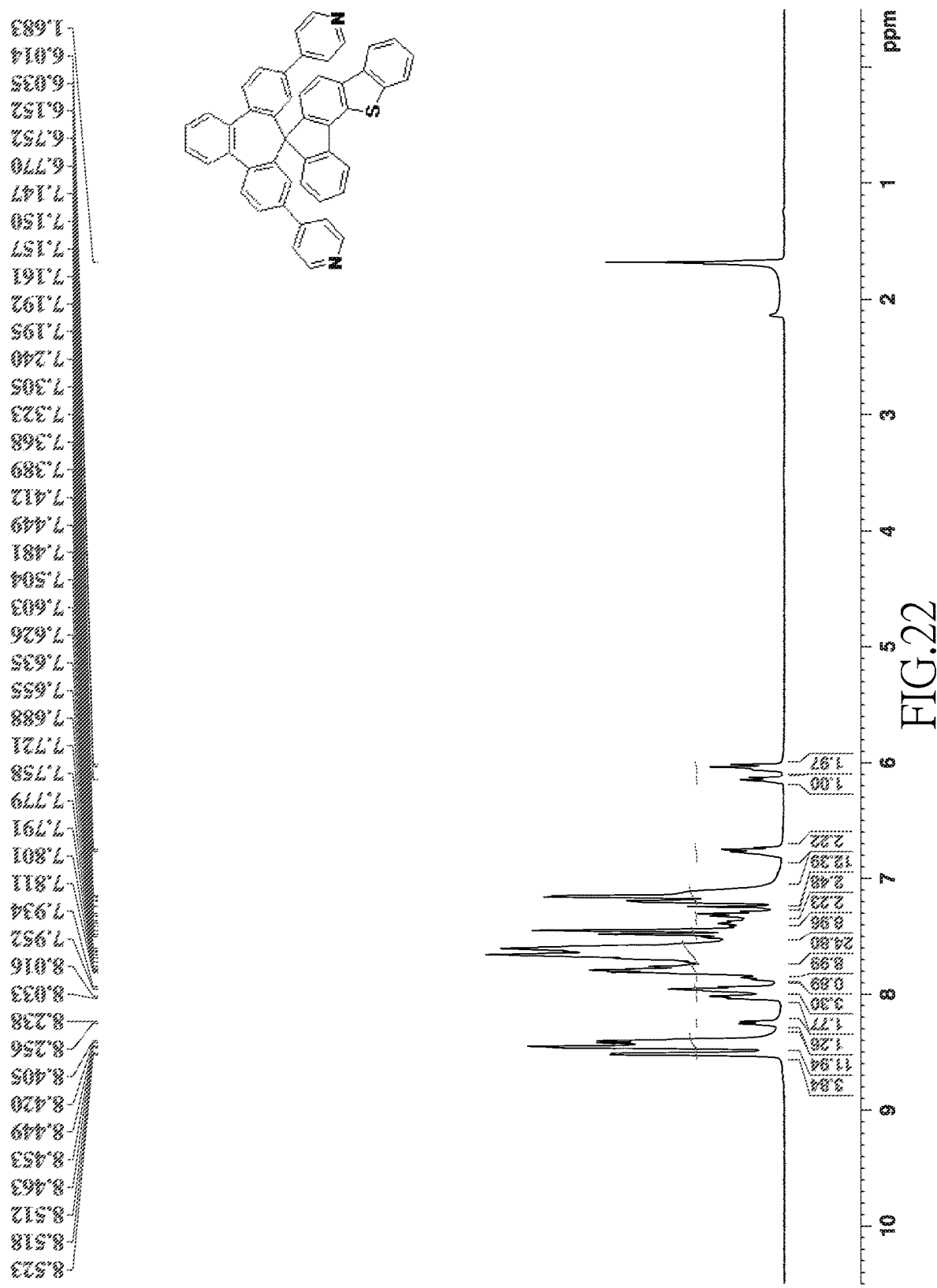
Figure 23:
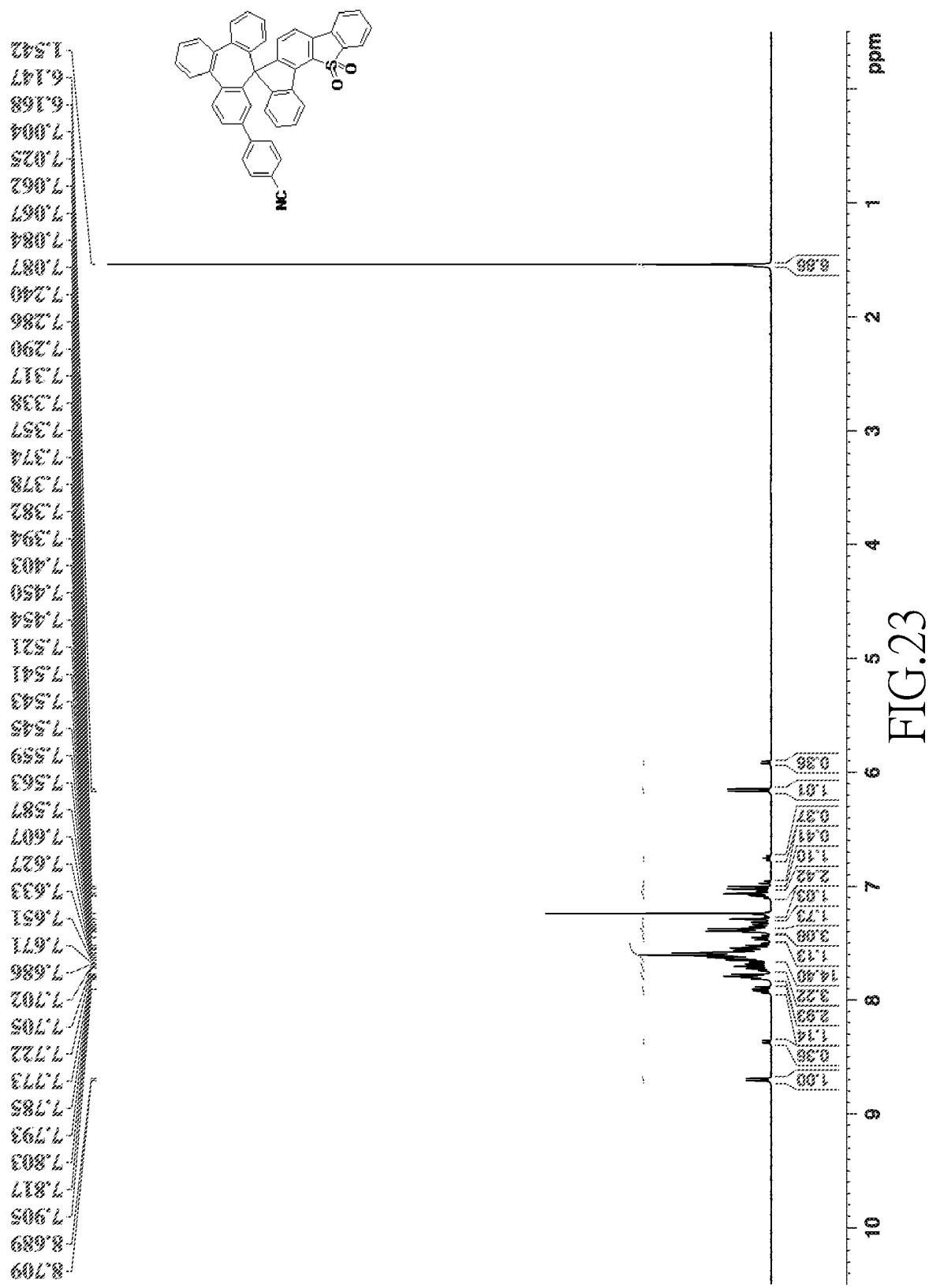
Figure 24:
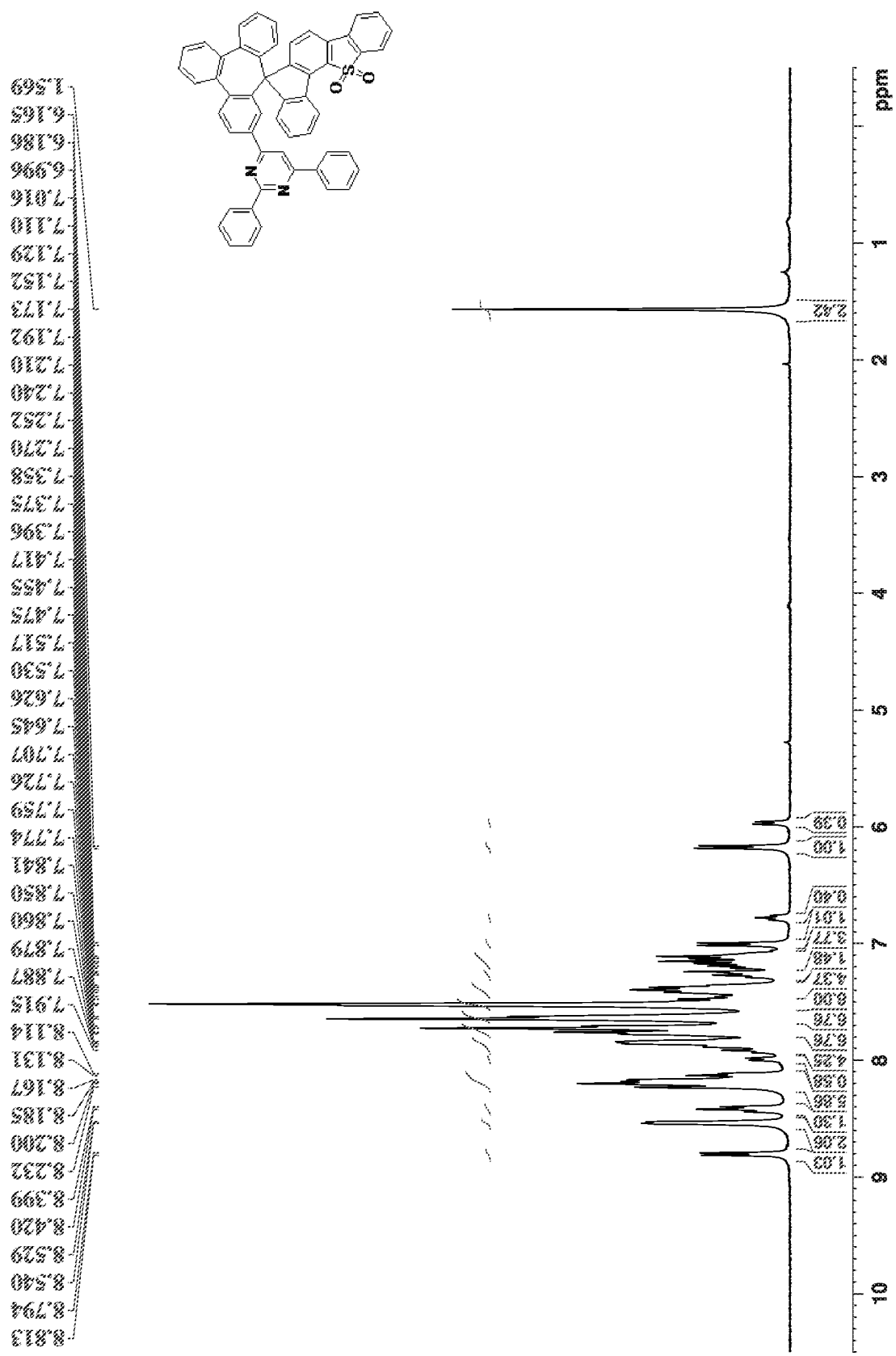
Figure 25:
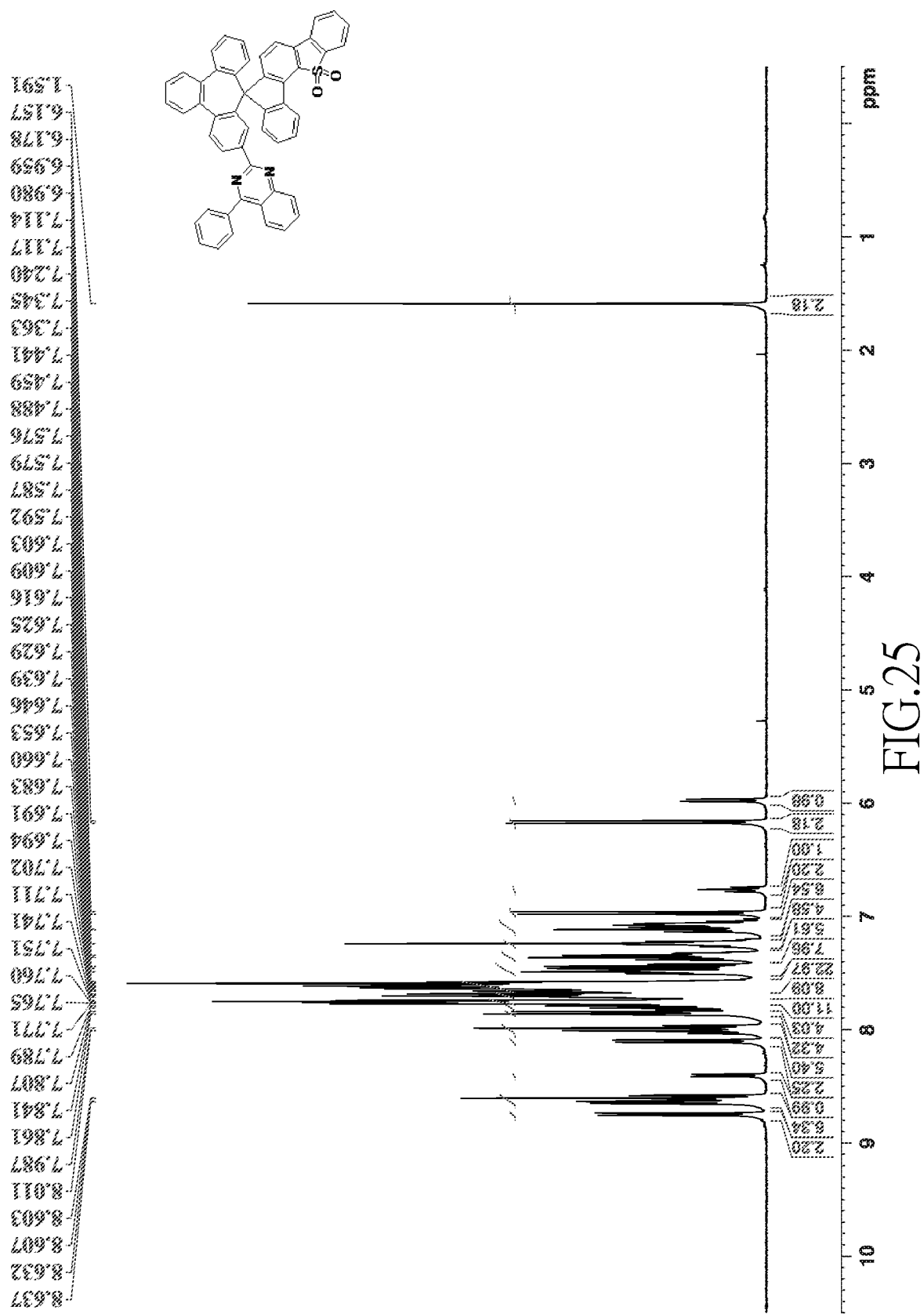
Figure 26:
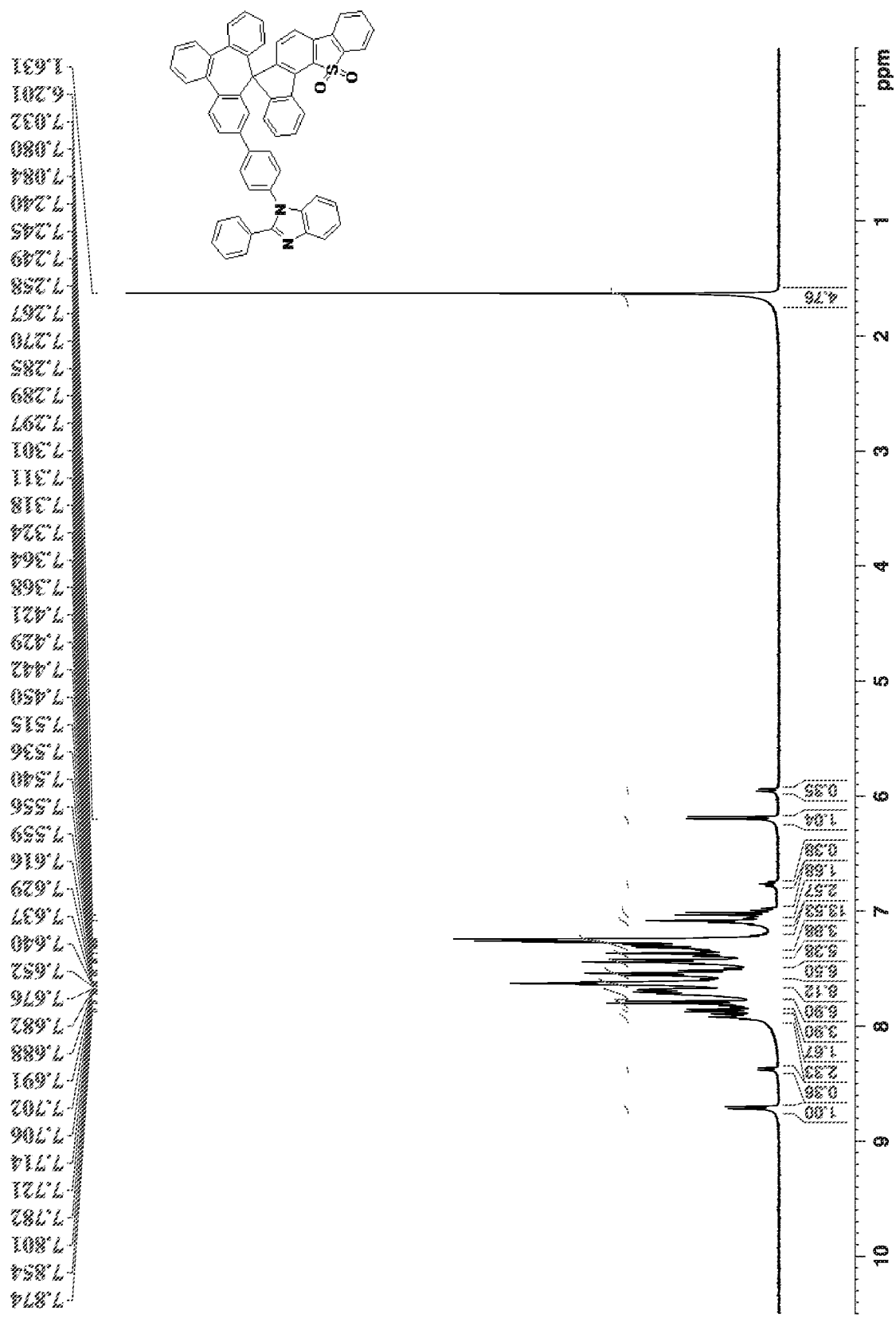
Figure 27:
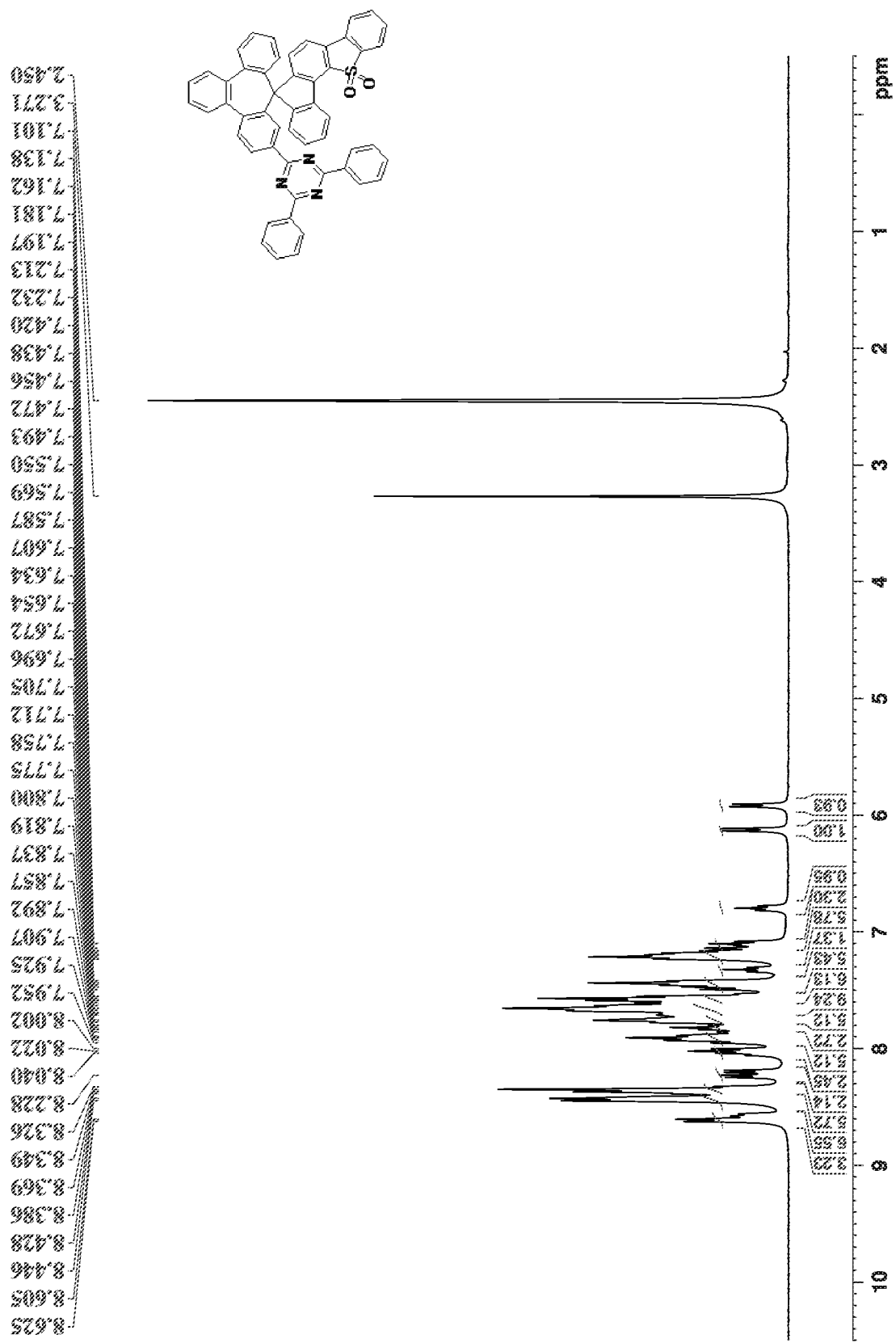
Figure 28:
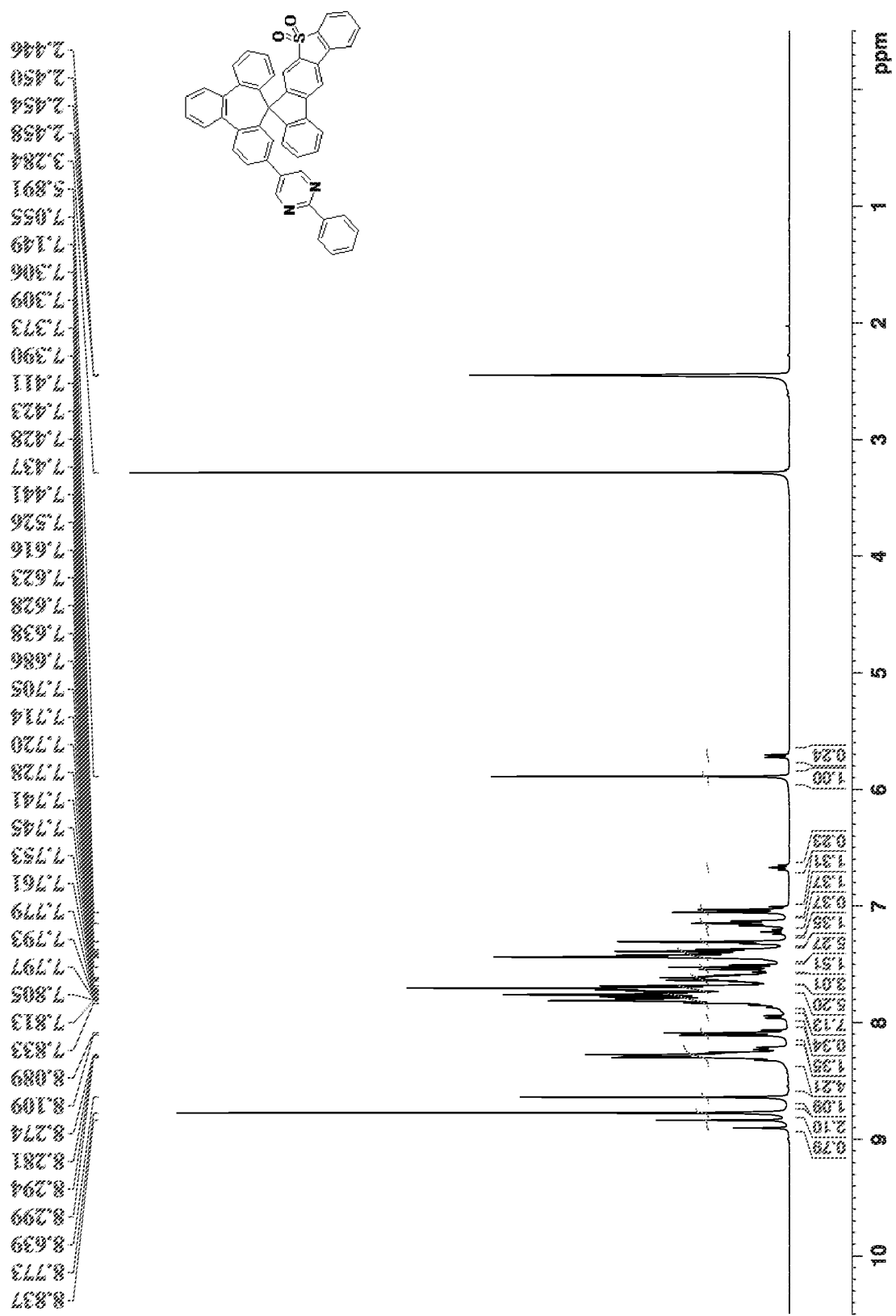

Reactant Bn and Intermediate C adopted to synthesize Compounds I to XXVII were listed in Table 5. Compounds I to XXVII were identified by H$^1$-NMR and FD-MS, and the chemical structure, yield, formula and mass of each of Compounds I to XXVII were also listed in Table 5. According to FIGS. 2 to 28 and the results of FD-MS, the chemical structure of Compounds I to XXVII were identified as follows.

TABLE 5 reactants and intermediates adopted to prepare Compounds I to XXVII and their yields, formulae, and FD-MS data.

| Intermediate No. | Reactant No. | Chemical Structure of Claimed Compound | Yield (%) | Formula/ Mass (M$^+$) |
|---|---|---|---|---|
| C1 | B1 | 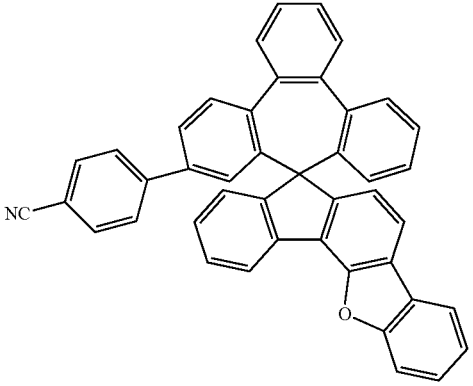<br>Compound I | 95 | C$_{44}$H$_{25}$NO/ 583.68 |
| C1 | B2 | 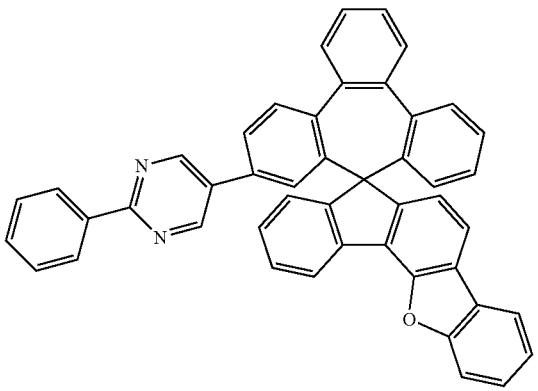<br>Compound II | 97 | C$_{47}$H$_{28}$N$_2$O/ 636.75 |

TABLE 5-continued reactants and intermediates adopted to prepare Compounds I to XXVII and their yields, formulae, and FD-MS data.

| Intermediate No. | Reactant No. | Chemical Structure of Claimed Compound | Yield (%) | Formula/ Mass (M+) |
|---|---|---|---|---|
| C1 | B4 | Compound III | 86 | $C_{47}H_{28}N_2O$/ 636.74 |
| C1-B | B5 | Compound IV | 72 | $C_{51}H_{30}N_2O$/ 686.80 |
| C1-B | B7 | Compound V | 83 | $C_{51}H_{31}N_3O$/ 713.82 |

TABLE 5-continued reactants and intermediates adopted to prepare Compounds I to XXVII and their yields, formulae, and FD-MS data.

| Intermediate No. | Reactant No. | Chemical Structure of Claimed Compound | Yield (%) | Formula/ Mass (M⁺) |
|---|---|---|---|---|
| C3-B | B6 | Compound VI | 73 | $C_{56}H_{34}N_2O$ / 750.88 |
| C3-B | B8 | Compound VII | 83 | $C_{53}H_{32}N_2O$ / 712.83 |
| C4-B | B7 | Compound VIII | 62 | $C_{52}H_{31}N_3O$ / 713.82 |

TABLE 5-continued reactants and intermediates adopted to prepare Compounds I to XXVII and their yields, formulae, and FD-MS data.

| Intermediate No. | Reactant No. | Chemical Structure of Claimed Compound | Yield (%) | Formula/ Mass (M+) |
|---|---|---|---|---|
| C2-B | B7 | Compound IX | 81 | $C_{52}H_{31}N_3O$ / 713.82 |
| C5 | B3 | Compound X | 63 | $C_{47}H_{28}N_2O$ / 636.74 |
| C6 | B1 | Compound XI | 84 | $C_{44}H_{25}NS$ / 599.74 |

TABLE 5-continued reactants and intermediates adopted to prepare Compounds I to XXVII and their yields, formulae, and FD-MS data.

| Intermediate No. | Reactant No. | Claimed Compound | | |
|---|---|---|---|---|
| | | Chemical Structure of Claimed Compound | Yield (%) | Formula/ Mass (M+) |
| C6 | B4 | Compound XII | 68 | $C_{47}H_{28}N_2S$/ 652.81 |
| C6-B | B8 | Compound XIII | 88 | $C_{53}H_{32}N_2S$/ 728.9 |
| C6-B | B9 | Compound XIV | 70 | $C_{49}H_{28}N_2S$/ 676.83 |

TABLE 5-continued
reactants and intermediates adopted to prepare Compounds I to XXVII and their yields, formulae, and FD-MS data.
| Intermediate No. | Reactant No. | Chemical Structure of Claimed Compound | Yield (%) | Formula/ Mass (M+) |
|---|---|---|---|---|
| C6-B | B5 | 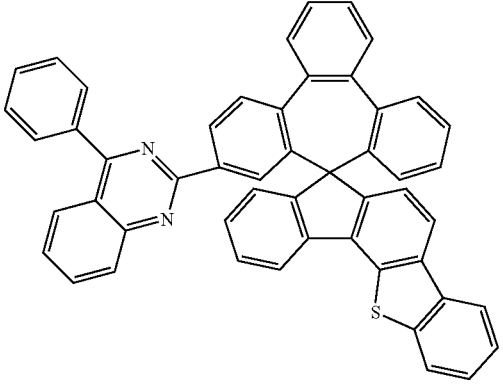<br>Compound XV | 72 | $C_{51}H_{30}N_2S$/ 702.86 |
| C6 | B10 | 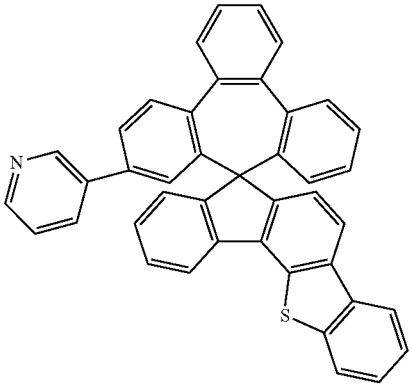<br>Compound XVI | 78 | $C_{42}H_{25}NS$/ 575.72 |
| C6 | B2 | 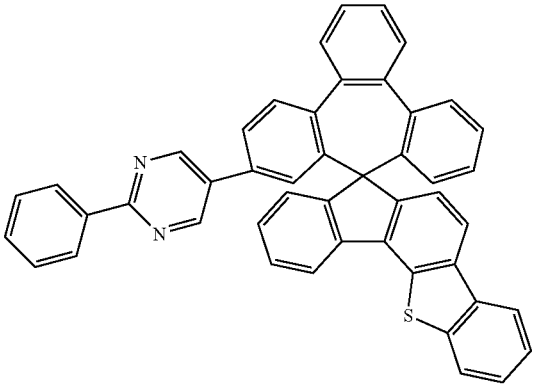<br>Compound XVII | 78 | $C_{47}H_{28}N_2S$/ 652.80 |

TABLE 5-continued reactants and intermediates adopted to prepare Compounds I to XXVII and their yields, formulae, and FD-MS data.

| Intermediate No. | Reactant No. | Chemical Structure of Claimed Compound | Yield (%) | Formula/ Mass (M+) |
|---|---|---|---|---|
| C7-B | B6 | Compound XVIII | 66 | $C_{56}H_{34}N_2S$/ 766.95 |
| C7-B | B7 | Compound XIX | 79 | $C_{52}H_{31}N_3S$/ 729.89 |
| C8-B | B7 | Compound XX | 66 | $C_{52}H_{31}N_3S$/ 729.89 |

TABLE 5-continued reactants and intermediates adopted to prepare Compounds I to XXVII and their yields, formulae, and FD-MS data.

| Intermediate No. | Reactant No. | Chemical Structure of Claimed Compound | Yield (%) | Formula/ Mass (M+) |
|---|---|---|---|---|
| C9 | B3 | Compound XXI | 85 | $C_{47}H_{28}N_2S$/ 652.80 |
| C34 | B1 | Compound XXII | 56 | $C_{44}H_{25}NO_2S$/ 631.74 |
| C34-B | B8 | Compound XXIII | 83 | $C_{53}H_{32}N_2O_2S$/ 760.90 |

TABLE 5-continued
reactants and intermediates adopted to prepare Compounds I to XXVII and their yields, formulae, and FD-MS data.
| Intermediate No. | Reactant No. | Chemical Structure of Claimed Compound | Yield (%) | Formula/ Mass (M⁺) |
|---|---|---|---|---|
| C34-B | B5 | 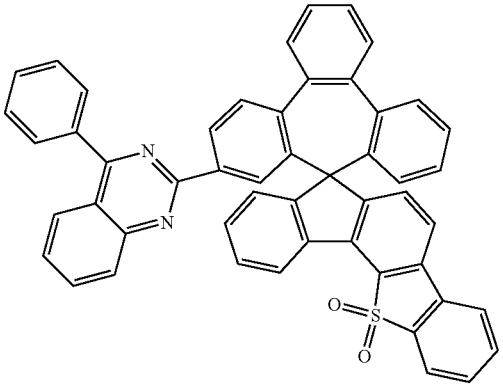<br>Compound XXIV | 83 | $C_{51}H_{30}N_2O_2S$/ 734.86 |
| C34-B | B6 | 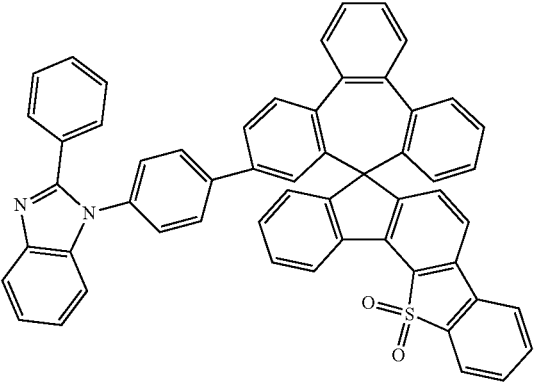<br>Compound XXV | 71 | $C_{56}H_{34}N_2O_2S$/ 798.95 |
| C34-B | B7 | 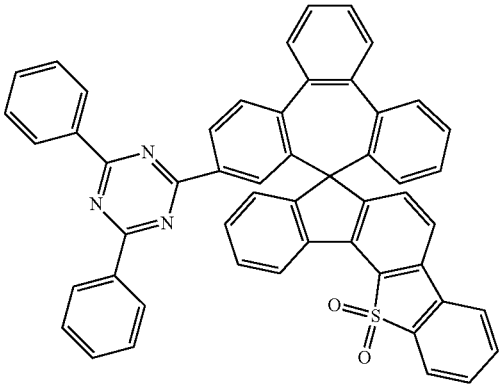<br>Compound XXVI | 63 | $C_{52}H_{31}N_3O_2S$/ 761.89 |

TABLE 5-continued reactants and intermediates adopted to prepare Compounds I to XXVII and their yields, formulae, and FD-MS data.

Claimed Compound

| Intermediate No. | Reactant No. | Chemical Structure of Claimed Compound | Yield (%) | Formula/ Mass (M+) |
|---|---|---|---|---|
| C35 | B2 | 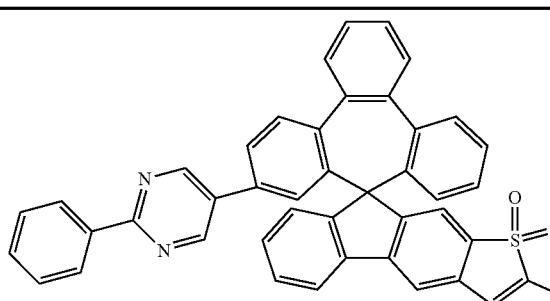<br>Compound XXVII | 66 | $C_{47}H_{28}N_2O_2S$/ 684.79 |

Modifications of Compounds I to XXVII

In addition to the Compounds I to XXVII, one person skilled in the art can react any Intermediate C, i.e., the foresaid Intermediate Cn or Cn-B, with any Reactant Bn through a reaction mechanism similar to Scheme I to synthesize other desired claimed novel compounds.

Preparation of OLED Devices

A glass substrate coated with an ITO layer (abbreviated as ITO substrate) in a thickness of 1500 Å was placed in distilled water containing a detergent dissolved therein, and was ultrasonically washed. The detergent was a product manufactured by Fischer Co., and the distilled water was distilled water filtered twice through a filter (Millipore Co.). After the ITO layer had been washed for 30 minutes, it was ultrasonically washed twice with distilled water for 10 minutes. After the completion of washing, the glass substrate was ultrasonically washed with isopropyl alcohol, acetone and methanol solvents and then dried, after which it was transported to a plasma cleaner. Then the substrate was cleaned with oxygen plasma for 5 minutes, and then transferred to a vacuum evaporator.

After that, various organic materials and metal materials were sequentially deposited on the ITO substrate to obtain the OLED device of Examples 1 to 19. The vacuum degree during the deposition was maintained at $1\times10^{-6}$ to $3\times10^{-7}$ torr. Herein, the ITO substrate was deposited with a first hole injection layer (HIL-1), a second hole injection layer (HIL-2), a first hole transporting layer(HTL-1), a second hole transporting layer (HTL-2), a blue/green/red emission layer (BEL/GEL/REL), an electron transporting layer (ETL), an electron injection layer (EIL), and a cathode (Cthd).

Herein, HAT was a material for forming HIL-1 and was a dopant for forming HIL-2; HI-2 was a material for forming HIL-2; HT-1 and HT-2 were respectively materials for forming HTL-1 and HTL-2; conventional ET and novel compounds of the present invention were materials for forming ETL; Liq was a dopant for forming ETL and was a material for forming EIL. RH/GH/BH were host materials for forming REL/GEL/BEL, and RD/GD/BD were dopants for forming REL/GEL/BEL. The main difference of the OLEDs between the Examples and Comparative Examples was that the ETL of OLED in the following comparative examples was made of BCP but the ETLs of OLEDs in following examples were made of the novel compounds of the present invention as listed in Table 5. The detailed chemical structures of foresaid commercial materials were listed in Table 6.

TABLE 6
chemical structures of commercial materials for OLED devices.
| HT-1 | 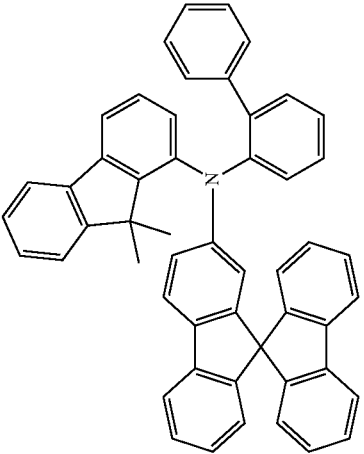 | BD |
| HI-2 | 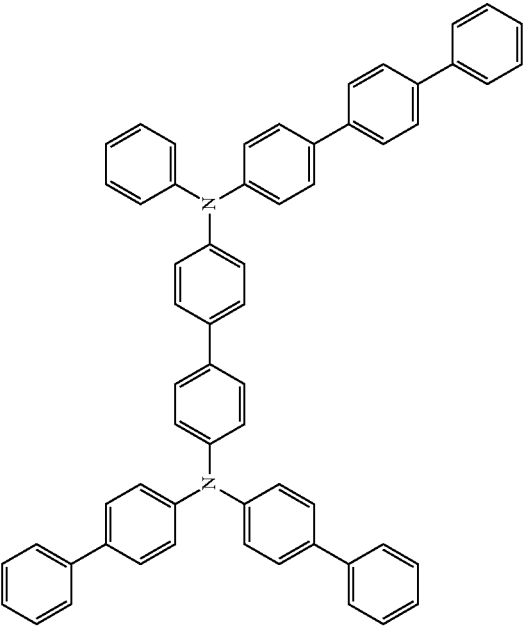 | BH |
| HAT | 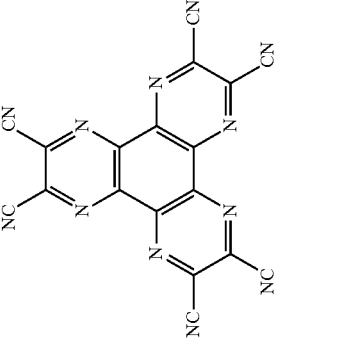 | HT-2 |

TABLE 6-continued
chemical structures of commercial materials for OLED devices.
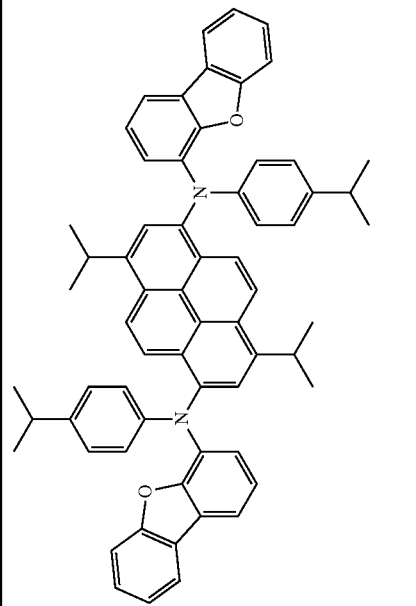
RH
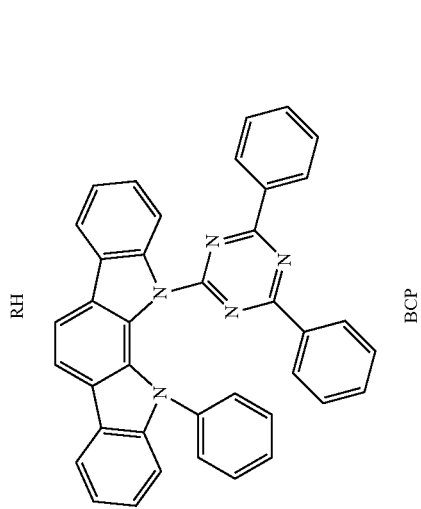
BCP
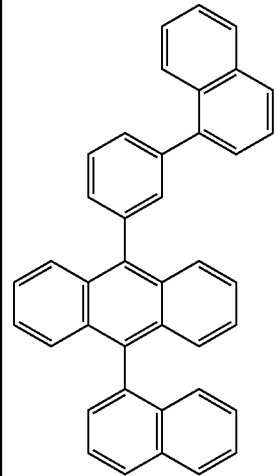
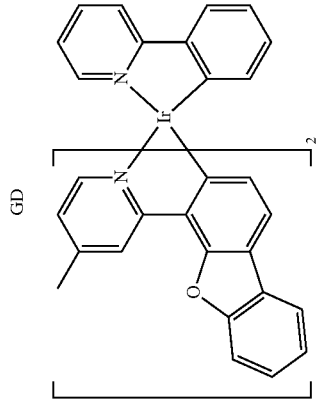
GD        Liq
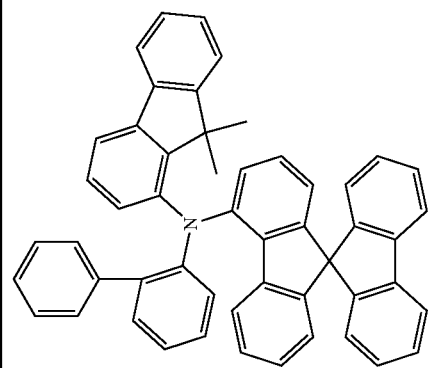
GH
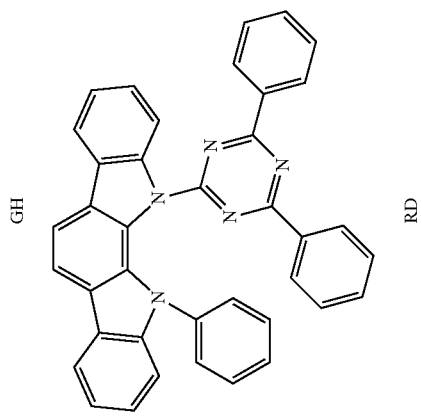
RD TABLE 6-continued
chemical structures of commercial materials for OLED devices.
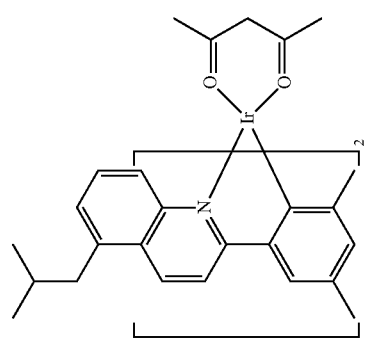
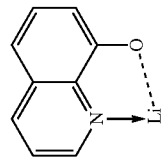
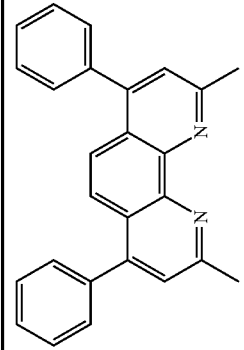

Preparation of Red OLED Devices

To prepare the red OLED device, multiple organic layers were respectively deposited on the ITO substrate according to the sequence as listed in Table 7, and the materials and the thicknesses of the organic layers in red OLED devices were also listed in Table 7.

TABLE 7 coating sequence, materials and thickness of the organic layers in red OLED device.

| Coating Sequence | Layer | Material | Thickness |
|---|---|---|---|
| 1 | HIL-1 | HAT | 100 Å |
| 2 | HIL-2 | HI-2 doped with 5.0 wt % of HAT | 2100 Å |
| 3 | HTL-1 | HT-1 | 100 Å |
| 4 | HTL-2 | HT-2 | 100 Å |
| 5 | REL | RH doped with 3.5 wt % of RD | 300 Å |
| 6 | ETL | Commercial ET/novel compounds doped with 35.0 wt % of Liq | 350 Å |
| 7 | EIL | Liq | 15 Å |
| 8 | Cthd | Al | 1500 Å |

Preparation of Green OLED Devices

To prepare the green OLED device, multiple organic layers were respectively deposited on the ITO substrate according to the sequence as listed in Table 8, and the materials and the thicknesses of the organic layers in green OLED devices were also listed in Table 8.

TABLE 8 coating sequence, materials and thickness of the layers in green OLED device.

| Coating Sequence | Layer | Material | Thickness |
|---|---|---|---|
| 1 | HIL-1 | HAT | 100 Å |
| 2 | HIL-2 | HI-2 doped with 5.0 wt % of HAT | 1300 Å |
| 3 | HTL-1 | HT-1 | 100 Å |
| 4 | HTL-2 | HT-2 | 100 Å |
| 5 | GEL | GH doped with 10.0 wt % of GD | 400 Å |
| 6 | ETL | Commercial ET/novel compounds doped with 35.0 wt % of Liq | 350 Å |
| 7 | EIL | Liq | 15 Å |
| 8 | Cthd | Al | 1500 Å |

Preparation of Blue OLED Devices

To prepare the blue OLED device, multiple organic layers were respectively deposited on the ITO substrate according to the sequence as listed in Table 9, and the materials and the thicknesses of the organic layers in blue OLED devices were also listed in Table 9.

TABLE 9 coating sequence, materials and thickness of the layers in blue OLED device.

| Coating Sequence | Layer | Material | Thickness |
|---|---|---|---|
| 1 | HIL-1 | HAT | 100 Å |
| 2 | HIL-2 | HI-2 doped with 5.0 wt % of HAT | 750 Å |
| 3 | HTL-1 | HT-1 | 100 Å |
| 4 | HTL-2 | HT-2 | 100 Å |
| 5 | BEL | BH doped with 3.5 wt % of BD | 250 Å |
| 6 | ETL | Commercial ET/novel compounds doped with 35.0 wt % of Liq | 250 Å |
| 7 | EIL | Liq | 15 Å |
| 8 | Cthd | Al | 1500 Å |

Performance of OLED Device

To evaluate the performance of OLED devices, red, green, and blue OLED devices were measured by PR650 as photometer and Keithley 2400 as power supply. Color coordinates (x,y) were determined according to the CIE chromaticity scale (Commission Internationale de L'Eclairage, 1931). The results were shown in Table 10. For the blue and red OLED devices, the data were collected at 1000 nits. For the green OLED devices, the data were collected at 3000 nits.

The materials of ETL, color and data of CIE, driving voltage, current efficiency, and external quantum efficiency (EQE) of each of Examples 1 to 19 and Comparative Example 1 to 3 were listed in Table 10.

TABLE 10 materials of ETL, colors, CIEs, voltages, current efficiencies, and EQE of OLED devices of Examples 1 to 19 and Comparative Examples 1 to 3.

| OLED device No. | Material of ETL | Color, CIE(x, y) | Voltage (V) | Current Efficiency (cd/A) | EQE (%) |
|---|---|---|---|---|---|
| Example 1 | Compound XXII | B(0.130, 0.149) | 4.94 | 9.46 | 6.69 |
| Example 2 | Compound XXV | B(0.129, 0.152) | 5.38 | 10.8 | 7.75 |
| Example 3 | Compound I | B(0.129, 0.160) | 5.49 | 9.89 | 7.36 |
| Example 4 | Compound XIX | B(0.129, 0.155) | 4.68 | 10.7 | 7.62 |
| Example 5 | Compound XIII | B(0.129, 0.154) | 4.73 | 11.5 | 6.27 |
| Example 6 | Compound XXVI | B(0.129, 0.155) | 4.58 | 10.2 | 7.54 |
| Example 7 | Compound IV | B(0.130, 0.146) | 5.59 | 8.47 | 6.05 |
| Example 8 | Compound XIV | B(0.129, 0.158) | 4.91 | 9.86 | 6.96 |
| Example 9 | Compound XXIV | B(0.129, 0.150) | 4.54 | 10.9 | 7.67 |
| Example 10 | Compound III | B(0.129, 0.149) | 5.23 | 9.86 | 6.88 |
| Example 11 | Compound XVIII | B(0.129, 0.149) | 5.23 | 9.86 | 6.88 |
| Comparative Example 1 | BCP | B(0.130, 0.142) | 6.71 | 6.98 | 4.88 |
| Example 12 | Compound IX | G(0.311, 0.640) | 3.87 | 72.6 | 17.27 |
| Example 13 | Compound XII | G(0.317, 0.637) | 4.45 | 72.0 | 17.79 |
| Example 14 | Compound XXIII | G(0.315, 0.638) | 3.75 | 74.4 | 17.86 |
| Example 15 | Compound XI | G(0.319, 0.636) | 4.52 | 72.8 | 17.66 |
| Comparative Example 2 | BCP | G(0.313, 0.638) | 4.67 | 70.3 | 16.95 |
| Example 16 | Compound VII | R(0.661, 0.338) | 4.06 | 26.6 | 18.19 |
| Example 17 | Compound XXI | R(0.661, 0.338) | 3.93 | 27.0 | 16.37 |
| Example 18 | Compound XV | R(0.660, 0.338) | 4.09 | 24.9 | 17.41 |
| Example 19 | Compound X | R(0.659, 0.339) | 3.85 | 24.5 | 16.14 |
| Comparative Example 3 | BCP | R(0.659, 0.340) | 4.16 | 24.1 | 16.05 |

Based on the results, in comparison with the commercial electron transport material (BCP), adopting Compounds I to XXVII as the electron transport material can reduce the driving voltage and improve the current efficiency and the external quantum efficiency of the red, green, or blue OLEDs. It demonstrated that the novel compound of the present invention is suitable as an electron transport material for any color OLEDs, and allows the OLEDs using the same to have low driving voltage and improved current efficiency as well as improved external quantum efficiency.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A compound represented by the following Formula (I):

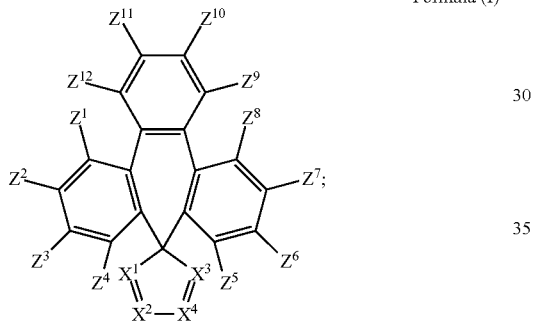

Formula (I)

wherein $X^1$ and $X^2$ are each independently $C(R^a)$, the two $(R^a)$s are the same or different, and the two $(R^a)$s are joined together to form an aryl ring;

wherein $X^3$ and $X^4$ are each independently $C(R^b)$, the two $(R^b)$s are the same or different, and the two $(R^b)$s are joined together to form a heteroaryl ring containing at least one furan group, at least one thiophene group, or at least one thiophene S,S-dioxide group;

wherein $Z^1$ to $Z^{12}$ are each independently selected from the group consisting of: a hydrogen atom, a deuterium atom, a trifuloromethyl group, a halogen group, a cyano group, a nitro group, an alkyl group having 1 to 40 carbon atoms, an alkenyl group having 2 to 40 carbon atoms, an alkynyl group having 2 to 40 carbon atoms, a cycloalkyl group having 3 to 60 ring carbon atoms, a heterocycloalkyl group having 3 to 60 ring carbon atoms, an aryl group having 6 to 60 ring carbon atoms, a heteroaryl group having 3 to 60 ring carbon atoms, an alkoxy group having 1 to 40 carbon atoms, an aryloxy group having 6 to 60 ring carbon atoms, an alkylsilyl group having 1 to 40 carbon atoms, an arylsilyl group having 6 to 60 ring carbon atoms, an alkylboron group having 1 to 40 carbon atoms, an arylboron group having 6 to 60 ring carbon atoms, a phosphine group having 1 to 40 carbon atoms, and a phosphine oxide group having 1 to 40 carbon atoms.

2. The compound as claimed in claim 1, wherein the compound is represented by the following Formulae (I-I) to (I-XVIII):

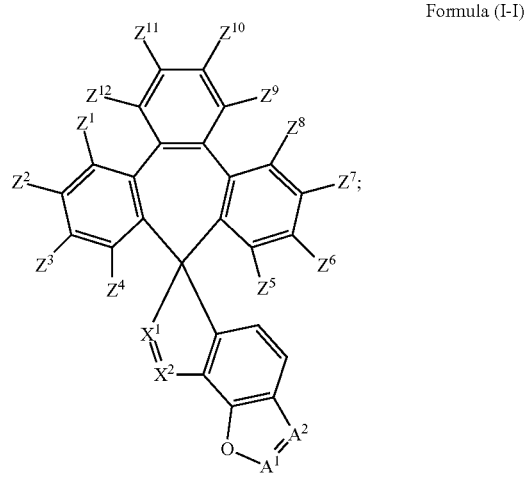

Formula (I-I)

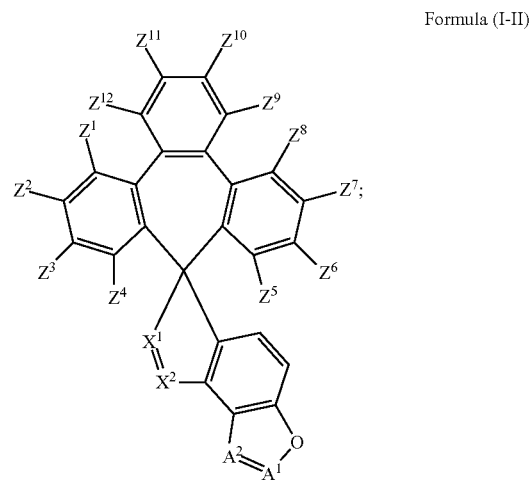

Formula (I-II)

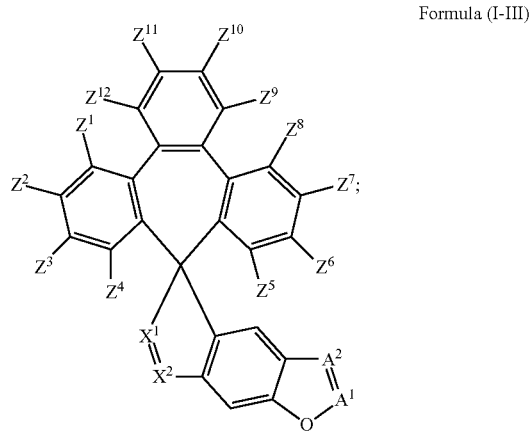

Formula (I-III)

-continued
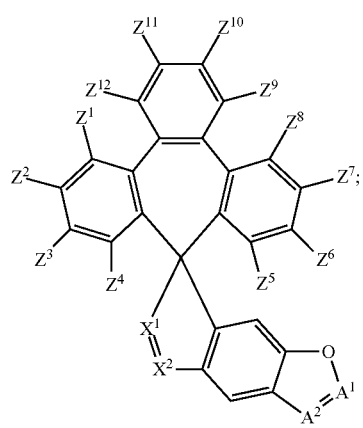
Formula (I-IV)
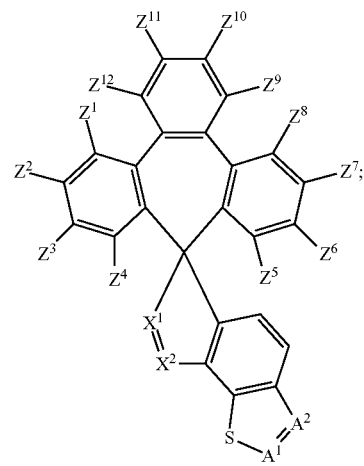
Formula (I-VII)
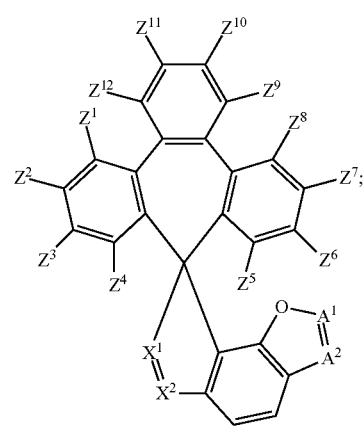
Formula (I-V)
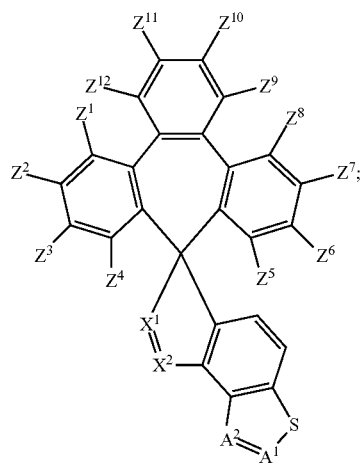
Formula (I-VIII)
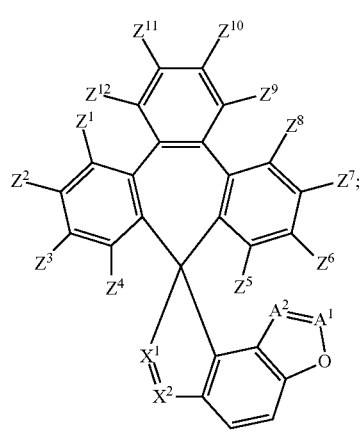
Formula (I-VI)
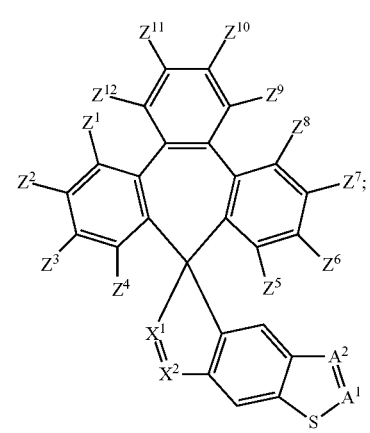
Formula (I-IX)

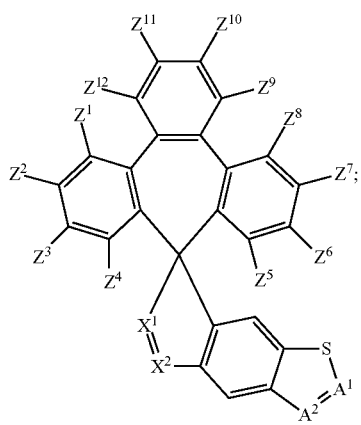
Formula (I-X)
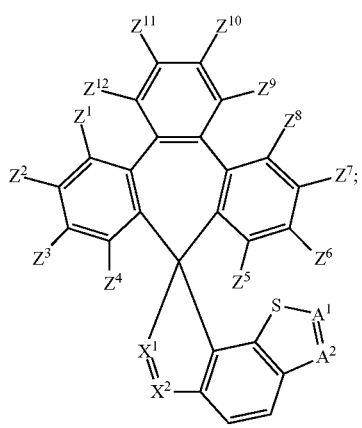
Formula (I-XI)
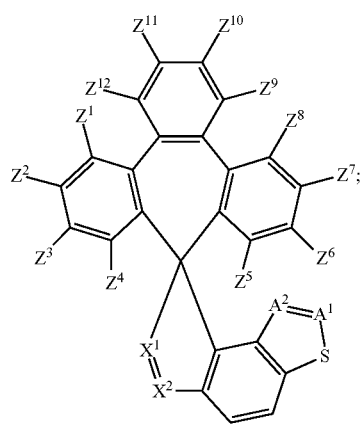
Formula (I-XII)
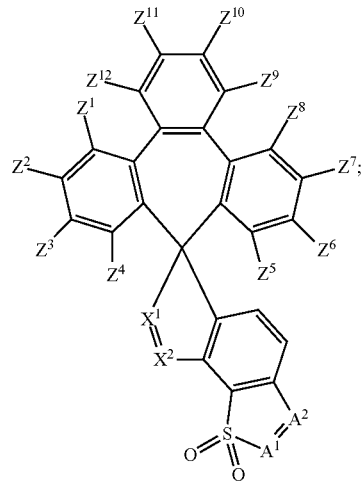
Formula (I-XIII)
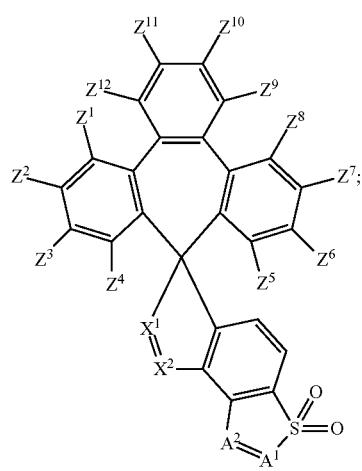
Formula (I-XIV)
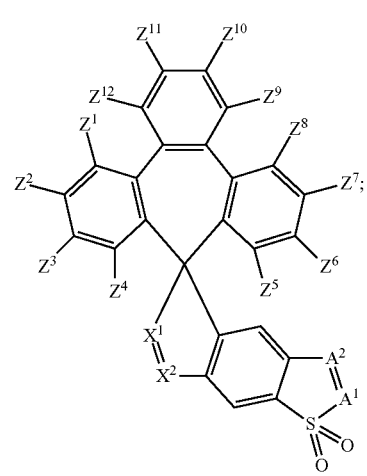
Formula (I-XV)

181

-continued

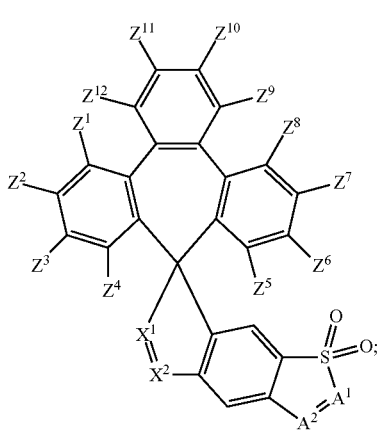

Formula (I-XVI)

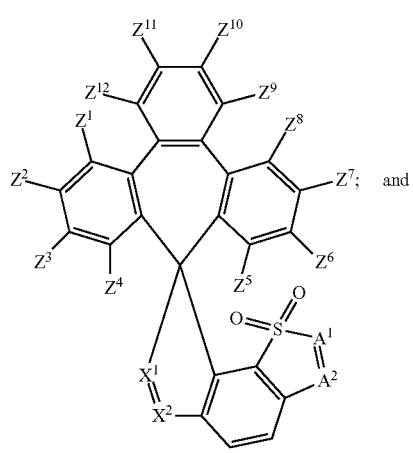

Formula (I-XVII)

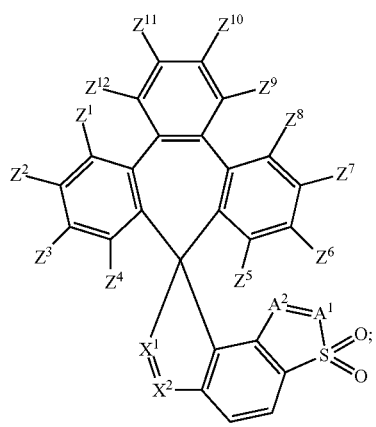

Formula (I-XVIII)

wherein $A^1$ and $A^2$ are each independently $C(R^c)$, the two $(R^c)$s are the same or different, and the two $(R^c)$s are joined together to form an aromatic structure contained in the heteroaryl ring extended from $X^3$ and $X^4$.

3. The compound as claimed in claim 2, wherein the aromatic structure contained in the heteroaryl ring is a substituted or unsubstituted 6 to 20-membered carbon aromatic cyclic structure.

4. The compound as claimed in claim 3, wherein the substituted or unsubstituted 6 to 20-membered carbon aromatic cyclic structure is selected from the group consisting of: a substituted or unsubstituted benzene structure, a substituted or unsubstituted naphthalene structure, a substituted or unsubstituted anthracene structure, a substituted or unsubstituted phenanthrene structure, a substituted or unsubstituted fluorene structure, a substituted or unsubstituted pyrene structure, a substituted or unsubstituted benzophenanthrene structure, a substituted or unsubstituted benzopyrene structure, a substituted or unsubstituted fluoranthene structure, and a substituted or unsubstituted benzofluoranthene structure.

5. The compound as claimed in claim 1, wherein the aryl ring extended from $X^1$ and $X^2$ is a substituted or unsubstituted 6 to 60-membered carbon ring.

6. The compound as claimed in claim 5, wherein the substituted or unsubstituted 6 to 60-membered carbon ring is selected from the group consisting of: a substituted or unsubstituted benzene ring, a substituted or unsubstituted naphthalene ring, a substituted or unsubstituted anthracene ring, a substituted or unsubstituted phenanthrene ring, a substituted or unsubstituted fluorene ring, a substituted or unsubstituted pyrene ring, a substituted or unsubstituted benzophenanthrene ring, a substituted or unsubstituted benzopyrene ring, a substituted or unsubstituted fluoranthene ring, and a substituted or unsubstituted benzofluoranthene ring.

7. The compound as claimed in claim 6, wherein the substituted or unsubstituted 6 to 60-membered carbon ring is a substituted or unsubstituted benzene structure.

8. The compound as claimed in claim 1, wherein at least one of $Z^1$ to $Z^8$ in Formula (I) is selected from the group consisting of: an alkyl group having 1 to 40 carbon atoms and substituted with at least one functional group, an alkenyl group having 2 to 40 carbon atoms and substituted with at least one functional group, an alkynyl group having 2 to 40 carbon atoms and substituted with at least one functional group, a cycloalkyl group having 3 to 60 ring carbon atoms and substituted with at least one functional group, a heterocycloalkyl group having 3 to 60 ring carbon atoms and substituted with at least one functional group, an aryl group having 6 to 60 ring carbon atoms and substituted with at least one functional group, a heteroaryl group having 3 to 60 ring carbon atoms containing at least one nitrogen atom, an alkoxy group having 1 to 40 carbon atoms and substituted with at least one functional group, an aryloxy group having 6 to 60 ring carbon atoms and substituted with at least one functional group, an alkylsilyl group having 1 to 40 carbon atoms and substituted with at least one functional group, an arylsilyl group having 6 to 60 ring carbon atoms and substituted with at least one functional group, an alkylboron group having 1 to 40 carbon atoms and substituted with at least one functional group, an arylboron group having 6 to 60 ring carbon atoms, a phosphine group having 1 to 40 ring carbon atoms and substituted with at least one functional group, and a phosphine oxide group having 1 to 40 carbon atoms and substituted with at least one functional group, wherein said functional group is selected from the group consisting of: a cyano group, a nitro group, a trifluoromethyl group, a fluoro group, and a chloro group.

9. The compound as claimed in claim 1, wherein at least one of $Z^1$ to $Z^8$ in Formula (I) is selected from the group consisting of:

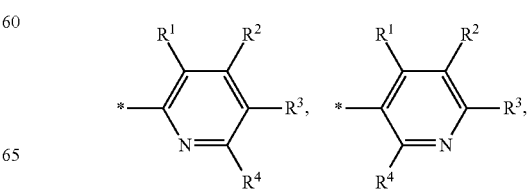

-continued
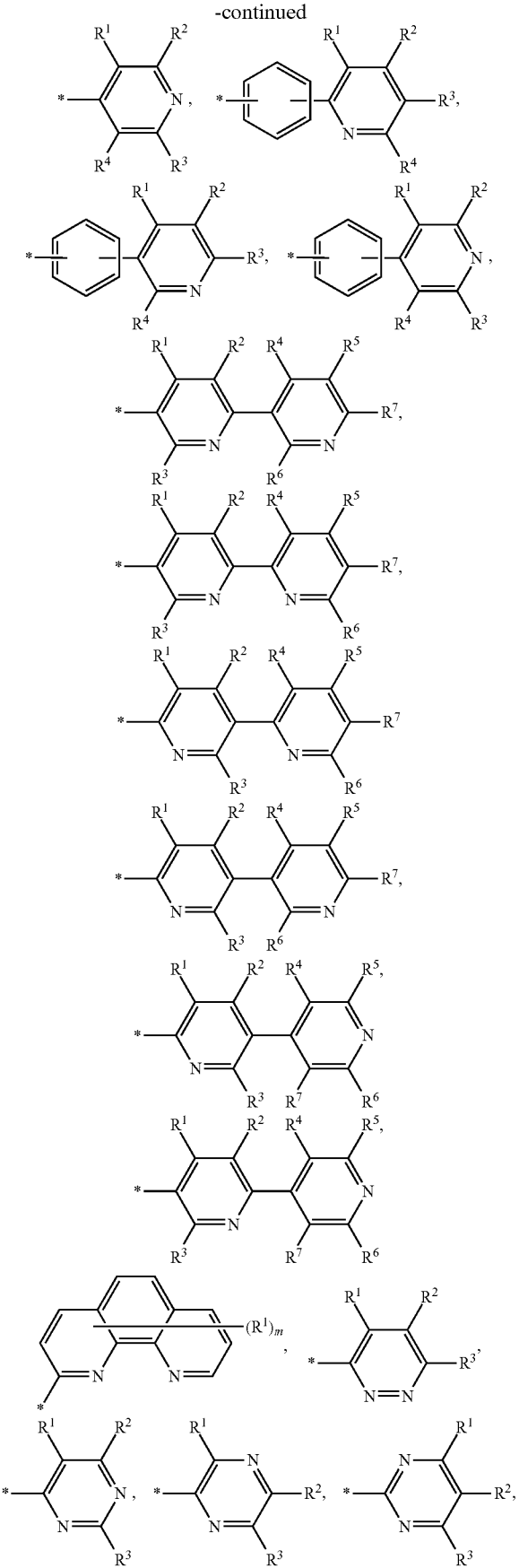
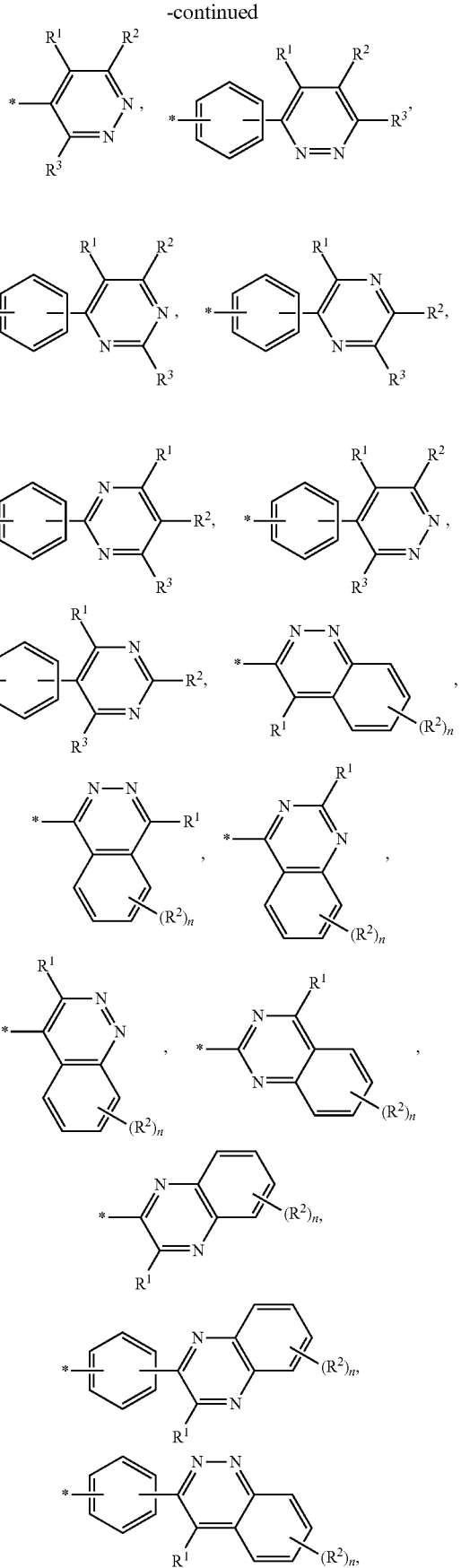

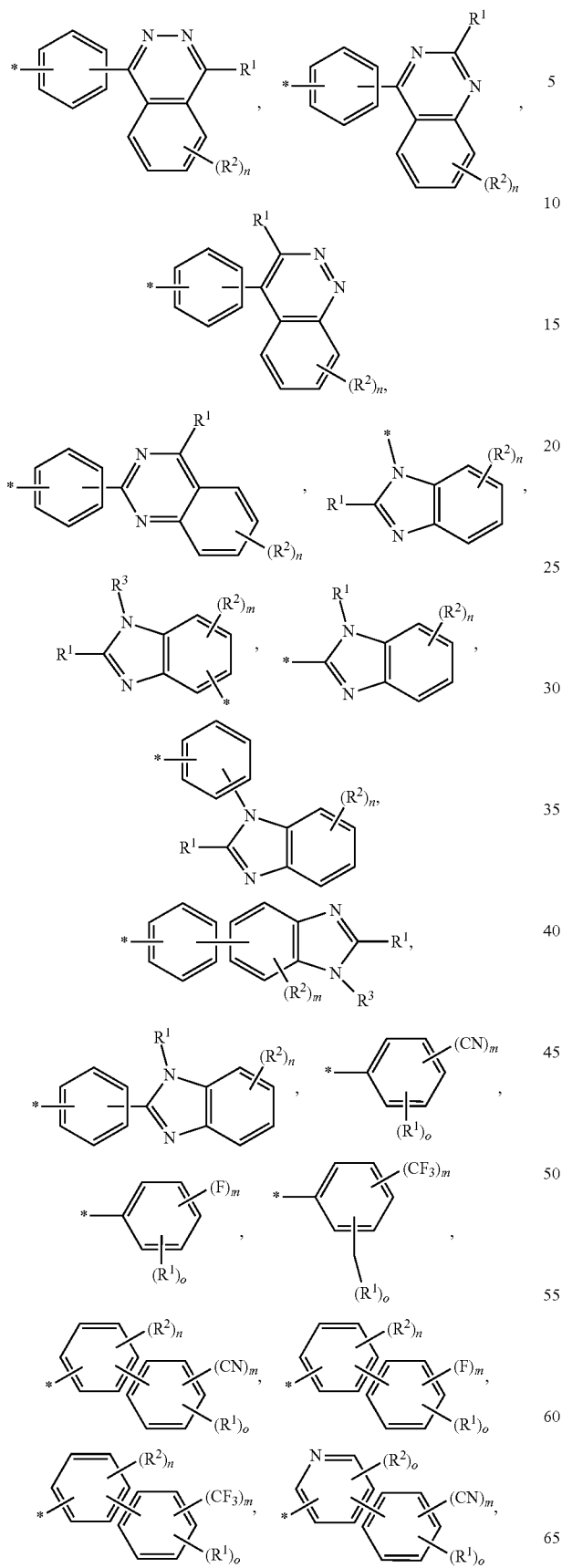
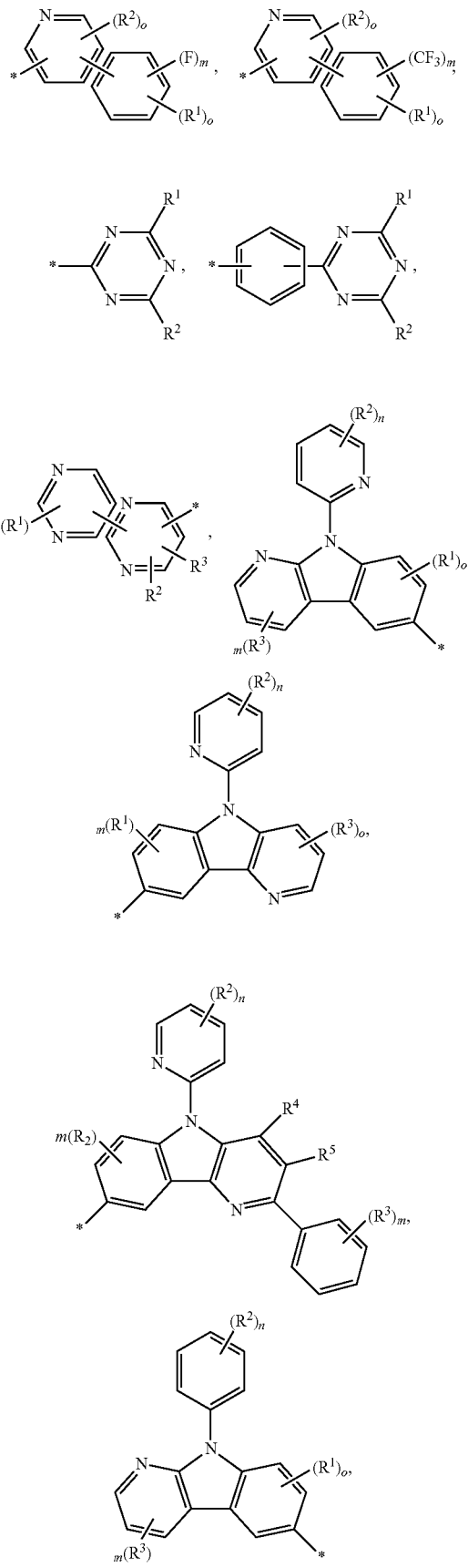

-continued

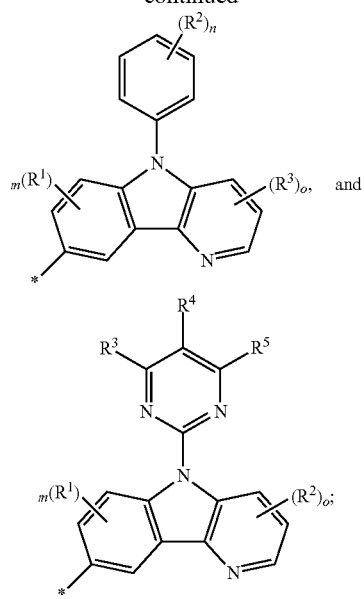

wherein R¹ to R⁷ are each independently selected from the group consisting of: a hydrogen atom, a deuterium atom, a trifluoromethyl group, a halogen group, a cyano group, a nitro group, an alkyl group having 1 to 12 carbon atoms, an alkenyl group having 2 to 12 carbon atoms, an alkynyl group having 2 to 12 carbon atoms, a cycloalkyl group having 3 to 30 ring carbon atoms, a heterocycloalkyl group having 3 to 30 ring carbon atoms, an aryl group having 6 to 30 ring carbon atoms, a heteroaryl group having 3 to 20 ring carbon atoms, an alkoxy group having 1 to 40 carbon atoms, an aryloxy group having 6 to 30 ring carbon atoms, an alkylsilyl group having 1 to 40 carbon atoms, an arylsilyl group having 6 to 30 ring carbon atoms, an alkylboron group having 1 to 40 carbon atoms, an arylboron group having 6 to 30 ring carbon atoms, a phosphine group having 1 to 30 carbon atoms, and a phosphine oxide group having 1 to 30 carbon atoms;

wherein n is a positive integral from 0 to 4, m is a positive integral from 0 to 3, o is a positive integral from 0 to 3, and the total of m and o is not more than 5.

10. The compound as claimed in claim 1, wherein at least one of $Z^2$, $Z^3$, $Z^6$, and $Z^7$ in Formula (I) is selected from the group consisting of:

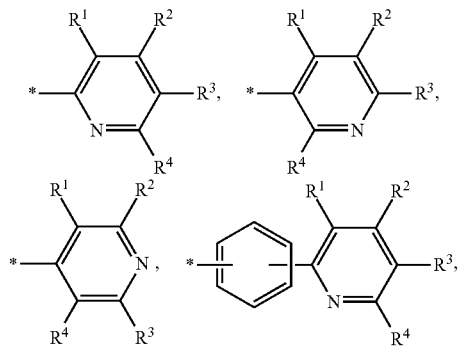

-continued

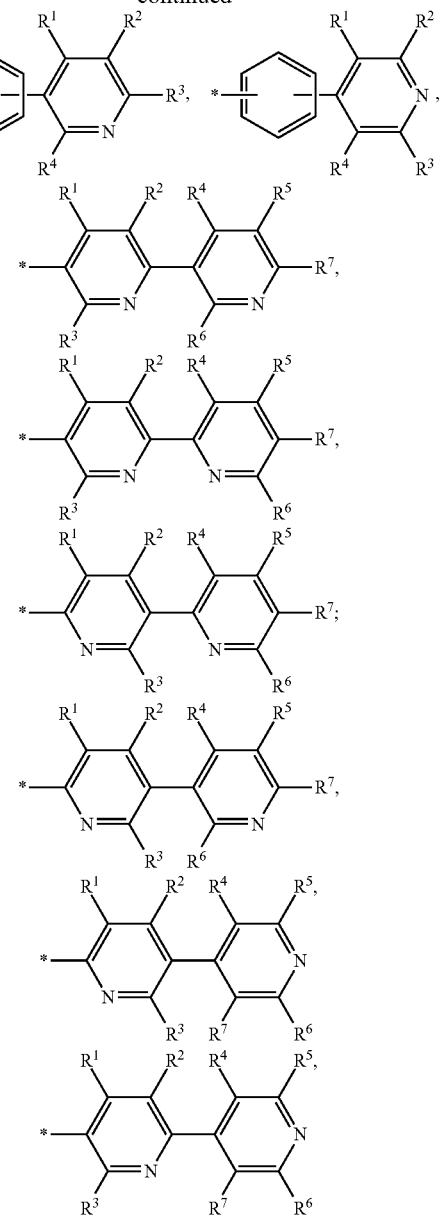

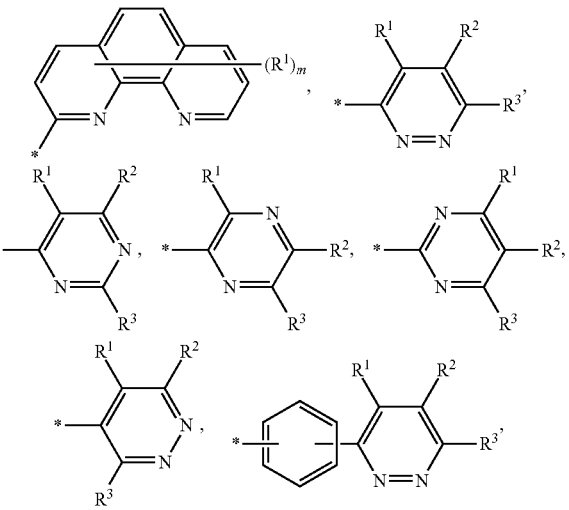

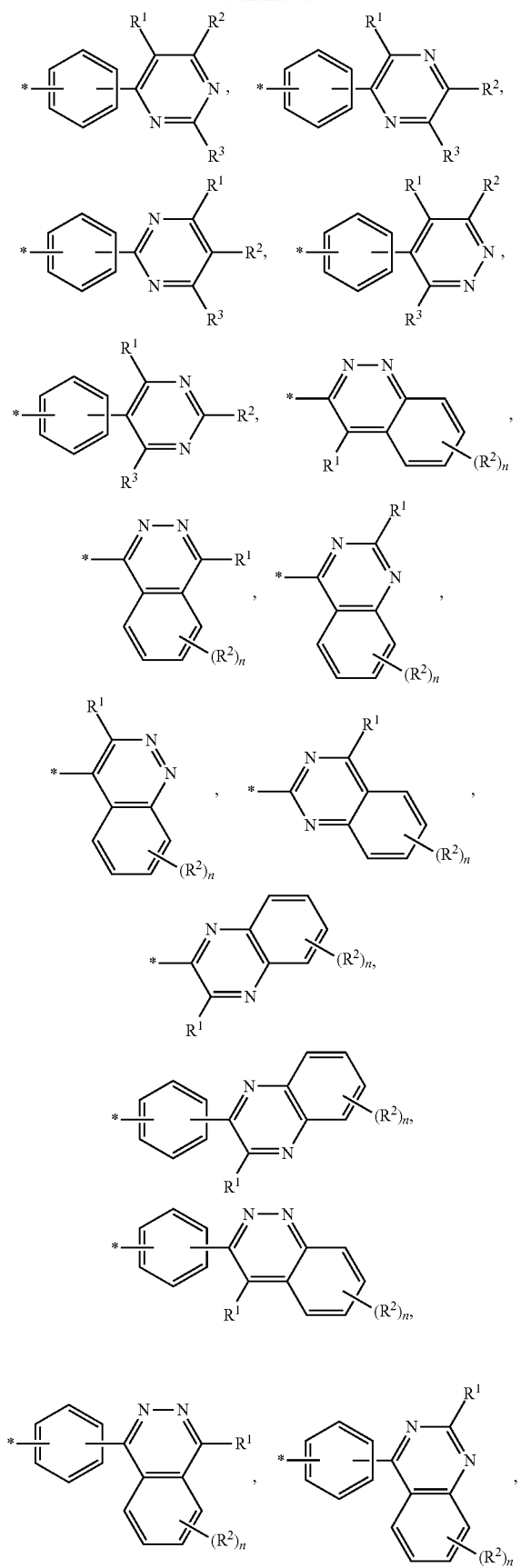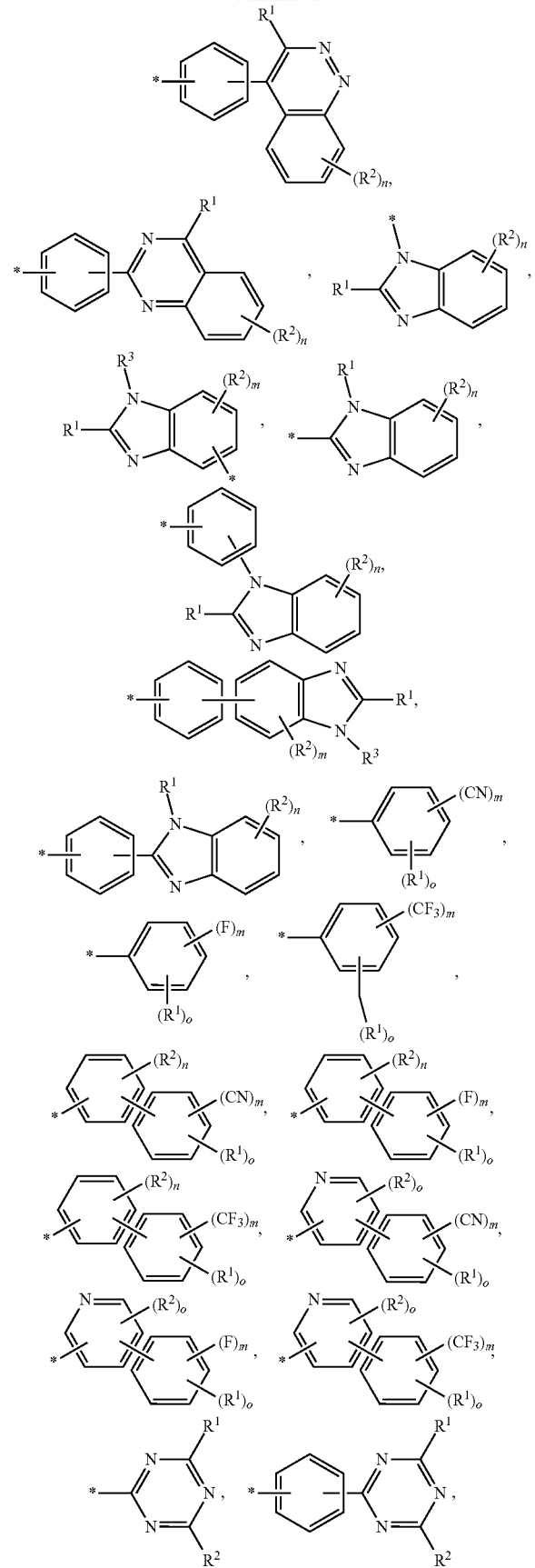

-continued

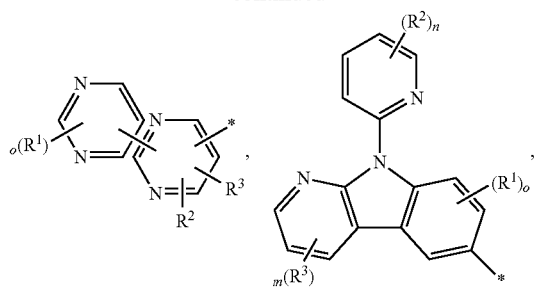

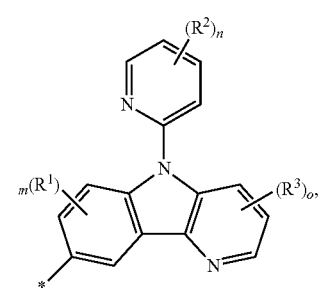

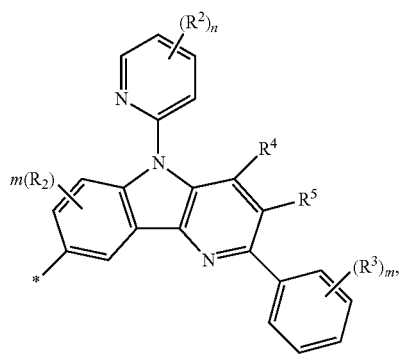

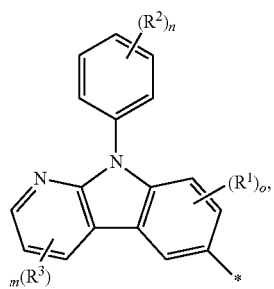

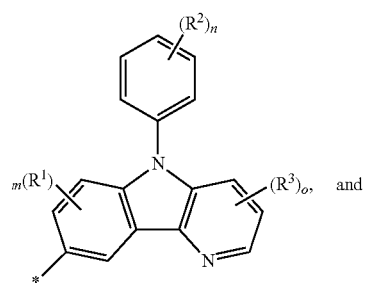

-continued

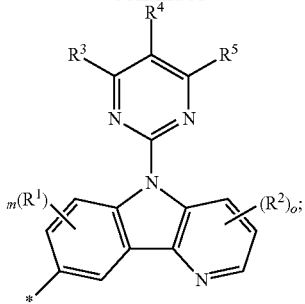

wherein $R^1$ to $R^7$ are each independently selected from the group consisting of: a hydrogen atom, a deuterium atom, a trifluoromethyl group, a halogen group, a cyano group, a nitro group, an alkyl group having 1 to 12 carbon atoms, an alkenyl group having 2 to 12 carbon atoms, an alkynyl group having 2 to 12 carbon atoms, a cycloalkyl group having 3 to 30 ring carbon atoms, a heterocycloalkyl group having 3 to 30 ring carbon atoms, an aryl group having 6 to 30 ring carbon atoms, a heteroaryl group having 3 to 20 ring carbon atoms, an alkoxy group having 1 to 40 carbon atoms, an aryloxy group having 6 to 30 ring carbon atoms, an alkylsilyl group having 1 to 40 carbon atoms, an arylsilyl group having 6 to 30 ring carbon atoms, an alkylboron group having 1 to 40 carbon atoms, an arylboron group having 6 to 30 ring carbon atoms, a phosphine group having 1 to 30 carbon atoms, and a phosphine oxide group having 1 to 30 carbon atoms;

wherein n is a positive integral from 0 to 4, m is a positive integral from 0 to 3, o is a positive integral from 0 to 3, and the total of m and o is not more than 5;

wherein $Z^1$, $Z^4$, $Z^5$, $Z^8$ are each independently selected from the group consisting of: a hydrogen atom, a deuterium atom, a halogen group, a cyano group, a nitro group, an alkyl group having 1 to 12 carbon atoms, an alkenyl group having 2 to 12 carbon atoms, and an alkynyl group having 2 to 12 carbon atoms.

11. The compound as claimed in claim 10, wherein at least one of $Z^2$, $Z^3$, $Z^6$, and $Z^7$ in Formula (I) is selected from the group consisting of:

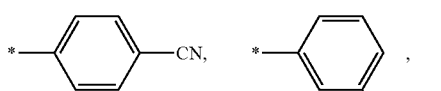

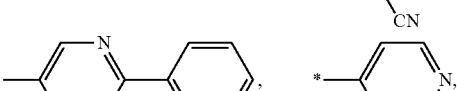

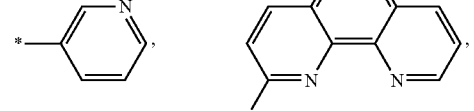

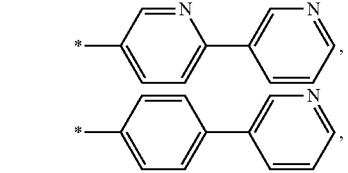

193
-continued
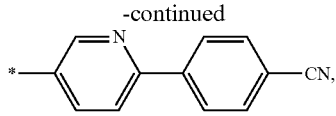
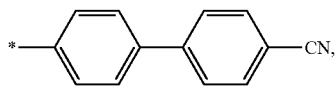
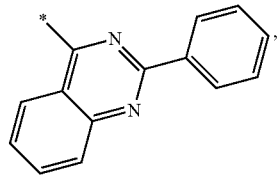
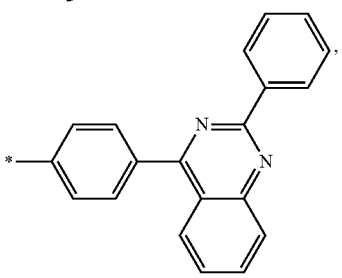
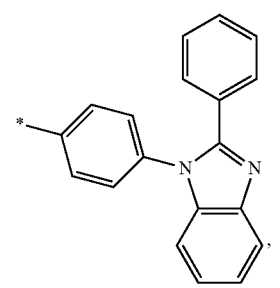
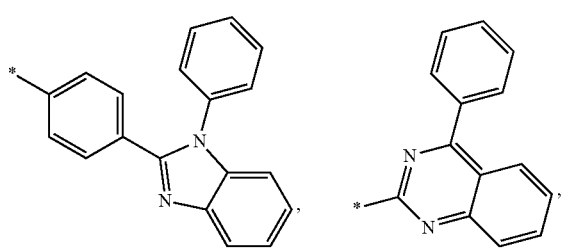
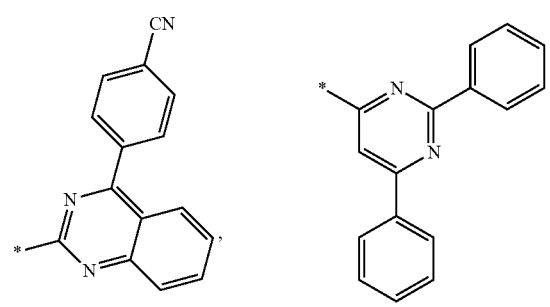
194
-continued
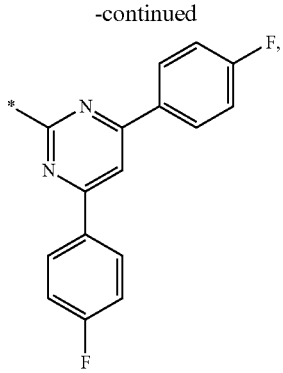
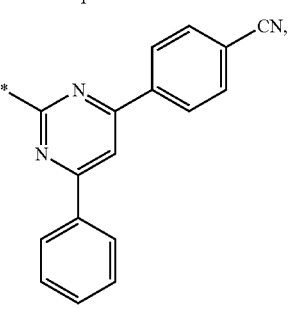
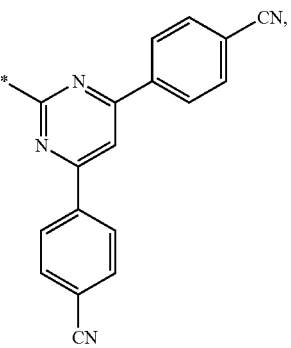
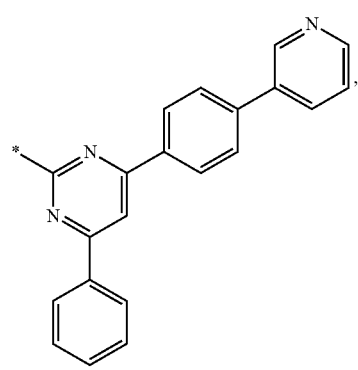
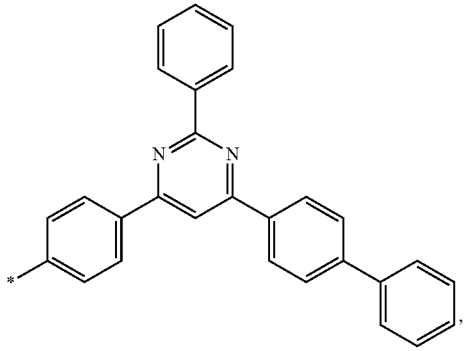

-continued
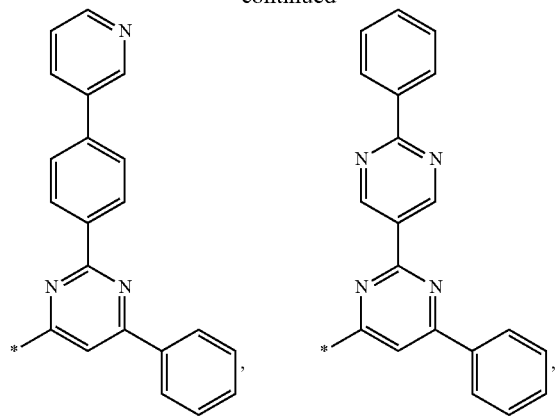
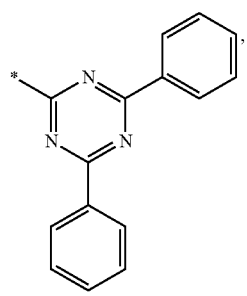
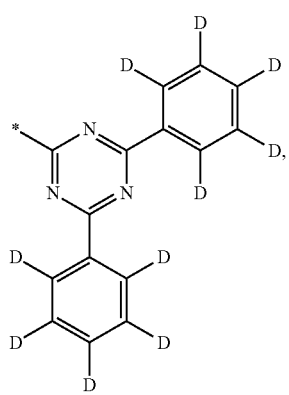
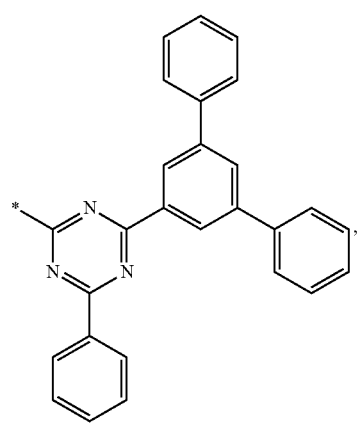
-continued
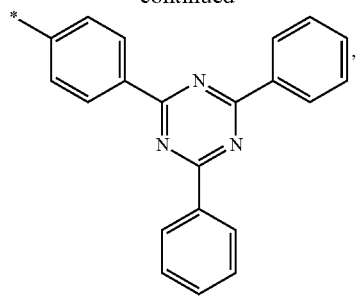
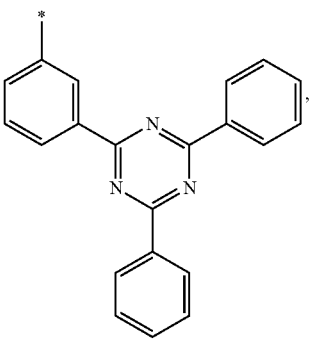
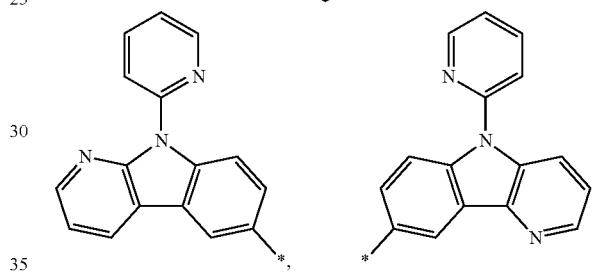
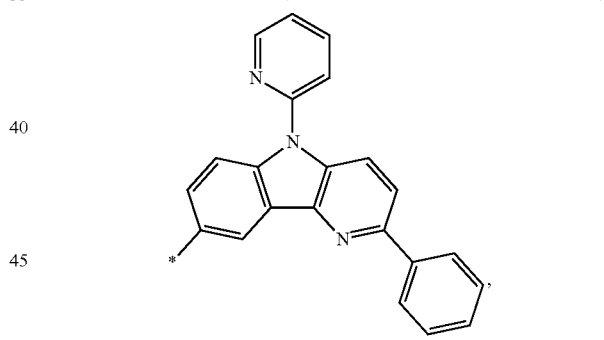
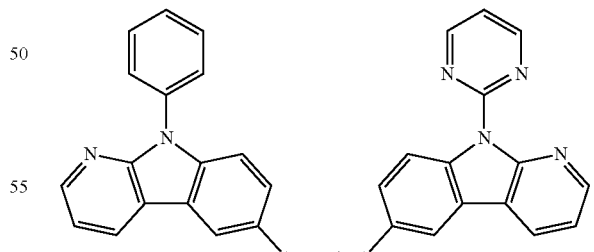
12. The compound as claimed in claim 1, wherein $Z^9$ to $Z^{12}$ in Formula (I) are each independently selected from the group consisting of: a hydrogen atom, a deuterium atom, a halogen group, a cyano group, a nitro group, an alkyl group having 1 to 12 carbon atoms, an alkenyl group having 2 to 12 carbon atoms, and an alkynyl group having 2 to 12 carbon atoms.

13. The compound as claimed in claim 1, wherein the compound is selected from the group consisting of:
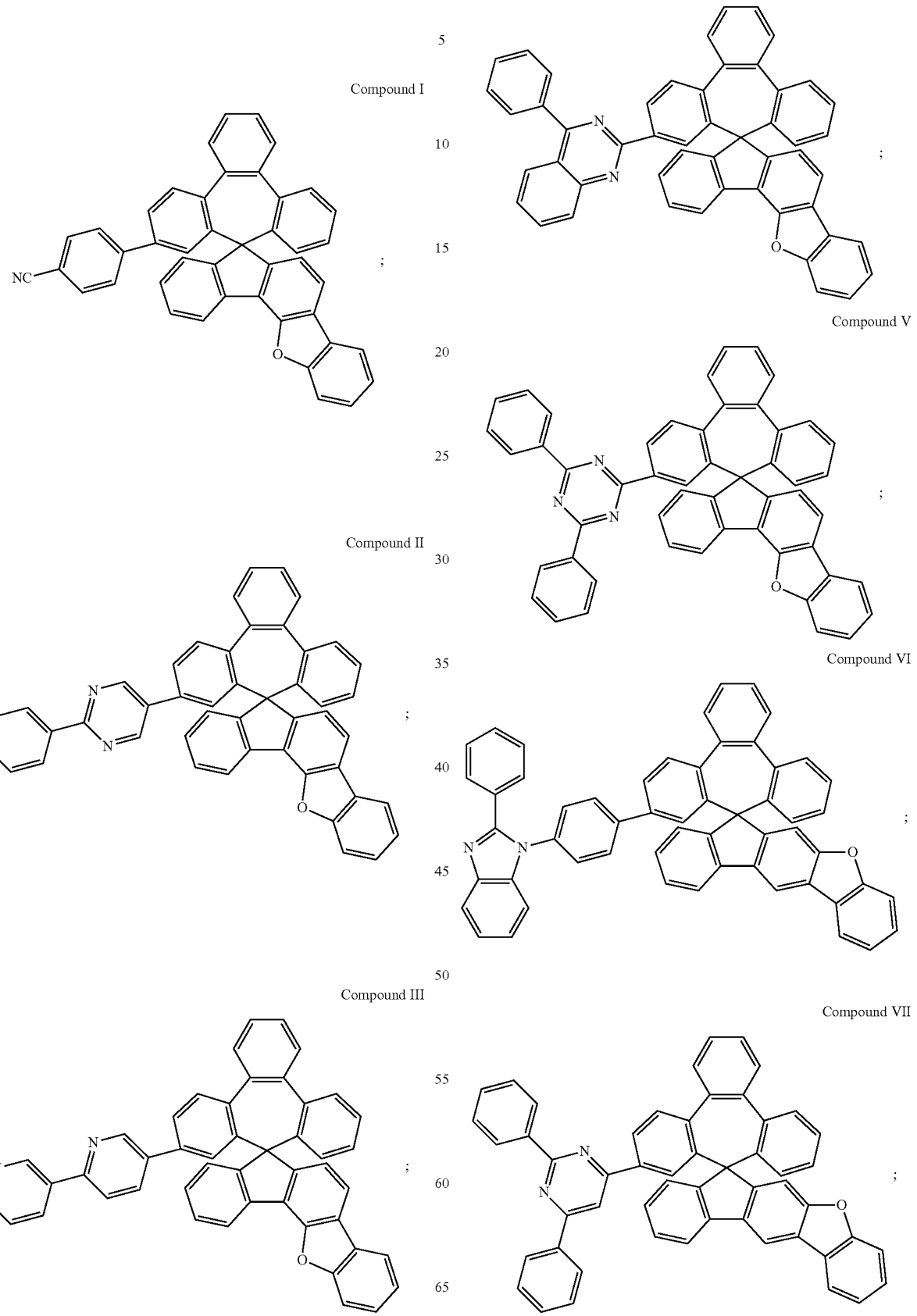

Compound VIII
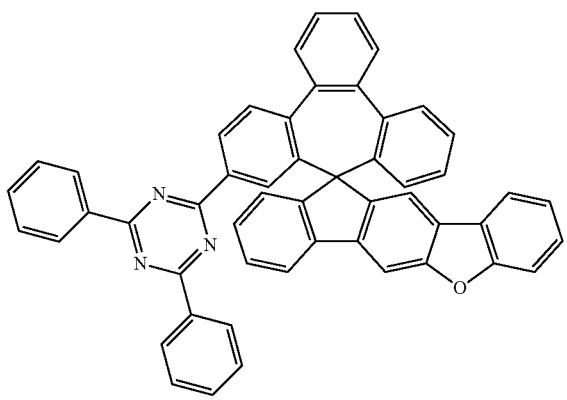
Compound IX
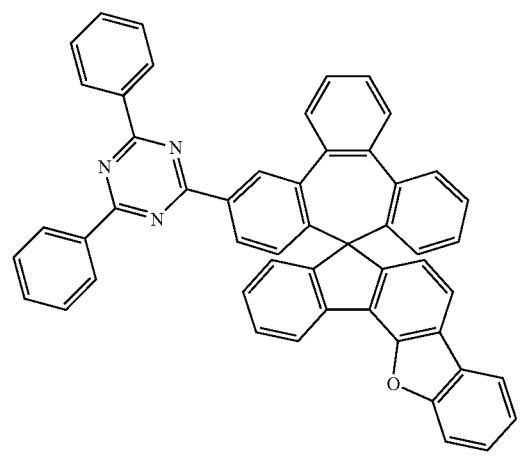
Compound X
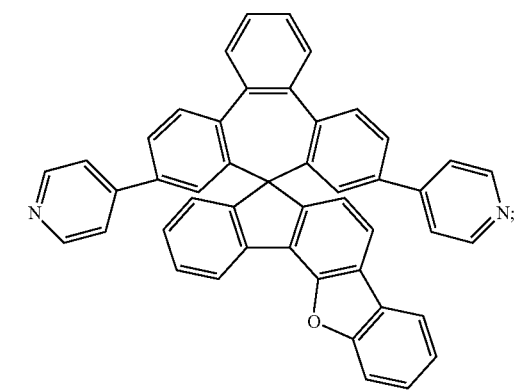
Compound XI
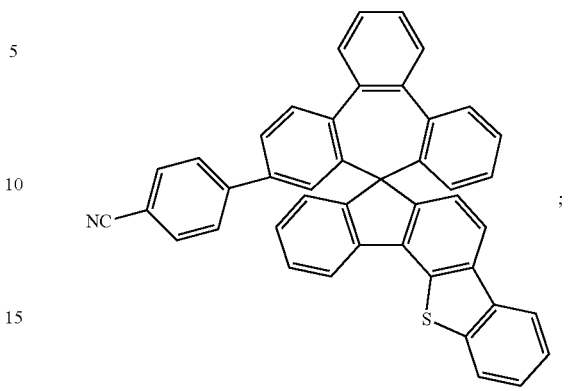
Compound XII
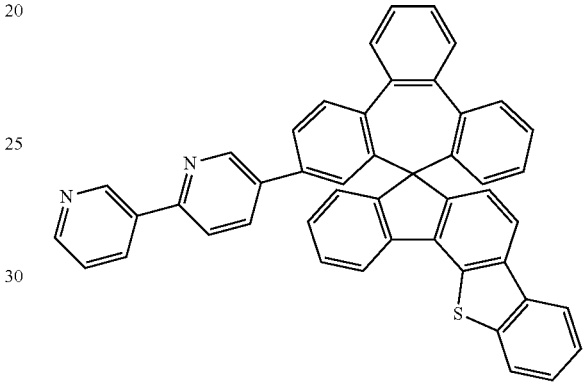
Compound XIII
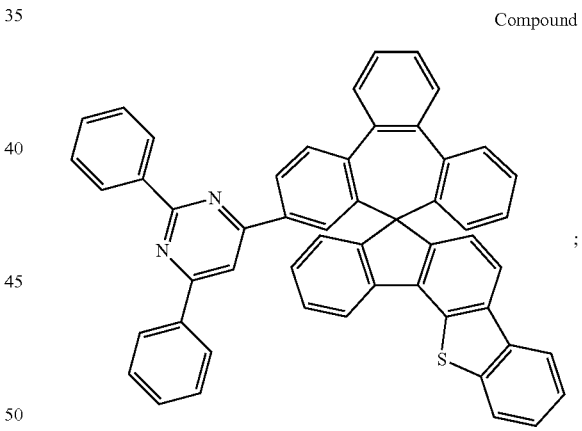
Compound XIV
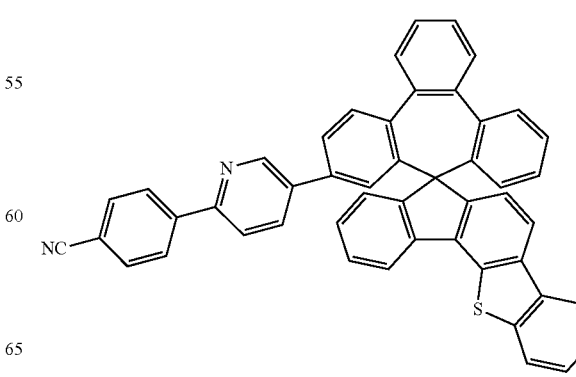

Compound XV
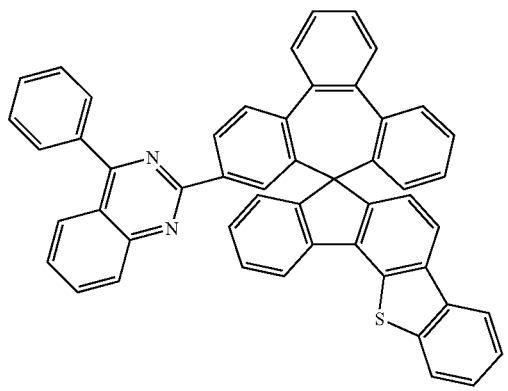
Compound XVI
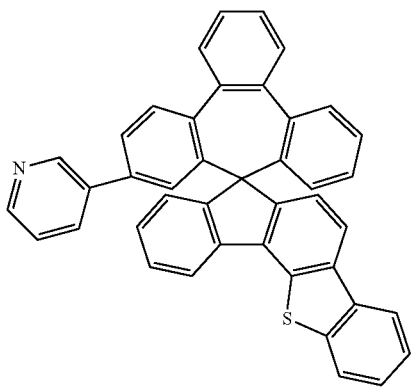
Compound XVII
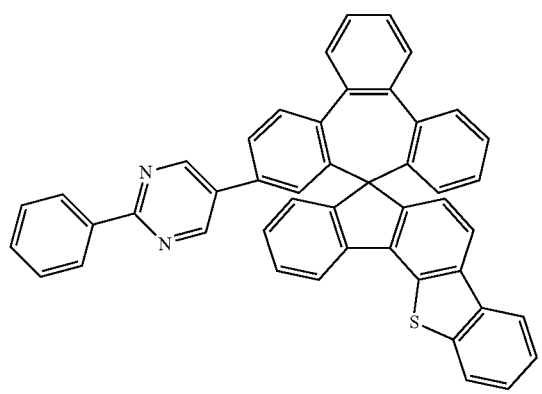
Compound XVIII
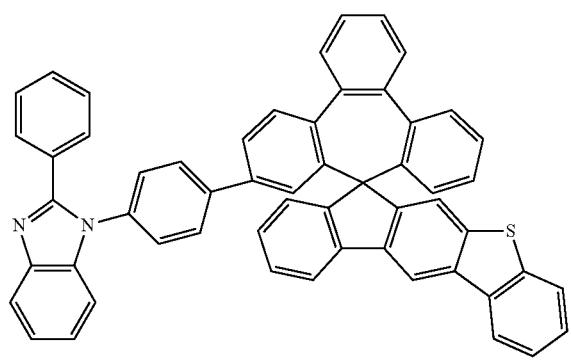
Compound XIX
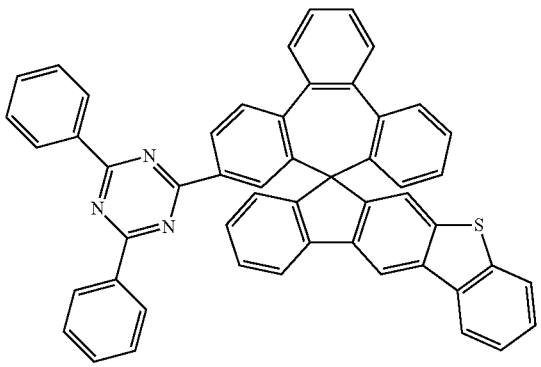
Compound XX
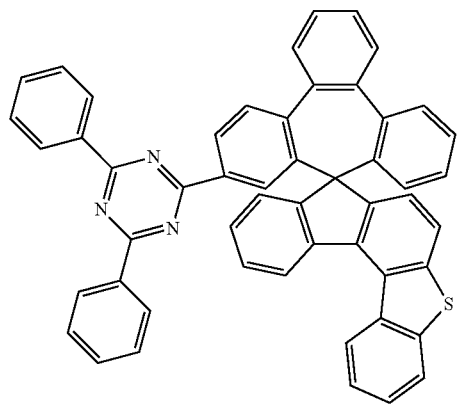
Compound XXI
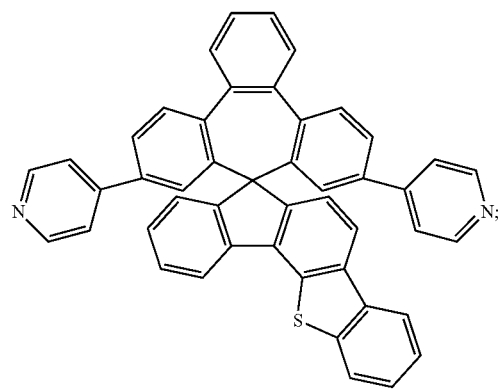
Compound XXII
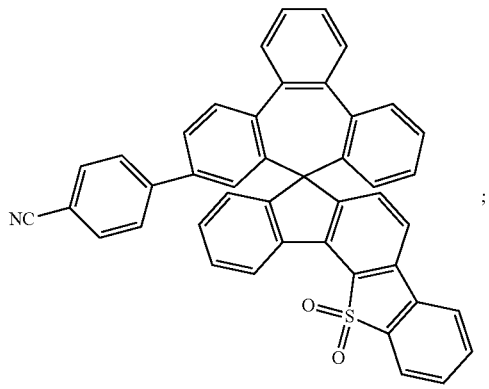

Compound XXIII

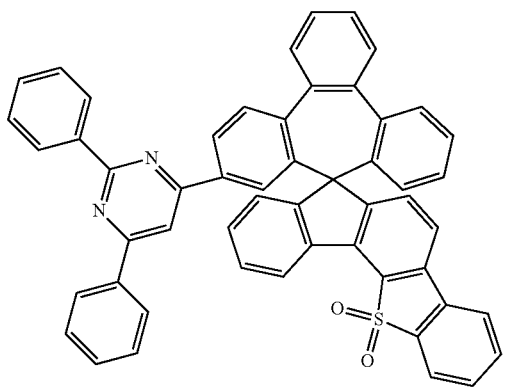

Compound XXIV

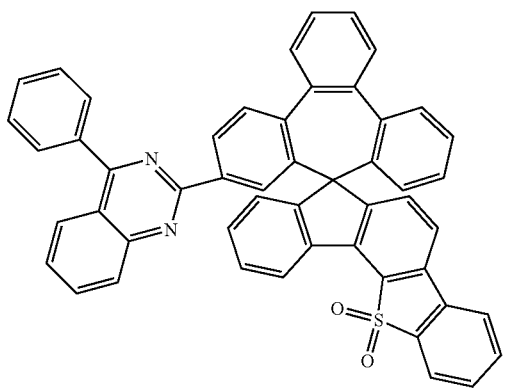

Compound XXV

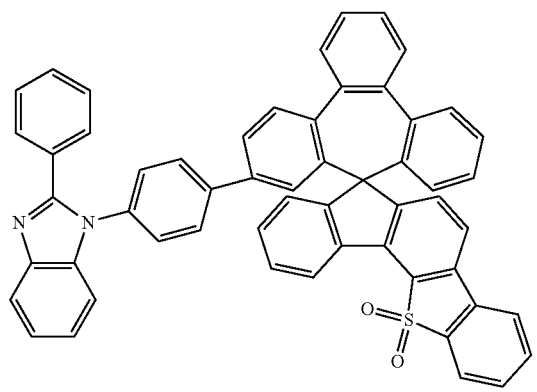

Compound XXVI

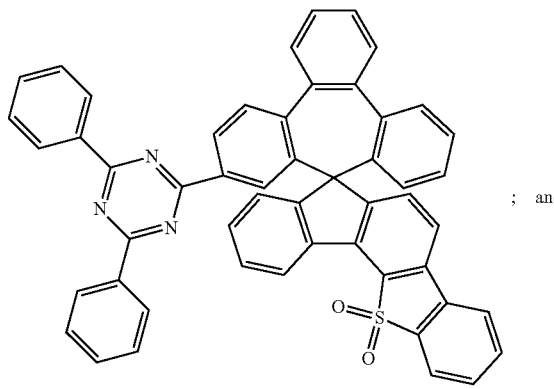
; and

Compound XXVII

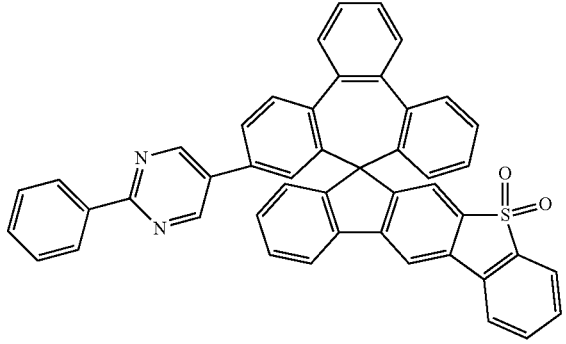

14. An organic electronic device, comprising a first electrode, a second electrode, and an organic layer disposed between the first electrode and the second electrode, wherein the organic layer comprises the compound as claimed in claim 1.

15. The organic electronic device as claimed in claim 14, wherein the organic electronic device is an organic light emitting device.

16. The organic electronic device as claimed in claim 15, wherein the organic light emitting device comprises:
   a hole injection layer formed on the first electrode;
   a hole transport layer formed on the hole injection layer;
   an emission layer formed on the hole transport layer;
   an electron transport layer formed on the emission layer, wherein the organic layer is the electron transport layer; and
   an electron injection layer formed between the electron transport layer and the second electrode.

17. The organic electronic device as claimed in claim 15, wherein the organic light emitting device comprises:
   a hole injection layer formed on the first electrode;
   a hole transport layer formed on the hole injection layer;
   an emission layer formed on the hole transport layer;
   a hole blocking layer formed on the emission layer, wherein the organic layer is the hole blocking layer;
   an electron transport layer formed on the hole blocking layer; and
   an electron injection layer formed between the electron transport layer and the second electrode.

18. The organic electronic device as claimed in claim 14, wherein the compound is selected from the group consisting of:

Compound I

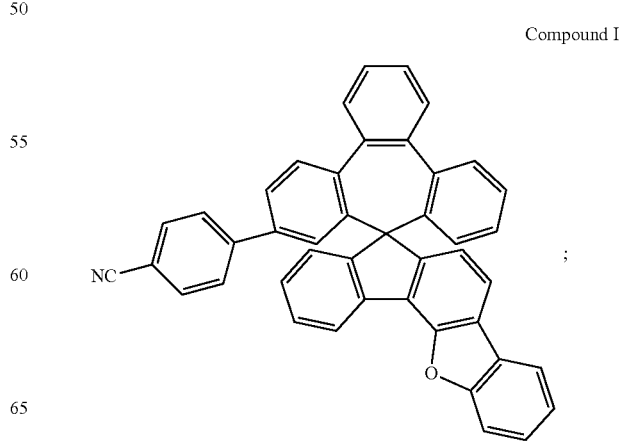
;

-continued
Compound II
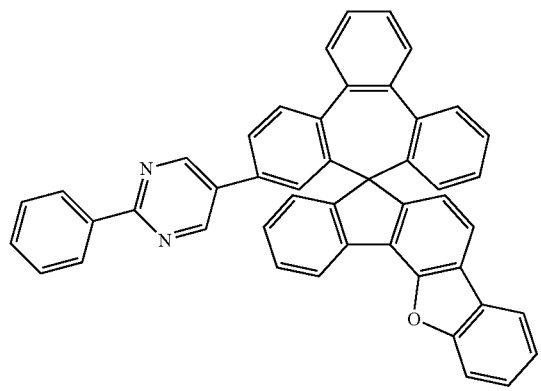
Compound III
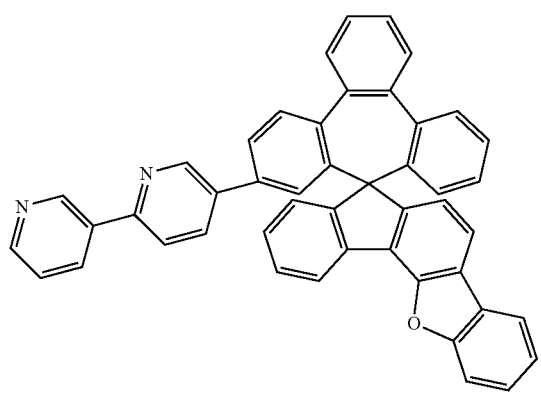
Compound IV
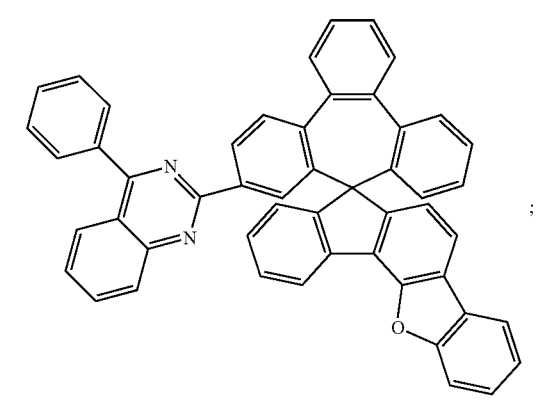
Compound V
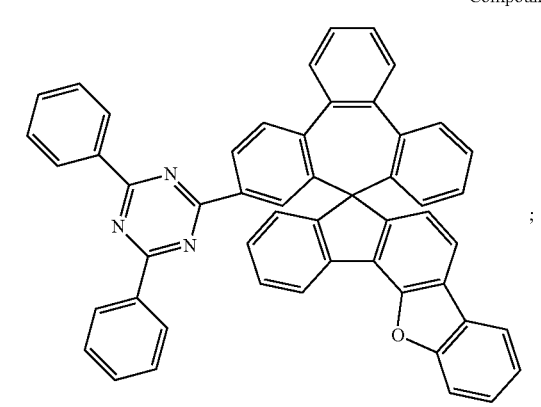
-continued
Compound VI
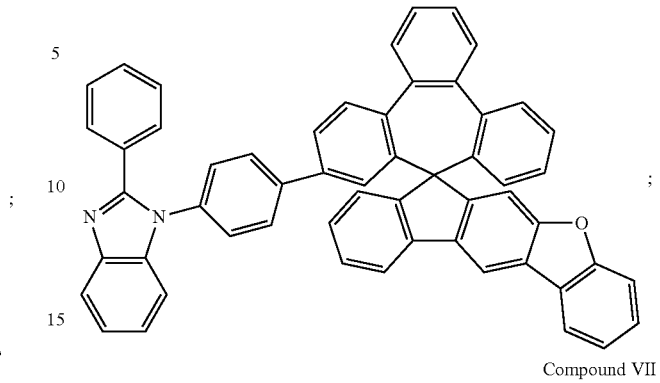
Compound VII
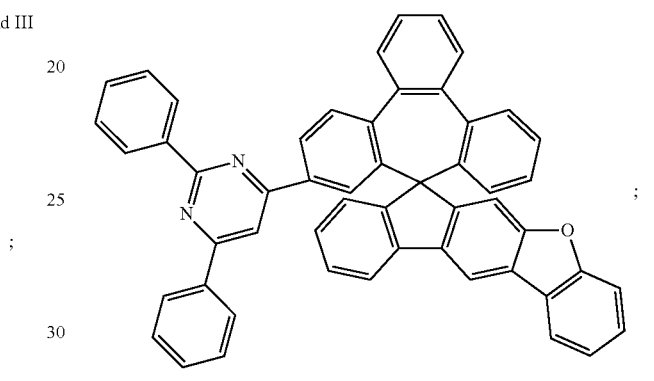
Compound VIII
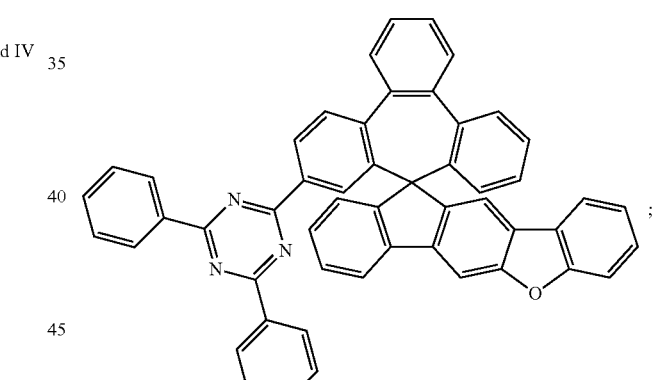
Compound IX
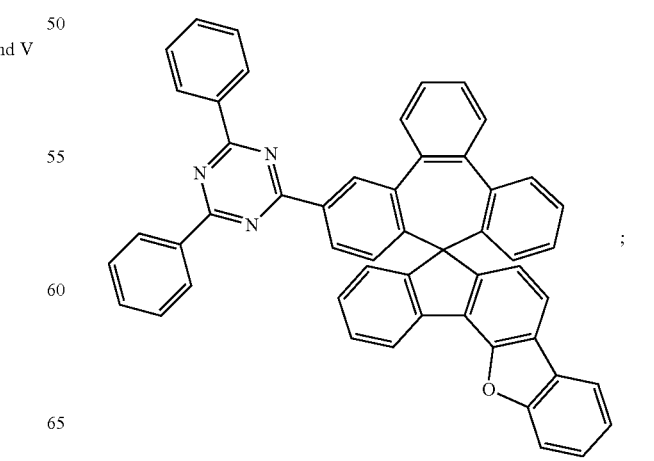

Compound X
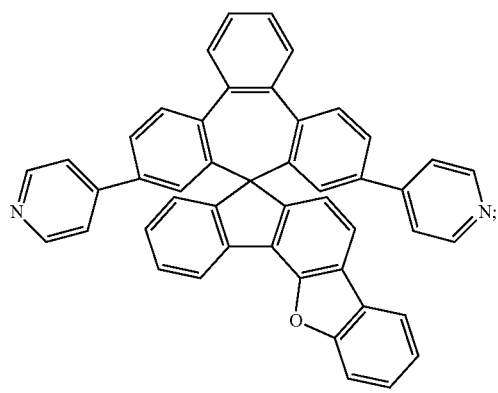
Compound XI
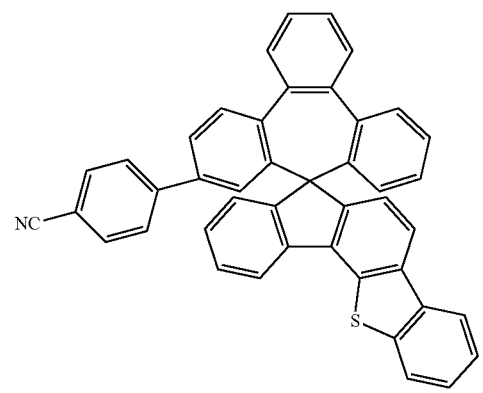
Compound XII
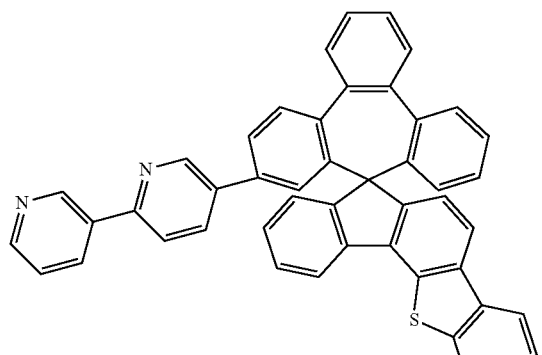
Compound XIII
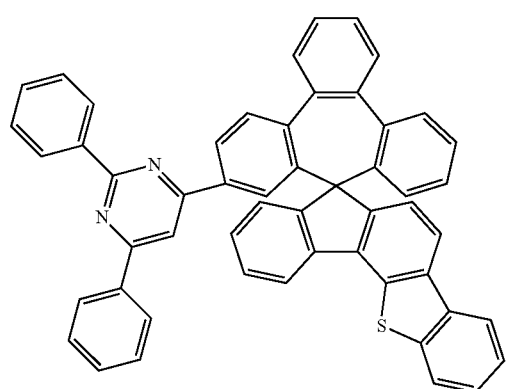
Compound XIV
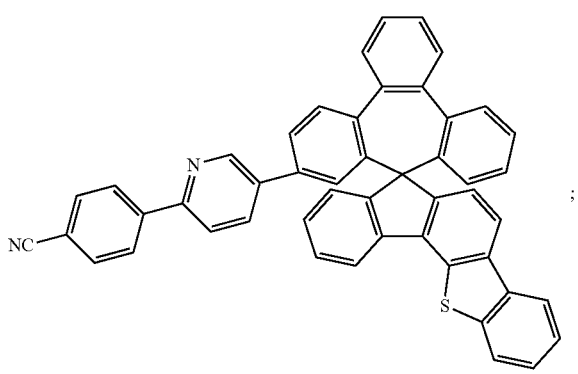
Compound XV
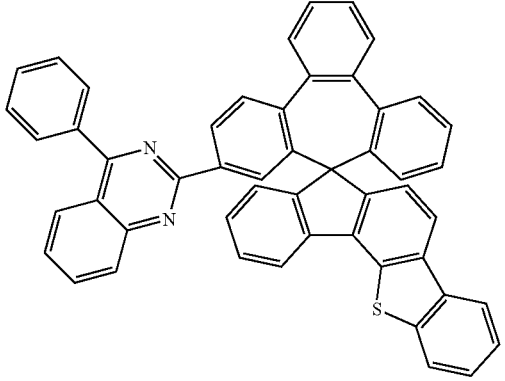
Compound XVI
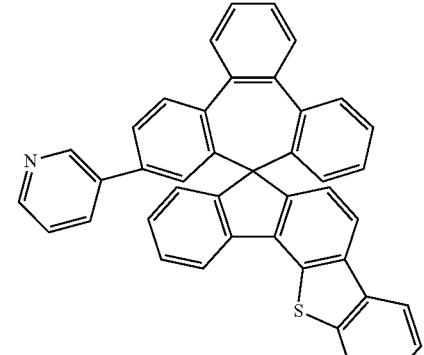
Compound XVII
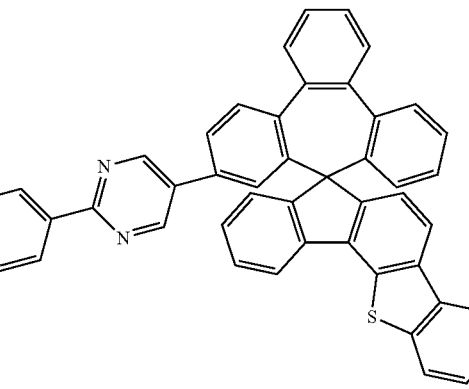

Compound XVIII
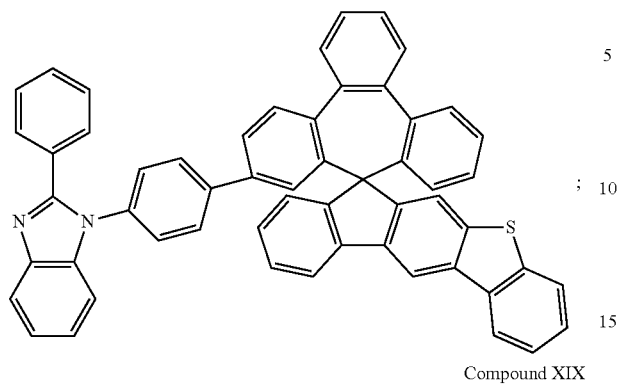
Compound XIX
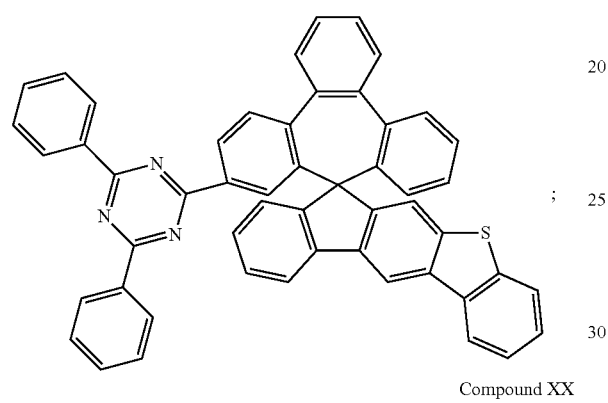
Compound XX
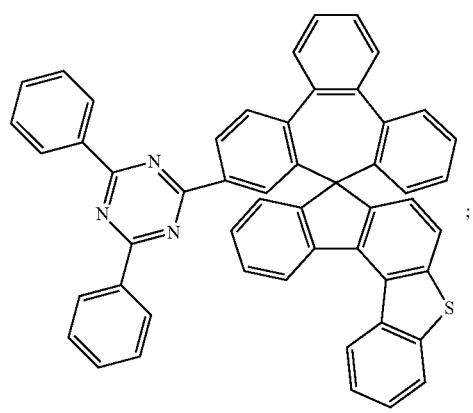
Compound XXI
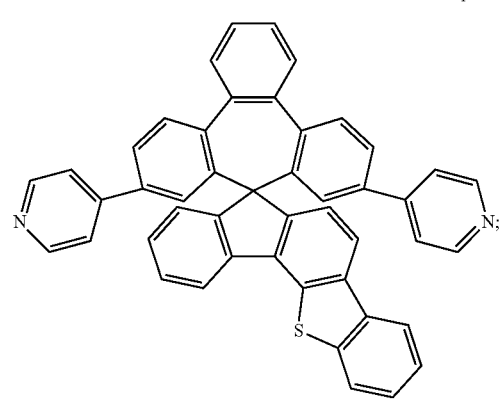
Compound XXII
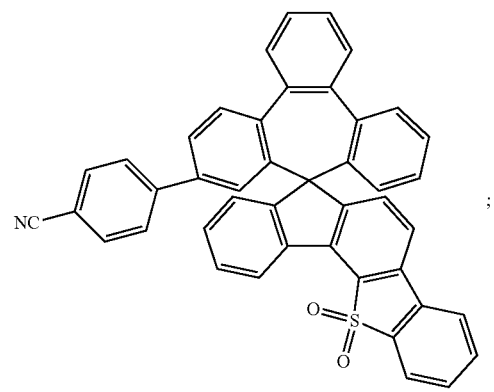
Compound XXIII
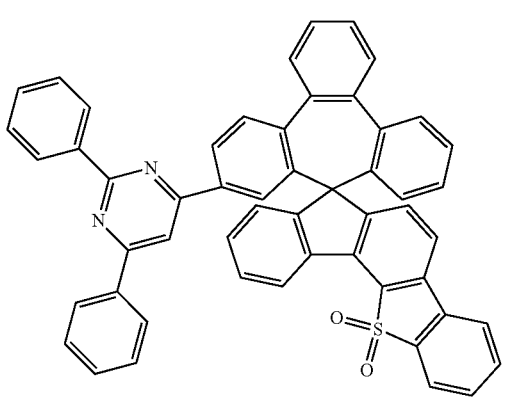
Compound XXIV
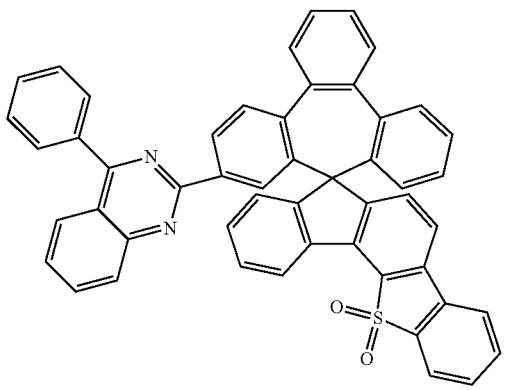
Compound XXV
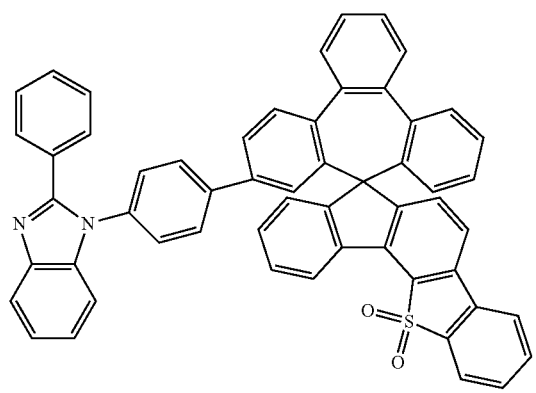

-continued
Compound XXVI
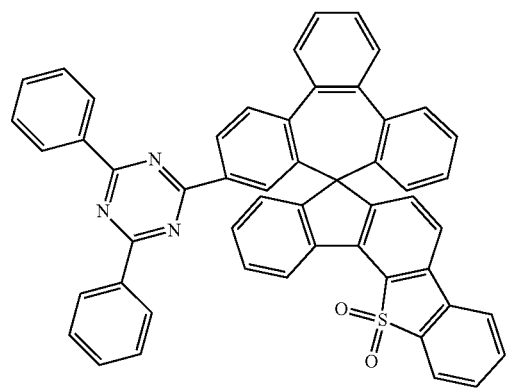
; and
-continued
Compound XXVII
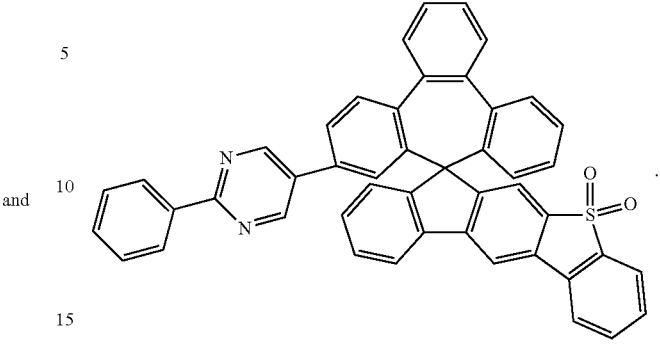
.
* * * * *